United States Patent
Vacca et al.

(10) Patent No.: US 10,745,379 B2
(45) Date of Patent: Aug. 18, 2020

(54) IRE1 SMALL MOLECULE INHIBITORS

(71) Applicant: Cornell University, Ithaca, NY (US)

(72) Inventors: Joseph P. Vacca, Telford, PA (US); Dansu Li, Warrington, PA (US); Sarah Bettigole, New York, NY (US)

(73) Assignee: Cornell University, Ithica, NY (US)

( * ) Notice: Subject to any disclaimer, the term of this patent is extended or adjusted under 35 U.S.C. 154(b) by 0 days.

(21) Appl. No.: 16/184,916

(22) Filed: Nov. 8, 2018

(65) Prior Publication Data

US 2019/0169160 A1 Jun. 6, 2019

Related U.S. Application Data

(60) Provisional application No. 62/584,575, filed on Nov. 10, 2017, provisional application No. 62/678,723, filed on May 31, 2018.

(51) Int. Cl.

| | | |
|---|---|---|
| *C07D 401/04* | (2006.01) | |
| *C07D 403/04* | (2006.01) | |
| *C07D 239/74* | (2006.01) | |
| *C07D 239/94* | (2006.01) | |
| *C07D 401/10* | (2006.01) | |
| *A61P 35/00* | (2006.01) | |
| *C07D 239/84* | (2006.01) | |
| *C07D 217/22* | (2006.01) | |
| *C07D 413/04* | (2006.01) | |
| *C07D 417/04* | (2006.01) | |
| *C07D 403/10* | (2006.01) | |

(52) U.S. Cl.
CPC ............ *C07D 401/10* (2013.01); *A61P 35/00* (2018.01); *C07D 217/22* (2013.01); *C07D 239/84* (2013.01); *C07D 401/04* (2013.01); *C07D 403/04* (2013.01); *C07D 403/10* (2013.01); *C07D 413/04* (2013.01); *C07D 417/04* (2013.01)

(58) Field of Classification Search
CPC .. C07D 401/04; C07D 403/04; C07D 239/74; C07D 239/94
See application file for complete search history.

(56) References Cited

FOREIGN PATENT DOCUMENTS

| WO | WO-2014052669 A1 | 4/2014 |
|---|---|---|
| WO | WO-2017152117 A1 | 9/2017 |
| WO | WO-2018222918 A1 | 12/2018 |
| WO | WO-2019094641 A1 | 5/2019 |

OTHER PUBLICATIONS

"International Application Serial No. PCT/US2018/059894, International Search Report dated Feb. 4, 2019", 4 pgs.
"International Application Serial No. PCT/US2018/059894, Written Opinion dated Feb. 4, 2019", 5 pgs.

*Primary Examiner* — Bruck Kifle
(74) *Attorney, Agent, or Firm* — Schwegman Lundberg & Woessner, P.A.

(57) ABSTRACT

Provided herein are small molecule inhibitors for the targeting or IRE1 protein family members. Binding may be direct or indirect. Further provided herein are methods of using IRE1 small molecule inhibitors for use in treating or ameliorating cancer in a subject. Moreover, IRE1 small molecule inhibitors described herein are for the treatment of cancer, where the cancer is a solid or hematologic cancer.

24 Claims, 10 Drawing Sheets
Specification includes a Sequence Listing.

* Kinase domain dimer interface residues
* KEN domain dimer interface residues
▼ Putative Nuclease active site residues

IRE1 SMALL MOLECULE INHIBITORS

CROSS-REFERENCE

This application claims the benefit of U.S. Provisional Patent Application No. 62/678,723 filed on May 31, 2018, and U.S. Provisional Patent Application No. 62/584,575 filed on Nov. 10, 2017, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 29, 2018, is named 51089-715_201_SL.txt and is 28,620 bytes in size.

BACKGROUND

Aggressive tumors have evolved strategies that enable them to thrive under constant adverse conditions. For example, cancer cells respond to hypoxia, nutrient starvation, oxidative stress, and high metabolic demand by adjusting their protein folding capacity via the endoplasmic reticulum (ER) stress response pathway. There exists a need for improved methods and compositions to target cancer cells and counter their mechanisms of survival.

BRIEF SUMMARY

Provided in one aspect is a compound of Formula (I), or a pharmaceutically acceptable salt, or solvate thereof:

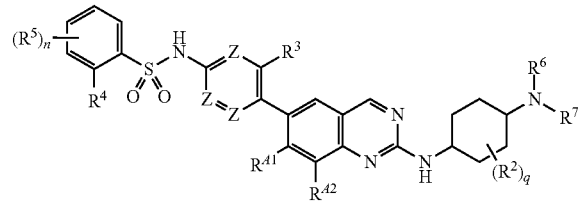

Formula (I)

wherein, each Z is independently N or $CR^1$, provided that at least one Z is N;

each $R^1$ is independently H, halogen, —CN, —$OR^8$, —$SR^8$, —S(=O)$R^9$, —S(=O)$_2R^9$, —S(=O)$_2N(R^8)_2$, —$NR^8$S(=O)$_2R^9$, —C(=O)$R^9$, —OC(=O)$R^9$, —C(=O)$OR^8$, —OC(=O)$OR^9$, —N($R^8$)$_2$, —OC(=O)N($R^8$)$_2$, —$NR^8$C(=O)$R^9$, —$NR^8$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^3$ is —CN, —$OR^8$, —$SR^8$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^4$ is halogen, —CN, —$OR^8$, optionally substituted $C_1$-$C_4$alkyl, optionally substituted $C_1$-$C_4$fluoroalkyl, or optionally substituted $C_1$-$C_4$heteroalkyl;

each $R^5$ is independently H, halogen, —CN, —$OR^8$, —$SR^8$, —N($R^8$)$_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^2$ is independently H, halogen, —CN, —$OR^8$, —$SR^8$, —S(=O)$R^9$, —S(=O)$_2R^9$, —S(=O)$_2N(R^8)_2$, —$NR^8$S(=O)$_2R^9$, —C(=O)$R^9$, —OC(=O)$R^9$, —C(=O)$OR^8$, —OC(=O)$OR^9$, —N($R^8$)$_2$, —OC(=O)N($R^8$)$_2$, —$NR^8$C(=O)$R^9$, —$NR^8$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^6$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

$R^7$ is optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cycloalkylalkyl, optionally substituted $C_2$-$C_{10}$heterocycloalkyl, optionally substituted aryl, or optionally substituted heteroaryl;

or $R^6$ and $R^7$ are taken together with the N atom to which they are attached to form an optionally substituted heterocycle;

each $R^8$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^8$ are taken together with the N atom to which they are attached to form an optionally substituted heterocycle;

each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

$R^{A1}$ and $R^{A2}$ are each independently H, halogen, —$OR^9$, optionally substituted $C_1$-$C_4$alkyl, optionally substituted $C_1$-$C_4$heteroalkyl, optionally substituted $C_1$-$C_4$fluoroalkyl, or optionally substituted aryl; provided that both $R^{A1}$ and $R^{A2}$ are not H;

n is 0, 1, 2, 3, or 4; and q is 0, 1, 2, 3, or 4.

Provided in another aspect is a compound of Formula (I), or a pharmaceutically acceptable salt, or solvate thereof:

Formula (I)

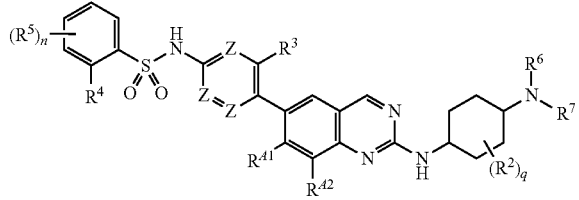

wherein, each Z is independently N or CR¹, provided that at least one Z is N;

each R¹ is independently H, halogen, —CN, —OR⁸, —SR⁸, —S(=O)R⁹, —S(=O)₂R⁹, —S(=O)₂N(R⁸)₂, —NR⁸S(=O)₂R⁹, —C(=O)R⁹, —OC(=O)R⁹, —C(=O)OR⁸, —OC(=O)OR⁹, —N(R⁸)₂, —OC(=O)N(R⁸)₂, —NR⁸C(=O)R⁹, —NR⁸C(=O)OR⁹, optionally substituted C₁-C₄alkyl, optionally substituted C₁-C₄fluoroalkyl, optionally substituted C₁-C₄heteroalkyl, optionally substituted C₃-C₆cycloalkyl, optionally substituted aryl, or optionally substituted heteroaryl;

R³ is —CN, —OR⁸, —SR⁸, optionally substituted C₁-C₄alkyl, optionally substituted C₁-C₄fluoroalkyl, optionally substituted —O—C₁-C₄alkyl, optionally substituted C₁-C₄heteroalkyl, optionally substituted C₃-C₆cycloalkyl, optionally substituted —O—C₃-C₆cycloalkyl, optionally substituted C₃-C₆heterocycloalkyl, optionally substituted —O—C₃-C₆heterocycloalkyl, optionally substituted aryl, or optionally substituted heteroaryl;

R⁴ is halogen, —CN, —OR⁸, optionally substituted C₁-C₄alkyl, optionally substituted C₁-C₄fluoroalkyl, or optionally substituted C₁-C₄heteroalkyl;

each R⁵ is independently H, halogen, —CN, —OR⁸, —SR⁸, —N(R⁸)₂, optionally substituted C₁-C₄alkyl, optionally substituted C₁-C₄fluoroalkyl, optionally substituted C₁-C₄heteroalkyl, optionally substituted C₃-C₆cycloalkyl, optionally substituted C₂-C₁₀heterocycloalkyl, optionally substituted aryl, or optionally substituted heteroaryl;

each R² is independently H, halogen, —CN, —OR⁸, —SR⁸, —S(=O)R⁹, —S(=O)₂R⁹, —S(=O)₂N(R⁸)₂, —NR⁸S(=O)₂R⁹, —C(=O)R⁹, —OC(=O)R⁹, —C(=O)OR⁸, —OC(=O)OR⁹, —N(R⁸)₂, —OC(=O)N(R⁸)₂, —NR⁸C(=O)R⁹, —NR⁸C(=O)OR⁹, optionally substituted C₁-C₄alkyl, optionally substituted C₁-C₄fluoroalkyl, optionally substituted C₁-C₄heteroalkyl, optionally substituted C₃-C₆cycloalkyl, optionally substituted aryl, or optionally substituted heteroaryl;

R⁶ is H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₃-C₆cycloalkylalkyl, optionally substituted C₂-C₁₀heterocycloalkyl, optionally substituted aryl, or optionally substituted heteroaryl;

R⁷ is optionally substituted C₃-C₆cyclooalkylalkyl or R⁷ is methyl, ethyl, —CH₂CF₃, —CH₂— cyclopropyl, or —CH₂CH₂OCH₃;

each R⁸ is independently H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

or two R⁸ are taken together with the N atom to which they are attached to form an optionally substituted heterocycle;

each R⁹ is independently optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

R^{A1} and R^{A2} are each independently H, halogen, —OR⁹, optionally substituted C₁-C₄alkyl, optionally substituted C₁-C₄heteroalkyl, optionally substituted C₁-C₄fluoroalkyl, or optionally substituted aryl; provided that both R^{A1} and R^{A2} are not H;

n is 0, 1, 2, 3, or 4; and q is 0, 1, 2, 3, or 4.

Any combination of the groups described above or below for the various variables is contemplated herein. Throughout the specification, groups and substituents thereof are chosen by one skilled in the field to provide stable moieties and compounds.

Provided herein are compounds or pharmaceutically acceptable salts, or solvates thereof, that selectively bind to IRE1a at one or more binding sites. In some embodiments, the IRE1a comprises an RNase domain, a kinase domain, or any combination thereof. In some embodiments, the kinase domain is an auto-transphosphorylation kinase domain. In some embodiments, the kinase domain comprises an ATP-binding pocket. In some embodiments, the kinase domain comprises an activation loop. In some embodiments, at least one binding site is within the RNase domain. In some embodiments, at least one binding site is within the kinase domain. In some embodiments, the at least one binding site is within the ATP-binding pocket of the kinase domain. In some embodiments, the at least one binding site is within the activation loop of the kinase domain. In some embodiments, binding occurs at a first binding site. In some embodiments, the first binding site is located within the RNase domain, kinase domain, ATP-binding pocket, or activation loop. In some embodiments, the first binding site comprises at least one amino acid residue of within amino acid residues 465-977 of SEQ ID NO: 1. In some embodiments, the first binding site comprises at least one amino acid residue within amino acid residues 568-833 of SEQ ID NO: 1. In some embodiments, the first binding site comprises at least one amino acid residue within amino acid residues 577-586, 597, 599, 626, 642-643, 645, 648, 688, 692-693, 695, or 711 of SEQ ID NO: 1. In some embodiments, the first binding site comprises at least one amino acid residue within amino acid residues 710-725 or 729-736 of SEQ ID NO: 1. In some embodiments, the first binding site comprises at least one amino acid residue within amino acid residues 835-963 of SEQ ID NO: 1. In some embodiments, binding further occurs at a second binding site. In some embodiments, the second binding site is located within the RNase domain, the kinase domain, the ATP-binding pocket, or the activation loop. In some embodiments, the second binding site comprises at least one amino acid residue of within amino acid residues 465-977 of SEQ ID NO: 1. In some embodiments, the second binding site comprises at least one amino acid residue within amino acid residues 568-833 of SEQ ID NO: 1. In some embodiments, the second binding site comprises at least one amino acid residue within amino acid residues 577-586, 597, 599, 626, 642-643, 645, 648, 688, 692-693, 695, or 711 of SEQ ID NO: 1. In some embodiments, the second binding site comprises at least one amino acid residue within amino acid residues 710-725 or 729-736 of SEQ ID NO: 1. In some embodiments, the second binding site comprises at least one amino acid residue within amino acid residues 835-963 of SEQ ID NO: 1. In some embodiments, binding occurs when the IRE1a is in a homodimerized conformation. In some embodiments, binding occurs when the IRE1a is in an oligomerized conformation. In some embodiments, binding occurs when the IRE1a is in a non-oligomerized or non-dimerized conformation. In some embodiments, binding occurs when the IRE1a is in an ATP-bound state. In some embodiments, binding occurs when the IRE1a is in a non-ATP-bound state. In some embodiments, the compound selectively binds to a first IRE1a. In some embodiments, selectively binding to the first IRE1a blocks dimerization of the first IRE1a to a second IRE1a. In some embodiments, selectively binding to the first IRE1a blocks auto-transphosphorylation of the first IRE1a. In some embodiments, selectively binding to the first IRE1a blocks auto-transphosphorylation of a second IRE1a to which the first IRE1a is dimerized. In some embodiments, selectively binding to the first IRE1a blocks activation of the first IRE1a. In some embodiments, selectively binding to the first IRE1a blocks activation a second IRE1a to which the first IRE1a is dimerized. In some embodiments, selectively binding to the first IRE1a blocks kinase activity of the first IRE1a. In some embodiments, selectively binding to the first IRE1a blocks kinase activity of a second IRE1a to which the first IRE1a is dimerized. In some embodiments, selectively binding to the first IRE1a blocks RNase activity of the first IRE1a. In some embodiments, selectively binding to the first IRE1a blocks RNase activity of a second IRE1a to which the first IRE1a is dimerized.

In another aspect, provided herein is a compound that selectively binds a first IRE1a at two or more sites, wherein when the compound is bound to the first IRE1a protein, the compound binds to an ATP-binding pocket of the first IRE1a and blocks the binding of ATP to the first IRE1a. In some embodiments, the ATP binding pocket is comprised within a kinase domain. In some embodiments, the ATP binding pocket is comprised within amino acid residues 465-977 of SEQ ID NO: 1. In some embodiments, the ATP binding pocket is comprised within amino acid residues 568-833 of SEQ ID NO: 1. In some embodiments, the ATP binding pocket comprises one or more of amino acid resides 577-586, 597, 599, 626, 642-643, 645, 648, 688, 692-693, 695, or 711 of SEQ ID NO: 1.

In another aspect, provided herein is a pharmaceutical composition comprising any one of the compounds described herein, or a pharmaceutically acceptable salt or solvate thereof. In some embodiments, the pharmaceutical composition further comprises one or more pharmaceutically acceptable excipients.

In another aspect, provided herein is a method for treating or ameliorating the effects of a disease associated with altered IRE1 signaling, the method comprising administering to a subject in need thereof a pharmaceutical composition, wherein the pharmaceutical composition comprises the compound of any one of the compounds described herein. In some embodiments, the disease is cancer. In some embodiments, the cancer is a solid cancer or a hematologic cancer. In some embodiments, the cancer is an ovarian cancer, a bladder cancer, a breast cancer, or a lung cancer. In some embodiments, the breast cancer is triple negative breast cancer (TNBC). In some embodiments, the cancer is a leukemia, lymphoma, or multiple myeloma. In some embodiments, the pharmaceutical composition administered to the subject intravenously or orally.

In another aspect, provided herein is a method for treating or ameliorating a cell proliferative disorder, the method comprising administering a pharmaceutical composition comprising a compound, or a pharmaceutically acceptable salt, or solvate thereof, that selectively binds to at least one amino acid residue of a IRE1 family protein comprising an RNase domain and kinase domain. In some embodiments, the IRE1 family protein is IRE1a. In some embodiments, the compound binds to an ATP-binding site of IRE1a. In some embodiments, the cell proliferative disorder is cancer. In some embodiments, the cancer is a solid cancer or a hematologic cancer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Certain Terminology

Figure 1:
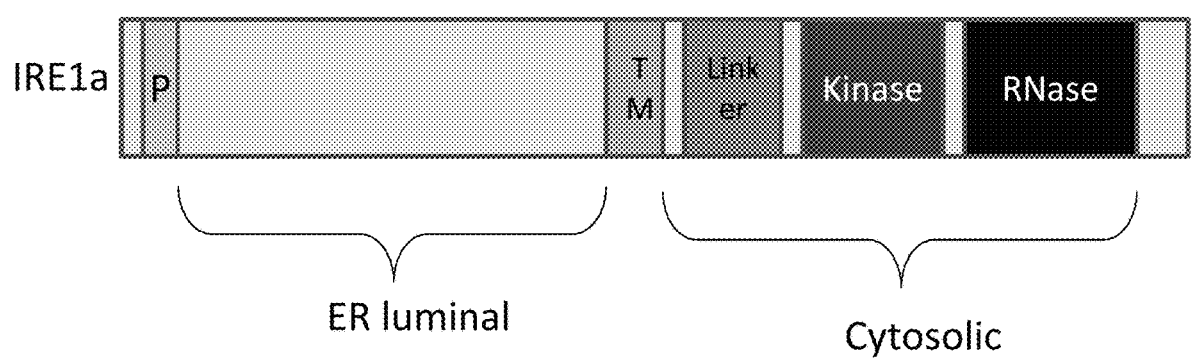
FIG. 1 shows an example diagram of the domain structure of IRE1a. A signal peptide (P) and transmembrane (TM) region are indicated.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. Unless otherwise noted, the "alkyl" group has 1 to 10 carbon atoms, i.e. a $C_1$-$C_{10}$alkyl, preferably 1 to 6 carbon atoms. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl. Alkyl includes alkenyls (one or more carbon-carbon double bonds) and alkynyls (one or more carbon-carbon triple bonds).

An "alkylene" group refers to a divalent alkyl radical. Any of the above mentioned monovalent alkyl groups may be an alkylene by abstraction of a hydrogen atom from the alkyl. Unless otherwise noted, an alkylene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

An "alkoxy" group refers to a (alkyl)O— group, where alkyl is as defined herein.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. Unless otherwise noted, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Unless otherwise noted, cycloalkyl groups have from 3 to 10 ring atoms, preferably from 3 to 6 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl. In some embodiments, a cycloalkyl is a monocyclic cycloalkyl.

Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1] heptanyl, and the like.

The term "cycloalkylalkyl" refers to a moiety of the formula —$R_bR_d$ where $R_b$ is an alkylene group as defined herein and $R_d$ is a cycloalkyl moiety as defined herein. In some embodiments, a cycloalkylalkyl moiety is a $C_3$-$C_{10}$cycloalkylalkyl moiety. In such a case, the $C_3$-$C_{10}$cycloalkylalkyl includes a $C_3$-$C_{10}$cycloalkyl radical. In some embodiments, a cycloalkylalkyl moiety is a $C_3$-$C_6$cycloalkylalkyl moiety. In such a case, the $C_3$-$C_6$cycloalkylalkyl includes a $C_3$-$C_6$cycloalkyl radical.

The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoralkyl is a $C_1$-$C_6$fluoroalkyl.

The term "fluoroalkyl" refers to an alkyl in which one or more hydrogen atoms are replaced by a fluorine atom. In one aspect, a fluoralkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to, unless otherwise stated, a straight or branched alkyl group comprising at least one carbon atom and at least one heteroatom, such as O, N (e.g. —NH—, —N(alkyl)-), P, Si, S, and Se. In some embodiments, one or more heteroatoms may be oxidized. Heteroatom(s) may be positioned within the alkyl moiety, e.g., —$CH_2$—O—$CH_2$—; at a point of connectivity with the remainder of the molecule, e.g., —S($=$O)$_2$CH(CH$_3$)CH$_2$—; or a combination thereof, e.g., —NHCH$_2$CH$_2$S($=$O)$_2$CH$_2$—. In one aspect, a heteroalkyl is a $C_1$-$C_6$heteroalkyl.

As used herein, the term "heteroatom" refers to an atom of any element other than carbon or hydrogen. Unless otherwise noted, the heteroatom is nitrogen, oxygen, or sulfur. In some embodiments, the heteroatom is nitrogen or oxygen. In some embodiments, the heteroatom is nitrogen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group comprises from 3 to 14 atoms in its ring system comprising 2 to 10 carbon atoms and from one to 4 heteroatoms, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo [4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d] imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo ($=$O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, a heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is a spirocyclic or bridged compound. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl.

The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein substituted with one or two of the preceding groups. In some embodiments, an optional substituent on an aliphatic carbon atom (acyclic or cyclic) includes oxo (=O).

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

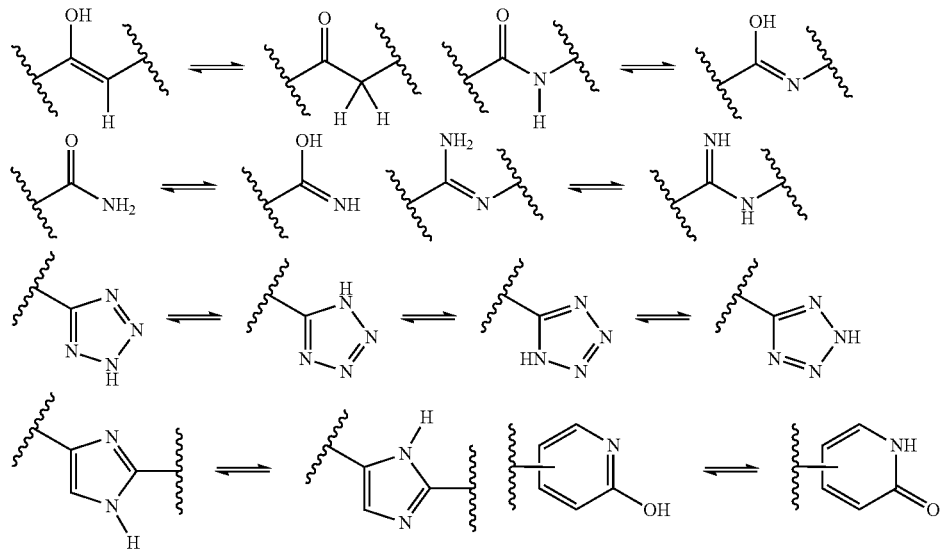

is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from deuterium, halogen, —CN, —NH$_2$, —NH (alkyl), —CH$_2$N(alkyl)$_2$, —N(alkyl)$_2$, —OH, —CO$_2$H, —CO$_2$alkyl, —CH$_2$NH$_2$, —C(=O)NH$_2$, —C(=O)NH (alkyl), —C(=O)N(alkyl)$_2$, —S(=O)$_2$NH$_2$, —S(=O)$_2$NH (alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —CH$_2$NH$_2$, —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH (C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O) C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CH$_2$NH$_2$, —CF$_3$, —OCH$_3$, and —OCF$_3$. In some embodiments, substituted groups are "Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Compounds

Compounds described herein, including pharmaceutically acceptable salts, and pharmaceutically acceptable solvates thereof, modulate IRE1 mediated signaling, directly or indirectly.

Provided in one aspect is a compound of Formula (I), or a pharmaceutically acceptable salt, or solvate thereof:

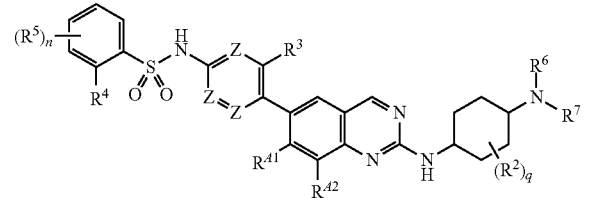

Formula (I)

wherein,
each Z is independently N or $CR^1$, provided that at least one Z is N;

each $R^1$ is independently H, halogen, —CN, —$OR^8$, —$SR^8$, —S(=O)$R^9$, —S(=O)$_2R^9$, —S(=O)$_2N(R^8)_2$, —$NR^8S(=O)_2R^9$, —C(=O)$R^9$, —OC(=O)$R^9$, —C(=O)$OR^8$, —OC(=O)$OR^9$, —N(R^8)_2$, —OC(=O)N(R^8)_2$, —$NR^8C(=O)R^9$, —$NR^8C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^3$ is —CN, —$OR^8$, —$SR^8$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^4$ is halogen, —CN, —$OR^8$, optionally substituted $C_1$-$C_4$alkyl, optionally substituted $C_1$-$C_4$fluoroalkyl, or optionally substituted $C_1$-$C_4$heteroalkyl;

each $R^5$ is independently H, halogen, —CN, —$OR^8$, —$SR^8$, —$N(R^8)_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^2$ is independently H, halogen, —CN, —$OR^8$, —$SR^8$, —S(=O)$R^9$, —S(=O)$_2R^9$, —S(=O)$_2N(R^8)_2$, —$NR^8S(=O)_2R^9$, —C(=O)$R^9$, —OC(=O)$R^9$, —C(=O)$OR^8$, —OC(=O)$OR^9$, —N(R^8)_2$, —OC(=O)N(R^8)_2$, —$NR^8C(=O)R^9$, —$NR^8C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^6$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cycloalkylalkyl, optionally substituted $C_2$-$C_{10}$heterocycloalkyl, optionally substituted aryl, or optionally substituted heteroaryl;

$R^7$ is optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cycloalkylalkyl, optionally substituted $C_2$-$C_{10}$heterocycloalkyl, optionally substituted aryl, or optionally substituted heteroaryl;

or $R^6$ and $R^7$ are taken together with the N atom to which they are attached to form an optionally substituted heterocycle;

each $R^8$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^8$ are taken together with the N atom to which they are attached to form an optionally substituted heterocycle;

each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

$R^{A1}$ and $R^{A2}$ are each independently H, halogen, —$OR^9$, optionally substituted $C_1$-$C_4$alkyl, optionally substituted $C_1$-$C_4$heteroalkyl, optionally substituted $C_1$-$C_4$fluoroalkyl, or optionally substituted aryl; provided that both $R^{A1}$ and $R^{A2}$ are not H;

n is 0, 1, 2, 3, or 4; and q is 0, 1, 2, 3, or 4.

Provided in a second aspect is a compound of Formula (I), or a pharmaceutically acceptable salt, or solvate thereof wherein Z, $R^1$, $R^3$, $R_4$, $R^5$, $R^2$, $R^8$, $R^9$, $R^{A1}$, $R^{A2}$, n and q are as provided in the preceding paragraph; $R^6$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cycloalkylalkyl, optionally substituted $C_2$-$C_{10}$heterocycloalkyl, optionally substituted aryl, or optionally substituted heteroaryl; and $R^7$ is optionally substituted $C_3$-$C_6$cyclooalkylalkyl or $R^7$ is methyl, ethyl, —$CH_2CF_3$, —$CH_2$-cyclopropyl, or —$CH_2CH_2OCH_3$. $R^7$ can be, for example, methyl, ethyl, —$CH_2CF_3$, —$CH_2$-cyclopropyl, or —$CH_2CH_2OCH_3$. Alternatively, $R^7$ can be, for example, optionally substituted $C_3$-$C_6$cyclooalkylalkyl or —$CH_2$-cyclobutyl. $R^6$ can be, for example, hydrogen, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cyclooalkyl, or optionally substituted $C_3$-$C_6$cycloalkylalkyl. Alternatively, $R^6$ can be, for example, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cyclooalkyl, or optionally substituted $C_3$-$C_6$cycloalkylalkyl. Alternatively, $R^6$ can be, for example, methyl.

In some embodiments,

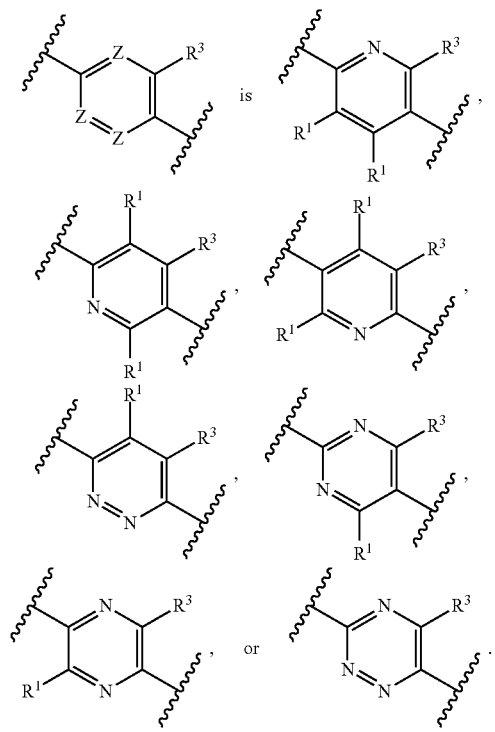

In such embodiments, $R^1$, $R^3$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments,

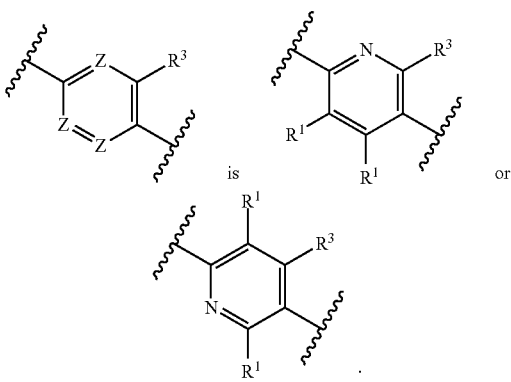

In such embodiments, $R^1$, $R^3$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments,

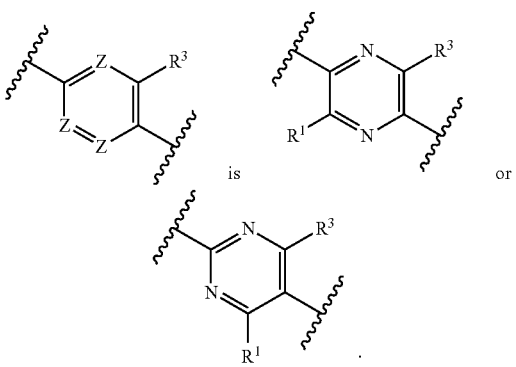

In such embodiments, $R^1$, $R^3$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments,

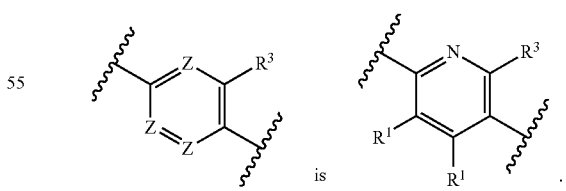

In such embodiments, $R^1$, $R^3$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, each $R^1$ is independently H, halogen, —CN, —$OR^8$, optionally substituted $C_1$-$C_4$alkyl, optionally substituted $C_1$-$C_4$fluoroalkyl, or optionally substituted $C_1$-$C_4$heteroalkyl. In such embodiments, Z, $R^3$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, each $R^1$ is independently H, halogen, —$OR^8$, optionally substituted $C_1$-$C_4$alkyl, or optionally substituted $C_1$-$C_4$heteroalkyl. In such embodiments, Z, $R^3$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, each $R^1$ is independently H. In some embodiments, each $R^1$ is independently halogen. In some embodiments, each $R^1$ is independently —CN. In some embodiments, each $R^1$ is independently —$OR^8$. In some embodiments, each $R^1$ is independently optionally substituted $C_1$-$C_4$alkyl. In some embodiments, each $R^1$ is independently optionally substituted $C_1$-$C_4$fluoroalkyl. In some embodiments, each $R^1$ is independently optionally substituted $C_1$-$C_4$heteroalkyl. In all such embodiments, Z, $R^3$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^3$ is —CN, —$OR^8$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, or optionally substituted —O—$C_3$-$C_6$cycloalkyl. In such embodiments, Z, $R^1$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^3$ is —$OR^8$, optionally substituted $C_1$-$C_4$alkyl, optionally substituted $C_1$-$C_4$fluoroalkyl, or optionally substituted $C_1$-$C_4$heteroalkyl. In such embodiments, Z, $R^1$, $R^4$, $R^5$, $R^2$, $R^6$, $R^7$, $R^8$, $R^9$, $R^{A1}$, $R^{A2}$, n and q are can be as defined above for Formula (I) or can be as defined in any of the embodiments described herein for those substituents in any combination thereof.

In some embodiments, $R^3$ is —CN. In some embodiments, $R^3$ is —$OR^8$. In some embodiments, $R^3$ is optionally substituted $C_1$-$C_4$alkyl. In some embodiments, $R^3$ is optionally substituted $C_1$-$C_4$fluoroalkyl. In some embodiments, $R^3$ is optionally substituted $C_1$-$C_4$heteroalkyl. In some embodiments, $R^3$ is optionally substituted $C_3$-$C_6$cycloalkyl. In some embodiments, $R^3$ is optionally substituted —O—$C_3$-$C_6$cycloalkyl. In all such embodiments, Z, $R^1$, $R^4$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^8$ is optionally substituted $C_1$-$C_4$alkyl, optionally substituted $C_1$-$C_4$heteroalkyl, optionally substituted $C_1$-$C_4$fluoroalkyl, or optionally substituted $C_3$-$C_6$cycloalkyl. In some embodiments, $R^8$ is optionally substituted $C_1$-$C_4$alkyl. In some embodiments, $R^8$ is optionally substituted $C_1$-$C_4$heteroalkyl. In some embodiments, $R^8$ is optionally substituted $C_1$-$C_4$fluoroalkyl. In some embodiments, $R^8$ is optionally substituted $C_3$-$C_6$cycloalkyl. In all such embodiments, Z, $R^1$, $R^3$, $R^4$, $R^5$, $R^2$, $R^6$, $R^7$, $R^9$, $R^{A1}$, $R^{A2}$, n and q can be as defined above for Formula (I) or can be as defined in any of the embodiments described herein for those substituents in any combination thereof In some embodiments, $R^4$ is halogen, —CN, —$OR^8$, optionally substituted $C_1$-$C_4$alkyl, or optionally substituted $C_1$-$C_4$fluoroalkyl. In such embodiments, Z, $R^1$, $R^3$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^4$ is halogen, —CN, —$OR^8$, optionally substituted $C_1$-$C_4$alkyl, or optionally substituted $C_1$-$C_4$fluoroalkyl. In such embodiments, Z, $R^1$, $R^3$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^4$ is halogen, optionally substituted $C_1$-$C_4$alkyl, or optionally substituted $C_1$-$C_4$fluoroalkyl. In such embodiments, Z, $R^1$, $R^3$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^4$ is halogen. In some embodiments, $R^4$ is —Cl, —Br, —F, or —I. In all such embodiments, Z, $R^1$, $R^3$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^4$ is —$OR^8$. In some embodiments, $R^8$ is H, optionally substituted $C_1$-$C_4$alkyl, or optionally substituted $C_1$-$C_4$fluoroalkyl. In all such embodiments, Z, $R^1$, $R^3$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof In some embodiments, $R^4$ is optionally substituted $C_1$-$C_4$alkyl. In some embodiments, $R^4$ is methyl, ethyl, propyl, or butyl. In all such embodiments, Z, $R^1$, $R^3$, $R^5$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^4$ is optionally substituted $C_1$-$C_4$fluoroalkyl. In some embodiments, $R^4$ is —$CF_3$, —$CF_2CH_3$, or —$CH_2CF_3$. In all such embodiments, Z, $R^1$, $R^3$, $R^5$, $R^2$, $R^6$, $R^7$, $R^8$, $R^9$, $R^4R^{A2}$, n and q can be as defined above for Formula (I) or can be as defined in any of the embodiments described herein for those substituents in any combination thereof.

In some embodiments, $R^5$ is H, halogen, —CN, —$OR^8$, —$SR^8$, —$N(R^8)_2$, optionally substituted $C_1$-$C_4$alkyl, or optionally substituted $C_1$-$C_4$fluoroalkyl. In such embodiments, Z, $R^1$, $R^3$, $R^4$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^5$ is H. In some embodiments, $R^5$ is halogen. In some embodiments, $R^5$ is —Cl, —Br, —F, or —I. In all such embodiments, Z, $R^1$, $R^3$, $R^4$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^5$ is —$OR^8$. In some embodiments, $R^8$ is H, optionally substituted $C_1$-$C_4$alkyl, or optionally substituted $C_1$-$C_4$fluoroalkyl. In all such embodiments, Z, $R^1$, $R^3$, $R^4$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^5$ is optionally substituted $C_1$-$C_4$alkyl. In some embodiments, $R^5$ is methyl, ethyl, propyl, or butyl. In all such embodiments, Z, $R^1$, $R^3$, $R^4$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, $R^5$ is optionally substituted $C_1$-$C_4$fluoroalkyl. In some embodiments, $R^5$ is —$CF_3$, —$CF_2CH_3$, or —$CH_2CF_3$. In all such embodiments, Z, $R^1$, $R^3$, $R^4$, $R^2$, $R^6$, $R^7$, $R^8$, $R^9$, $R^{A1}$, $R^{A2}$, n and q can be as defined above for Formula (I) or can be as defined in any of the embodiments described herein for those substituents in any combination thereof.

In some embodiments, the compound of Formula (I) has the structure of formula (Ia)

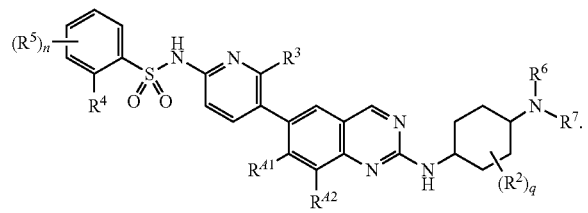

(Ia)

In some embodiments, the compound of Formula (I) has the structure of formula (Ib)

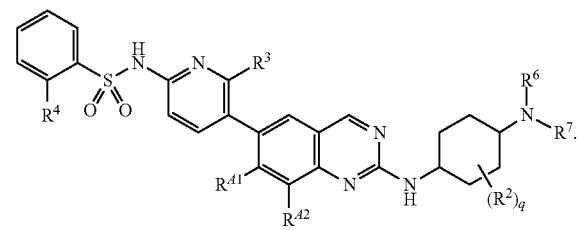

(Ib)

In some embodiments, each $R^2$ is independently H, halogen, —$OR^8$, optionally substituted $C_1$-$C_4$alkyl, optionally substituted $C_1$-$C_4$heteroalkyl, or optionally substituted $C_1$-$C_4$fluoroalkyl. In such embodiments, Z, $R^1$, $R^3$, $R^4$, $R^5$, $R^6$, $R^7$, $R^8$, $R^9$, $R^{A1}$, $R^{A2}$, n and q can be as defined above for Formula (I) or can be as defined in any of the embodiments described herein in any combination thereof.

In some embodiments, q is 0, 1, 2, or 3. In some embodiments, q is 0, 1, or 2. In some embodiments, q is 0. In some embodiments, q is 1. In some embodiments, q is 2. In all such embodiments, Z, $R^1$, $R^3$, $R^4$, $R^5$, $R^2$, $R^6$, $R^7$, $R^8$, $R^9$, $R^{A1}$, $R^{A2}$, and n can be as defined above for Formula (I) or can be as defined in any of the embodiments described herein in any combination thereof.

In some embodiments, $R^6$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cyclooalkyl, or optionally substituted $C_3$-$C_6$cycloalkylalkyl. In such embodiments, Z, $R^1$, $R^3$, $R^4$, $R^5$, $R^2$, $R^7$, $R^8$, $R^9$, $R^{A1}$, $R^{A2}$, n and q can be as defined above for Formula (I) or can be as defined in any of the embodiments described herein in any combination thereof.

In some embodiments, $R^6$ is optionally substituted $C_1$-$C_4$alkyl. In some embodiments, $R^6$ is methyl. In some embodiments, $R^6$ is ethyl. In some embodiments, $R^6$ is propyl. In all such embodiments, Z, $R^1$, $R^3$, $R^4$, $R^5$, $R^2$, $R^7$, $R^8$, $R^9$, $R^{A1}$, $R^{A2}$, n and q can be as defined above for Formula (I) or can be as defined in any of the embodiments described herein in any combination thereof.

In some embodiments, $R^6$ is optionally substituted $C_1$-$C_4$heteroalkyl. In some embodiments, $R^6$ is optionally substituted $C_1$-$C_4$fluoroalkyl. In some embodiments, $R^6$ is optionally substituted $C_3$-$C_6$cyclooalkyl. In some embodiments, $R^6$ is optionally substituted $C_3$-$C_6$cycloalkylalkyl. In some embodiments, $R^6$ is H. In all such embodiments, Z, $R^1$, $R^3$, $R^4$, $R^5$, $R^2$, $R^7$, $R^8$, $R^9$, $R^{A1}$, $R^{A2}$, n and q can be as defined above for Formula (I) or can be as defined in any of the embodiments described herein in any combination thereof.

In some embodiments, $R^7$ is optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cyclooalkyl, or optionally substituted $C_3$-$C_6$cycloalkylalkyl. In such embodiments, Z, $R^1$, $R^3$, $R^4$, $R^5$, $R^2$, $R^6$, $R^8$, $R^9$, $R^{A1}$, $R^{A2}$, n and q can be as defined above for Formula (I) or can be as defined in any of the embodiments described herein in any combination thereof.

In some embodiments, $R^7$ is optionally substituted $C_1$-$C_4$alkyl. In some embodiments, $R^7$ is optionally substituted $C_1$-$C_4$heteroalkyl. In some embodiments, $R^7$ is optionally substituted $C_3$-$C_6$cyclooalkyl. In some embodiments, $R^7$ is optionally substituted $C_1$-$C_4$alkyl. In some embodiments, $R^7$ is optionally substituted $C_3$-$C_6$cycloalkylalkyl. In some embodiments, $R^7$ is selected from the group of methyl, ethyl, —$CH_2CF_3$, —$CH_2$-cyclopropyl, or —$CH_2CH_2OCH_3$. In all such embodiments, Z, $R^1$, $R^3$, $R^4$, $R^5$, $R^2$, $R^6$, $R^8$, $R^9$, $R^{A1}$, $R^{A2}$, n and q can be as defined above for Formula (I) or can be as defined in any of the embodiments described herein in any combination thereof.

In some embodiments, $R^{A1}$ is H, optionally substituted $C_1$-$C_4$alkyl, optionally substituted $C_1$-$C_4$heteroalkyl, or optionally substituted $C_1$-$C_4$fluoroalkyl. In such embodiments, Z, $R^1$, $R^3$, $R^4$, $R^5$, $R^2$, $R^6$, $R^7$, $R^8$, $R^9$, $R^{A2}$, n and q can be as defined above for Formula (I) or can be as defined in any of the embodiments described herein in any combination thereof.

In some embodiments, $R^{A1}$ is H. In some embodiments, $R^{A1}$ is optionally substituted $C_1$-$C_4$alkyl. In some embodiments, $R^{A1}$ is optionally substituted $C_1$-$C_4$heteroalkyl. In some embodiments, $R^{A1}$ is optionally substituted $C_1$-$C_4$fluoroalkyl. In all such embodiments, Z, $R^1$, $R^3$, $R^4$, $R^5$, $R^2$, $R^6$, $R^7$, $R^8$, $R^9$, $R^{A2}$, n and q can be as defined above for Formula (I) or can be as defined in any of the embodiments described herein in any combination thereof.

In some embodiments, $R^{A2}$ is H, optionally substituted $C_1$-$C_4$alkyl, optionally substituted $C_1$-$C_4$heteroalkyl, or optionally substituted $C_1$-$C_4$fluoroalkyl. In such embodiments, Z, $R^1$, $R^3$, $R^4$, $R^5$, $R^2$, $R^6$, $R^7$, $R^8$, $R^9$, $R^{A1}$, n and q can be as defined above for Formula (I) or can be as defined in any of the embodiments described herein in any combination thereof.

In some embodiments, $R^{A2}$ is optionally substituted $C_1$-$C_4$alkyl. In some embodiments, $R^{A2}$ is methyl, ethyl, propyl, or butyl. In some embodiments, $R^{A2}$ is ethyl. In some embodiments, $R^{A2}$ is optionally substituted $C_1$-$C_4$heteroalkyl. In some embodiments, $R^{A2}$ is optionally substituted $C_1$-$C_4$fluoroalkyl. In some embodiments, $R^{A2}$ is H. In all such embodiments, Z, $R^1$, $R^3$, $R^4$, $R^5$, $R^2$, $R^6$, $R^7$, $R^8$, $R^9$, $R^{A1}$, n and q can be as defined above for Formula (I) or can be as defined in any of the embodiments described herein in any combination thereof.

In some embodiments, the compound of Formula (I) has the structure of formula (Ic)

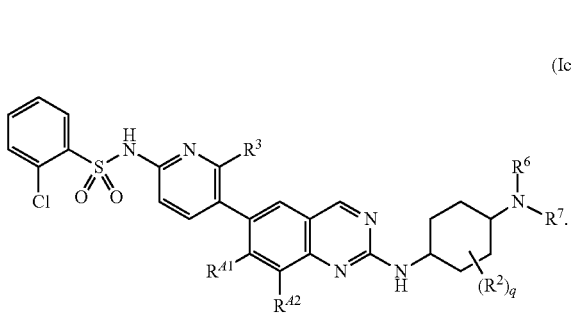

(Ic)

In some embodiments, the compound of Formula (I) has the structure of formula (Id)

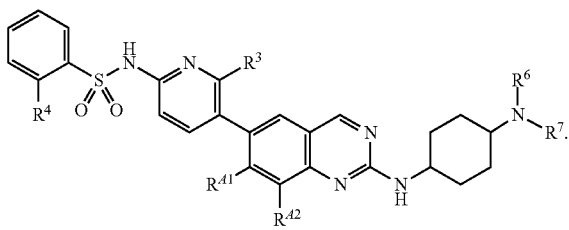

(Id)

In some embodiments, the compound of Formula (I) has the structure of formula (Ie)

(Ie)

In another aspect, provided herein is a compound of Formula (I*), (Ib*), or (Ic*) or a pharmaceutically acceptable salt, or solvate thereof:

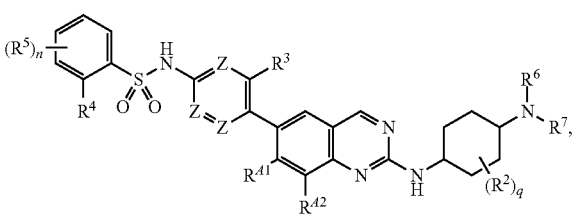

Formula (I*)

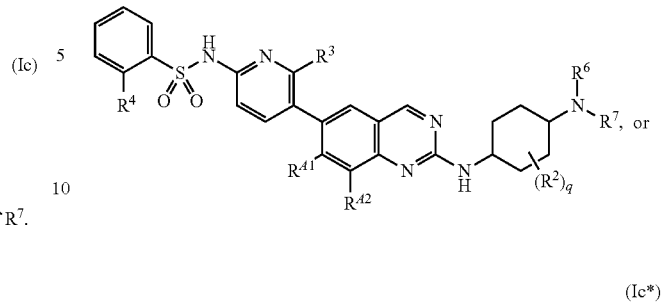

(Ib*)

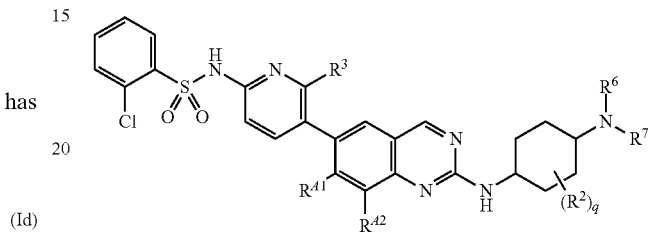

(Ic*)

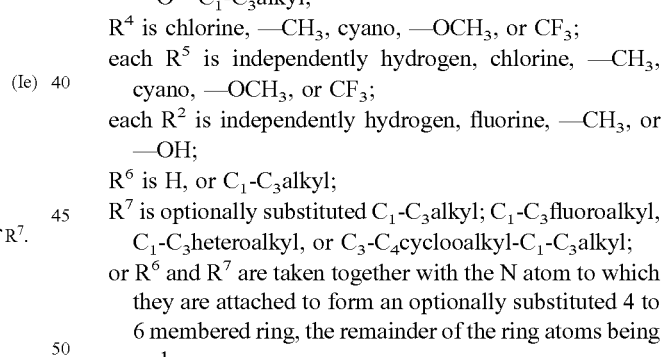

wherein,
each Z is independently N or CR$^1$, provided that at least one Z is N;
each R$^1$ is independently hydrogen, fluorine, chlorine or cyano;
R$^3$ is —CN, optionally substituted C$_1$-C$_3$alkyl, optionally substituted C$_3$-C$_4$cycloalkyl, optionally substituted —O—C$_3$-C$_4$cycloalkyl, or optionally substituted —O—C$_1$-C$_3$alkyl;
R$^4$ is chlorine, —CH$_3$, cyano, —OCH$_3$, or CF$_3$;
each R$^5$ is independently hydrogen, chlorine, —CH$_3$, cyano, —OCH$_3$, or CF$_3$;
each R$^2$ is independently hydrogen, fluorine, —CH$_3$, or —OH;
R$^6$ is H, or C$_1$-C$_3$alkyl;
R$^7$ is optionally substituted C$_1$-C$_3$alkyl; C$_1$-C$_3$fluoroalkyl, C$_1$-C$_3$heteroalkyl, or C$_3$-C$_4$cyclooalkyl-C$_1$-C$_3$alkyl;
or R$^6$ and R$^7$ are taken together with the N atom to which they are attached to form an optionally substituted 4 to 6 membered ring, the remainder of the ring atoms being carbon;
R$^{A1}$ and R$^{A2}$ are each independently H, optionally substituted C$_1$-C$_3$alkyl; C$_1$-C$_3$fluoroalkyl, C$_1$-C$_3$heteroalkyl, or C$_3$-C$_4$cyclooalkyl-C$_1$-C$_3$alkyl, provided that both R$^{A1}$ and R$^{A2}$ are not hydrogen;
n is 0, 1, 2, 3, or 4; and
q is 0, 1, 2, 3, or 4.

In some such aspects of Formulas (I*), (Ib*) or (Ic*), R$^{A1}$ is H or C$_{1-3}$ alkyl and Z, R$^1$, R$^3$, R$^4$, R$^5$, R$^2$, R$^6$, R$^7$, R$^8$, R$^9$, R$^{A2}$, n and q can be as defined above for Formulas (I*), (Ib*) or (Ic*) or can be as defined in any of the embodiments described herein for Formulas (I*), (Ib*) or (Ic*) in any combination thereof.

In some such aspects of Formulas (I*), (Ib*) or (Ic*), one or more of R$^3$, R$^7$, R$^{A1}$, and R$^{A2}$ are optionally substituted, wherein optional substituents are each independently selected from fluorine, —OH, —OCH$_3$, —OCH$_2$CH$_3$, —OCH$_2$CH$_2$CH$_3$, —NH$_2$, —NH(CH$_3$), or —N(CH$_3$)$_2$ and Z, R$^1$, R$^4$, R$^5$, R$^2$, R$^6$, R$^8$, R$^9$, n and q can be as defined above for Formulas (I*), (Ib*) or (Ic*) or can be as defined in any of the embodiments described herein for Formulas (I*), (Ib*) or (Ic*) in any combination thereof.

In some such aspects of Formulas (I*), (Ib*) or (Ic*), one or more of R$^3$, R$^7$, R$^{41}$, and R$^{42}$ are optionally substituted, wherein optional substituents are each independently selected from fluorine, —OH, —OCH$_3$, —OCH$_2$CH$_3$, —OCH$_2$CH$_2$CH$_3$, —NH(CH$_3$), or —N(CH$_3$)$_2$ and Z, R$^1$, R$^4$, R$^5$, R$^2$, R$^6$, R$^8$, R$^9$, n and q can be as defined above for Formulas (I*), (Ib*) or (Ic*) or can be as defined in any of the embodiments described herein for Formulas (I*), (Ib*) or (Ic*) in any combination thereof.

In some such aspects of Formulas (I*), (Ib*) or (Ic*), one or more of R$^7$, R$^{41}$, and R$^{42}$ are C$_1$-C$_3$heteroalkyl, wherein a heteroatom in the C$_1$-C$_3$heteroalkyl is oxygen and Z, R$^1$, R$^3$, R$^4$, R$^5$, R$^2$, R$^6$, R$^8$, R$^9$, n and q can be as defined above for Formulas (I*), (Ib*) or (Ic*) or can be as defined in any of the embodiments described herein for Formulas (I*), (Ib*) or (Ic*) in any combination thereof.

In some such aspects of Formulas (I*), (Ib*) or (Ic*), R$^6$ is H, or methyl and R$^7$ is methyl, ethyl, CH$_2$CF$_3$, CH$_2$-cyclopropyl or CH$_2$CH$_2$OCH$_3$ and Z, R$^1$, R$^3$, R$^4$, R$^5$, R$^2$, R$^8$, R$^9$, R$^{41}$, and R$^{42}$, n and q can be as defined above for Formulas (I*), (Ib*) or (Ic*) or can be as defined in any of the embodiments described herein for Formulas (I*), (Ib*) or (Ic*) in any combination thereof.

In some such aspects of Formulas (I*), (Ib*) or (Ic*), R$^6$ is methyl and R$^7$ is methyl, ethyl, CH$_2$CF$_3$, CH$_2$-cyclopropyl or CH$_2$CH$_2$OCH$_3$ and Z, R$^1$, R$^3$, R$^4$, R$^5$, R$^2$, R$^8$, R$^9$, R$^{41}$, and R$^{42}$, n and q can be as defined above for Formulas (I*), (Ib*) or (Ic*) or can be as defined in any of the embodiments described herein for Formulas (I*), (Ib*) or (Ic*) in any combination thereof.

In some such aspects of Formulas (I*), (Ib*) or (Ic*), q is zero.

In some such aspects of Formulas (I*), (Ib*) or (Ic*), each Z is independently N or CR$^1$, provided that at least one Z is N; each R$^1$ is independently hydrogen, fluorine, chlorine or cyano; R$^3$ is C$_1$-C$_3$alkyl or —OC$_1$-C$_3$alkyl; R$^{41}$ is hydrogen, or C$_1$-C$_3$alkyl; R$^{42}$ is C$_1$-C$_3$alkyl, C$_1$-C$_3$fluoroalkyl, or C$_1$-C$_3$heteroalkyl; provided that both R$^{41}$ and R$^{42}$ are not hydrogen; R$^4$ is chlorine; each R$^5$ is independently hydrogen, chlorine, —CH$_3$, cyano, —OCH$_3$, or CF$_3$; n is 0, 1, 2, 3, or 4; and q is zero.

In some such aspects of Formulas (I*), (Ib*) or (Ic*) of Formulas (I*), (Ib*) or (Ic*),
R$^1$ is fluorine;
R$^3$ is methyl, ethyl, or —OCH$_3$,
R$^4$ is chlorine, or —CH$_3$;
R$^6$ is H, or methyl;
R$^7$ is methyl, ethyl, CH$_2$CF$_3$, CH$_2$-cyclopropyl or CH$_2$CH$_2$OCH$_3$;
R$^{42}$ is ethyl, hydrogen, CF$_2$CH$_3$, CF$_3$, CH$_2$OCH$_3$, or CH$_3$;
R$^{42}$ is methyl or H;
n is 0; and
q is 0.

In another aspect, provided herein is a compound of Formula (Id*) or a pharmaceutically acceptable salt, or solvate thereof:

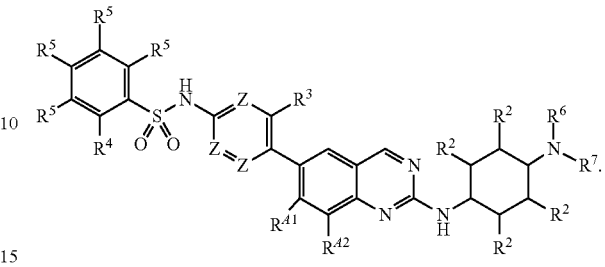

(Id*)

wherein Z, R$^1$, R$^3$, R$^4$, R$^5$, R$^2$, R$^6$, R$^7$, R$^8$, R$^9$, R$^{41}$, and R$^{42}$ are as described for Formula (I). In some such embodiments, each Z is independently N or CR$^1$, provided that at least one Z is N; each R$^5$ is independently hydrogen, chlorine, fluorine, or C$_1$-C$_3$alkyl; R$^4$ is chlorine or C$_1$-C$_3$alkyl; R$^3$ is C$_1$-C$_3$alkyl or —OC$_1$-C$_3$alkyl; R$^{41}$ is fluorine, chlorine, hydrogen, or C$_1$-C$_3$alkyl; R$^{42}$ is C$_1$-C$_3$alkyl, —OC$_1$-C$_3$alkyl, hydrogen, C$_1$-C$_3$fluoroalkyl, fluorine, chlorine, or C$_1$-C$_3$heteroalkyl; provided that both R$^{41}$ and R$^{42}$ are not hydrogen; each R$^2$ is independently hydrogen or fluorine; and R$^1$ is hydrogen or fluorine; and wherein one, two or three Zs are nitrogen. In an illustrative example,

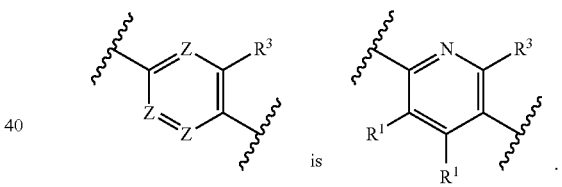

is

In some such aspects, each R$^5$ is independently hydrogen, chlorine, fluorine, or —CH$_3$;
R$^4$ is chlorine or —CH$_3$; R$^3$ is —CH$_3$, —CH$_2$CH$_3$, or —OCH$_3$;
R$^{41}$ is fluorine, chlorine, hydrogen, or —CH$_3$; R$^{42}$ is hydrogen, —CH$_3$, —CH$_2$CH$_3$, —OCH$_3$, CF$_3$, CF$_2$CH$_3$, CH$_2$OCH$_3$, or fluorine; provided that both R$^{41}$ and R$^{42}$ are not hydrogen; each R$^2$ is independently hydrogen or fluorine; and R$^1$ is hydrogen or fluorine. R$^6$ and R$^7$ can be as described in any of the embodiments set forth herein. For example, R$^7$ can be optionally substituted C$_3$-C$_6$cyclooalkylalkyl or R$^7$ can be selected from the group of methyl, ethyl, —CH$_2$CF$_3$, —CH$_2$— cyclopropyl, or —CH$_2$CH$_2$OCH$_3$ or R$^7$ can be selected from the group of methyl, ethyl, —CH$_2$CF$_3$, —CH$_2$-cyclopropyl, —CH$_2$-cyclobutyl, or —CH$_2$CH$_2$OCH$_3$; and R$^6$ is as described herein for any of the embodiments. For example, R$^6$ can be hydrogen or C$_{1-4}$ alkyl or R$^6$ can be hydrogen or methyl. In some such embodiments, each R$^5$ is hydrogen; R$^4$ is chlorine; each R$^2$ is hydrogen; and R$^1$ is hydrogen.

In some embodiments, a compound described herein is selected from any one of the compounds from Table 1.

TABLE 1

| Compound No. | Structure | Name |
|---|---|---|
| 23 | 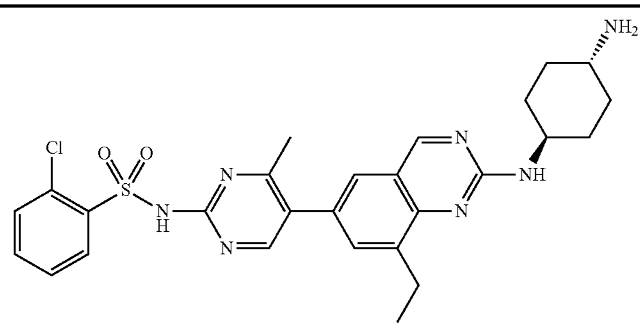 | N-(5-(2-(((1r,4r)-4-aminocyclohexyl)amino)-8-ethylquinazolin-6-yl)-4-methylpyrimidin-2-yl)-2-chlorobenzenesulfonamide |
| 24 | 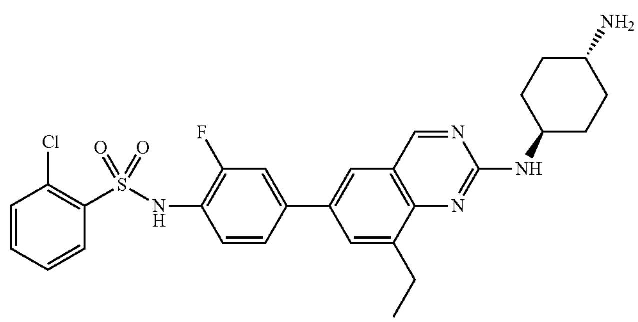 [SMILES: CCc1cc(-c2ccc(NS(=O)(=O)c3ccccc3Cl)c(F)c2)cc2cnc(N[C@H]3CC[C@H](N)CC3)nc12] | N-(4-(2-(((1r,4r)-4-aminocyclohexyl)amino)-8-ethylquinazolin-6-yl)-2-fluorophenyl)-2-chlorobenzenesulfonamide |
| 25 | 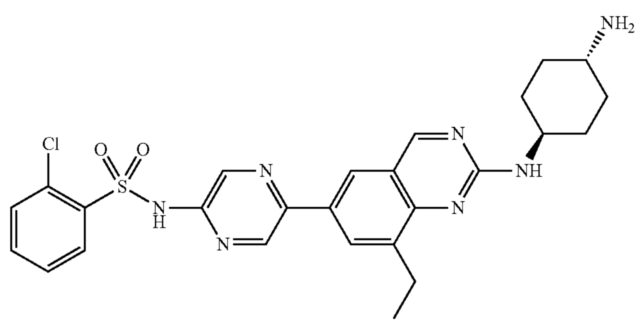 [SMILES: CCc1cc(-c2cnc(NS(=O)(=O)c3ccccc3Cl)cn2)cc2cnc(N[C@H]3CC[C@H](N)CC3)nc12] | N-(5-(2-(((1r,4r)-4-aminocyclohexyl)amino)-8-ethylquinazolin-6-yl)pyrazin-2-yl)-2-chlorobenzenesulfonamide |
| 26 | 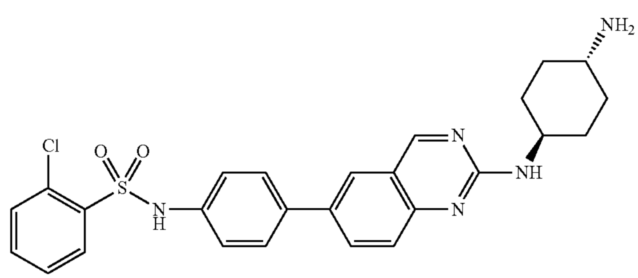 [SMILES: N[C@H]1CC[C@H](Nc2ncc3cc(-c4ccc(NS(=O)(=O)c5ccccc5Cl)cc4)ccc3n2)CC1] | N-(4-(2-(((1r,4r)-4-aminocyclohexyl)amino)quinazolin-6-yl)phenyl)-2-chlorobenzenesulfonamide |
| 27 | 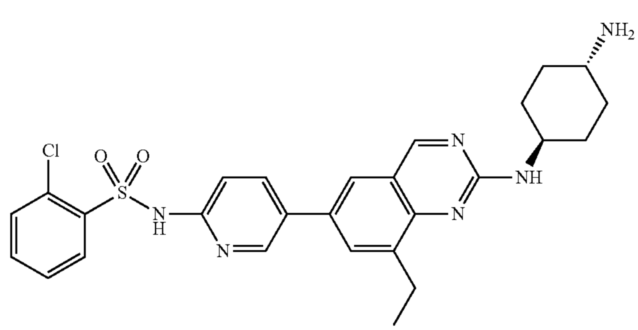 [SMILES: CCc1cc(-c2ccc(NS(=O)(=O)c3ccccc3Cl)nc2)cc2cnc(N[C@H]3CC[C@H](N)CC3)nc12] | N-(5-(2-(((1r,4r)-4-aminocyclohexyl)amino)-8-ethylquinazolin-6-yl)pyridin-2-yl)-2-chlorobenzenesulfonamide |

TABLE 1-continued

| Compound No. | Structure | Name |
|---|---|---|
| 28 | 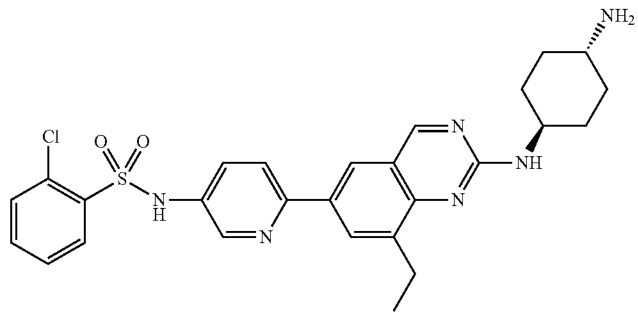 [SMILES: CCc1cc(-c2ccc(NS(=O)(=O)c3ccccc3Cl)cn2)cc2cnc(N[C@H]3CC[C@H](N)CC3)nc12] | N-(6-(2-(((1r,4r)-4-aminocyclohexyl)amino)-8-ethylquinazolin-6-yl)pyridin-3-yl)-2-chlorobenzenesulfonamide |
| 29 | 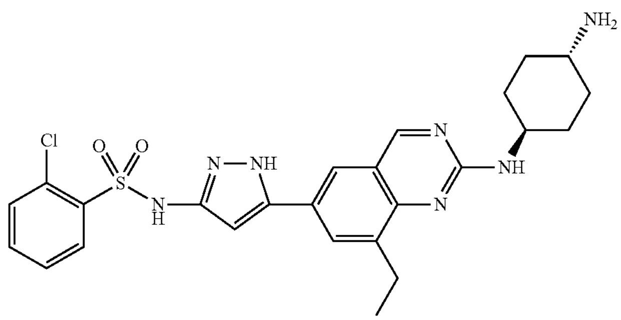 [SMILES: CCc1cc(-c2cc(NS(=O)(=O)c3ccccc3Cl)n[nH]2)cc2cnc(N[C@H]3CC[C@H](N)CC3)nc12] | N-(5-(2-(((1r,4r)-4-aminocyclohexyl)amino)-8-ethylquinazolin-6-yl)-1H-pyrazol-3-yl)-2-chlorobenzenesulfonamide |
| 30 | 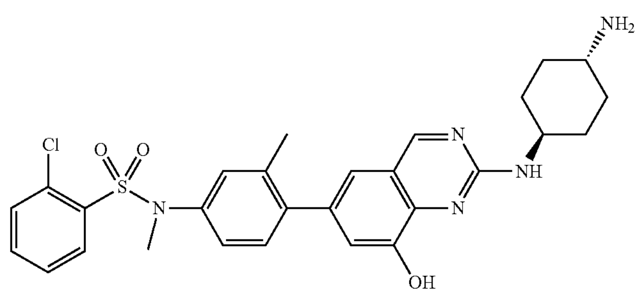 [SMILES: Cc1cc(N(C)S(=O)(=O)c2ccccc2Cl)ccc1-c1cc(O)c2nc(N[C@H]3CC[C@H](N)CC3)ncc2c1] | N-(4-(2-(((1r,4r)-4-aminocyclohexyl)amino)-8-hydroxyquinazolin-6-yl)-3-methylphenyl)-2-chloro-N-methylbenzenesulfonamide |
| 31 | 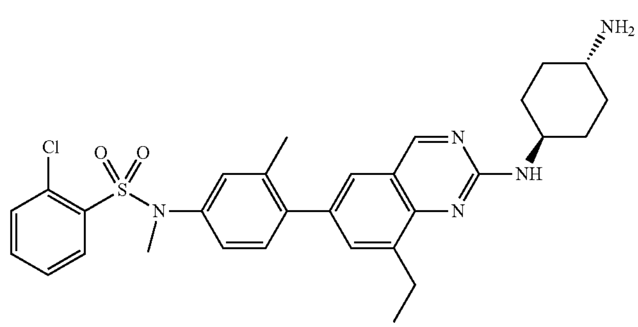 [SMILES: CCc1cc(-c2ccc(N(C)S(=O)(=O)c3ccccc3Cl)cc2C)cc2cnc(N[C@H]3CC[C@H](N)CC3)nc12] | N-(4-(2-(((1r,4r)-4-aminocyclohexyl)amino)-8-ethylquinazolin-6-yl)-3-methylphenyl)-2-chloro-N-methylbenzenesulfonamide |
| 32 | 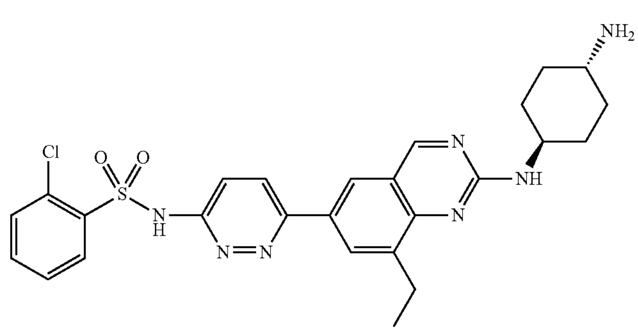 [SMILES: CCc1cc(-c2ccc(NS(=O)(=O)c3ccccc3Cl)nn2)cc2cnc(N[C@H]3CC[C@H](N)CC3)nc12] | N-(6-(2-(((1r,4r)-4-aminocyclohexyl)amino)-8-ethylquinazolin-6-yl)pyridazin-3-yl)-2-chlorobenzenesulfonamide |

TABLE 1-continued

| Compound No. | Structure | Name |
|---|---|---|
| 33 | 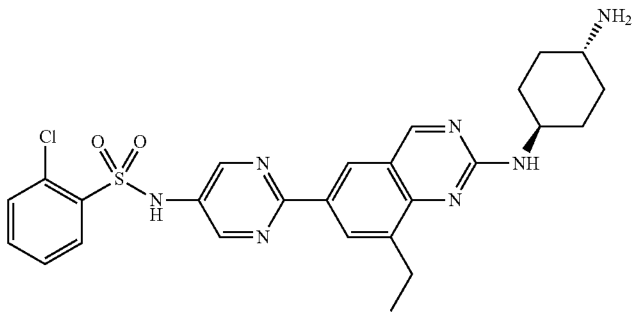 [SMILES: CCc1cc(-c2ncc(NS(=O)(=O)c3ccccc3Cl)cn2)cc2cnc(N[C@H]3CC[C@H](N)CC3)nc12] | N-(2-(2-(((1r,4r)-4-aminocyclohexyl)amino)-8-ethylquinazolin-6-yl)pyrimidin-5-yl)-2-chlorobenzenesulfonamide |
| 34 | 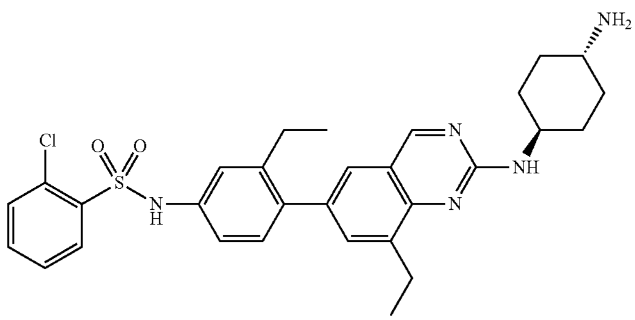 [SMILES: CCc1cc(NS(=O)(=O)c2ccccc2Cl)ccc1-c1cc(CC)c2nc(N[C@H]3CC[C@H](N)CC3)ncc2c1] | N-(4-(2-(((1r,4r)-4-aminocyclohexyl)amino)-8-ethylquinazolin-6-yl)-3-ethylphenyl)-2-chlorobenzenesulfonamide |
| 35 | 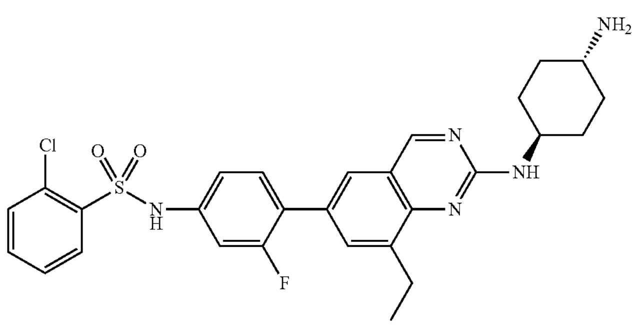 [SMILES: CCc1cc(-c2ccc(NS(=O)(=O)c3ccccc3Cl)cc2F)cc2cnc(N[C@H]3CC[C@H](N)CC3)nc12] | N-(4-(2-(((1r,4r)-4-aminocyclohexyl)amino)-8-ethylquinazolin-6-yl)-3-fluorophenyl)-2-chlorobenzenesulfonamide |
| 36 | 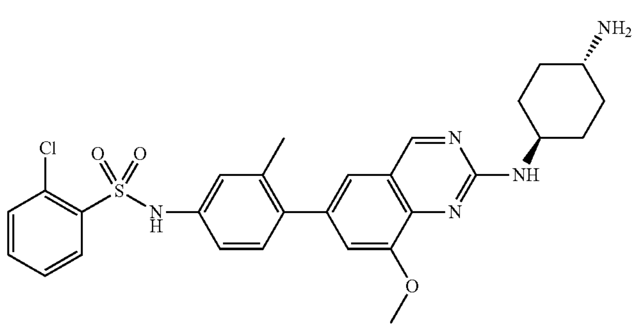 [SMILES: COc1cc(-c2ccc(NS(=O)(=O)c3ccccc3Cl)cc2C)cc2cnc(N[C@H]3CC[C@H](N)CC3)nc12] | N-(4-(2-(((1r,4r)-4-aminocyclohexyl)amino)-8-methoxyquinazolin-6-yl)-3-methylphenyl)-2-chlorobenzenesulfonamide |

TABLE 1-continued

| Compound No. | Structure | Name |
|---|---|---|
| 37 | 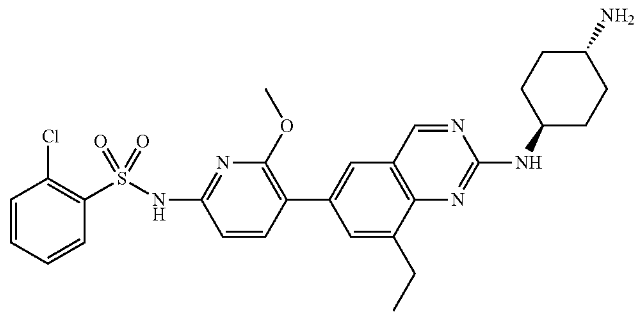 [SMILES: CCc1cc(-c2ccc(NS(=O)(=O)c3ccccc3Cl)nc2OC)cc2cnc(N[C@H]3CC[C@H](N)CC3)nc12] | N-(5-(2-(((1r,4r)-4-aminocyclohexyl)amino)-8-ethylquinazolin-6-yl)-6-methoxypyridin-2-yl)-2-chlorobenzenesulfonamide |
| 38 | 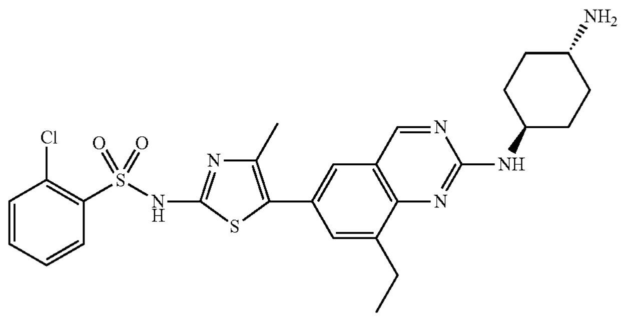 [SMILES: CCc1cc(-c2sc(NS(=O)(=O)c3ccccc3Cl)nc2C)cc2cnc(N[C@H]3CC[C@H](N)CC3)nc12] | N-(5-(2-(((1r,4r)-4-aminocyclohexyl)amino)-8-ethylquinazolin-6-yl)-4-methylthiazol-2-yl)-2-chlorobenzenesulfonamide |
| 39 | 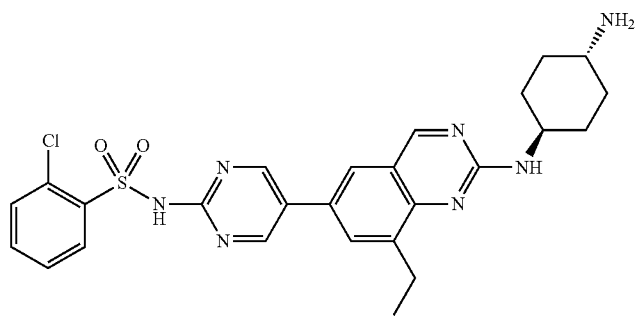 [SMILES: CCc1cc(-c2cnc(NS(=O)(=O)c3ccccc3Cl)nc2)cc2cnc(N[C@H]3CC[C@H](N)CC3)nc12] | N-(5-(2-(((1r,4r)-4-aminocyclohexyl)amino)-8-ethylquinazolin-6-yl)pyrimidin-2-yl)-2-chlorobenzenesulfonamide |
| 40 | 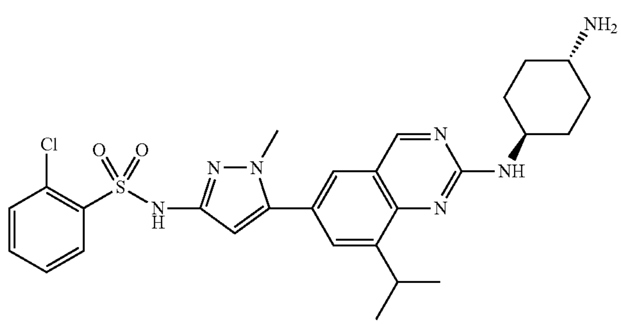 [SMILES: CC(C)c1cc(-c2cc(NS(=O)(=O)c3ccccc3Cl)nn2C)cc2cnc(N[C@H]3CC[C@H](N)CC3)nc12] | N-(5-(2-(((1r,4r)-4-aminocyclohexyl)amino)-8-isopropylquinazolin-6-yl)-1-methyl-1H-pyrazol-3-yl)-2-chlorobenzenesulfonamide |
| 41 | 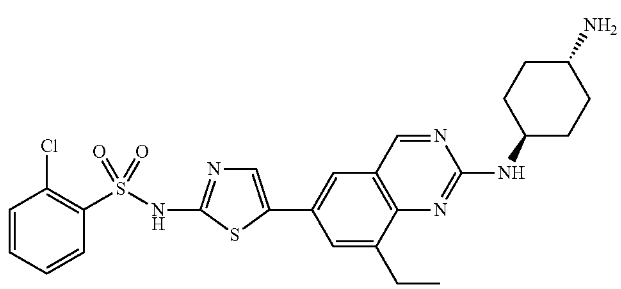 [SMILES: CCc1cc(-c2cnc(NS(=O)(=O)c3ccccc3Cl)s2)cc2cnc(N[C@H]3CC[C@H](N)CC3)nc12] | N-(5-(2-(((1r,4r)-4-aminocyclohexyl)amino)-8-ethylquinazolin-6-yl)thiazol-2-yl)-2-chlorobenzenesulfonamide |

TABLE 1-continued

| Compound No. | Structure | Name |
|---|---|---|
| 42 | 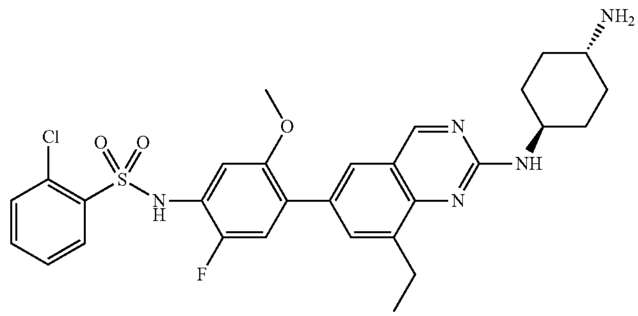 [SMILES: CCc1cc(-c2cc(F)c(NS(=O)(=O)c3ccccc3Cl)cc2OC)cc2cnc(N[C@H]3CC[C@H](N)CC3)nc12] | N-(4-(2-(((1r,4r)-4-aminocyclohexyl)amino)-8-ethylquinazolin-6-yl)-2-fluoro-5-methoxyphenyl)-2-chlorobenzenesulfonamide |
| 43 | 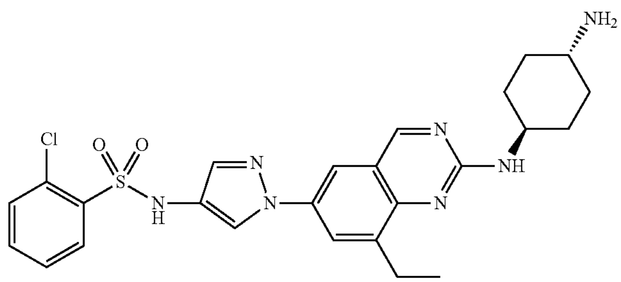 [SMILES: CCc1cc(-n2cc(NS(=O)(=O)c3ccccc3Cl)cn2)cc2cnc(N[C@H]3CC[C@H](N)CC3)nc12] | N-(1-(2-(((1r,4r)-4-aminocyclohexyl)amino)-8-ethylquinazolin-6-yl)-1H-pyrazol-4-yl)-2-chlorobenzenesulfonamide |
| 44 | 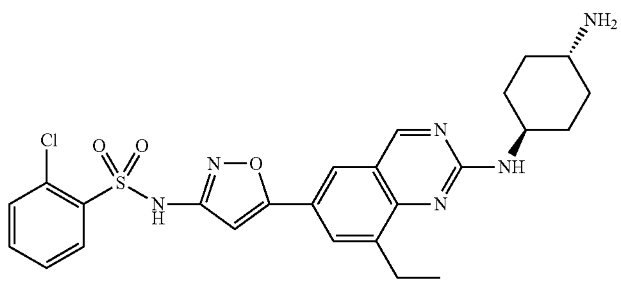 [SMILES: CCc1cc(-c2cc(NS(=O)(=O)c3ccccc3Cl)no2)cc2cnc(N[C@H]3CC[C@H](N)CC3)nc12] | N-(5-(2-(((1r,4r)-4-aminocyclohexyl)amino)-8-ethylquinazolin-6-yl)isoxazol-3-yl)-2-chlorobenzenesulfonamide |
| 45 | 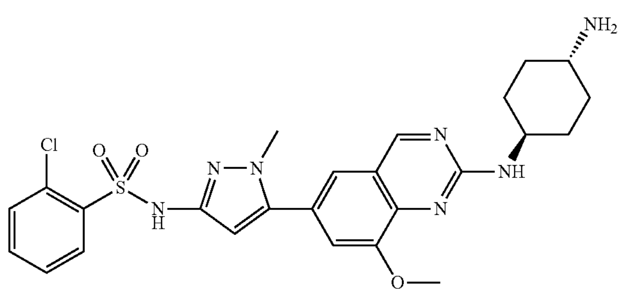 [SMILES: COc1cc(-c2cc(NS(=O)(=O)c3ccccc3Cl)nn2C)cc2cnc(N[C@H]3CC[C@H](N)CC3)nc12] | N-(5-(2-(((1r,4r)-4-aminocyclohexyl)amino)-8-methoxyquinazolin-6-yl)-1-methyl-1H-pyrazol-3-yl)-2-chlorobenzenesulfonamide |
| 46 | 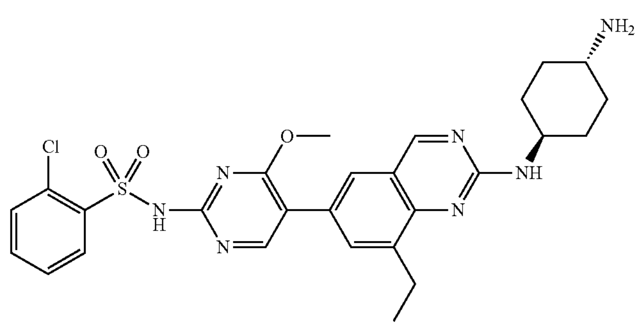 [SMILES: CCc1cc(-c2cnc(NS(=O)(=O)c3ccccc3Cl)nc2OC)cc2cnc(N[C@H]3CC[C@H](N)CC3)nc12] | N-(5-(2-(((1r,4r)-4-aminocyclohexyl)amino)-8-ethylquinazolin-6-yl)-4-methoxypyrimidin-2-yl)-2-chlorobenzenesulfonamide |

TABLE 1-continued

| Compound No. | Structure | Name |
|---|---|---|
| 47 | 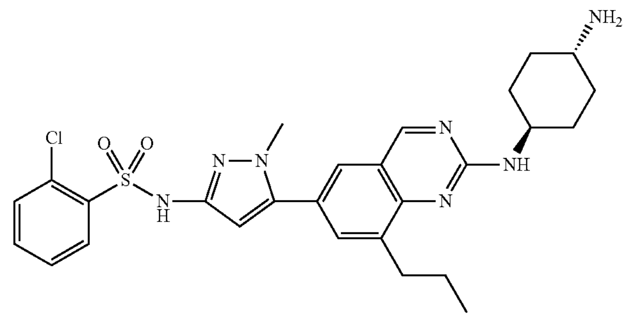 [SMILES: CCCc1cc(-c2cc(NS(=O)(=O)c3ccccc3Cl)nn2C)cc2cnc(N[C@H]3CC[C@H](N)CC3)nc12] | N-(5-(2-(((1r,4r)-4-aminocyclohexyl)amino)-8-propylquinazolin-6-yl)-1-methyl-1H-pyrazol-3-yl)-2-chlorobenzenesulfonamide |
| 48 | 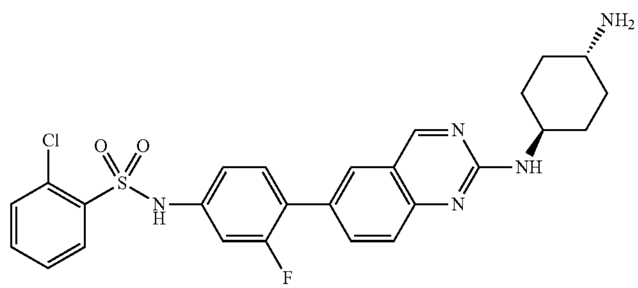 [SMILES: N[C@H]1CC[C@H](Nc2ncc3cc(-c4ccc(NS(=O)(=O)c5ccccc5Cl)cc4F)ccc3n2)CC1] | N-(4-(2-(((1r,4r)-4-aminocyclohexyl)amino)quinazolin-6-yl)-3-fluorophenyl)-2-chlorobenzenesulfonamide |
| 49 | 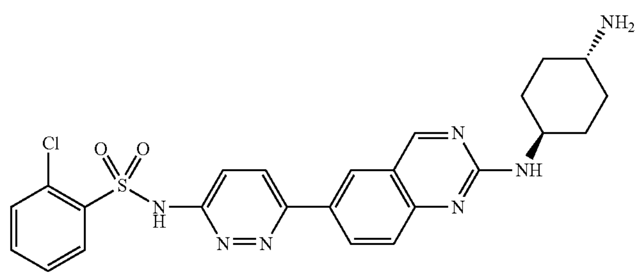 [SMILES: N[C@H]1CC[C@H](Nc2ncc3cc(-c4ccc(NS(=O)(=O)c5ccccc5Cl)nn4)ccc3n2)CC1] | N-(6-(2-(((1r,4r)-4-aminocyclohexyl)amino)quinazolin-6-yl)pyridazin-3-yl)-2-chlorobenzenesulfonamide |
| 50 | 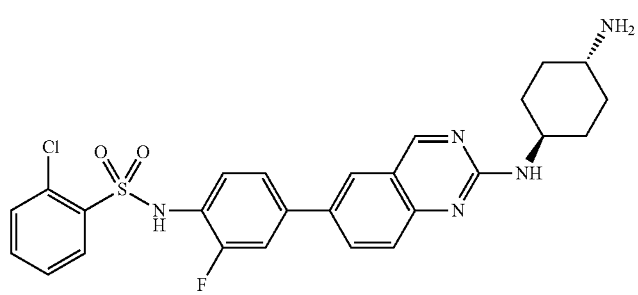 [SMILES: N[C@H]1CC[C@H](Nc2ncc3cc(-c4ccc(NS(=O)(=O)c5ccccc5Cl)c(F)c4)ccc3n2)CC1] | N-(4-(2-(((1r,4r)-4-aminocyclohexyl)amino)quinazolin-6-yl)-2-fluorophenyl)-2-chlorobenzenesulfonamide |
| 51 | 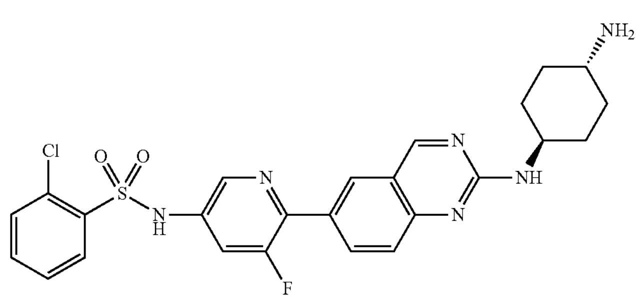 [SMILES: N[C@H]1CC[C@H](Nc2ncc3cc(-c4ncc(NS(=O)(=O)c5ccccc5Cl)cc4F)ccc3n2)CC1] | N-(6-(2-(((1r,4r)-4-aminocyclohexyl)amino)quinazolin-6-yl)-5-fluoropyridin-3-yl)-2-chlorobenzenesulfonamide |

TABLE 1-continued

| Compound No. | Structure | Name |
|---|---|---|
| 52 | 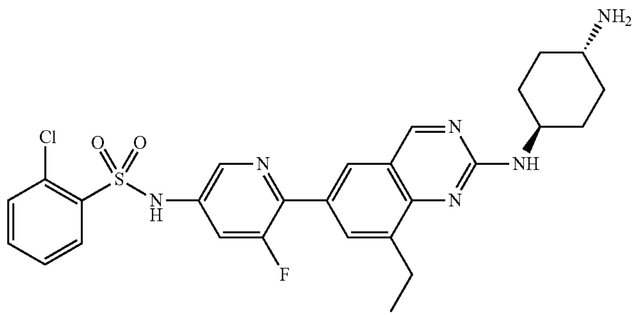 [SMILES: CCc1cc(-c2ncc(NS(=O)(=O)c3ccccc3Cl)cc2F)cc2cnc(N[C@H]3CC[C@H](N)CC3)nc12] | N-(6-(2-(((1r,4r)-4-aminocyclohexyl)amino)-8-ethylquinazolin-6-yl)-5-fluoropyridin-3-yl)-2-chlorobenzenesulfonamide |
| 53 | 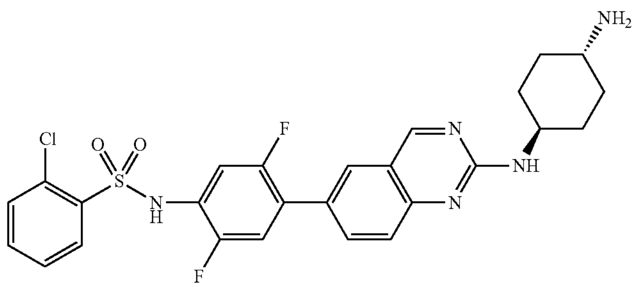 [SMILES: N[C@H]1CC[C@H](Nc2ncc3cc(-c4cc(F)c(NS(=O)(=O)c5ccccc5Cl)cc4F)ccc3n2)CC1] | N-(4-(2-(((1r,4r)-4-aminocyclohexyl)amino)quinazolin-6-yl)-2,5-difluorophenyl)-2-chlorobenzenesulfonamide |
| 54 | 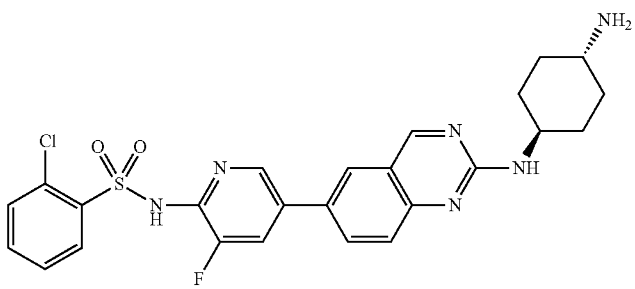 [SMILES: N[C@H]1CC[C@H](Nc2ncc3cc(-c4cnc(NS(=O)(=O)c5ccccc5Cl)c(F)c4)ccc3n2)CC1] | N-(5-(2-(((1r,4r)-4-aminocyclohexyl)amino)quinazolin-6-yl)-3-fluoropyridin-2-yl)-2-chlorobenzenesulfonamide |
| 55 | 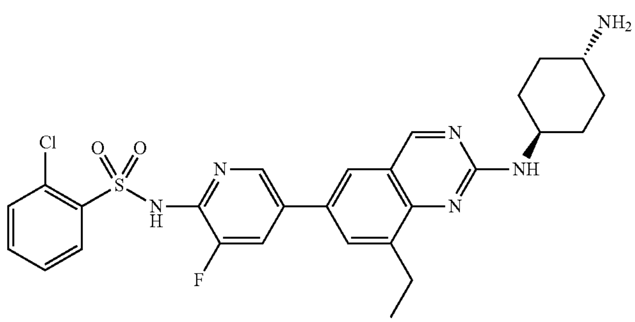 [SMILES: CCc1cc(-c2cnc(NS(=O)(=O)c3ccccc3Cl)c(F)c2)cc2cnc(N[C@H]3CC[C@H](N)CC3)nc12] | N-(5-(2-(((1r,4r)-4-aminocyclohexyl)amino)-8-ethylquinazolin-6-yl)-3-fluoropyridin-2-yl)-2-chlorobenzenesulfonamide |
| 56 | 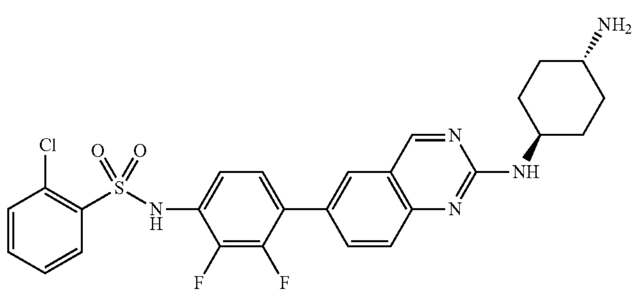 [SMILES: N[C@H]1CC[C@H](Nc2ncc3cc(-c4ccc(NS(=O)(=O)c5ccccc5Cl)c(F)c4F)ccc3n2)CC1] | N-(4-(2-(((1r,4r)-4-aminocyclohexyl)amino)quinazolin-6-yl)-2,3-difluorophenyl)-2-chlorobenzenesulfonamide |

TABLE 1-continued

| Compound No. | Structure | Name |
|---|---|---|
| 57 | 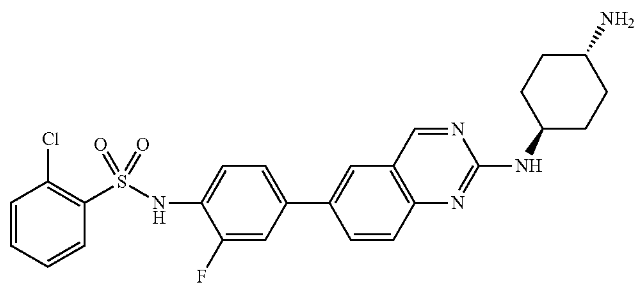 [SMILES: N[C@H]1CC[C@H](Nc2ncc3cc(-c4ccc(NS(=O)(=O)c5ccccc5Cl)c(F)c4)ccc3n2)CC1] | N-(4-(3-(((1r,4r)-4-aminocyclohexyl)amino)isoquinolin-7-yl)-2-fluorophenyl)-2-chlorobenzenesulfonamide |
| 58 | 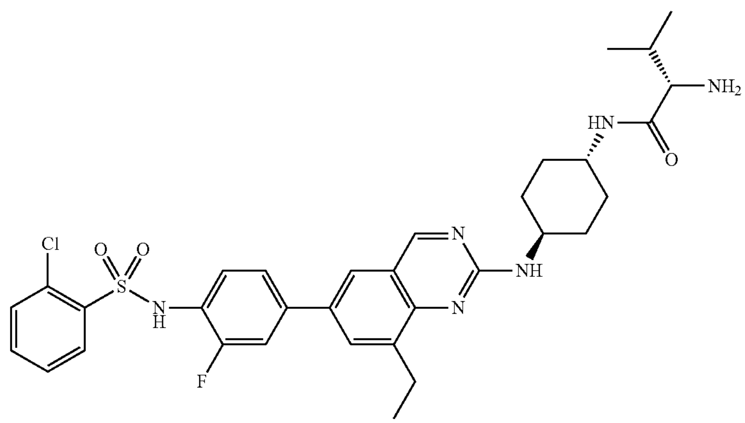 [SMILES: CCc1cc(-c2ccc(NS(=O)(=O)c3ccccc3Cl)c(F)c2)cc2cnc(N[C@H]3CC[C@H](NC(=O)[C@@H](N)C(C)C)CC3)nc12] | (S)-2-amino-N-((1r,4S)-4-((6-(4-((2-chlorophenyl)sulfonamido)-3-fluorophenyl)-8-ethylquinazolin-2-yl)amino)cyclohexyl)-3-methylbutanamide |
| 59 | 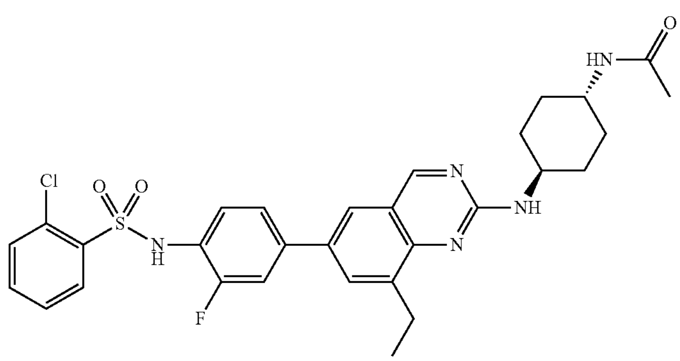 [SMILES: CCc1cc(-c2ccc(NS(=O)(=O)c3ccccc3Cl)c(F)c2)cc2cnc(N[C@H]3CC[C@H](NC(C)=O)CC3)nc12] | N-((1r,4r)-4-((6-(4-((2-chlorophenyl)sulfonamido)-3-fluorophenyl)-8-ethylquinazolin-2-yl)amino)cyclohexyl)acetamide |
| 60 | 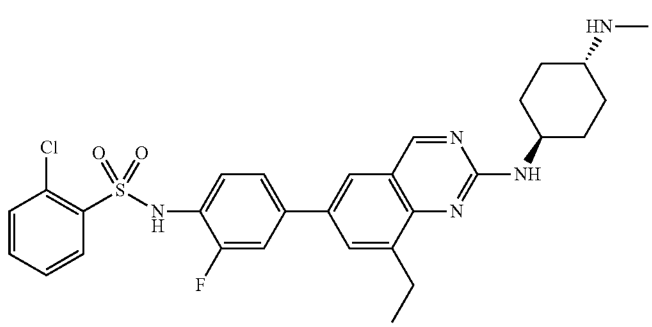 [SMILES: CCc1cc(-c2ccc(NS(=O)(=O)c3ccccc3Cl)c(F)c2)cc2cnc(N[C@H]3CC[C@H](NC)CC3)nc12] | 2-chloro-N-(4-(8-ethyl-2-(((1r,4r)-4-(methylamino)cyclohexyl)amino)quinazolin-6-yl)-2-fluorophenyl)benzenesulfonamide |

TABLE 1-continued

| Compound No. | Structure | Name |
|---|---|---|
| 61 | 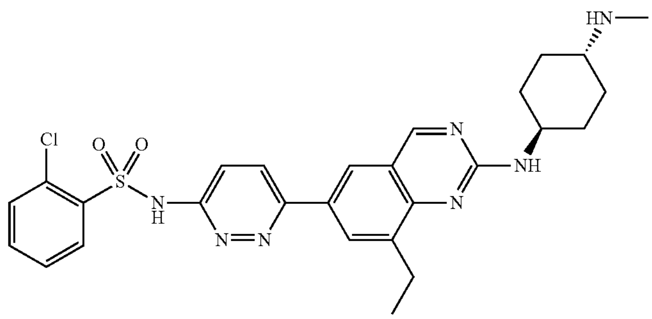 [SMILES: CCc1cc(-c2ccc(NS(=O)(=O)c3ccccc3Cl)nn2)cc2cnc(N[C@H]3CC[C@H](NC)CC3)nc12] | 2-chloro-N-(6-(8-ethyl-2-(((1r,4r)-4-(methylamino)cyclohexyl)amino)quinazolin-6-yl)pyridazin-3-yl)benzenesulfonamide |
| 62 | 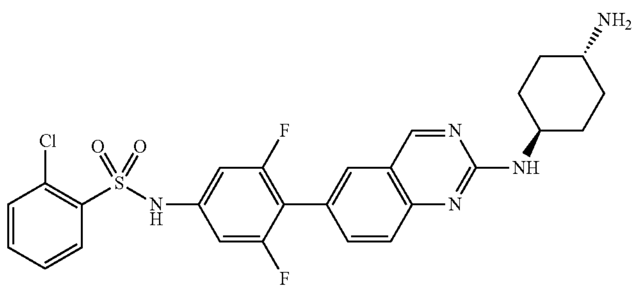 [SMILES: N[C@H]1CC[C@H](Nc2ncc3cc(-c4c(F)cc(NS(=O)(=O)c5ccccc5Cl)cc4F)ccc3n2)CC1] | N-(4-(2-(((1r,4r)-4-aminocyclohexyl)amino)quinazolin-6-yl)-3,5-difluorophenyl)-2-chlorobenzenesulfonamide |
| 63 | 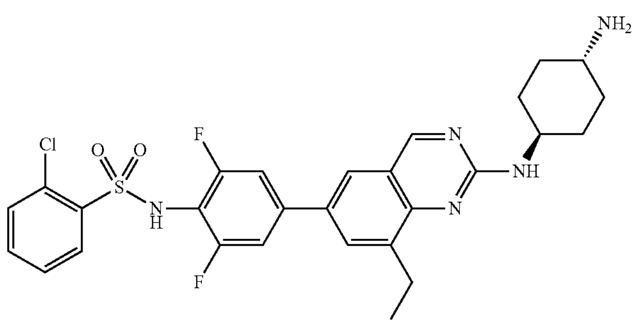 [SMILES: CCc1cc(-c2cc(F)c(NS(=O)(=O)c3ccccc3Cl)c(F)c2)cc2cnc(N[C@H]3CC[C@H](N)CC3)nc12] | N-(4-(2-(((1r,4r)-4-aminocyclohexyl)amino)-8-ethylquinazolin-6-yl)-2,6-difluorophenyl)-2-chlorobenzenesulfonamide |
| 64 | 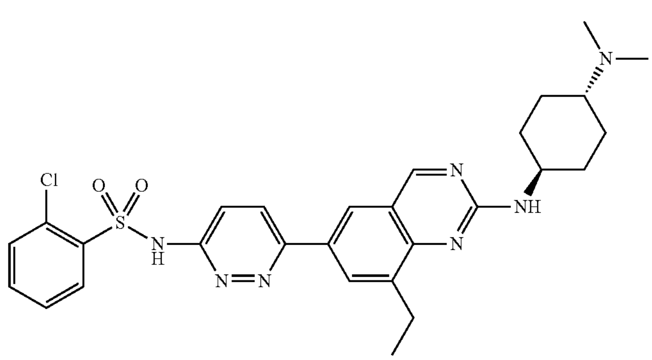 [SMILES: CCc1cc(-c2ccc(NS(=O)(=O)c3ccccc3Cl)nn2)cc2cnc(N[C@H]3CC[C@H](N(C)C)CC3)nc12] | 2-chloro-N-(6-(2-(((1r,4r)-4-(dimethylamino)cyclohexyl)amino)-8-ethylquinazolin-6-yl)pyridazin-3-yl)benzenesulfonamide |

TABLE 1-continued

| Compound No. | Structure | Name |
|---|---|---|
| 65 | 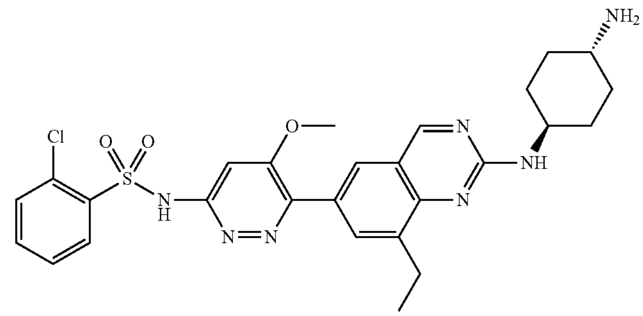 [SMILES: CCc1cc(-c2nnc(NS(=O)(=O)c3ccccc3Cl)cc2OC)cc2cnc(N[C@H]3CC[C@H](N)CC3)nc12] | N-(6-(2-(((1r,4r)-4-aminocyclohexyl)amino)-8-ethylquinazolin-6-yl)-5-methoxypyridazin-3-yl)-2-chlorobenzenesulfonamide |
| 66 | 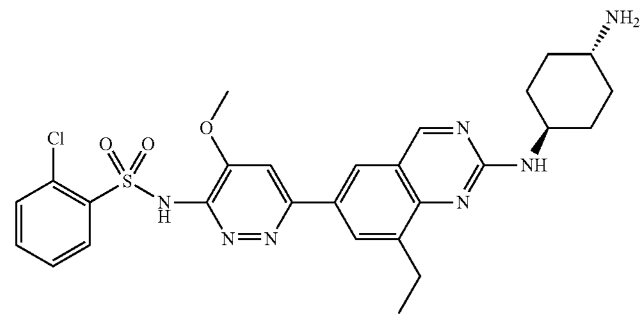 [SMILES: CCc1cc(-c2cc(OC)c(NS(=O)(=O)c3ccccc3Cl)nn2)cc2cnc(N[C@H]3CC[C@H](N)CC3)nc12] | N-(6-(2-(((1r,4r)-4-aminocyclohexyl)amino)-8-ethylquinazolin-6-yl)-4-methoxypyridazin-3-yl)-2-chlorobenzenesulfonamide |
| 67 | 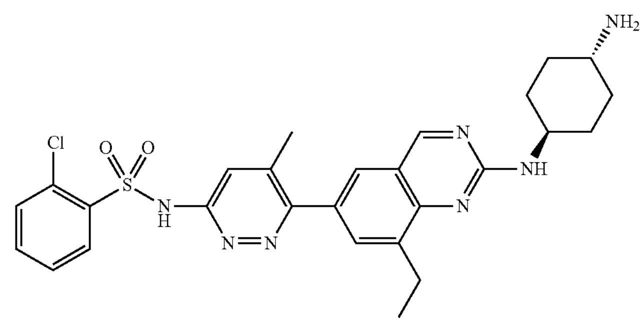 [SMILES: CCc1cc(-c2nnc(NS(=O)(=O)c3ccccc3Cl)cc2C)cc2cnc(N[C@H]3CC[C@H](N)CC3)nc12] | N-(6-(2-(((1r,4r)-4-aminocyclohexyl)amino)-8-ethylquinazolin-6-yl)-5-methylpyridazin-3-yl)-2-chlorobenzenesulfonamide |
| 68 | 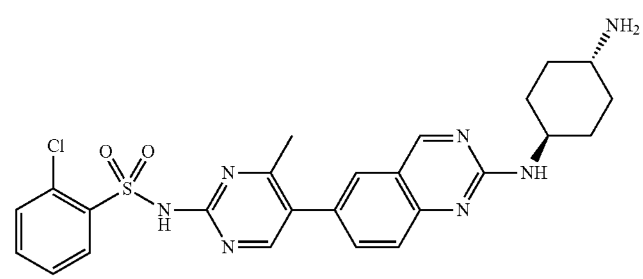 [SMILES: Cc1nc(NS(=O)(=O)c2ccccc2Cl)ncc1-c1ccc2nc(N[C@H]3CC[C@H](N)CC3)ncc2c1] | N-(5-(2-(((1r,4r)-4-aminocyclohexyl)amino)quinazolin-6-yl)-4-methylpyrimidin-2-yl)-2-chlorobenzenesulfonamide |
| 69 | 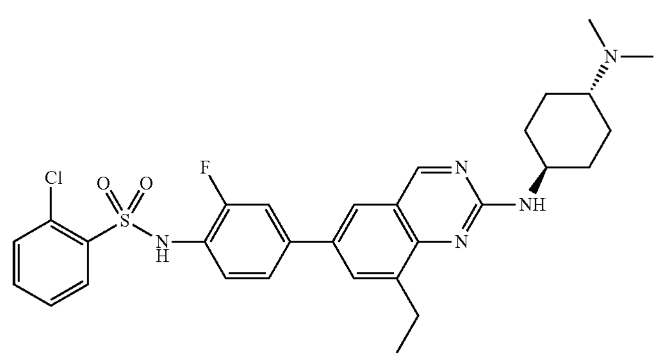 [SMILES: CCc1cc(-c2ccc(NS(=O)(=O)c3ccccc3Cl)c(F)c2)cc2cnc(N[C@H]3CC[C@H](N(C)C)CC3)nc12] | 2-chloro-N-(4-(2-(((1r,4r)-4-(dimethylamino)cyclohexyl)amino)-8-ethylquinazolin-6-yl)-2-fluorophenyl)benzenesulfonamide |

TABLE 1-continued

| Compound No. | Structure | Name |
|---|---|---|
| 70 | 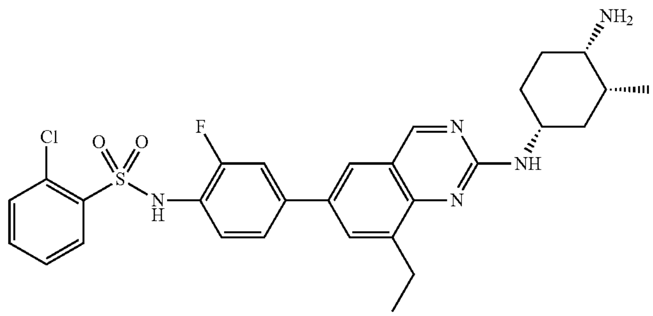 [SMILES: CCc1cc(-c2ccc(NS(=O)(=O)c3ccccc3Cl)c(F)c2)cc2cnc(N[C@@H]3CC[C@H](N)[C@H](C)C3)nc12] | N-(4-(2-(((1R,3R,4S)-4-amino-3-methylcyclohexyl)amino)-8-ethylquinazolin-6-yl)-2-fluorophenyl)-2-chlorobenzenesulfonamide |
| 71 | 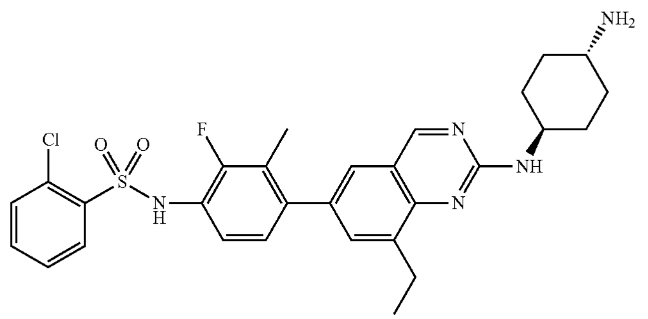 [SMILES: CCc1cc(-c2ccc(NS(=O)(=O)c3ccccc3Cl)c(F)c2C)cc2cnc(N[C@H]3CC[C@H](N)CC3)nc12] | N-(4-(2-(((1r,4r)-4-aminocyclohexyl)amino)-8-ethylquinazolin-6-yl)-2-fluoro-3-methylphenyl)-2-chlorobenzenesulfonamide |
| 72 | 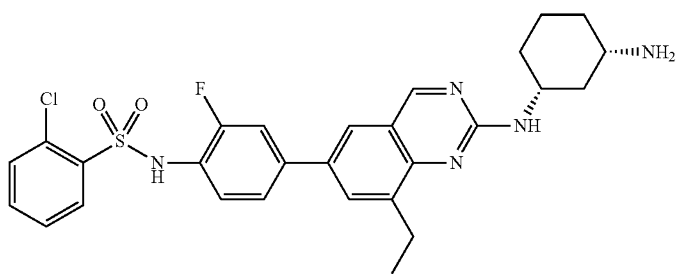 [SMILES: CCc1cc(-c2ccc(NS(=O)(=O)c3ccccc3Cl)c(F)c2)cc2cnc(N[C@@H]3CCC[C@H](N)C3)nc12] | N-(4-(2-(((1R,3S)-3-aminocyclohexyl)amino)-8-ethylquinazolin-6-yl)-2-fluorophenyl)-2-chlorobenzenesulfonamide |
| 73 | 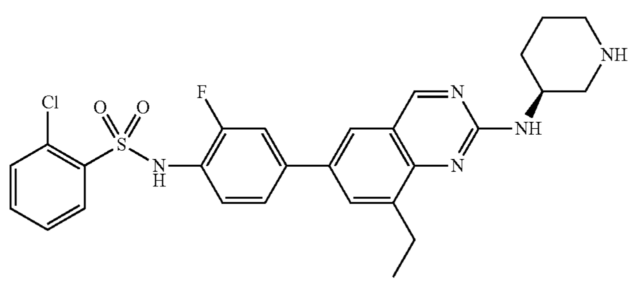 [SMILES: CCc1cc(-c2ccc(NS(=O)(=O)c3ccccc3Cl)c(F)c2)cc2cnc(N[C@H]3CCCNC3)nc12] | (S)-2-chloro-N-(4-(8-ethyl-2-(piperidin-3-ylamino)quinazolin-6-yl)-2-fluorophenyl)benzenesulfonamide |
| 74 | 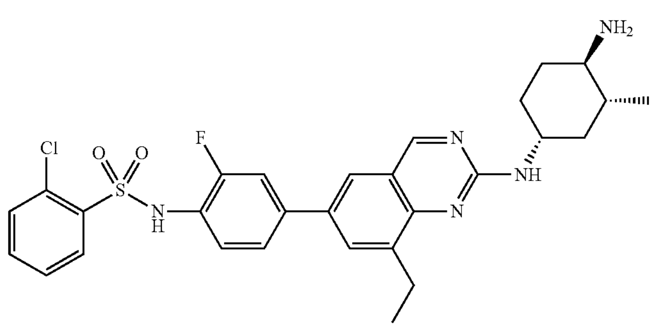 [SMILES: CCc1cc(-c2ccc(NS(=O)(=O)c3ccccc3Cl)c(F)c2)cc2cnc(N[C@@H]3CC[C@@H](N)[C@H](C)C3)nc12] | N-(4-(2-(((1R,3R,4R)-4-amino-3-methylcyclohexyl)amino)-8-ethylquinazolin-6-yl)-2-fluorophenyl)-2-chlorobenzenesulfonamide |

TABLE 1-continued

| Compound No. | Structure | Name |
|---|---|---|
| 75 | 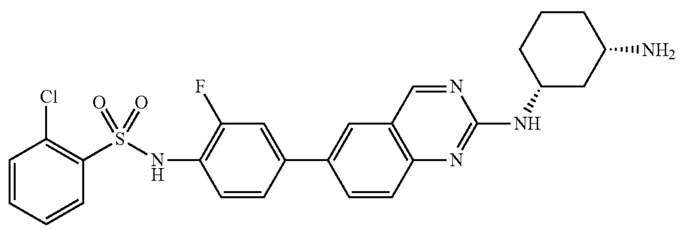 [SMILES: N[C@H]1CCC[C@@H](Nc2ncc3cc(-c4ccc(NS(=O)(=O)c5ccccc5Cl)c(F)c4)ccc3n2)C1] | N-(4-(2-(((1R,3S)-3-aminocyclohexyl)amino)quinazolin-6-yl)-2-fluorophenyl)-2-chlorobenzenesulfonamide |
| 76 | 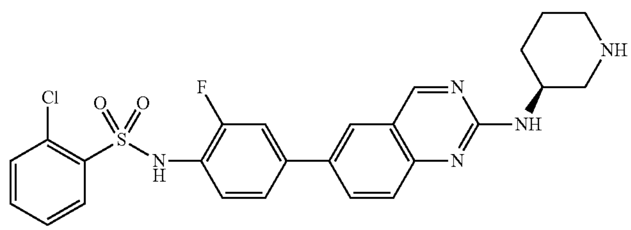 [SMILES: O=S(=O)(Nc1ccc(-c2ccc3nc(N[C@H]4CCCNC4)ncc3c2)cc1F)c1ccccc1Cl] | (S)-2-chloro-N-(2-fluoro-4-(2-(piperidin-3-ylamino)quinazolin-6-yl)phenyl)benzenesulfonamide |
| 77 | 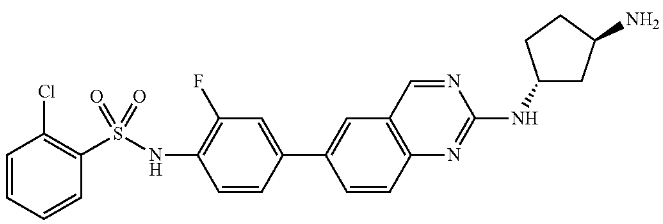 [SMILES: N[C@@H]1CC[C@@H](Nc2ncc3cc(-c4ccc(NS(=O)(=O)c5ccccc5Cl)c(F)c4)ccc3n2)C1] | N-(4-(2-(((1R,3R)-3-aminocyclopentyl)amino)quinazolin-6-yl)-2-fluorophenyl)-2-chlorobenzenesulfonamide |
| 78 | 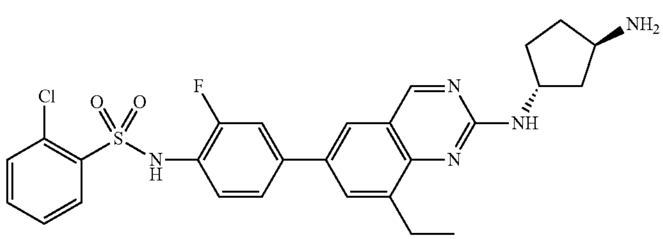 [SMILES: CCc1cc(-c2ccc(NS(=O)(=O)c3ccccc3Cl)c(F)c2)cc2cnc(N[C@@H]3CC[C@@H](N)C3)nc12] | N-(4-(2-(((1R,3R)-3-aminocyclopentyl)amino)-8-ethylquinazolin-6-yl)-2-fluorophenyl)-2-chlorobenzenesulfonamide |
| 79 | 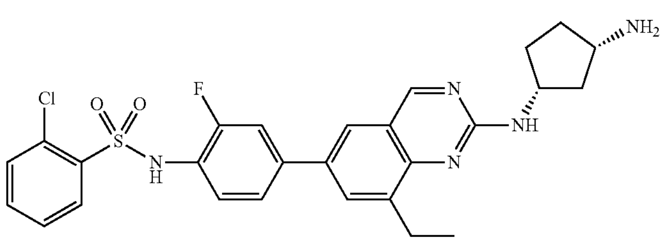 [SMILES: CCc1cc(-c2ccc(NS(=O)(=O)c3ccccc3Cl)c(F)c2)cc2cnc(N[C@@H]3CC[C@H](N)C3)nc12] | N-(4-(2-(((1R,3S)-3-aminocyclopentyl)amino)-8-ethylquinazolin-6-yl)-2-fluorophenyl)-2-chlorobenzenesulfonamide |
| 80 | 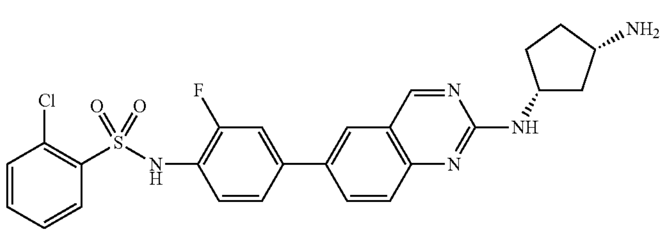 [SMILES: N[C@H]1CC[C@@H](Nc2ncc3cc(-c4ccc(NS(=O)(=O)c5ccccc5Cl)c(F)c4)ccc3n2)C1] | N-(4-(2-(((1R,3S)-3-aminocyclopentyl)amino)quinazolin-6-yl)-2-fluorophenyl)-2-chlorobenzenesulfonamide |

TABLE 1-continued

| Compound No. | Structure | Name |
|---|---|---|
| 81 | 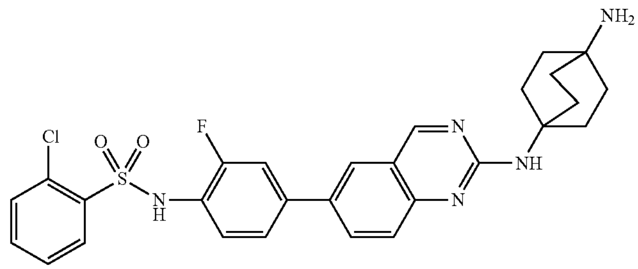 [SMILES: NC12CCC(Nc3ncc4cc(-c5ccc(NS(=O)(=O)c6ccccc6Cl)c(F)c5)ccc4n3)(CC1)CC2] | N-(4-(2-((4-aminobicyclo[2.2.2]octan-1-yl)amino)quinazolin-6-yl)-2-fluorophenyl)-2-chlorobenzenesulfonamide |
| 82 | 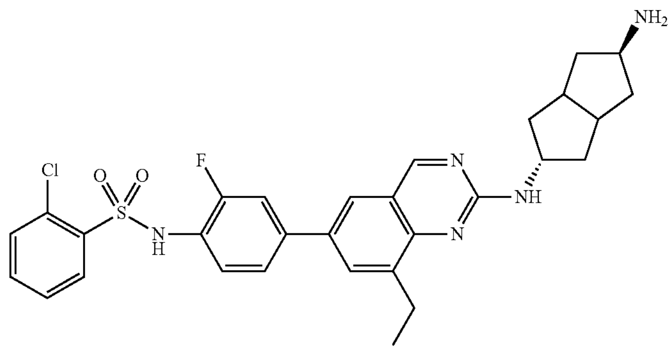 [SMILES: CCc1cc(-c2ccc(NS(=O)(=O)c3ccccc3Cl)c(F)c2)cc2cnc(N[C@H]3CC4C[C@H](N)CC4C3)nc12] | N-(4-(2-(((2r,5r)-5-aminooctahydropentalen-2-yl)amino)-8-ethylquinazolin-6-yl)-2-fluorophenyl)-2-chlorobenzenesulfonamide |
| 83 | 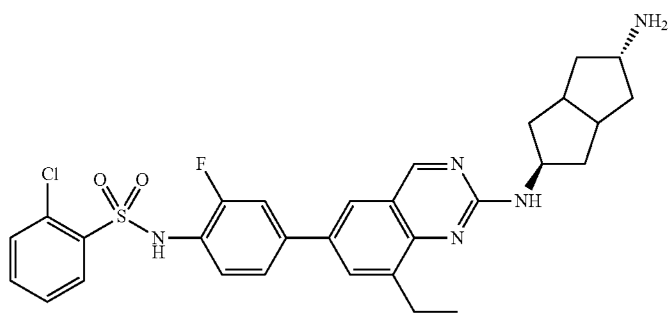 [SMILES: CCc1cc(-c2ccc(NS(=O)(=O)c3ccccc3Cl)c(F)c2)cc2cnc(N[C@H]3CC4C[C@H](N)CC4C3)nc12] | N-(4-(2-(((2r,5r)-5-aminooctahydropentalen-2-yl)amino)-8-ethylquinazolin-6-yl)-2-fluorophenyl)-2-chlorobenzenesulfonamide |
| 84 | 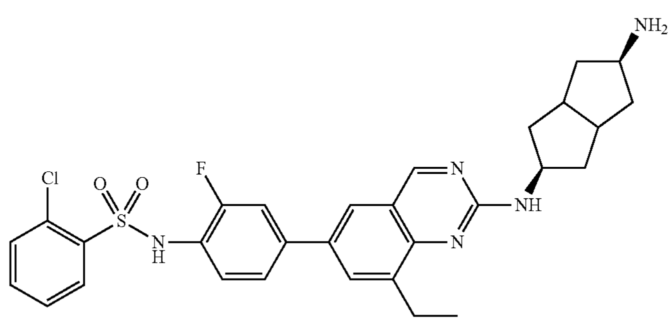 [SMILES: CCc1cc(-c2ccc(NS(=O)(=O)c3ccccc3Cl)c(F)c2)cc2cnc(N[C@H]3CC4C[C@@H](N)CC4C3)nc12] | N-(4-(2-(((2s,5s)-5-aminooctahydropentalen-2-yl)amino)-8-ethylquinazolin-6-yl)-2-fluorophenyl)-2-chlorobenzenesulfonamide |
| 85 | 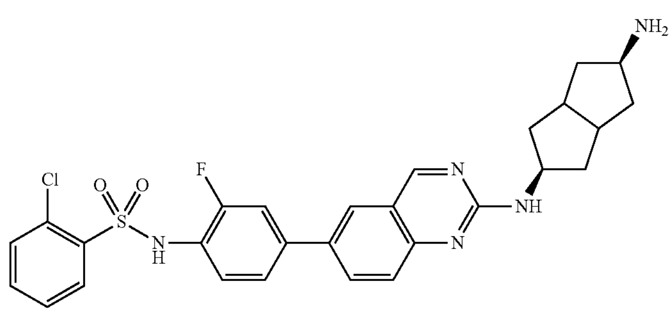 [SMILES: N[C@H]1CC2C[C@@H](Nc3ncc4cc(-c5ccc(NS(=O)(=O)c6ccccc6Cl)c(F)c5)ccc4n3)CC2C1] | N-(4-(2-(((2s,5s)-5-aminooctahydropentalen-2-yl)amino)quinazolin-6-yl)-2-fluorophenyl)-2-chlorobenzenesulfonamide |

TABLE 1-continued

| Compound No. | Structure | Name |
|---|---|---|
| 86 | 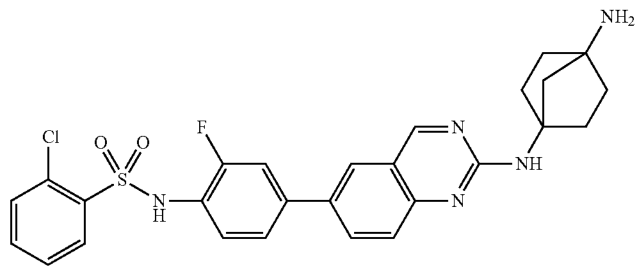 [SMILES: NC12CCC(Nc3ncc4cc(-c5ccc(NS(=O)(=O)c6ccccc6Cl)c(F)c5)ccc4n3)(CC1)C2] | N-(4-(2-((4-aminobicyclo[2.2.1]heptan-1-yl)amino)quinazolin-6-yl)-2-fluorophenyl)-2-chlorobenzenesulfonamide |
| 87 | 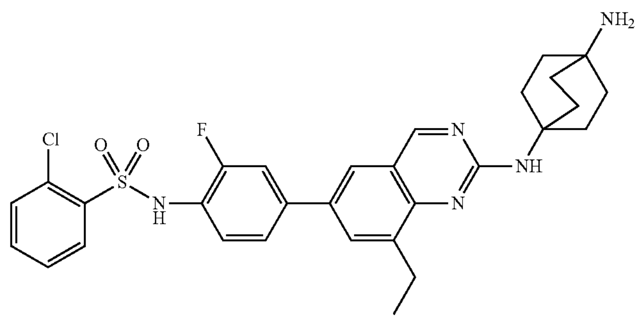 [SMILES: CCc1cc(-c2ccc(NS(=O)(=O)c3ccccc3Cl)c(F)c2)cc2cnc(NC34CCC(N)(CC3)CC4)nc12] | N-(4-(2-((4-aminobicyclo[2.2.2]octan-1-yl)amino)-8-ethylquinazolin-6-yl)-2-fluorophenyl)-2-chlorobenzenesulfonamide |
| 88 | 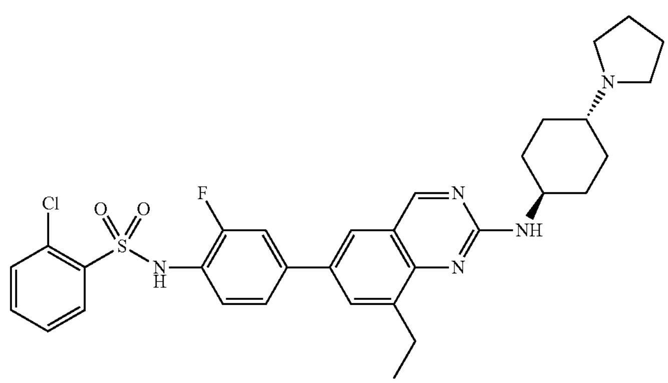 [SMILES: CCc1cc(-c2ccc(NS(=O)(=O)c3ccccc3Cl)c(F)c2)cc2cnc(N[C@H]3CC[C@H](N4CCCC4)CC3)nc12] | 2-chloro-N-(4-(8-ethyl-2-(((1r,4r)-4-(pyrrolidin-1-yl)cyclohexyl)amino)quinazolin-6-yl)-2-fluorophenyl)benzenesulfonamide |
| 89 | 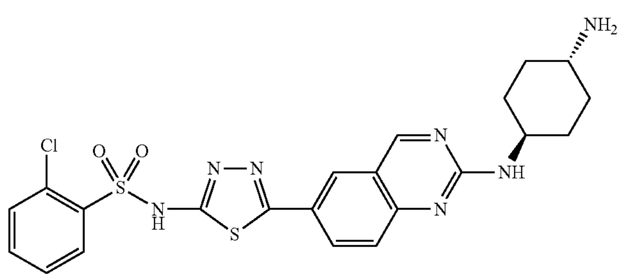 [SMILES: N[C@H]1CC[C@H](Nc2ncc3cc(-c4nnc(NS(=O)(=O)c5ccccc5Cl)s4)ccc3n2)CC1] | N-(5-(2-(((1r,4r)-4-aminocyclohexyl)amino)quinazolin-6-yl)-1,3,4-thiadiazol-2-yl)-2-chlorobenzenesulfonamide |
| 90 | 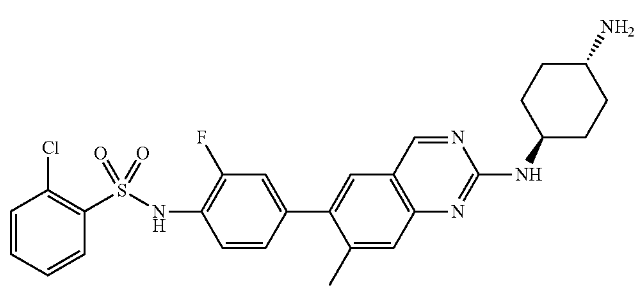 [SMILES: Cc1cc2nc(N[C@H]3CC[C@H](N)CC3)ncc2cc1-c1ccc(NS(=O)(=O)c2ccccc2Cl)c(F)c1] | N-(4-(2-(((1r,4r)-4-aminocyclohexyl)amino)-7-methylquinazolin-6-yl)-2-fluorophenyl)-2-chlorobenzenesulfonamide |

TABLE 1-continued

| Compound No. | Structure | Name |
|---|---|---|
| 91 | 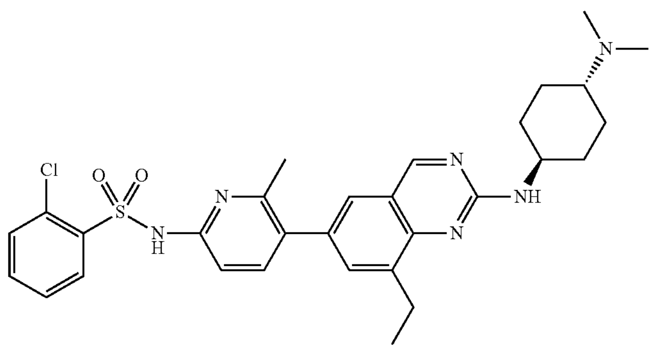 [SMILES: CCc1cc(-c2ccc(NS(=O)(=O)c3ccccc3Cl)nc2C)cc2cnc(N[C@H]3CC[C@H](N(C)C)CC3)nc12] | 2-chloro-N-(5-(2-(((1r,4r)-4-(dimethylamino)cyclohexyl)amino)-8-ethylquinazolin-6-yl)-6-methylpyridin-2-yl)benzenesulfonamide |
| 92 | 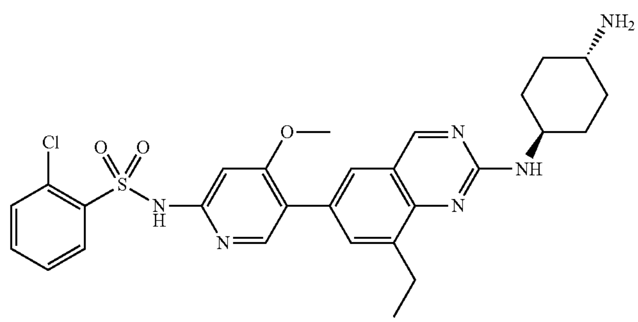 [SMILES: CCc1cc(-c2cnc(NS(=O)(=O)c3ccccc3Cl)cc2OC)cc2cnc(N[C@H]3CC[C@H](N)CC3)nc12] | N-(5-(2-(((1r,4r)-4-aminocyclohexyl)amino)-8-ethylquinazolin-6-yl)-4-methoxypyridin-2-yl)-2-chlorobenzenesulfonamide |
| 93 | 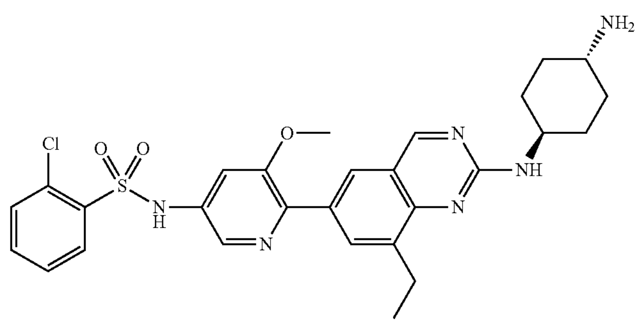 [SMILES: CCc1cc(-c2ncc(NS(=O)(=O)c3ccccc3Cl)cc2OC)cc2cnc(N[C@H]3CC[C@H](N)CC3)nc12] | N-(6-(2-(((1r,4r)-4-aminocyclohexyl)amino)-8-ethylquinazolin-6-yl)-5-methoxypyridin-3-yl)-2-chlorobenzenesulfonamide |
| 94 | 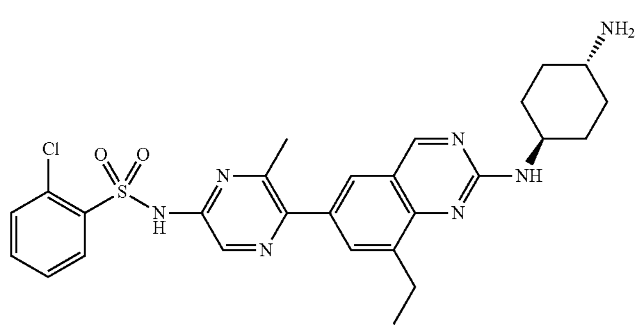 [SMILES: CCc1cc(-c2ncc(NS(=O)(=O)c3ccccc3Cl)nc2C)cc2cnc(N[C@H]3CC[C@H](N)CC3)nc12] | N-(5-(2-(((1r,4r)-4-aminocyclohexyl)amino)-8-ethylquinazolin-6-yl)-6-methylpyrazin-2-yl)-2-chlorobenzenesulfonamide |

TABLE 1-continued

| Compound No. | Structure | Name |
|---|---|---|
| 95 | 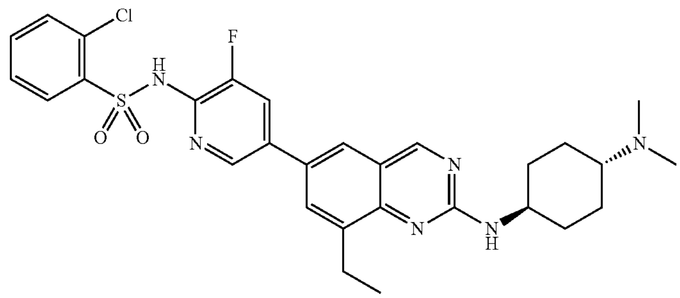 [SMILES: CCc1cc(-c2cnc(NS(=O)(=O)c3ccccc3Cl)c(F)c2)cc2cnc(N[C@H]3CC[C@H](N(C)C)CC3)nc12] | 2-chloro-N-(5-(2-(((1r,4r)-4-(dimethylamino)cyclohexyl)amino)-8-ethylquinazolin-6-yl)-3-fluoropyridin-2-yl)benzenesulfonamide |
| 96 | 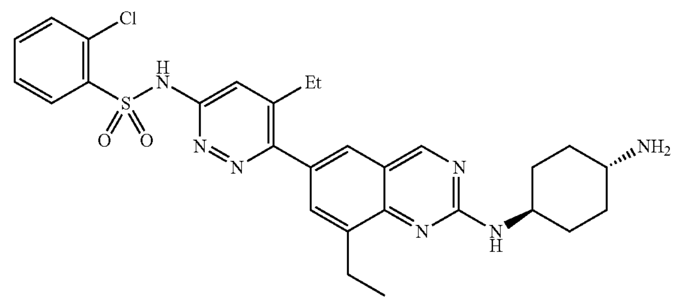 [SMILES: CCc1cc(NS(=O)(=O)c2ccccc2Cl)nnc1-c1cc(CC)c2nc(N[C@H]3CC[C@H](N)CC3)ncc2c1] | N-(6-(2-(((1r,4r)-4-aminocyclohexyl)amino)-8-ethylquinazolin-6-yl)-5-ethylpyridazin-3-yl)-2-chlorobenzenesulfonamide |
| 97 | 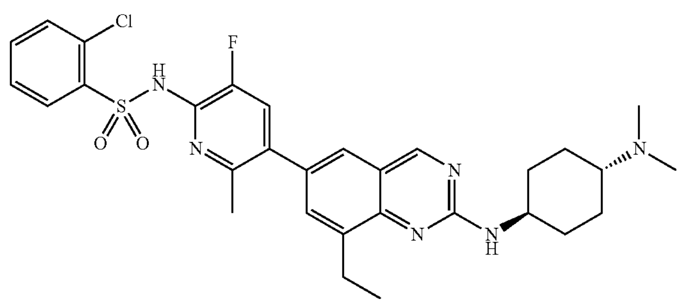 [SMILES: CCc1cc(-c2cc(F)c(NS(=O)(=O)c3ccccc3Cl)nc2C)cc2cnc(N[C@H]3CC[C@H](N(C)C)CC3)nc12] | 2-chloro-N-(5-(2-(((1r,4r)-4-(dimethylamino)cyclohexyl)amino)-8-ethylquinazolin-6-yl)-3-fluoro-6-methylpyridin-2-yl)benzenesulfonamide |
| 98 | 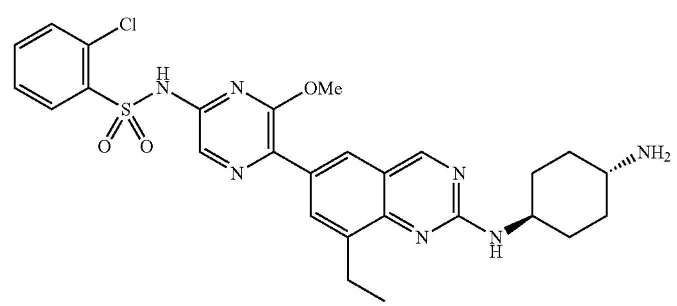 [SMILES: CCc1cc(-c2ncc(NS(=O)(=O)c3ccccc3Cl)nc2OC)cc2cnc(N[C@H]3CC[C@H](N)CC3)nc12] | N-(5-(2-(((1r,4r)-4-aminocyclohexyl)amino)-8-ethylquinazolin-6-yl)-6-methoxypyrazin-2-yl)-2-chlorobenzenesulfonamide |
| 99 | 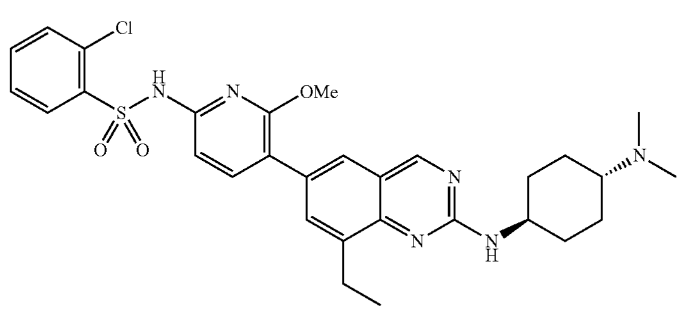 [SMILES: CCc1cc(-c2ccc(NS(=O)(=O)c3ccccc3Cl)nc2OC)cc2cnc(N[C@H]3CC[C@H](N(C)C)CC3)nc12] | 2-chloro-N-(5-(2-(((1r,4r)-4-(dimethylamino)cyclohexyl)amino)-8-ethylquinazolin-6-yl)-6-methoxypyridin-2-yl)benzenesulfonamide |

TABLE 1-continued

| Compound No. | Structure | Name |
|---|---|---|
| 108 | 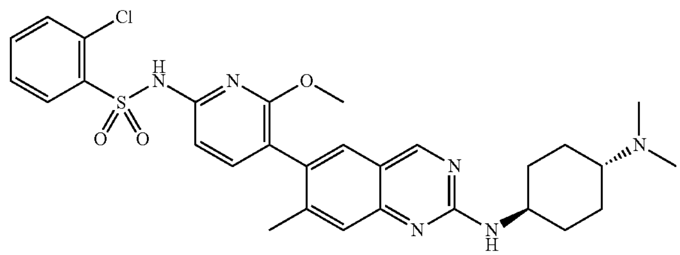 [SMILES: COc1nc(NS(=O)(=O)c2ccccc2Cl)ccc1-c1cc2cnc(N[C@H]3CC[C@H](N(C)C)CC3)nc2cc1C] | 2-chloro-N-(5-(2-(((1r,4r)-4-(dimethylamino)cyclohexyl)amino)-7-methylquinazolin-6-yl)-6-methoxypyridin-2-yl)benzenesulfonamide |
| 116 | 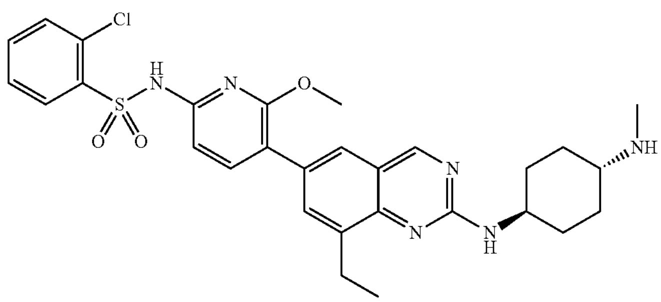 [SMILES: CCc1cc(-c2ccc(NS(=O)(=O)c3ccccc3Cl)nc2OC)cc2cnc(N[C@H]3CC[C@H](NC)CC3)nc12] | 2-chloro-N-(5-(8-ethyl-2-(((1r,4r)-4-(methylamino)cyclohexyl)amino)quinazolin-6-yl)-6-methoxypyridin-2-yl)benzenesulfonamide |
| 117 | 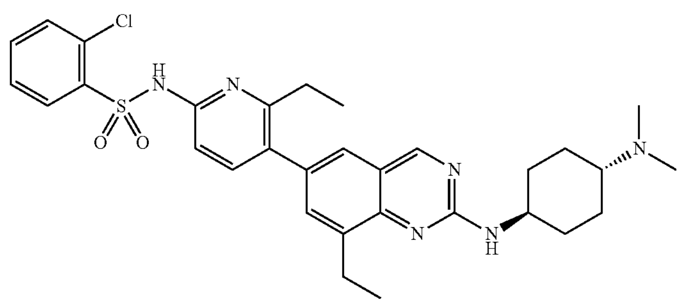 [SMILES: CCc1nc(NS(=O)(=O)c2ccccc2Cl)ccc1-c1cc(CC)c2nc(N[C@H]3CC[C@H](N(C)C)CC3)ncc2c1] | 2-chloro-N-(5-(2-(((1r,4r)-4-(dimethylamino)cyclohexyl)amino)-8-ethylquinazolin-6-yl)-6-ethylpyridin-2-yl)benzenesulfonamide |
| 118 | 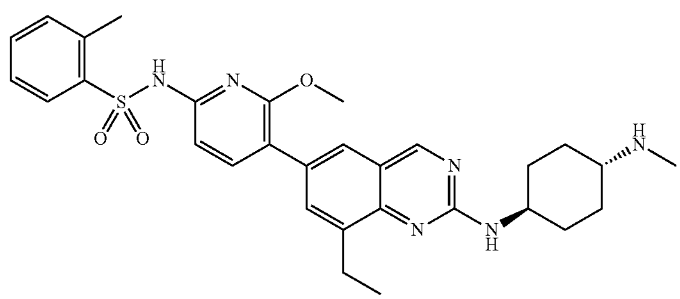 [SMILES: CCc1cc(-c2ccc(NS(=O)(=O)c3ccccc3C)nc2OC)cc2cnc(N[C@H]3CC[C@H](NC)CC3)nc12] | N-(5-(8-ethyl-2-(((1r,4r)-4-(methylamino)cyclohexyl)amino)quinazolin-6-yl)-6-methoxypyridin-2-yl)-2-methylbenzenesulfonamide |
| 119 | 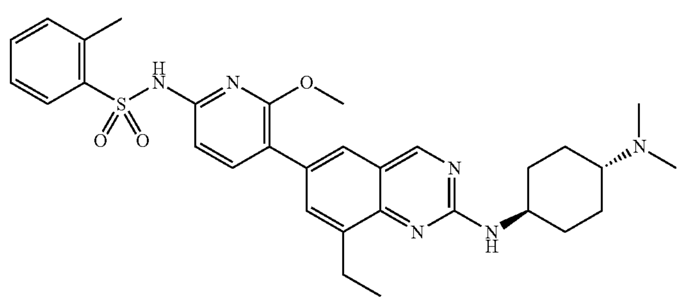 [SMILES: CCc1cc(-c2ccc(NS(=O)(=O)c3ccccc3C)nc2OC)cc2cnc(N[C@H]3CC[C@H](N(C)C)CC3)nc12] | N-(5-(2-(((1r,4r)-4-(dimethylamino)cyclohexyl)amino)-8-ethylquinazolin-6-yl)-6-methoxypyridin-2-yl)-2-methylbenzenesulfonamide |

TABLE 1-continued

| Compound No. | Structure | Name |
|---|---|---|
| 122 | 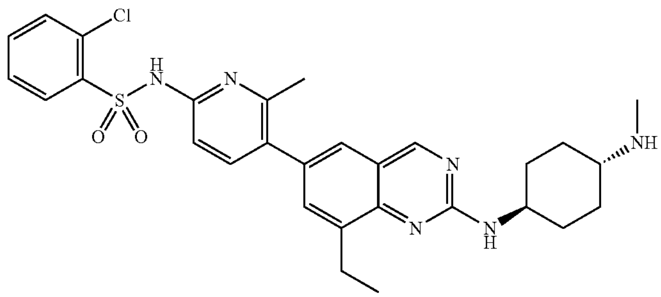 [SMILES: CCc1cc(-c2ccc(NS(=O)(=O)c3ccccc3Cl)nc2C)cc2cnc(N[C@H]3CC[C@H](NC)CC3)nc12] | 2-chloro-N-(5-(8-ethyl-2-(((1r,4r)-4-(methylamino)cyclohexyl)amino)quinazolin-6-yl)-6-methylpyridin-2-yl)benzenesulfonamide |
| 124 | 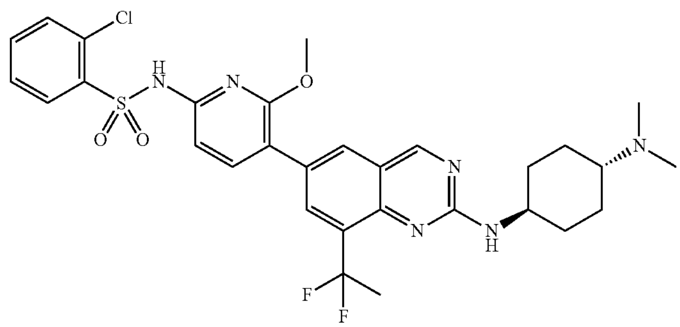 [SMILES: COc1nc(NS(=O)(=O)c2ccccc2Cl)ccc1-c1cc(C(C)(F)F)c2nc(N[C@H]3CC[C@H](N(C)C)CC3)ncc2c1] | 2-chloro-N-(5-(8-(1,1-difluoroethyl)-2-(((1r,4r)-4-(dimethylamino)cyclohexyl)amino)quinazolin-6-yl)-6-methoxypyridin-2-yl)benzenesulfonamide |
| 125 | 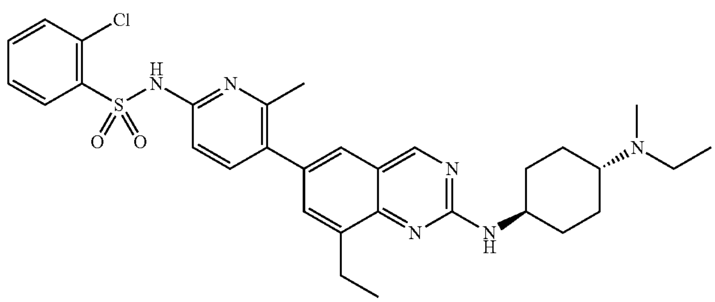 [SMILES: CCc1cc(-c2ccc(NS(=O)(=O)c3ccccc3Cl)nc2C)cc2cnc(N[C@H]3CC[C@H](N(C)CC)CC3)nc12] | 2-chloro-N-(5-(8-ethyl-2-(((1r,4r)-4-(ethyl(methyl)amino)cyclohexyl)amino)quinazolin-6-yl)-6-methylpyridin-2-yl)benzenesulfonamide |
| 126 | 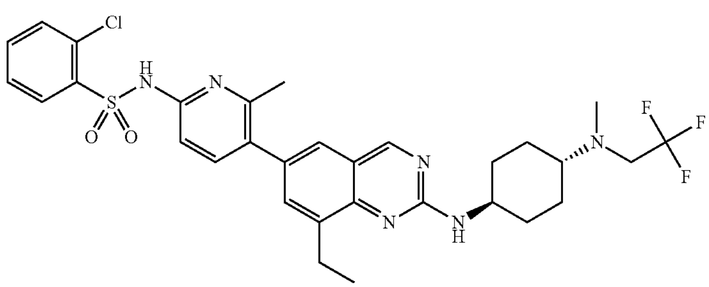 [SMILES: CCc1cc(-c2ccc(NS(=O)(=O)c3ccccc3Cl)nc2C)cc2cnc(N[C@H]3CC[C@H](N(C)CC(F)(F)F)CC3)nc12] | 2-chloro-N-(5-(8-ethyl-2-(((1r,4r)-4-(methyl(2,2,2-trifluoroethyl)amino)cyclohexyl)amino)quinazolin-6-yl)-6-methylpyridin-2-yl)benzenesulfonamide |
| 127 | 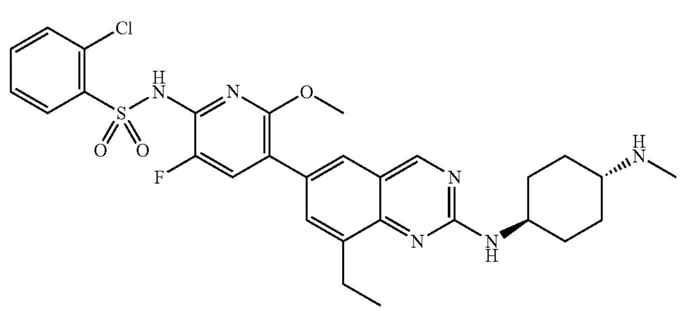 [SMILES: CCc1cc(-c2cc(F)c(NS(=O)(=O)c3ccccc3Cl)nc2OC)cc2cnc(N[C@H]3CC[C@H](NC)CC3)nc12] | 2-chloro-N-(5-(8-ethyl-2-(((1r,4r)-4-(methylamino)cyclohexyl)amino)quinazolin-6-yl)-3-fluoro-6-methoxypyridin-2-yl)benzenesulfonamide |

TABLE 1-continued

| Compound No. | Structure | Name |
|---|---|---|
| 128 | 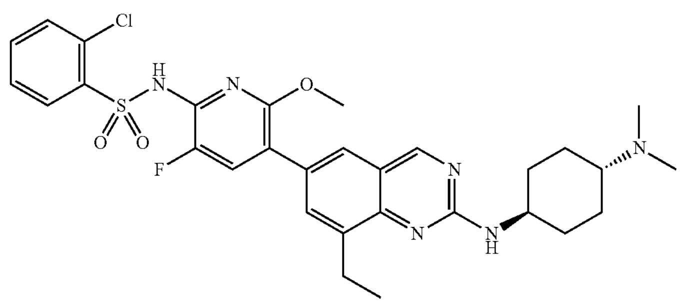 [SMILES: CCc1cc(-c2cc(F)c(NS(=O)(=O)c3ccccc3Cl)nc2OC)cc2cnc(N[C@H]3CC[C@H](N(C)C)CC3)nc12] | 2-chloro-N-(5-(2-(((1r,4r)-4-(dimethylamino)cyclohexyl)amino)-8-ethylquinazolin-6-yl)-3-fluoro-6-methoxypyridin-2-yl)benzenesulfonamide |
| 130 | 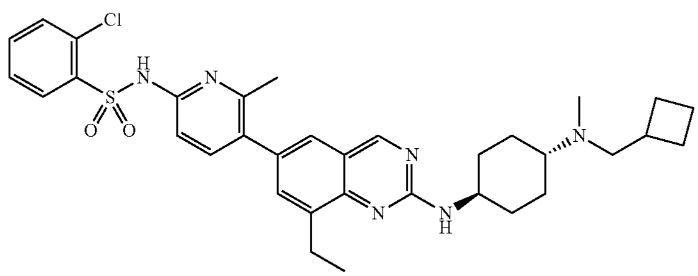 [SMILES: CCc1cc(-c2ccc(NS(=O)(=O)c3ccccc3Cl)nc2C)cc2cnc(N[C@H]3CC[C@H](N(C)CC4CCC4)CC3)nc12] | 2-chloro-N-(5-(2-(((1r,4r)-4-((cyclobutylmethyl)(methyl)amino)cyclohexyl)amino)-8-ethylquinazolin-6-yl)-6-methylpyridin-2-yl)benzenesulfonamide |
| 131 | 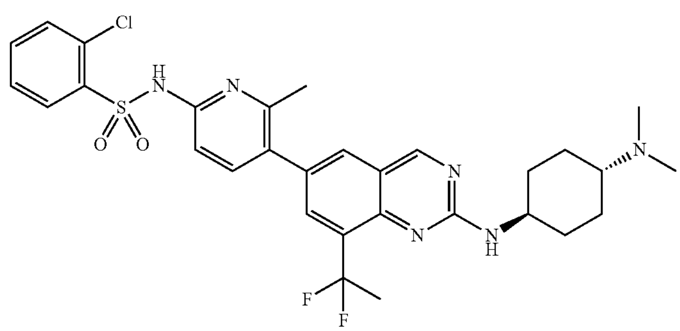 [SMILES: Cc1nc(NS(=O)(=O)c2ccccc2Cl)ccc1-c1cc(C(C)(F)F)c2nc(N[C@H]3CC[C@H](N(C)C)CC3)ncc2c1] | 2-chloro-N-(5-(8-(1,1-difluoroethyl)-2-(((1r,4r)-4-(dimethylamino)cyclohexyl)amino)quinazolin-6-yl)-6-methylpyridin-2-yl)benzenesulfonamide |
| 132 | 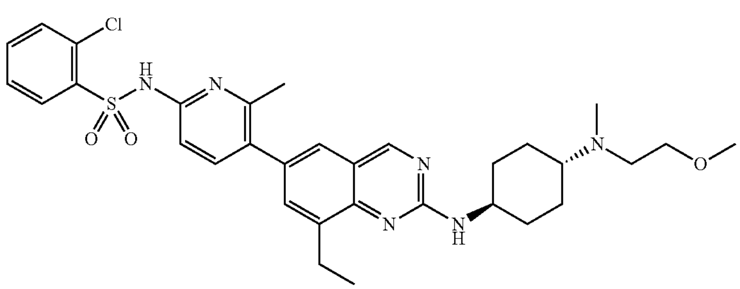 [SMILES: CCc1cc(-c2ccc(NS(=O)(=O)c3ccccc3Cl)nc2C)cc2cnc(N[C@H]3CC[C@H](N(C)CCOC)CC3)nc12] | 2-chloro-N-(5-(8-ethyl-2-(((1r,4r)-4-((2-methoxyethyl)(methyl)amino)cyclohexyl)amino)quinazolin-6-yl)-6-methylpyridin-2-yl)benzenesulfonamide |
| 133 | 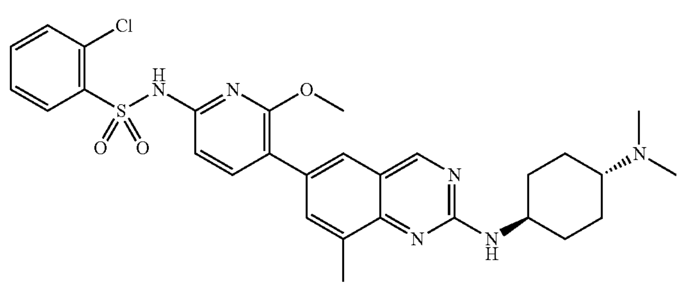 [SMILES: COc1nc(NS(=O)(=O)c2ccccc2Cl)ccc1-c1cc(C)c2nc(N[C@H]3CC[C@H](N(C)C)CC3)ncc2c1] | 2-chloro-N-(5-(2-(((1r,4r)-4-(dimethylamino)cyclohexyl)amino)-8-methylquinazolin-6-yl)-6-methoxypyridin-2-yl)benzenesulfonamide |

TABLE 1-continued

| Compound No. | Structure | Name |
|---|---|---|
| 135 | 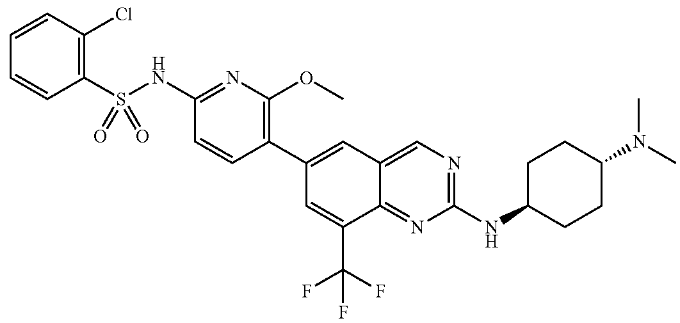 [SMILES: COc1nc(NS(=O)(=O)c2ccccc2Cl)ccc1-c1cc(C(F)(F)F)c2nc(N[C@H]3CC[C@H](N(C)C)CC3)ncc2c1] | 2-chloro-N-(5-(2-(((1r,4r)-4-(dimethylamino)cyclohexyl)amino)-8-(trifluoromethyl)quinazolin-6-yl)-6-methoxypyridin-2-yl)benzenesulfonamide |
| 137 | 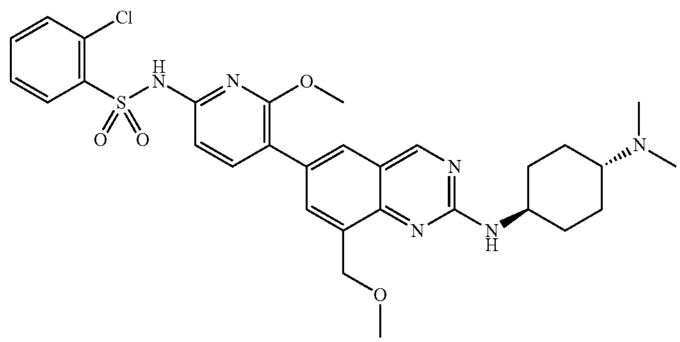 [SMILES: COCc1cc(-c2ccc(NS(=O)(=O)c3ccccc3Cl)nc2OC)cc2cnc(N[C@H]3CC[C@H](N(C)C)CC3)nc12] | 2-chloro-N-(5-(2-(((1r,4r)-4-(dimethylamino)cyclohexyl)amino)-8-(methoxymethyl)quinazolin-6-yl)-6-methoxypyridin-2-yl)benzenesulfonamide |
| 139 | 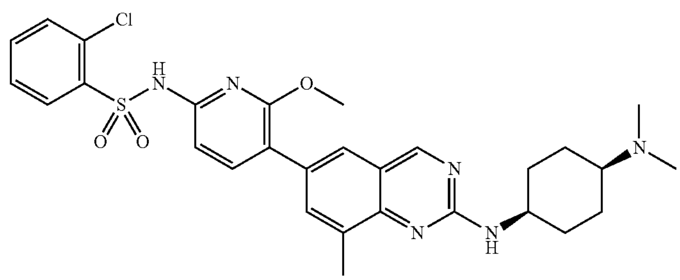 [SMILES: COc1nc(NS(=O)(=O)c2ccccc2Cl)ccc1-c1cc(C)c2nc(N[C@H]3CC[C@@H](N(C)C)CC3)ncc2c1] | 2-chloro-N-(5-(2-(((1s,4s)-4-(dimethylamino)cyclohexyl)amino)-8-methylquinazolin-6-yl)-6-methoxypyridin-2-yl)benzenesulfonamide |
| 141 | 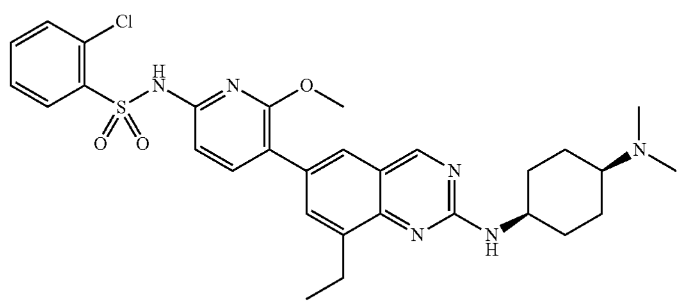 [SMILES: CCc1cc(-c2ccc(NS(=O)(=O)c3ccccc3Cl)nc2OC)cc2cnc(N[C@H]3CC[C@@H](N(C)C)CC3)nc12] | 2-chloro-N-(5-(2-(((1s,4s)-4-(dimethylamino)cyclohexyl)amino)-8-ethylquinazolin-6-yl)-6-methoxypyridin-2-yl)benzenesulfonamide |
| 142 | 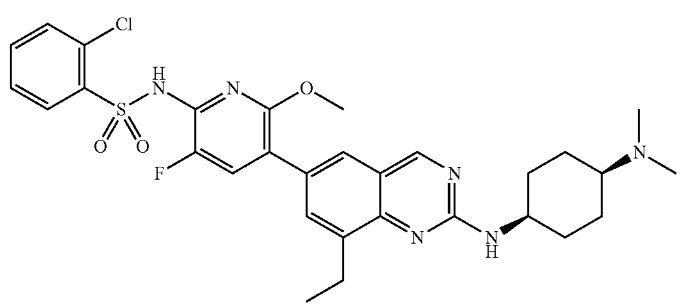 [SMILES: CCc1cc(-c2cc(F)c(NS(=O)(=O)c3ccccc3Cl)nc2OC)cc2cnc(N[C@H]3CC[C@@H](N(C)C)CC3)nc12] | 2-chloro-N-(5-(2-(((1s,4s)-4-(dimethylamino)cyclohexyl)amino)-8-ethylquinazolin-6-yl)-3-fluoro-6-methoxypyridin-2-yl)benzenesulfonamide |

TABLE 1-continued

| Compound No. | Structure | Name |
|---|---|---|
| 143 | 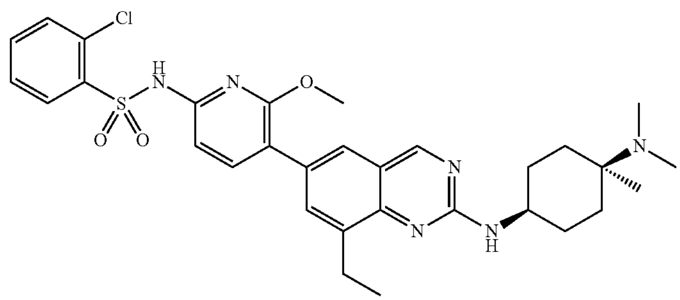 [SMILES: CCc1cc(-c2ccc(NS(=O)(=O)c3ccccc3Cl)nc2OC)cc2cnc(N[C@H]3CC[C@@](C)(N(C)C)CC3)nc12] | 2-chloro-N-(5-(2-(((1s,4s)-4-(dimethylamino)-4-methylcyclohexyl)amino)-8-ethylquinazolin-6-yl)-6-methoxypyridin-2-yl)benzenesulfonamide |
| 144 | 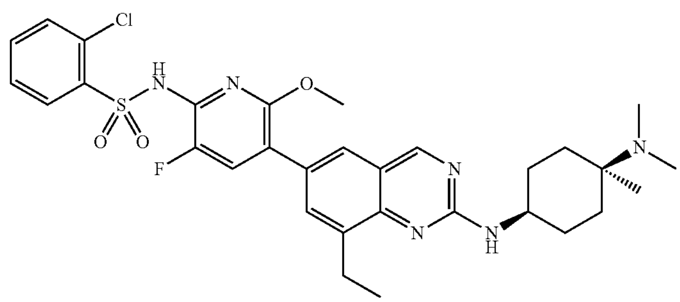 [SMILES: CCc1cc(-c2cc(F)c(NS(=O)(=O)c3ccccc3Cl)nc2OC)cc2cnc(N[C@H]3CC[C@@](C)(N(C)C)CC3)nc12] | 2-chloro-N-(5-(2-(((1s,4s)-4-(dimethylamino)-4-methylcyclohexyl)amino)-8-ethylquinazolin-6-yl)-3-fluoro-6-methoxypyridin-2-yl)benzenesulfonamide |
| 145 | 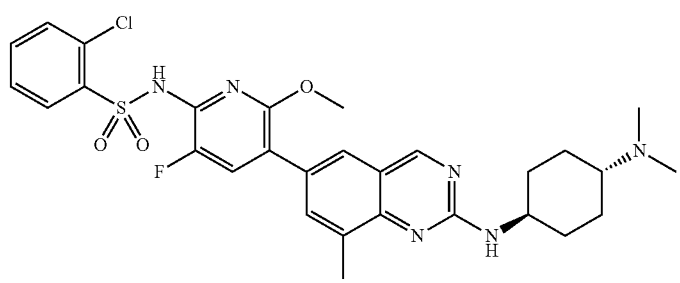 [SMILES: COc1nc(NS(=O)(=O)c2ccccc2Cl)c(F)cc1-c1cc(C)c2nc(N[C@H]3CC[C@H](N(C)C)CC3)ncc2c1] | 2-chloro-N-(5-(2-(((1r,4r)-4-(dimethylamino)cyclohexyl)amino)-8-methylquinazolin-6-yl)-3-fluoro-6-methoxypyridin-2-yl)benzenesulfonamide |
| 147 | 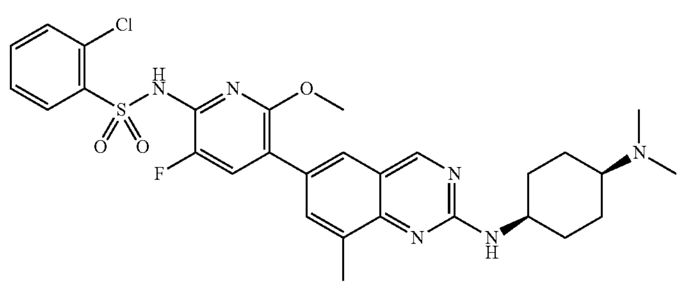 [SMILES: COc1nc(NS(=O)(=O)c2ccccc2Cl)c(F)cc1-c1cc(C)c2nc(N[C@H]3CC[C@@H](N(C)C)CC3)ncc2c1] | 2-chloro-N-(5-(2-(((1s,4s)-4-(dimethylamino)cyclohexyl)amino)-8-methylquinazolin-6-yl)-3-fluoro-6-methoxypyridin-2-yl)benzenesulfonamide |
| 148 | 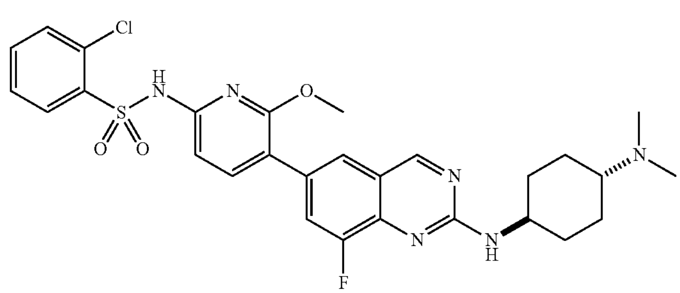 | 2-chloro-N-(5-(2-(((1r,4r)-4-(dimethylamino)cyclohexyl)amino)-8-fluoroquinazolin-6-yl)-6-methoxypyridin-2-yl)benzenesulfonamide |

TABLE 1-continued

| Compound No. | Structure | Name |
|---|---|---|
| 149 | 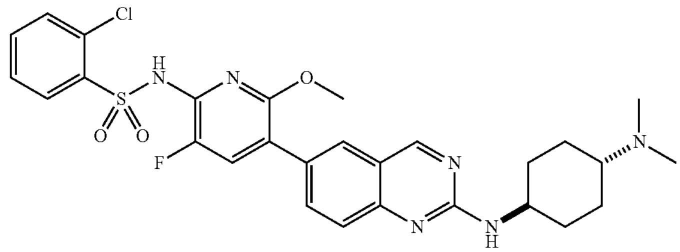 | 2-chloro-N-(5-(2-(((1r,4r)-4-(dimethylamino)cyclohexyl)amino)quinazolin-6-yl)-3-fluoro-6-methoxypyridin-2-yl)benzenesulfonamide |
| 150 | 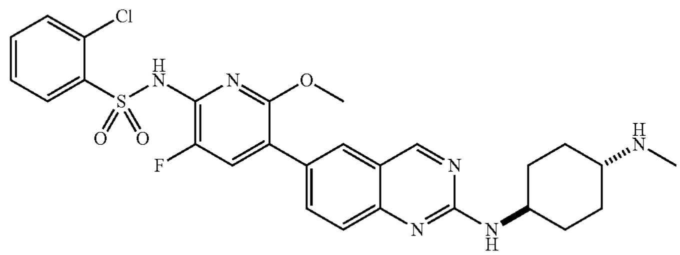 | 2-chloro-N-(3-fluoro-6-methoxy-5-(2-(((1r,4r)-4-(methylamino)cyclohexyl)amino)quinazolin-6-yl)pyridin-2-yl)benzenesulfonamide |
| 151 | 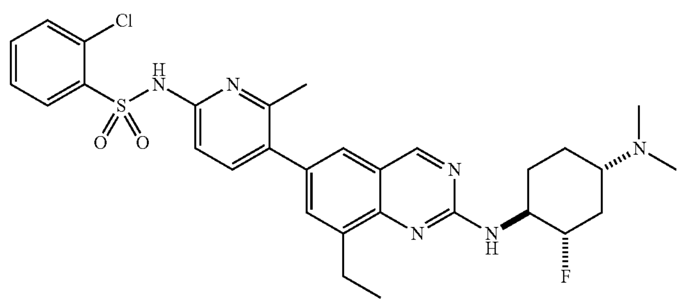 | 2-chloro-N-(5-(2-(((1S,2S,4S)-4-(dimethylamino)-2-fluorocyclohexyl)amino)-8-ethylquinazolin-6-yl)-6-methylpyridin-2-yl)benzenesulfonamide |
| 152 | 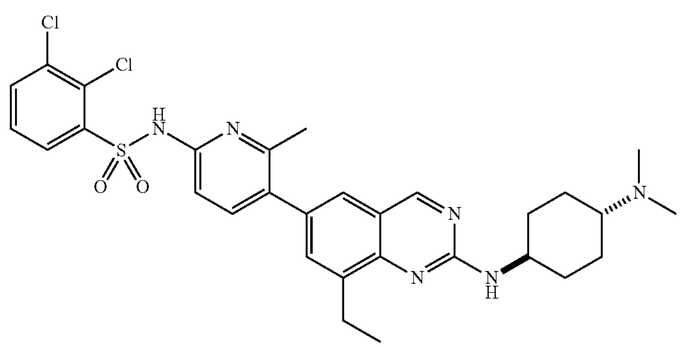 | 2,3-dichloro-N-(5-(2-(((1r,4r)-4-(dimethylamino)cyclohexyl)amino)-8-ethylquinazolin-6-yl)-6-methylpyridin-2-yl)benzenesulfonamide |
| 153 | 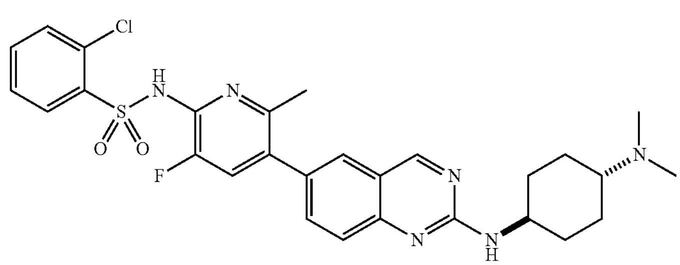 | 2-chloro-N-(5-(2-(((1r,4r)-4-(dimethylamino)cyclohexyl)amino)quinazolin-6-yl)-3-fluoro-6-methylpyridin-2-yl)benzenesulfonamide |

TABLE 1-continued

| Compound No. | Structure | Name |
|---|---|---|
| 154 | 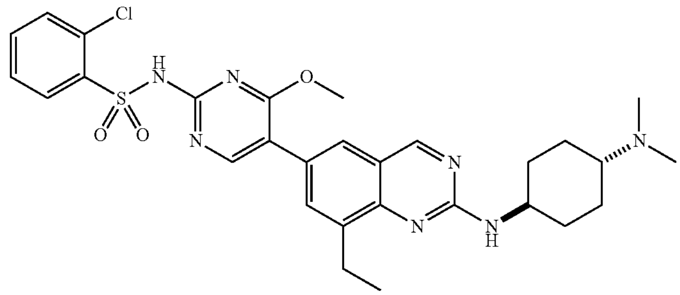 | 2-chloro-N-(5-(2-(((1r,4r)-4-(dimethylamino)cyclohexyl)amino)-8-ethylquinazolin-6-yl)-4-methoxypyrimidin-2-yl)benzenesulfonamide |
| 155 | 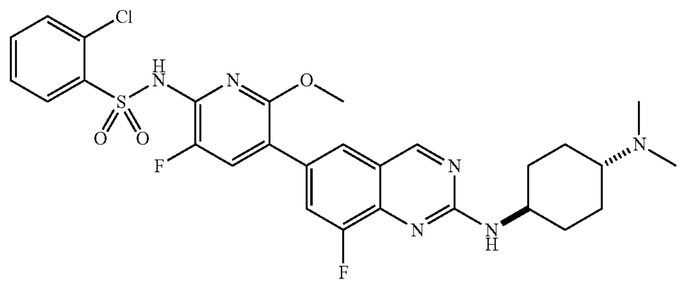 | 2-chloro-N-(5-(2-(((1r,4r)-4-(dimethylamino)cyclohexyl)amino)-8-fluoroquinazolin-6-yl)-3-fluoro-6-methoxypyridin-2-yl)benzenesulfonamide |
| 156 | 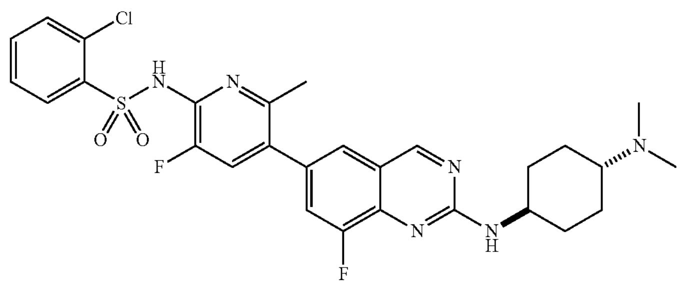 | 2-chloro-N-(5-(2-(((1r,4r)-4-(dimethylamino)cyclohexyl)amino)-8-fluoroquinazolin-6-yl)-3-fluoro-6-methylpyridin-2-yl)benzenesulfonamide |
| 157 | 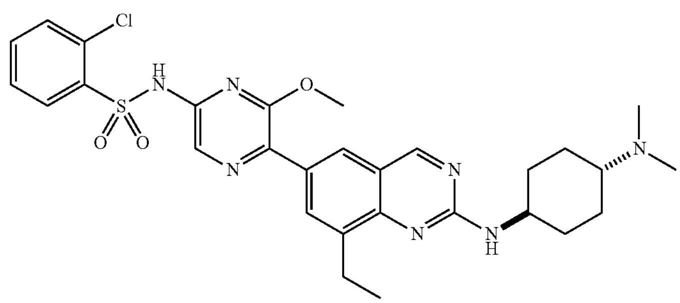 | 2-chloro-N-(5-(2-(((1r,4r)-4-(dimethylamino)cyclohexyl)amino)-8-ethylquinazolin-6-yl)-6-methoxypyrazin-2-yl)benzenesulfonamide |
| 158 | 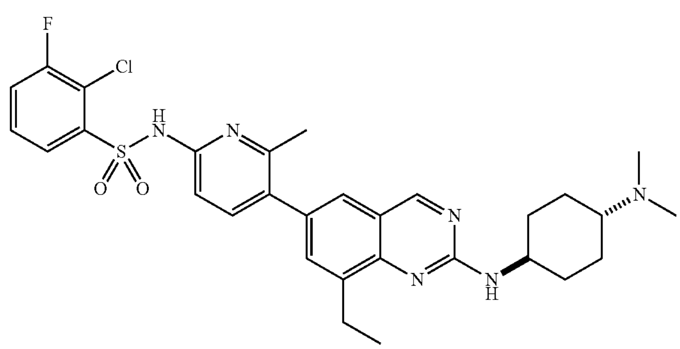 | 2-chloro-N-(5-(2-(((1r,4r)-4-(dimethylamino)cyclohexyl)amino)-8-ethylquinazolin-6-yl)-6-methylpyridin-2-yl)-3-fluorobenzenesulfonamide |

TABLE 1-continued

| Compound No. | Structure | Name |
|---|---|---|
| 159 | 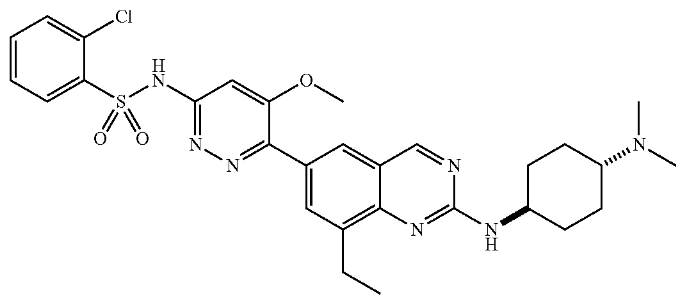 | 2-chloro-N-(6-(2-(((1r,4r)-4-(dimethylamino)cyclohexyl)amino)-8-ethylquinazolin-6-yl)-5-methoxypyridazin-3-yl)benzenesulfonamide |
| 160 | 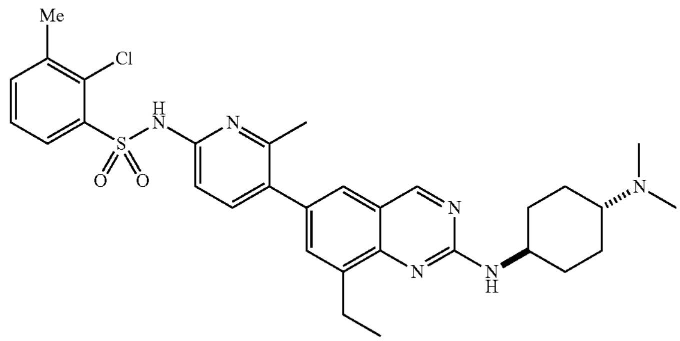 | 2-chloro-N-(5-(2-(((1r,4r)-4-(dimethylamino)cyclohexyl)amino)-8-ethylquinazolin-6-yl)-6-methylpyridin-2-yl)-3-methylbenzenesulfonamide |
| 161 | 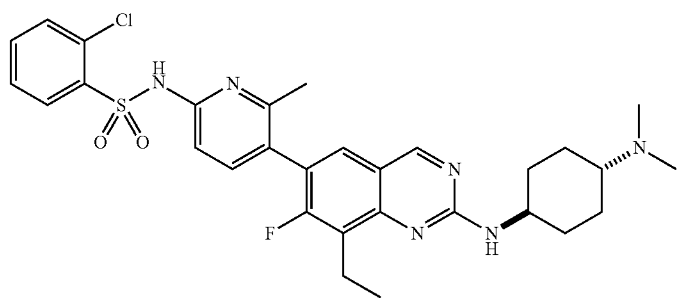 | 2-chloro-N-(5-(2-(((1r,4r)-4-(dimethylamino)cyclohexyl)amino)-8-ethyl-7-fluoroquinazolin-6-yl)-6-methylpyridin-2-yl)benzenesulfonamide |
| 162 | 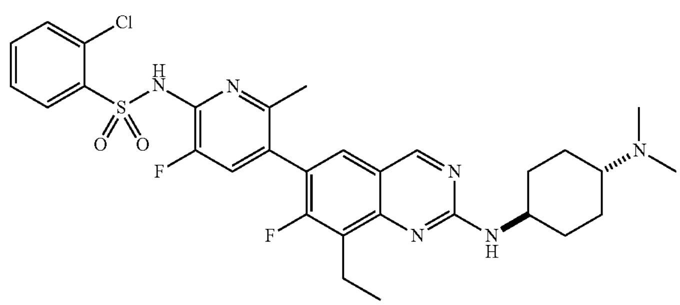 | 2-chloro-N-(5-(2-(((1r,4r)-4-(dimethylamino)cyclohexyl)amino)-8-ethyl-7-fluoroquinazolin-6-yl)-3-fluoro-6-methylpyridin-2-yl)benzenesulfonamide |
| 163 | 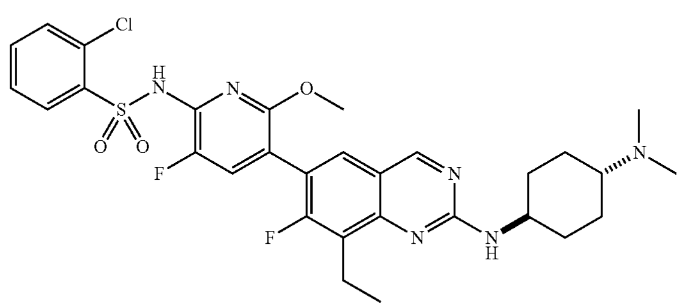 | 2-chloro-N-(5-(2-(((1r,4r)-4-(dimethylamino)cyclohexyl)amino)-8-ethyl-7-fluoroquinazolin-6-yl)-3-fluoro-6-methoxypyridin-2-yl)benzenesulfonamide |

In one aspect, provided herein is a pharmaceutically acceptable salt or solvate thereof of a compound described in Table 1. Any combination of the groups described above or below for the various variables is contemplated herein. Throughout the specification, groups and substituents thereof are chosen by one skilled in the field to provide stable moieties and compounds.

IRE1-Like Family of Proteins

In some embodiments, a compound disclosed herein selectively binds to a protein of the serine/threonine-protein kinase/endoribonuclease inositol-requiring enzyme 1 (IRE1) family of proteins. In humans, IRE1 is encoded by the ERN1 gene. Exemplary IRE1 family proteins include isoforms IRE1 and IRE1a. Other exemplary IRE1 family proteins include IRE1 homologues or orthologues in other organisms. Exemplary organisms include human, non-human primate, mouse, rat, chicken, fruit fly, yeast, and others listed in Table 2. In some embodiments, the IRE1 protein is human IRE1a.

TABLE 2

| Organism | Accession # |
|---|---|
| Homo sapiens | NP_001424.3 |
| Mus musculus | NP_076402.1 |
| Rattus norvegicus | XP_006247696.1 |

Figure 2:
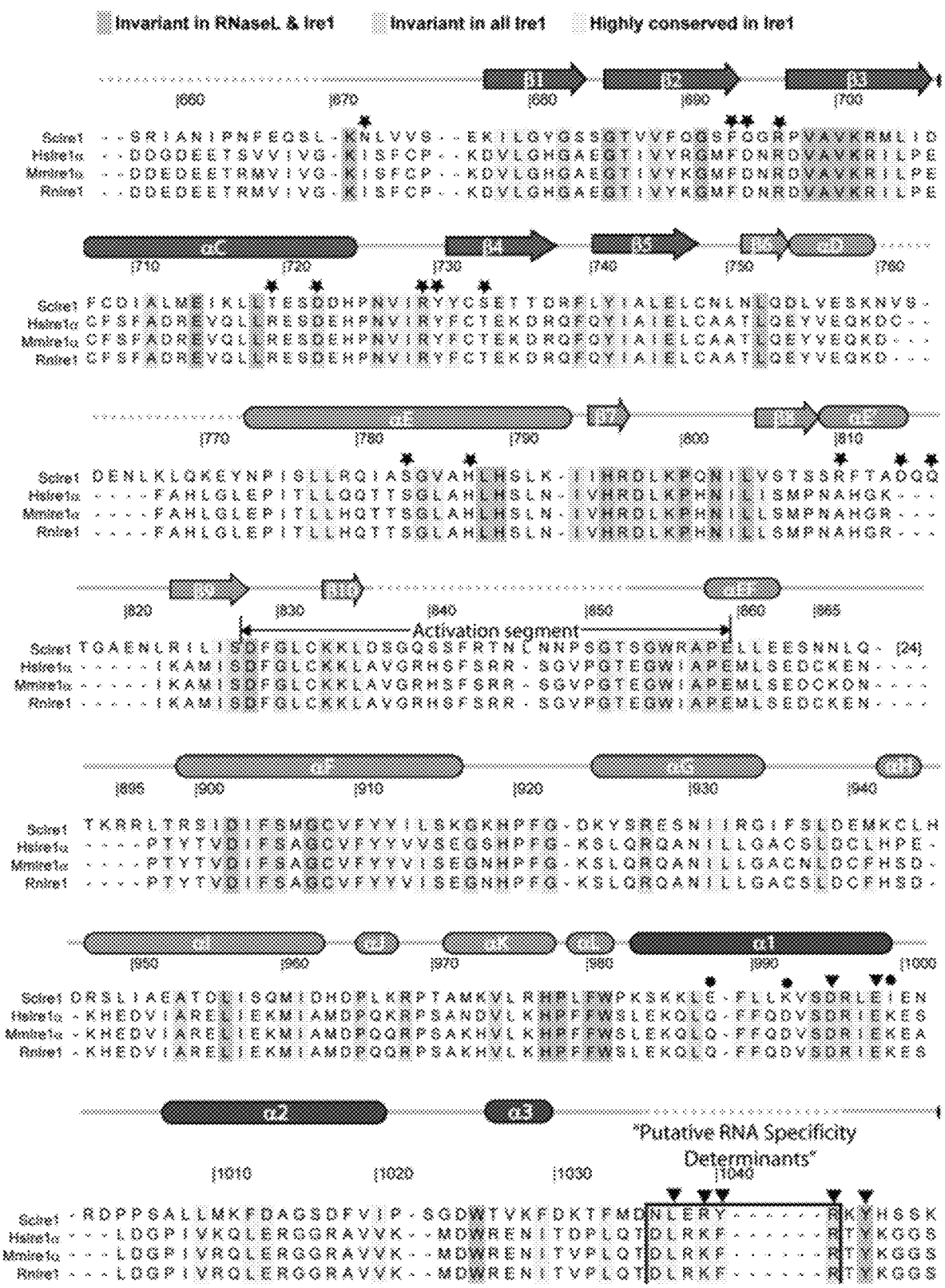
FIG. 2 shows an example alignment of the C-terminal half IRE1 orthologues from yeast (ScIre1), human (HsIre1), mouse (MmIre1), and rat (RnIRE1). Stars indicate kinase domain dimer interface residues. Circles indicate Kinase extension nuclease (KEN) domain dimer interface residues. Triangles indicate putative nuclease active site residues.
Figure 2:
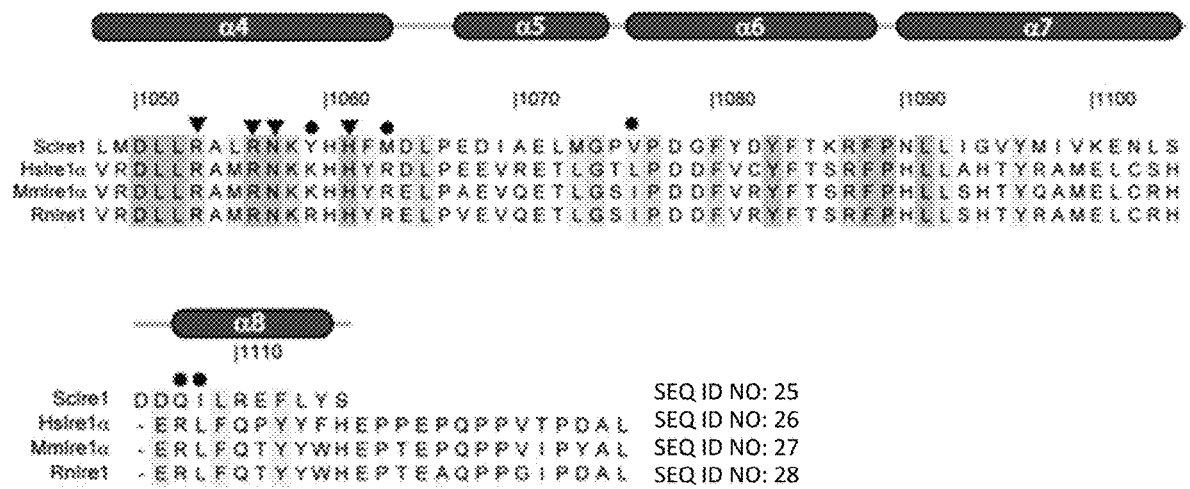

In some embodiments, a compound disclosed herein selectively binds to an IRE1 family protein comprising a kinase domain and/or an RNase domain. In some embodiments, the kinase domain is a trans-autophosphorylation kinase domain. In some embodiments, the IRE1 family protein is IRE1a. An example arrangement of domains within an IRE1a protein is depicted in FIG. 1. An example alignment of IRE1 family protein orthologues is depicted in FIG. 2.

In some embodiments, a compound disclosed herein selectively binds to a trans-autophosphorylation kinase domain region of IRE1a. In some embodiments, a compound disclosed herein selectively binds to a trans-autophosphorylation kinase domain region of IRE1a, for example within amino acid residues 568-833 of SEQ ID NO: 1, or equivalent amino acid residues thereof.

In some embodiments, a compound disclosed herein selectively binds to an ATP-binding pocket within a trans-autophosphorylation kinase domain region of IRE1a. In some embodiments, a compound disclosed herein selectively binds to an ATP-binding pocket within a trans-autophosphorylation kinase domain region of IRE1a, for example, one or more of amino acid resides 577-711, 577-586, 597, 599, 626, 642-643, 645, 648, 688, 692-693, 695, or 711 of SEQ ID NO: 1, or equivalent amino acid residues thereof.

In some embodiments, a compound disclosed herein selectively binds to an activation loop within a trans-autophosphorylation kinase domain region of IRE1a. In some embodiments, a compound disclosed herein selectively binds to an activation loop within a trans-autophosphorylation kinase domain region of IRE1a, for example, one or more of amino acid residues 710-736, 710-725, or 729-736 of SEQ ID NO: 1, or equivalent amino acid residues thereof.

In some embodiments, a compound disclosed herein selectively binds to an RNase domain region of IRE1a. In some embodiments, a compound disclosed herein selectively binds to an RNase domain region of IRE1a, for example within amino acid residues 835-963 of SEQ ID NO: 1, or equivalent amino acid residues thereof.

In some embodiments, a compound disclosed herein selectively binds to a kinase domain dimer interface amino acid residue. In some embodiments, a compound disclosed herein selectively binds to a kinase domain dimer interface amino acid residue, such as one or more of amino acid residues 569-701, 569, 591, 592, 594, 617, 620, 627, 628, 631, 674, 678, or 701 of SEQ ID NO: 1.

In some embodiments, a compound disclosed herein selectively binds to a first IRE1a and blocks dimerization between kinase domain dimer interface amino acid residues of the first IRE1a and a second IRE1a. In some embodiments, a compound disclosed herein selectively binds to a first IRE1a, and inhibit dimerization at one or more of amino acid residues 569-701, 569, 591, 592, 594, 617, 620, 627, 628, 631, 674, 678, or 701 of SEQ ID NO: 1.

In some embodiments, a compound disclosed herein selectively binds to a kinase-extension nuclease (KEN) domain dimer interface amino acid residue of an IRE1a. In some embodiments, a compound disclosed herein selectively binds to a KEN domain dimer interface amino acid residue, such as one or more of amino acid residues 840-925, 840, 844, 851, 908, 912, or 925 of SEQ ID NO: 1.

In some embodiments, a compound disclosed herein selectively binds to amino acid residues of a nuclease active site. In some embodiments, a compound disclosed herein selectively binds to amino acid residues of a nuclease active site, such as one or more of amino acid residues 847-910, 847, 850, 886, 888, 889, 890, 892, 902, 905, 906, or 910 of SEQ ID NO: 1.

In some embodiments, a compound disclosed herein selectively binds to an RNase domain and a trans-autophosphorylation kinase domain region of IRE1a. In some embodiments, a compound disclosed herein selectively binds to an RNase domain and an ATP-binding pocket within a trans-autophosphorylation kinase domain region of IRE1a. In some embodiments, a compound disclosed herein selectively binds to an RNase domain and an activation loop within a trans autophosphorylation kinase domain region of IRE1a.

In some embodiments, a compound disclosed herein selectively binds to IRE1a at two sites located in an RNase domain, trans-autophosphorylation kinase domain region, ATP-binding pocket, activation loop, or any combination thereof. In some embodiments, a compound disclosed herein selectively binds to IRE1a at two or more sites. In some embodiments, a compound disclosed herein selectively binds to IRE1a at two or more sites located in an RNase domain, trans-autophosphorylation kinase domain region, ATP-binding pocket, activation loop, or any combination thereof. In some embodiments, a compound disclosed herein selectively binds to IRE1a at three sites located in an RNase domain, trans-autophosphorylation kinase domain region, ATP-binding pocket, activation loop, or any combination thereof.

In some embodiments, a compound disclosed herein selectively binds to IRE1a at a first site located in an RNase domain, trans-autophosphorylation kinase domain region, ATP-binding pocket, or activation loop. In some embodiments, a first site comprises one or more of any amino acid residue within amino acid residues 465-977 of SEQ ID NO: 1. In some embodiments, a compound disclosed herein selectively binds to IRE1a at a second site located in an RNase domain, trans-autophosphorylation kinase domain region, ATP-binding pocket, or activation loop. In some examples, the first site is located within the same domain or region as the second site. In some examples, the first site is located within a different domain or region as the second site.

In some embodiments, a compound disclosed herein selectively binds to first IRE1a, thereby blocking dimerization of the first IRE1a to a second IRE1a. In some embodiments, a compound disclosed herein selectively binds to first IRE1a, thereby blocking auto-transphosphorylation of the first IRE1a or a second IRE1a to which the first IRE1a is dimerized. In some embodiments, a compound disclosed herein selectively binds to a first IRE1a, thereby blocking activation of the first IRE1a or a second IRE1a to which the first IRE1a is dimerized. In some embodiments, a compound disclosed herein selectively binds to a first IRE1a, thereby blocking kinase activity of the first IRE1a or a second IRE1a to which the first IRE1a is dimerized. In some embodiments, a compound disclosed herein selectively binds to a first IRE1a, thereby blocking RNase activity of the first IRE1a or a second IRE1a to which the first IRE1a is dimerized.

In some embodiments, a compound disclosed herein selectively binds to IRE1a when in a homo-dimerized conformation. In some embodiments, a compound disclosed herein selectively binds to IRE1a when in an oligomerized conformation. In some embodiments, a compound disclosed herein selectively binds to IRE1a when in a non-oligomerized or non-dimerized conformation. In some embodiments, a compound disclosed herein selectively binds to IRE1a when in an ATP-bound state. In some embodiments, a compound disclosed herein selectively binds to an IRE1 family protein when in a non-ATP-bound state. In some embodiments, the compound is a pharmaceutically acceptable salt, or solvate thereof.

IRE1 Signaling Pathway

In some embodiments, a compound disclosed herein selectively binds to an IRE1 family protein and alters a downstream signaling pathway. In some embodiments, a compound disclosed herein selectively binds to an IRE1 family protein and alters signaling of immunoglobulin heavy-chain binding protein (BIP), protein kinase R (PKR)-like endoplasmic reticulum kinase (PERK), glucose regulate protein 78 (Grp78), eukaryotic translation initiation factor 2α (eIF2α), X-box binding protein 1 (XBP1), activating transcription factor 6α (ATF6α), C/EBP homologous protein (CHOP), growth arrest and DNA damage-inducible protein 34 (GADD34), tumor necrosis factor receptor-associated factor 2 (TRAF2), JUN N-terminal kinase (JNK), regulated IRE1-dependent decay (RIDD), transcriptionally active XBP1 (XBP1s), or unspliced XBP1 (XBP1u). In some embodiments, a compound disclosed herein selectively binds to an IRE1 family protein and alters a downstream cellular process. In some embodiments, an IRE1 family protein is IRE1, IRE1a, or ERN1.

In some embodiments, a compound disclosed herein selectively binds to an IRE1 family protein and decreases or blocks a downstream signaling pathway. In some embodiments, a compound disclosed herein selectively binds to an IRE1 family protein and decreases or blocks activity or signaling of TXNIP, Caspase 1, Interleukin 1-beta, JNK, Bim, cytochrome C, Caspase 3, Caspase 8, mRNA degradation, miRNA degradation, apoptosis-inducing proteins, or inflammation-inducing proteins. In some embodiments, a compound disclosed herein selectively binds to an IRE1 family protein and decreases XBP1 mRNA levels. In some embodiments, a compound disclosed herein selectively binds to an IRE1 family protein and decreases transcriptionally active XBP1 (XBP i1s) mRNA levels. In some embodiments, a compound disclosed herein selectively binds to an IRE1 family protein and decreases spliced XBP1 mRNA levels. In some embodiments, an IRE1 family protein is IRE1, IRE1a, or ERN1.

In some embodiments, a compound disclosed herein selectively binds to an IRE1 family protein and increases, activates, or removes a block of a downstream signaling pathway. In some embodiments, a compound disclosed herein selectively binds to an IRE1 family protein and increases, activates, or removes a block of activity or signaling of Bcl2, Bcl-XL, Mcl-1, Bax, Bak, other anti-apoptotic proteins, or an mRNA translocon proteins. In some embodiments, an IRE1 family protein is IRE1, IRE1a, or ERN1.

In some embodiments, a compound disclosed herein selectively binds to an IRE1 family protein and disrupts binding with an effector protein. In some cases, the effector protein binds to the IRE1 family protein when in a dimerized or oligomerized state. In some cases, the effector protein binds to the IRE1 family protein when in a non-dimerized or non-oligomerized state. In some cases, the effector protein is immunoglobulin heavy-chain binding protein (BIP), protein kinase R (PKR)-like endoplasmic reticulum kinase (PERK), glucose regulate protein 78 (Grp78), tumor necrosis factor receptor-associated factor 2 (TRAF2), JUN N-terminal kinase (JNK), transcriptionally active XBP1 (XBP1s), unspliced XBP1 (XBP1u), regulated IRE1-dependent decay (RIDD), Heat shock protein 90 kDa alpha (HSP 90-alpha), or misfolded protein. In some embodiments, an IRE1 family protein is IRE1, IRE1a, or ERN1.

In some embodiments, a compound disclosed herein selectively binds to an IRE1 family protein and alters activity of a cellular process or cellular function, such as regulated IRE1-dependent decay (RIDD), RNA decay, translation, autophagy, cell survival, ER protein folding, ERAD, reactive oxygen species generation, transport, ER-associated protein degradation (ERAD), protein synthesis, or apoptosis. In some embodiments, where an altered or lack of a cellular process or cellular function is associate with a disease state, selective binding of a compound disclosed herein results in inhibiting or alleviating the disease state, or inhibiting a deleterious activity associated with the disease state. In some embodiments, an IRE1 family protein is IRE1, IRE1a, or ERN1.

Diseases Associated with Altered IRE1 Pathway Signaling

In some cases, a compound disclosed herein is used to treat or ameliorate a disease associated with altered IRE1a pathway signaling when administered to a subject in need thereof. In some cases, a compound disclosed herein is used to treat or ameliorate the effects of a disease associated with altered IRE1a pathway signaling when administered to a subject in need thereof. Exemplary disease associated with altered IRE1a signaling include cancer. In some cases, a compound disclosed herein is used to treat or ameliorate a cancer when administered to a subject in need thereof. Exemplary cancers include tumors, solid and hematologic cancers. In some cases, a compound disclosed herein is used to treat or ameliorate a cell proliferative disorder when administered to a subject in need thereof. In some cases, the cell proliferative disorder is a cancer. In some cases, the solid cancer is ovarian cancer, lung cancer, breast cancer, bladder cancer, or triple negative breast cancer (TNBC). In some cases, the hematological cancer is a leukemia, lymphoma, and multiple myeloma.

An IRE1a pathway can be involved in a variety of pathological conditions, including neurodegenerative diseases, inflammation, metabolic disorders, liver dysfunction, brain ischemia, heart ischemia, autoimmune diseases, and cancer. In some cases, modulation of this pathway provides therapeutic methods useful for treatment of such diseases.

In some instances, a compound disclosed herein is used to reinforce anti-tumor mechanisms. In some cases, an anti-tumor mechanism comprises direct inhibition of tumor growth. In some cases, an anti-tumor mechanism comprises induction of anti-tumor immunity. In some cases, anti-tumor mechanisms comprise direct inhibition of tumor growth and simultaneous induction of anti-tumor immunity. In some cases, a compound disclosed herein can prevent lipid accumulation in myeloid cells exposed to ovarian cancer-derived ascites supernatants. In some cases, a compound disclosed herein can block myeloid cell immunosuppression mediated by tumor-associated factors. In some cases, a compound disclosed herein can be employed as therapeutic compound that enhances dendritic cell and T cell anti-tumor activity in mammals. For example, the compounds disclosed herein can be used to treat murine and human ovarian cancers.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (e.g., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%), 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg to 5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 mg/kg to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day, e.g., two, three, four or more times daily.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In one embodiment, the therapeutic effectiveness of one of the compounds described herein is enhanced by administration of an adjuvant {i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Conjugates

In some embodiments, a compound described herein is conjugated, optionally via a linker, to a molecule that allows for directing the compound to a target. Exemplary targets include, without limitation, a tumor, a bacterium, a fungus, a virus, or a parasite. In some embodiments, a compound described herein is conjugated, optionally via a linker, to a molecule that allows for directing the compound to a cell surface target. Exemplary cell surface targets include, without limitation, proteins, lipids, and sugars. In some embodiments, the molecule conjugated to a compound described herein is a peptide, an antibody or an antibody fragment. In some embodiments, mmunoglobulins of IgA, IgD, IgE, IgG or IgM class are used. In some embodiments, conjugated inhibitor/cell targeting compositions provide for targeting the compound to specific cells, internalization of the conjugated composition, separation of the compound from the vehicle in the cell, and then targeting of the compound to the intracellular target. In some embodiments, antibody fragments for use in the conjugate include, without limitation, half antibody molecules (a single heavy/light chain pair), Fab, Fab', (Fab')$_2$ (monospecific, bispecific or trispecific), scFv, bispecific diabody, trispecific diabody, scFv-Fc, or minibody fragments. In some embodiments, a compound described herein is conjugated to a molecule that allows for recruitment to cellular machinery for degradation. For example, in some embodiments, a proteolysis-targeting chimeric molecule (PROTAC) system is used. In such a composition, a ubiquitin E3 ligase binding protein is joined by a linker to a compound described herein. In some embodiments, the compound, or a pharmaceutically acceptable salt or solvate thereof, is a compound described herein in Table 1.

Representative Illustrative Embodiments

In a first illustrative embodiment, the present invention comprises a compound of Formula (I), or a pharmaceutically acceptable salt, or solvate thereof:

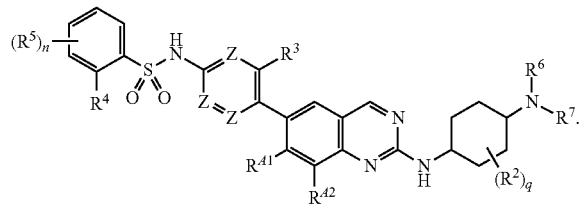

Formula (I)

wherein, each Z is independently N or $CR^1$, provided that at least one Z is N;

each $R^1$ is independently H, halogen, —CN, —$OR^8$, —$SR^8$, —S(=O)$R^9$, —S(=O)$_2R^9$, —S(=O)$_2N(R^8)_2$, —$NR^8S(=O)_2R^9$, —C(=O)$R^9$, —OC(=O)$R^9$, —C(=O)$OR^8$, —OC(=O)$OR^9$, —N$(R^8)_2$, —OC(=O)N$(R^8)_2$, —$NR^8C(=O)R^9$, —$NR^8C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^3$ is —CN, —$OR^8$, —$SR^8$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^4$ is halogen, —CN, —$OR^8$, optionally substituted $C_1$-$C_4$alkyl, optionally substituted $C_1$-$C_4$fluoroalkyl, or optionally substituted $C_1$-$C_4$heteroalkyl;

each $R^5$ is independently H, halogen, —CN, —$OR^8$, —$SR^8$, —N$(R^8)_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^2$ is independently H, halogen, —CN, —$OR^8$, —$SR^8$, —S(=O)$R^9$, —S(=O)$_2R^9$, —S(=O)$_2N(R^8)_2$, —$NR^8S(=O)_2R^9$, —C(=O)$R^9$, —OC(=O)$R^9$, —C(=O)$OR^8$, —OC(=O)$OR^9$, —N$(R^8)_2$, —OC(=O)N$(R^8)_2$, —$NR^8C(=O)R^9$, —$NR^8C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^6$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cycloalkylalkyl, optionally substituted $C_2$-$C_{10}$heterocycloalkyl, optionally substituted aryl, or optionally substituted heteroaryl;

$R^7$ is optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cycloalkylalkyl, optionally substituted $C_2$-$C_{10}$heterocycloalkyl, optionally substituted aryl, or optionally substituted heteroaryl;

or $R^6$ and $R^7$ are taken together with the N atom to which they are attached to form an optionally substituted heterocycle;

each $R^8$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

$R^{A1}$ and $R^{A2}$ are each independently H, halogen, —$OR^9$, optionally substituted $C_1$-$C_4$alkyl, optionally substituted $C_1$-$C_4$heteroalkyl, optionally substituted $C_1$-$C_4$fluoroalkyl, or optionally substituted aryl; provided that both $R^{A1}$ and $R^{A2}$ are not H;

n is 0, 1, 2, 3, or 4; and q is 0, 1, 2, 3, or 4.

In second embodiment, provided are any of the compounds of embodiment 1, or a pharmaceutically acceptable salt, or solvate thereof, wherein:

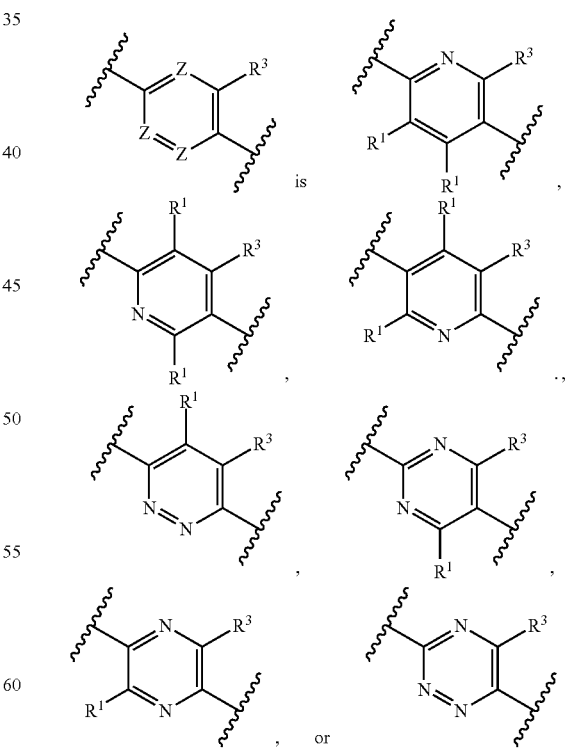

In a third embodiment, provided are any of the compounds of embodiments 1 or 2, or a pharmaceutically acceptable salt, or solvate thereof, wherein:

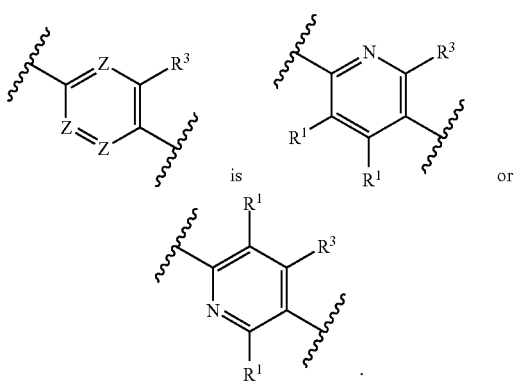

In a fourth embodiment, provided are any of the compounds of embodiment 1 or 2, or a pharmaceutically acceptable salt, or solvate thereof, wherein:

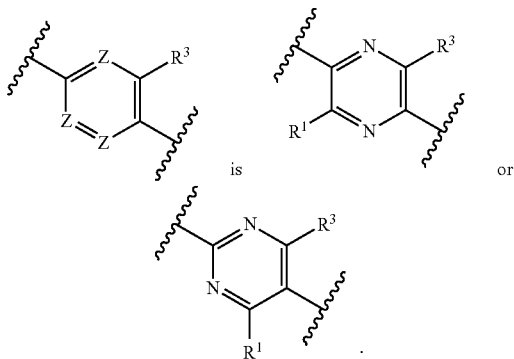

In a fifth embodiment, provided are any of the compounds of embodiments 1-3, or a pharmaceutically acceptable salt, or solvate thereof, wherein:

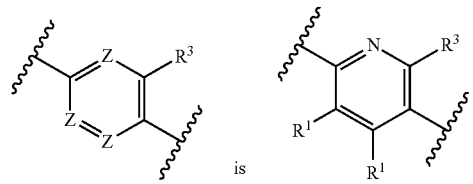

In a sixth embodiment, provided are any of the compounds of embodiments 1-5, or a pharmaceutically acceptable salt, or solvate thereof, wherein each $R^1$ is independently H, halogen, —CN, —$OR^8$, optionally substituted $C_1$-$C_4$alkyl, optionally substituted $C_1$-$C_4$fluoroalkyl, or optionally substituted $C_1$-$C_4$heteroalkyl.

In a seventh embodiment, provided are any of the compounds of embodiment 1-6, or a pharmaceutically acceptable salt, or solvate thereof, wherein each $R^1$ is independently H, halogen, —$OR^8$, optionally substituted $C_1$-$C_4$alkyl, or optionally substituted $C_1$-$C_4$heteroalkyl.

In an eighth embodiment, provided are any of the compounds of embodiments 1-7, or a pharmaceutically acceptable salt, or solvate thereof, wherein $R^3$ is —CN, —$OR^8$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, or optionally substituted —O—$C_3$-$C_6$cycloalkyl.

In a ninth embodiment, provided are any of the compounds of embodiments 1-8, or a pharmaceutically acceptable salt, or solvate thereof, wherein $R^3$ is —$OR^8$, optionally substituted $C_1$-$C_4$alkyl, optionally substituted $C_1$-$C_4$fluoroalkyl, or optionally substituted $C_1$-$C_4$heteroalkyl.

In a tenth embodiment, provided are any of the compounds of embodiments 1-9, or a pharmaceutically acceptable salt, or solvate thereof, wherein $R^3$ is optionally substituted $C_1$-$C_4$alkyl.

In an eleventh embodiment, provided are any of the compounds of embodiment 10, or a pharmaceutically acceptable salt, or solvate thereof, wherein $R^3$ is methyl, ethyl, propyl, or butyl.

In a twelfth embodiment, provided are any of the compounds of embodiments 1-9, or a pharmaceutically acceptable salt, or solvate thereof, wherein $R^3$ is —$OR^8$.

In a thirteenth embodiment, provided are any of the compounds of embodiment 12, or a pharmaceutically acceptable salt, or solvate thereof, wherein $R^8$ is optionally substituted $C_1$-$C_4$alkyl, optionally substituted $C_1$-$C_4$heteroalkyl, optionally substituted $C_1$-$C_4$fluoroalkyl, or optionally substituted $C_3$-$C_6$cycloalkyl.

In a fourteenth embodiment, provided are any of the compounds of embodiments 1-13, or a pharmaceutically acceptable salt, or solvate thereof, wherein $R^4$ is halogen, —CN, —$OR^8$, optionally substituted $C_1$-$C_4$alkyl, or optionally substituted $C_1$-$C_4$fluoroalkyl.

In a fifteenth embodiment, provided are any of the compounds of embodiments 1-14, or a pharmaceutically acceptable salt, or solvate thereof, wherein $R^4$ is halogen, —CN, —$OR^8$, optionally substituted $C_1$-$C_4$alkyl, or optionally substituted $C_1$-$C_4$fluoroalkyl.

In a sixteenth embodiment, provided are any of the compounds of embodiments 1-14, or a pharmaceutically acceptable salt, or solvate thereof, wherein $R^4$ is halogen, optionally substituted $C_1$-$C_4$alkyl, or optionally substituted $C_1$-$C_4$fluoroalkyl.

In a seventeenth embodiment, provided are any of the compounds of embodiment 15, or a pharmaceutically acceptable salt, or solvate thereof, wherein $R^4$ is halogen.

In an eighteenth embodiment, provided are any of the compounds of embodiment 17, or a pharmaceutically acceptable salt, or solvate thereof, wherein $R^4$ is —Cl, —Br, —F, or —I or when $R^4$ is —$C_1$.

In a nineteenth embodiment, provided are any of the compounds of embodiment 15, or a pharmaceutically acceptable salt, or solvate thereof, wherein $R^4$ is —$OR^8$.

In a twentieth embodiment, provided are any of the compounds of embodiment 19, or a pharmaceutically acceptable salt, or solvate thereof, wherein $R^8$ is H, optionally substituted $C_1$-$C_4$alkyl, or optionally substituted $C_1$-$C_4$fluoroalkyl.

In a twenty-first embodiment, provided are any of the compounds of embodiment 15, or a pharmaceutically acceptable salt, or solvate thereof, wherein $R^4$ is optionally substituted $C_1$-$C_4$alkyl.

In a twenty-second embodiment, provided are any of the compounds of embodiment 21, or a pharmaceutically acceptable salt, or solvate thereof, wherein $R^4$ is methyl, ethyl, propyl, or butyl.

In a twenty-third embodiment, provided are any of the compounds of embodiment 15, or a pharmaceutically acceptable salt, or solvate thereof, wherein $R^4$ is optionally substituted $C_1$-$C_4$fluoroalkyl.

In a twenty-fourth embodiment, provided are any of the compounds of embodiment 23, or a pharmaceutically acceptable salt, or solvate thereof, wherein $R^4$ is —$CF_3$, —$CF_2CH_3$, or —$CH_2CF_3$.

In a twenty-fifth embodiment, provided are any of the compounds of embodiments 1-24, or a pharmaceutically acceptable salt, or solvate thereof, wherein $R^5$ is H, halogen, —CN, —$OR^8$, —$SR^8$, —$N(R^8)_2$, optionally substituted $C_1$-$C_4$alkyl, or optionally substituted $C_1$-$C_4$fluoroalkyl.

In a twenty-sixth embodiment, provided are any of the compounds of embodiment 25, or a pharmaceutically acceptable salt, or solvate thereof, wherein $R^5$ is H.

In a twenty-seventh embodiment, provided are any of the compounds of embodiment 25, or a pharmaceutically acceptable salt, or solvate thereof, wherein $R^5$ is halogen.

In a twenty-eighth embodiment, provided are any of the compounds of embodiment 27, or a pharmaceutically acceptable salt, or solvate thereof, wherein $R^5$ is —Cl, —Br, —F, or —I.

In a twenty-ninth embodiment, provided are any of the compounds of embodiment 25, or a pharmaceutically acceptable salt, or solvate thereof, wherein $R^5$ is —$OR^8$.

In a thirtieth embodiment, provided are any of the compounds of embodiment 29, or a pharmaceutically acceptable salt, or solvate thereof, wherein $R^8$ is H, optionally substituted $C_1$-$C_4$alkyl, or optionally substituted $C_1$-$C_4$fluoroalkyl.

In a thirty-first embodiment, provided are any of the compounds of embodiment 25, or a pharmaceutically acceptable salt, or solvate thereof, wherein $R^5$ is optionally substituted $C_1$-$C_4$alkyl.

In a thirty-second embodiment, provided are any of the compounds of embodiment 31, or a pharmaceutically acceptable salt, or solvate thereof, wherein $R^5$ is methyl, ethyl, propyl, or butyl.

In a thirty-third embodiment, provided are any of the compounds of embodiment 25, or a pharmaceutically acceptable salt, or solvate thereof, wherein $R^5$ is optionally substituted $C_1$-$C_4$fluoroalkyl.

In a thirty-fourth embodiment, provided are any of the compounds of embodiment 33, or a pharmaceutically acceptable salt, or solvate thereof, wherein $R^5$ is —$CF_3$, —$CF_2CH_3$, or —$CH_2CF_3$.

In a thirty-fifth embodiment, embodiment, provided are any of the compounds of embodiment 1, wherein the compound has the structure of formula (Ia), or a pharmaceutically acceptable salt, or solvate thereof

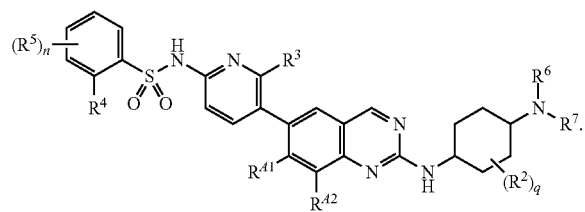

(Ia)

In a thirty-sixth embodiment, provided are any of the compounds of embodiment 1, wherein the compound has the structure of formula (Ib), or a pharmaceutically acceptable salt, or solvate thereof,

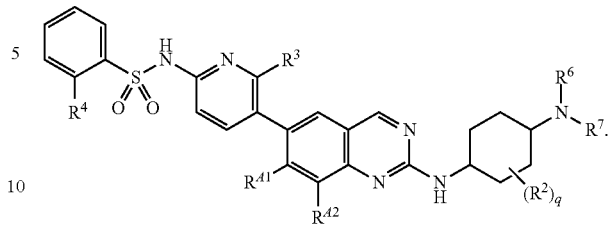

(Ib)

In a thirty-seventh embodiment, provided are any of the compounds of embodiments 1-36, or a pharmaceutically acceptable salt, or solvate thereof, wherein each $R^2$ is independently H, halogen, —$OR^8$, optionally substituted $C_1$-$C_4$alkyl, optionally substituted $C_1$-$C_4$heteroalkyl, or optionally substituted $C_1$-$C_4$fluoroalkyl or alternatively wherein each $R^2$ is hydrogen.

In a thirty-eighth embodiment, provided are any of the compounds of embodiments 1-37, or a pharmaceutically acceptable salt, or solvate thereof, wherein q is 0, 1, or 2 or alternatively wherein q is 0.

In a thirty-ninth embodiment, provided are any of the compounds of embodiments 1-38, or a pharmaceutically acceptable salt, or solvate thereof, wherein $R^6$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, or optionally substituted $C_3$-$C_6$cycloalkylalkyl.

In a fortieth embodiment, provided are any of the compounds of embodiment 39, or a pharmaceutically acceptable salt, or solvate thereof, wherein $R^6$ is optionally substituted $C_1$-$C_4$alkyl.

In a forty-first embodiment, provided are any of the compounds of embodiment 40, or a pharmaceutically acceptable salt, or solvate thereof, wherein $R^6$ is methyl.

In a forty-second embodiment, provided are any of the compounds of embodiment 39, or a pharmaceutically acceptable salt, or solvate thereof, wherein $R^6$ is optionally substituted $C_1$-$C_4$heteroalkyl.

In a forty-third embodiment, provided are any of the compounds of embodiment 39, or a pharmaceutically acceptable salt, or solvate thereof, wherein $R^6$ is optionally substituted $C_1$-$C_4$fluoroalkyl.

In a forty-fourth embodiment, provided are any of the compounds of embodiment 39, or a pharmaceutically acceptable salt, or solvate thereof, wherein $R^6$ is optionally substituted $C_3$-$C_6$cycloalkyl.

In a forty-fifth embodiment, provided are any of the compounds of embodiment 39, or a pharmaceutically acceptable salt, or solvate thereof, wherein $R^6$ is optionally substituted $C_3$-$C_6$cycloalkylalkyl.

In a forty-sixth embodiment, provided are any of the compounds of embodiment 39, or a pharmaceutically acceptable salt, or solvate thereof, wherein $R^6$ is H.

In a forty-seventh embodiment, provided are any of the compounds of embodiments 1-46, or a pharmaceutically acceptable salt, or solvate thereof, wherein $R^7$ is optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, or optionally substituted $C_3$-$C_6$cycloalkylalkyl.

In a forty-eighth embodiment, provided are any of the compounds of embodiment 47, or a pharmaceutically acceptable salt, or solvate thereof, wherein $R^7$ is optionally substituted $C_1$-$C_4$alkyl.

In a forty-ninth embodiment, provided are any of the compounds of embodiment 47, or a pharmaceutically acceptable salt, or solvate thereof, wherein $R^7$ is optionally substituted $C_1$-$C_4$heteroalkyl.

In a fiftieth embodiment, provided are any of the compounds of embodiment 47, or a pharmaceutically acceptable salt, or solvate thereof, wherein $R^7$ is optionally substituted $C_3$-$C_6$cyclooalkyl.

In a fifty-first embodiment, provided are any of the compounds of embodiment 47, or a pharmaceutically acceptable salt, or solvate thereof, wherein $R^7$ is optionally substituted $C_1$-$C_4$alkyl.

In a fifty-second embodiment, provided are any of the compounds of embodiment 47, or a pharmaceutically acceptable salt, or solvate thereof, wherein $R^7$ is optionally substituted $C_3$-$C_6$cycloalkylalkyl.

In a fifty-third embodiment, provided are any of the compounds of embodiment 47, or a pharmaceutically acceptable salt, or solvate thereof, wherein $R^7$ is selected from the group of methyl, ethyl, —$CH_2CF_3$, —$CH_2$-cyclopropyl, or —$CH_2CH_2OCH_3$ or alternatively $R^7$ is $CH_2$-cyclobutyl.

In a fifty-fourth embodiment, provided are any of the compounds of embodiments 1-53, or a pharmaceutically acceptable salt, or solvate thereof, wherein $R^{41}$ is H, optionally substituted $C_1$-$C_4$alkyl, optionally substituted $C_1$-$C_4$heteroalkyl, or optionally substituted $C_1$-$C_4$fluoroalkyl.

In a fifty-fifth embodiment, provided are any of the compounds of embodiment 54, or a pharmaceutically acceptable salt, or solvate thereof, wherein $R^{41}$ is H.

In a fifty-sixth embodiment, provided are any of the compounds of embodiment 54, or a pharmaceutically acceptable salt, or solvate thereof, wherein $R^{41}$ is optionally substituted $C_1$-$C_4$alkyl.

In a fifty-seventh embodiment, provided are any of the compounds of embodiments 1-56, or a pharmaceutically acceptable salt, or solvate thereof, wherein $R^{42}$ is H, optionally substituted $C_1$-$C_4$alkyl, optionally substituted $C_1$-$C_4$heteroalkyl, or optionally substituted $C_1$-$C_4$fluoroalkyl.

In a fifty-eighth embodiment, provided are any of the compounds of embodiment 57, or a pharmaceutically acceptable salt, or solvate thereof, wherein $R^{42}$ is optionally substituted $C_1$-$C_4$alkyl.

In a fifty-ninth embodiment, provided are any of the compounds of embodiment 58, or a pharmaceutically acceptable salt, or solvate thereof, wherein $R^{42}$ is methyl, ethyl, propyl, or butyl.

In a sixtieth embodiment, provided are any of the compounds of embodiment 59, or a pharmaceutically acceptable salt, or solvate thereof, wherein $R^{42}$ is ethyl.

In a sixty-first embodiment, provided are any of the compounds of embodiment 57, or a pharmaceutically acceptable salt, or solvate thereof, wherein $R^{42}$ is optionally substituted $C_1$-$C_4$heteroalkyl.

In a sixty-second embodiment, provided are any of the compounds of embodiment 57, or a pharmaceutically acceptable salt, or solvate thereof, wherein $R^{42}$ is optionally substituted $C_1$-$C_4$fluoroalkyl.

In a sixty-third embodiment, provided are any of the compounds of embodiment 57, or a pharmaceutically acceptable salt, or solvate thereof, wherein $R^{42}$ is H.

In a sixty-fourth embodiment, provided are any of the compounds of embodiments 1-63 wherein the compound has the structure of formula (Ic), (Id), or (Ie), or a pharmaceutically acceptable salt, or solvate thereof:

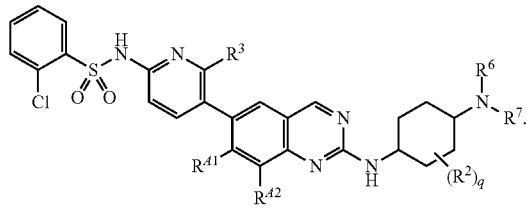

(Ic)

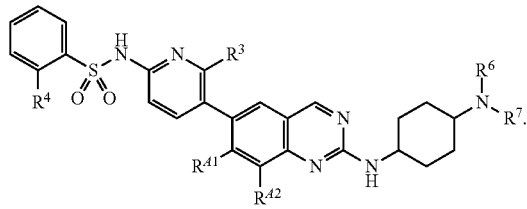

(Id)

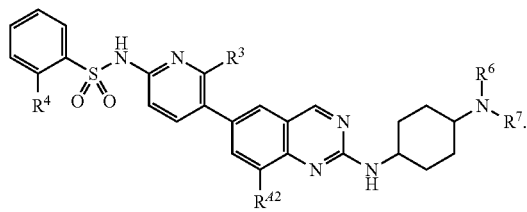

(Ie)

In a sixty-fifth embodiment, provided are the compounds of any one of embodiments 1 to 64 or a pharmaceutically acceptable salt, or solvate thereof wherein each $R^8$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, or optionally substituted $C_2$-$C_{10}$heterocycloalkyl and each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, or optionally substituted $C_2$-$C_{10}$heterocycloalkyl.

In a sixty-sixth embodiment, provided are the compounds of any one of embodiments 1 to 65 or a pharmaceutically acceptable salt, or solvate thereof wherein optional substituents are independently selected from D, halogen, —CN, —$NH_2$, —$NH(CH_3)$, —$N(CH_3)_2$, —OH, —$CO_2H$, —$CO_2(C_1$-$C_4$alkyl), —$CH_2NH_2$, —$C(=O)NH_2$, —$C(=O)NH(C_1$-$C_4$alkyl), —$C(=O)N(C_1$-$C_4$alkyl)_2$, —$S(=O)_2NH_2$, —$S(=O)_2NH(C_1$-$C_4$alkyl), —$S(=O)_2N(C_1$-$C_4$alkyl)_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —$SC_1$-$C_4$alkyl, —$S(=O)C_1$-$C_4$alkyl, and —$S(=O)_2C_1$-$C_4$alkyl (more preferably from D, halogen, —CN, —$NH_2$, —OH, —$NH(CH_3)$, —$N(CH_3)_2$, —$CH_3$, —$CH_2CH_3$, —$CH_2NH_2$, —$CF_3$, —$OCH_3$, and —$OCF_3$).

In a sixty-seventh embodiment, provided are the compounds of any one of embodiments 1 to 65, or a pharmaceutically acceptable salt or solvate thereof, wherein there are no optional substituents.

In a sixty-eighth embodiment, provided is a compound of Formula (I*), or a pharmaceutically acceptable salt, or solvate thereof:

Formula (I*)

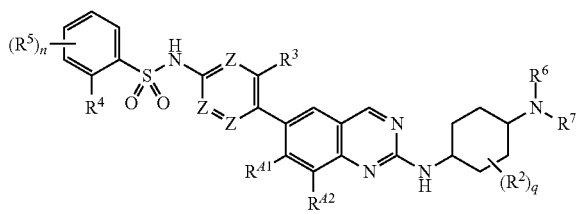

wherein, each Z is independently N or CR$^1$, provided that at least one Z is N;

each R$^1$ is independently hydrogen, fluorine, chlorine or cyano;

R$^3$ is —CN, optionally substituted C$_1$-C$_3$alkyl, optionally substituted C$_3$-C$_4$cycloalkyl, optionally substituted —O—C$_3$-C$_4$cycloalkyl, or optionally substituted —O—C$_1$-C$_3$alkyl;

R$^4$ is chlorine, —CH$_3$, cyano, —OCH$_3$, or CF$_3$;

each R$^5$ is independently hydrogen, chlorine, —CH$_3$, cyano, —OCH$_3$, or CF$_3$;

each R$^2$ is independently hydrogen, fluorine, —CH$_3$, or —OH;

R$^6$ is H, or C$_1$-C$_3$alkyl;

R$^7$ is optionally substituted C$_1$-C$_3$alkyl; C$_1$-C$_3$fluoroalkyl, C$_1$-C$_3$heteroalkyl, or C$_3$-C$_4$cyclooalkyl-C$_1$-C$_3$alkyl;

or R$^6$ and R$^7$ are taken together with the N atom to which they are attached to form an optionally substituted 4 to 6 membered ring, the remainder of the ring atoms being carbon;

R$^{A1}$ and R$^{A2}$ are each independently H, optionally substituted C$_1$-C$_3$alkyl; optionally substituted C$_1$-C$_3$fluoroalkyl, optionally substituted C$_1$-C$_3$heteroalkyl, or optionally substituted C$_3$-C$_4$cyclooalkyl-C$_1$-C$_3$alkyl, provided that both R$^{A1}$ and R$^{A2}$ are not hydrogen; or alternatively R$^{A1}$ and R$^{A2}$ are each independently H; C$_1$-C$_3$fluoroalkyl, C$_1$-C$_3$heteroalkyl, or C$_3$-C$_4$cyclooalkyl-C$_1$-C$_3$alkyl or optionally substituted C$_1$-C$_3$alkyl provided that both R$^{A1}$ and R$^{A2}$ are not hydrogen;

n is 0, 1, 2, 3, or 4; and q is 0, 1, 2, 3, or 4.

In a sixty-ninth embodiment, provided are any of the compounds of embodiment 68, wherein the compound has the structure of formula (Ib*) or (Ic*) or a pharmaceutically acceptable salt, or solvate thereof:

(Ib*)

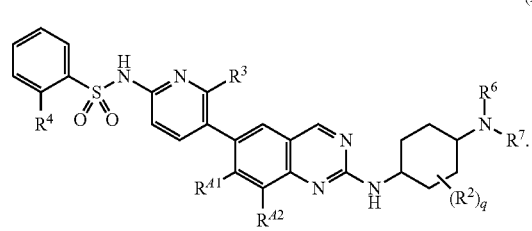

-continued (Ic*)

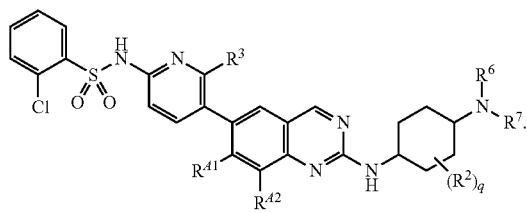

In a seventieth embodiment, provided are any of the compounds of embodiments 68-69, or a pharmaceutically acceptable salt, or solvate thereof, wherein R$^{A1}$ is H or C$_1$-C$_3$alkyl.

In a seventy-first embodiment, provided are any of the compounds of embodiments 68-70, or a pharmaceutically acceptable salt, or solvate thereof, wherein one or more of R$^3$, R$^7$, R$^{A1}$, and R$^{A2}$ are optionally substituted, wherein optional substituents are each independently selected from fluorine, —OH, —OCH$_3$, —OCH$_2$CH$_3$, —OCH$_2$CH$_2$CH$_3$, —NH$_2$, —NH(CH$_3$), or —N(CH$_3$)$_2$.

In a seventy-second embodiment, provided are any of the compounds of embodiments 68-70, or a pharmaceutically acceptable salt, or solvate thereof, wherein one or more of R$^3$, R$^7$, R$^{A1}$, and R$^{A2}$ are optionally substituted, wherein optional substituents are each independently selected from fluorine, —OH, —OCH$_3$, —OCH$_2$CH$_3$, —OCH$_2$CH$_2$CH$_3$, —NH(CH$_3$), or —N(CH$_3$)$_2$.

In a seventy-third embodiment, provided are any of the compounds of embodiments 68-72, or a pharmaceutically acceptable salt, or solvate thereof, wherein one or more of R$^7$, R$^{A1}$, and R$^{A2}$ are C$_1$-C$_3$heteroalkyl, wherein a heteroatom in the C$_1$-C$_3$heteroalkyl is oxygen.

In a seventy-fourth embodiment, provided are any of the compounds of embodiments 68-73 or a pharmaceutically acceptable salt, or solvate thereof wherein R$^6$ is H or methyl and R$^7$ is methyl, ethyl, CH$_2$CF$_3$, CH$_2$-cyclopropyl, or CH$_2$CH$_2$OCH$_3$.

In a seventy-fifth embodiment, provided are any of the compounds of embodiments 68-74 or a pharmaceutically acceptable salt, or solvate thereof wherein R$^6$ is methyl and R$^7$ is methyl, ethyl, CH$_2$CF$_3$, CH$_2$-cyclopropyl or CH$_2$CH$_2$OCH$_3$.

In a seventy-sixth embodiment, provided are the compounds of any of the embodiments 68-75 wherein q is zero.

In a seventy-seventh embodiment, provided are the compounds of any of the embodiments 68-76 wherein each Z is independently N or CR$^1$, provided that at least one Z is N; each R$^1$ is independently hydrogen, fluorine, chlorine or cyano; R$^3$ is C$_1$-C$_3$alkyl or —OC$_1$-C$_3$alkyl; R$^{A1}$ is hydrogen, or C$_1$-C$_3$alkyl; R$^{A2}$ is C$_1$-C$_3$alkyl, C$_1$-C$_3$fluoroalkyl, or C$_1$-C$_3$heteroalkyl; provided that both R$^{A1}$ and R$^{A2}$ are not hydrogen; R$^4$ is chlorine; each R$^5$ is independently hydrogen, chlorine, —CH$_3$, cyano, —OCH$_3$, or CF$_3$; n is 0, 1, 2, 3, or 4; and q is zero.

In a seventy-eighth embodiment, provided are the compounds of embodiment 1 having Formula (Id*), or a pharmaceutically acceptable salt or solvate thereof:

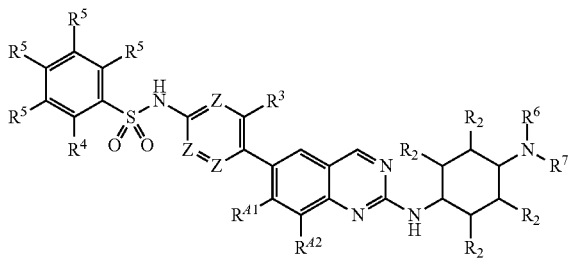

wherein Z, $R^1$, $R^2$, $R^3$, $R^4$, $R^5$, $R^6$, $R^7$, $R^8$, $R^9$, $R^{A1}$, and $R^{A2}$ are as described for compounds of embodiment 1.

In a seventy-ninth embodiment, provided are the compounds of embodiment 78, or a pharmaceutically acceptable salt or solvate thereof:

wherein:
- each $R^5$ is independently hydrogen, chlorine, fluorine, or $C_1$-$C_3$alkyl (preferably hydrogen);
- $R^4$ is chlorine or $C_1$-$C_3$alkyl (preferably chlorine);
- $R^3$ is $C_1$-$C_3$alkyl or —$OC_1$-$C_3$alkyl;
- $R^{41}$ is fluorine, chlorine, hydrogen, or $C_1$-$C_3$alkyl;
- $R^{42}$ is $C_1$-$C_3$alkyl, —$OC_1$-$C_3$alkyl, hydrogen, $C_1$-$C_3$fluoroalkyl, fluorine, chlorine, or $C_1$-$C_3$heteroalkyl; provided that both $R^{41}$ and $R^{42}$ are not hydrogen;
- Each $R^2$ is independently hydrogen or fluorine (preferably hydrogen);
- $R^1$ is hydrogen or fluorine (preferably hydrogen);
- Z is independently N or $CR^1$;
- and wherein one Z is nitrogen, two of Z are nitrogen, or three of Z are nitrogen or wherein:

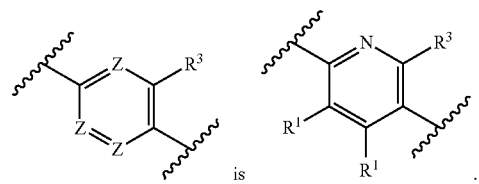

In an eightieth embodiment, provided are the compounds of embodiment 79, or a pharmaceutically acceptable salt or solvate thereof, wherein
- each $R^5$ is independently hydrogen, chlorine, fluorine, or —$CH_3$ (preferably hydrogen);
- $R^4$ is chlorine or —$CH_3$ (preferably chlorine);
- $R^3$ is —$CH_3$, —$CH_2CH_3$, or —$OCH_3$;
- $R^{41}$ is fluorine, chlorine, hydrogen, or —$CH_3$;
- $R^{42}$ is hydrogen, —$CH_3$, —$CH_2CH_3$, —$OCH_3$, $CF_3$, $CF_2CH_3$, $CH_2OCH_3$, or fluorine; provided that both $R^{41}$ and $R^{42}$ are not hydrogen;
- Each $R^2$ is independently hydrogen or fluorine (preferably hydrogen);
- $R^1$ is hydrogen or fluorine (preferably hydrogen);
- and Z is as set forth for compounds of embodiment 79.

In an eighty-first embodiment, provided are the compounds of embodiment 78, 79, or 80 wherein $R^6$ and $R^7$ can be as described in any of the embodiments set forth herein. (For example, $R^7$ can be optionally substituted $C_3$-$C_6$cyclooalkylalkyl or $R^7$ can be selected from the group of methyl, ethyl, —$CH_2CF_3$, —$CH_2$-cyclopropyl, or —$CH_2CH_2OCH_3$ or $R^7$ can be selected from the group of methyl, ethyl, —$CH_2CF_3$, —$CH_2$-cyclopropyl, —$CH_2$-cyclobutyl, or —$CH_2CH_2OCH_3$; and $R^6$ can be as described herein for any of the embodiments (For example, $R^6$ can be hydrogen or $C_{1-4}$ alkyl, more preferably hydrogen or methyl).

Also provided are pharmaceutical compositions comprising any of the compounds described herein including pharmaceutically acceptable salts and solvates thereof and one or more pharmaceutically acceptable excipients as well as methods of using the compounds and compositions to treat or ameliorate the effects of a disease associated with altered IRE1 signaling. Such methods comprise administering to a subject in need thereof a pharmaceutical composition or compound of the present invention. The disease can be, for example, any of the disease described herein.

The compound and compositions provided herein can be for use as medicament. The medicament can be used, for example, to treat disease, including any of the diseases described herein.

EXAMPLES

The following examples are intended to illustrate but not limit the disclosed embodiments.

I. Chemical Synthesis

Example 1A: Synthesis of tert-butyl ((1r,4r)-4-((6-(4,4,5,5-tetramethyl-1,3,2-dioxaborolan-2-yl)quinazolin-2-yl)amino)cyclohexyl)carbamate (1A)

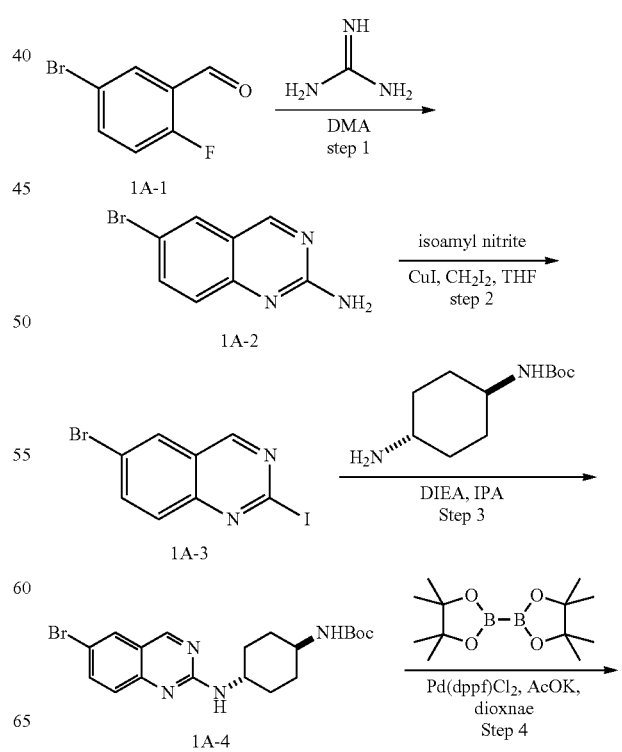

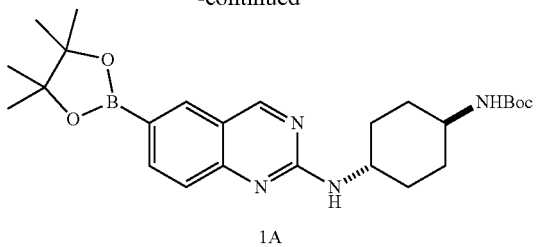

1A

Step 1: 6-bromoquinazolin-2-amine (1A-2)

To a solution of 5-bromo-2-fluoro-benzaldehyde (20.0 g, 98.5 mmol) in DMA (700 mL) was added guanidine-carbonic acid (26.6 g, 147.7 mmol). The mixture was stirred at 160° C. for 0.5 h, cooled to rt and concentrated. The residue was diluted with $H_2O$ (300 mL) and extracted with ethyl acetate (200 mL×3). The combined organic layers were washed with brine (100 mL×3), dried over $Na_2SO_4$, filtered and concentrated under reduced pressure to give a residue. The residue was washed with DCM (300 mL) to get compound 1A-2 (4.0 g, crude).

Step 2: 6-bromo-2-iodoquinazoline (1A-3)

To a solution of compound 1A-2 (2.0 g, 8.9 mmol) in THF (20.0 mL) under $N_2$ were added of isoamylnitrite (3.1 g, 26.8 mmol, 3.6 mL), diiodomethane (11.9 g, 44.7 mmol, 3.6 mL) and CuI (1.7 g, 8.9 mmol). The mixture was stirred at 80° C. for 2 h, cooled to rt, quenched by addition of ice water (100 mL), and extracted with ethyl acetate (100 mL×3). The combined organic layers were washed with brine (100 mL×3), dried over anhydrous $Na_2SO_4$, filtered and concentrated. The residue was purified by column chromatography ($SiO_2$) to afford compound 1A-3 (2.1 g, crude).

Step 3: 1-tert-butyl ((1r, 4r)-4-((6-bromoquinazolin-2-yl)amino)cyclohexyl)carbamate (1A-4)

To a solution of compound 1A-3 (4.0 g, 11.9 mmol) in IPA (120.0 mL) was added DIEA (4.6 g, 35.8 mmol, 6.2 mL) and tert-butyl ((1r,4r)-4-aminocyclohexyl)carbamate (7.6 g, 35.8 mmol). The mixture was stirred at 80° C. for 12 h, cooled to rt and filtered. The collected solid was washed with Dichloromethane/Methanol (10/1, 60 mL). The combined filtrate was concentrated to give a residue which was purified by column chromatography ($SiO_2$) to afford compound 1A-4 (3.6 g, 6.8 mmol, 57.2% yield). $M+H^+=421.1$ (LCMS); $^1H$ NMR (CHLOROFORM-d, 400 MHz) δ 8.87 (s, 1H), 7.78 (d, J=1.8 Hz, 1H), 7.71 (dd, J=2.0, 9.0 Hz, 1H), 7.44 (d, J=9.2 Hz, 1H), 5.19 (br d, J=7.9 Hz, 1H), 4.43 (br s, 1H), 3.93 (br d, J=7.5 Hz, 1H), 3.49 (br s, 1H), 2.27-2.00 (m, 4H), 1.46 (s, 9H), 1.40-1.29 (m, 4H).

Step 4: tert-butyl ((1r,4r)-4-((6-(4,4,5,5-tetramethyl-1,3,2-dioxaborolan-2-yl)quinazolin-2-yl)amino)cyclohexyl)carbamate (1A)

A mixture of compound 1A-4 (2.0 g, 4.7 mmol), 4,4,5,5-tetramethyl-2-(4,4,5,5-tetramethyl-1,3,2-dioxaborolan-2-yl)-1,3,2-dioxaborolane (1.3 g, 5.2 mmol), AcOK (1.4 g, 14.2 mmol) and Pd(dppf)$Cl_2$ (347 mg, 474.6 umol) in dioxane (50 mL) was degassed and purged with $N_2$ three times, and heated at 90° C. for 12 h under $N_2$. The reaction was cooled to rt and concentrated to give a residue. The residue was purified by column chromatography ($SiO_2$) to afford compound 1A (2.7 g, crude). $M+H^+=469.2$ (LCMS).

Example 2A: Synthesis of tert-butyl ((1r,4r)-4-((8-ethyl-6-(4,4,5,5-tetramethyl-1,3,2-dioxaborolan-2-yl)quinazolin-2-yl)amino)cyclohexyl)carbamate (2A)

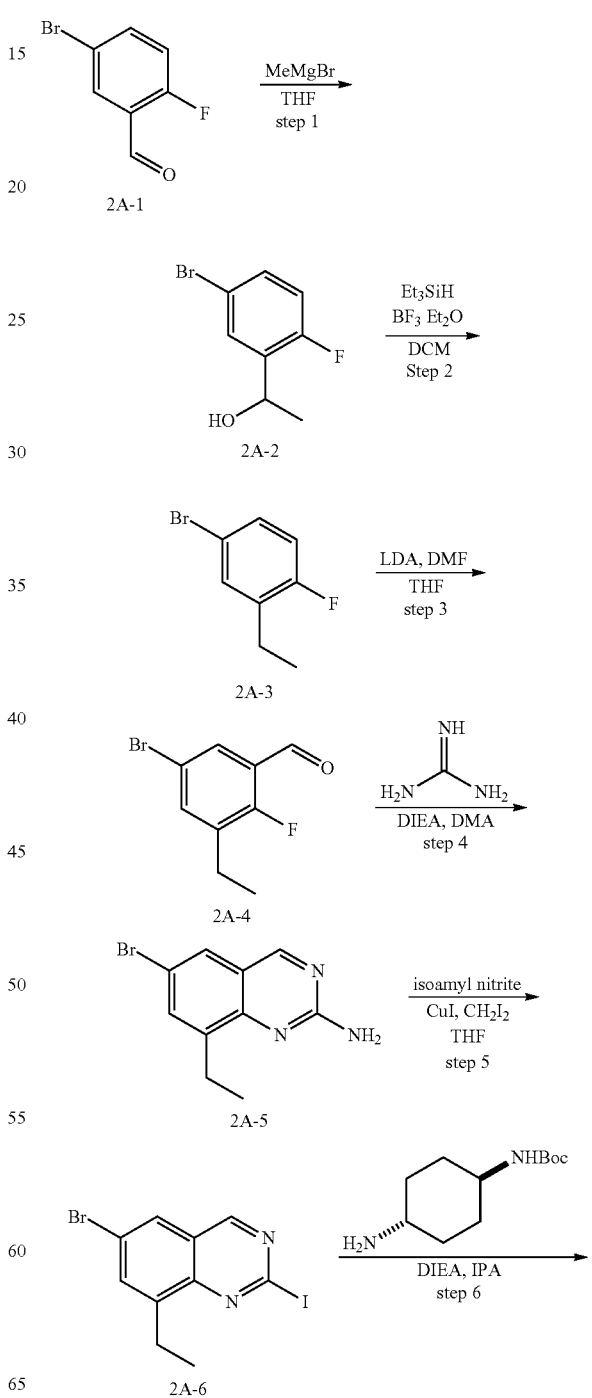

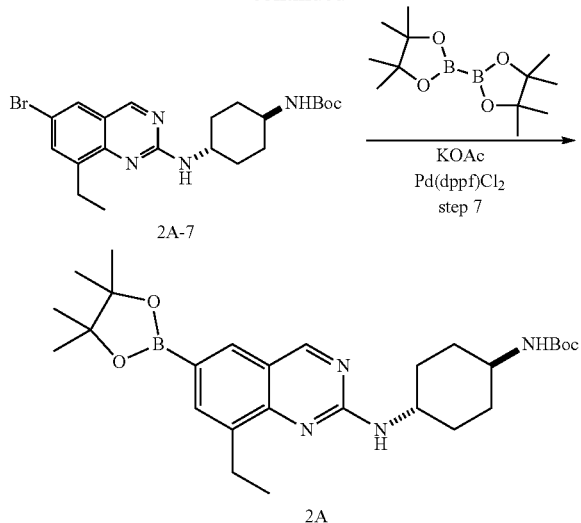

Step 1: 1-(5-bromo-2-fluorophenyl)ethan-1-ol (2A-2)

A solution of 5-bromo-2-fluoro-benzaldehyde (55.0 g, 270.9 mmol) in THF (500.0 mL) was cooled to 0° C. Then MeMgBr (3 M, 94.8 mL) was added. The mixture was stirred at 0° C. for 0.5 h, quenched with NH$_4$Cl (500 mL) and extracted with ethyl acetate (500 mL×3). The combined organic layers were washed with brine (500 mL×3), dried over Na$_2$SO$_4$, filtered and concentrated under reduced pressure to give a residue. The residue was purified by column chromatography (SiO$_2$) to afford compound 2A-2 (46.0 g, crude).

Step 2: 4-bromo-2-ethyl-1-fluorobenzene (2A-3)

To a solution of compound 2A-2 (46.0 g, 210.0 mmol) and triethylsilane (48.8 g, 420.0 mmol, 66.9 mL) in DCM (500.0 mL) was added BF$_3$.Et$_2$O (59.6 g, 420.0 mmol, 51.8 mL) at 0° C. The mixture was stirred at 25° C. for 2 h, concentrated, quenched by addition of Sat.NaHCO$_3$ (200 mL) at 0° C., and extracted with ethyl acetate (200 mL×3). The combined organic layers were washed with brine (200 mL×3), dried over Na$_2$SO$_4$, filtered and concentrated. The residue was purified by column chromatography (SiO$_2$) to afford compound 2A-3 (24.0 g, crude). $^1$H NMR (CHLOROFORM-d, 400 MHz) δ 7.31 (dd, J=2.2, 6.6 Hz, 1H), 7.27-7.21 (m, 1H), 6.87 (t, J=9.2 Hz, 1H), 2.62 (q, J=7.5 Hz, 2H), 1.20 (t, J=7.6 Hz, 3H).

Step 3: 5-bromo-3-ethyl-2-fluorobenzaldehyde (2A-4)

To a solution of compound 2A-3 (24.0 g, 82.7 mmol) in THF (500 mL) was added LDA (2 M, 49.6 mL) at −78° C. The mixture was stirred at −78° C. for 1 h. Then dimethyl formamide (7.8 g, 107.5 mmol, 8.3 mL) was added and stirred for 1 h at −78° C. The reaction mixture was quenched by addition of NH$_4$Cl (100 mL) and the resulting mixture was extracted with ethyl acetate (200 mL×3). The combined organic layers were washed with brine (100 mL×3), dried over Na$_2$SO$_4$, filtered and concentrated under reduced pressure to give a residue. The residue was purified by column chromatography (SiO$_2$) to afford compound 2A-4 (13.0 g, crude). $^1$H NMR (CDCl$_3$, 400 MHz) δ 10.30 (s, 1H), 7.81 (dd, J=2.6, 5.7 Hz, 1H), 7.58 (dd, J=2.6, 6.4 Hz, 1H), 2.73 (q, J=7.6 Hz, 2H), 1.30-1.25 (m, 3H).

Step 4: 6-bromo-8-ethylquinazolin-2-amine (2A-5)

To a solution of carbonic acid-guanidine (3.5 g, 19.4 mmol) and DIEA (5.0 g, 38.9 mmol, 6.8 mL) in DMA (20 mL) was added a solution of compound 2A-4 (3.0 g, 12.98 mmol) in DMA (5 mL). The mixture was stirred at 160° C. for 1 h, poured into ice water (30 mL) and extracted with ethyl acetate (40 mL×3). The combined organic layers were washed with brine (30 mL×3), dried over Na$_2$SO$_4$, filtered and concentrated under reduced pressure to give a residue. The residue was purified by column chromatography (SiO$_2$) to afford compound 2A-5 (1.2 g, crude). $^1$H NMR (DMSO-d$_6$, 400 MHz) δ 9.03 (s, 1H), 7.85 (d, J=2.4 Hz, 1H), 7.60 (d, J=2.4 Hz, 1H), 6.94 (s, 2H), 2.98-2.88 (m, 2H), 1.22-1.17 (m, 3H).

Step 5: 6-bromo-8-ethyl-2-iodoquinazoline (2A-6)

To a mixture of compound 2A-5 (1.2 g, 4.76 mmol) and CH$_2$I$_2$ (6.3 g, 23.8 mmol, 1.92 mL) in tetrahydrofuran (24.0 mL) were added CuI (906 mg, 4.7 mmol) and isoamyl nitrite (1.6 g, 14.3 mmol, 2.0 mL). After the mixture was stirred at 80° C. for 2 h under N$_2$, NH$_3$.H$_2$O (30 mL) was added. The resulting mixture was extracted with ethyl acetate (50 mL×3) and the combined organic layers were washed with brine (50 mL×3), dried over Na$_2$SO$_4$, filtered and concentrated. The residue was purified by column chromatography (SiO$_2$) to afford compound 2A-6 (400 mg, crude).

Step 6: tert-butyl ((1r,4r)-4-((6-bromo-8-ethylquinazolin-2-yl)amino)cyclohexyl)carbamate (2A-7)

To a mixture of compound 2A-6 (350 mg, 964.2 umol) and DIEA (373 mg, 2.8 mmol, 505.2 uL) in isopropanol (10 mL) was added tert-butyl ((1r,4r)-4-aminocyclohexyl)carbamate (413 mg, 1.9 mmol). The mixture was stirred at 80° C. for 12 h, cooled to rt and concentrated. The residue was purified by prep-TLC (SiO$_2$) to afford compound 2A-7 (350 mg, crude).

Step 7: tert-butyl ((1r,4r)-4-((8-ethyl-6-(4,4,5,5-tetramethyl-1,3,2-dioxaborolan-2-yl)quinazolin-2-yl)amino)cyclohexyl)carbamate (2A)

To a mixture of compound 2A-7 (150 mg, 333.7 umol) and KOAc (98 mg, 1.0 mmol) in dioxane (2 mL) were added 4,4,5,5-tetramethyl-2-(4,4,5,5-tetramethyl-1,3,2-dioxaborolan-2-yl)-1,3,2-dioxaborolane (101 mg, 400.5 umol) and Pd(dppf)Cl$_2$ (24 mg, 33.3 umol). The mixture was stirred at 90° C. for 12 h under N$_2$, cooled to rt and concentrated. The residue was purified by prep-TLC (SiO$_2$) to afford compound 2A (100 mg, crude).

Exemplary compounds were synthesized according to procedures described herein. For compounds that do not have a specific synthetic scheme described herein, such compounds can be routinely synthesized by a skilled artisan armed with the guidance presented herein and skill in the art.

| Comp ID | Structure | Chemical Name | Mass (M + H+) | 1H NMR (CD3OD, 400 MHz) |
|---|---|---|---|---|
| 23 | 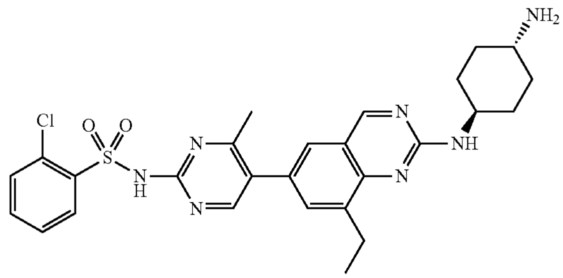 [SMILES: CCc1cc(-c2cnc(NS(=O)(=O)c3ccccc3Cl)nc2C)cc2cnc(N[C@H]3CC[C@H](N)CC3)nc12] | N-(5-(2-(((1r,4r)-4-aminocyclohexyl)amino)-8-ethylquinazolin-6-yl)-4-methylpyrimidin-2-yl)-2-chlorobenzenesulfonamide | Calc'd for C27H31ClN7O2S: 552.1; Found: 552.1 | δ 9.01 (s, 1H), 8.58 (br s, 1H), 8.34 (br d, J = 7.0 Hz, 1H), 8.23 (br s, 1H), 7.61-7.46 (m, 5H), 4.05-3.89 (m, 1H), 3.26-3.13 (m, 1H), 3.07 (q, J = 7.5 Hz, 2H), 2.31 (m, 5H), 2.16 (br d, J = 10.6 Hz, 2H), 1.71-1.43 (m, 4H), 1.33 (t, J = 7.5 Hz, 3H) |
| 24 | 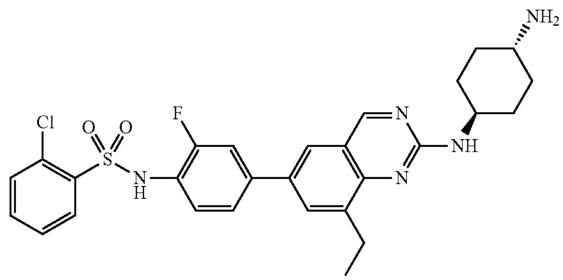 [SMILES: CCc1cc(-c2ccc(NS(=O)(=O)c3ccccc3Cl)c(F)c2)cc2cnc(N[C@H]3CC[C@H](N)CC3)nc12] | N-(4-(2-(((1r,4r)-4-aminocyclohexyl)amino)-8-ethylquinazolin-6-yl)-2-fluorophenyl)-2-chlorobenzenesulfonamide | Calc'd for C28H30ClFN5O2S: 554.2; Found: 554.1 | δ 9.03 (s, 1H), 8.56 (br s, 1H), 8.03 (dd, J = 1.3, 7.9 Hz, 1H), 7.80 (s, 2H), 7.68-7.54 (m, 2H), 7.54-7.34 (m, 4H), 4.05-3.91 (m, 1H), 3.25-3.15 (m, 1H), 3.09 (q, J = 7.4 Hz, 2H), 2.33 (br d, J = 11.5 Hz, 2H), 2.16 (br d, J = 11.7 Hz, 2H), 1.71-1.43 (m, 4H), 1.41-1.27 (m, 3H) |
| 25 | 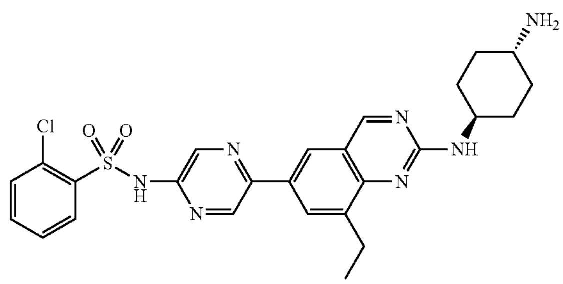 [SMILES: CCc1cc(-c2cnc(NS(=O)(=O)c3ccccc3Cl)cn2)cc2cnc(N[C@H]3CC[C@H](N)CC3)nc12] | N-(5-(2-(((1r,4r)-4-aminocyclohexyl)amino)-8-ethylquinazolin-6-yl)pyrazin-2-yl)-2-chlorobenzenesulfonamide | Calc'd for C26H29ClN7O2S: 538.2; Found: 538.1 | δ 9.03 (s, 1H), 8.58 (br s, 2H), 8.33-8.23 (m, 2H), 8.13 (d, J = 1.7 Hz, 1H), 8.08 (d, J = 1.8 Hz, 1H), 7.57-7.44 (m, 3H), 4.06-3.91 (m, 1H), 3.26-3.14 (m, 1H), 3.08 (q, J = 7.4 Hz, 2H), 2.32 (br d, J = 10.5 Hz, 2H), 2.16 (br d, J = 13.0 Hz, 2H), 1.73-1.44 (m, 4H), 1.38-1.27 (m, 3H) |
| 26 | 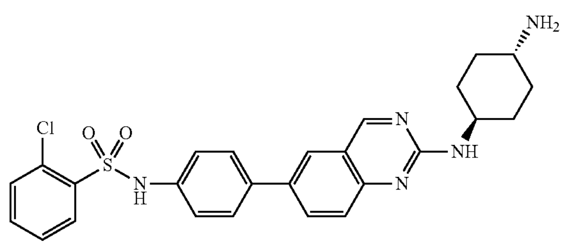 [SMILES: N[C@H]1CC[C@H](Nc2ncc3cc(-c4ccc(NS(=O)(=O)c5ccccc5Cl)cc4)ccc3n2)CC1] | N-(4-(2-(((1r,4r)-4-aminocyclohexyl)amino)quinazolin-6-yl)phenyl)-2-chlorobenzenesulfonamide | M + H+ = 508.1 (LCMS) | δ 9.06 (s, 1H), 8.41 (br s, 1H), 8.14-8.06 (m, 1H), 7.99-7.88 (m, 2H), 7.62-7.49 (m, 5H), 7.43 (m, 1H), 7.25 (d, J = 8.7 Hz, 2H), 4.02-3.89 (m, 1H), 3.21-3.10 (m, 1H), 2.23 (br d, J = 12.0 Hz, 2H), 2.12 (br d, J = 11.0 Hz, 2H), 1.67-1.55 (m, 2H), 1.53-1.41 (m, 2H) |
| 27 | 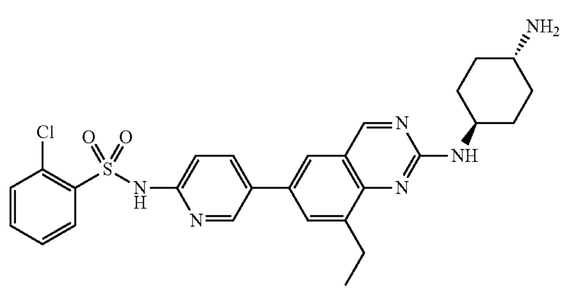 | N-(5-(2-(((1r,4r)-4-aminocyclohexyl)amino)-8-ethylquinazolin-6-yl)pyridin-2-yl)-2-chlorobenzenesulfonamide | Calc'd for C27H30ClN6O2S: 537.2; Found: 537.1 | δ 9.03 (s, 1 H), 8.55 (br s, 1 H), 8.40 (d, J = 2.45 Hz, 1 H), 8.05-8.15 (m, 3 H), 7.80 (d, J = 8.80 Hz, 1 H), 7.68 (dd, J = 8.56, 2.69 Hz, 1 H), 7.53-7.61 (m, 2 H), 7.41-7.50 (m, 1 H), 3.92-4.03 (m, 1 H), 3.12-3.21 (m, 1 H), 3.08 (q, J = 7.34 Hz, 2 H), 2.31 (br d, J = 11.25 Hz, 2 H), 2.14 (br d, J = 11.74 Hz, 2 H), 1.42-1.64 (m, 4 H), 1.34 (t, J = 7.58 Hz, 3H) |

-continued

| Comp ID | Structure | Chemical Name | Mass (M + H⁺) | ¹H NMR (CD₃OD, 400 MHz) |
|---|---|---|---|---|
| 28 | 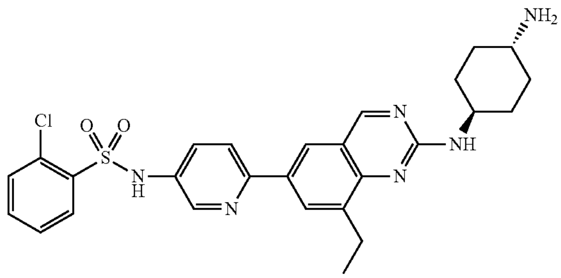 [SMILES: CCc1cc(-c2ccc(NS(=O)(=O)c3ccccc3Cl)cn2)cc2cnc(N[C@H]3CC[C@H](N)CC3)nc12] | N-(6-(2-(((1r,4r)-4-aminocyclohexyl)amino)-8-ethylquinazolin-6-yl)pyridin-3-yl)-2-chlorobenzenesulfonamide | Calc'd for $C_{27}H_{30}ClN_6O_2S$: 537.2; Found: 537.2 | δ 9.00 (s, 1H), 8.53 (br s, 1H), 8.30 (s, 1H), 8.23 (d, J = 7.7 Hz, 1H), 8.06 (dd, J = 2.0, 8.8 Hz, 1H), 7.76 (s, 2H), 7.55-7.44 (m, 3H), 7.29 (d, J = 9.0 Hz, 1H), 4.01-3.90 (m, 1H), 3.21-3.11 (m, 1H), 3.07 (q, J = 7.4 Hz, 2H), 2.30 (br d, J = 10.8 Hz, 2H), 2.13 (br d, J = 12.1 Hz, 2H), 1.66-1.40 (m, 4H), 1.33 (t, J = 7.5 Hz, 3H) |
| 29 | 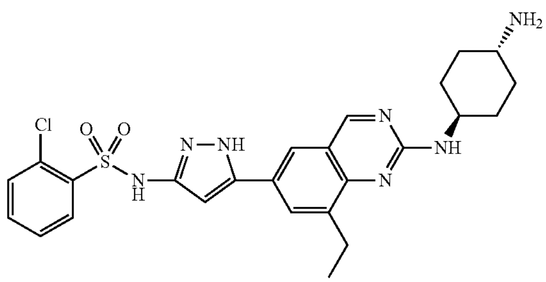 [SMILES: CCc1cc(-c2cc(NS(=O)(=O)c3ccccc3Cl)n[nH]2)cc2cnc(N[C@H]3CC[C@H](N)CC3)nc12] | N-(5-(2-(((1r,4r)-4-aminocyclohexyl)amino)-8-ethylquinazolin-6-yl)-1H-pyrazol-3-yl)-2-chlorobenzenesulfonamide | Calc'd for $C_{25}H_{29}ClN_7O_2S$: 526.2; Found: 526.1 | δ 8.99 (s, 1H), 8.09 (d, J = 7.3 Hz, 1H), 7.78 (br s, 2H), 7.62-7.52 (m, 2H), 7.43 (t, J = 7.2 Hz, 1H), 6.37 (s, 1H), 3.96 (m, 1H), 3.17 (m, 1H), 3.05 (q, J = 7.3 Hz, 2H), 2.30 (br d, J = 11.5 Hz, 2H), 2.14 (br d, J = 11.9 Hz, 2H), 1.65-1.54 (m, 2H), 1.53-1.43 (m, 2H), 1.33 (t, J = 7.5 Hz, 3H) |
| 30 | 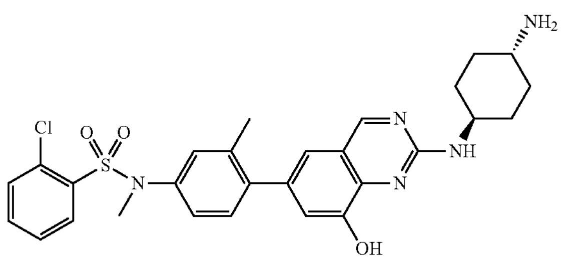 [SMILES: Cc1cc(N(C)S(=O)(=O)c2ccccc2Cl)ccc1-c1cc(O)c2nc(N[C@H]3CC[C@H](N)CC3)ncc2c1] | N-(4-(2-(((1r,4r)-4-aminocyclohexyl)amino)-8-hydroxyquinazolin-6-yl)-3-methylphenyl)-2-chloro-N-methylbenzenesulfonamide | M + H⁺ = 552.2 | δ 8.99 (s, 1H), 8.51 (s, 1H), 7.92 (d, J = 7.9 Hz, 1H), 7.68-7.53 (m, 2H), 7.43 (t, J = 7.0 Hz, 1H), 7.22-7.06 (m, 4H), 7.01 (s, 1H), 4.09 (br s, 1H), 3.42 (s, 3H), 3.15 (br t, J = 11.6 Hz, 1H), 2.30-2.20 (m, 5H), 2.12 (br d, J = 12.7 Hz, 2H), 1.73-1.55 (m, 2H), 1.53-1.35 (m, 2H). |
| 31 | 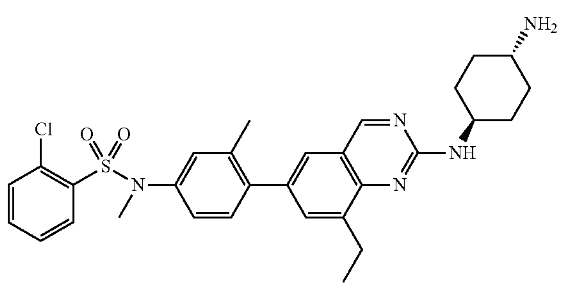 [SMILES: CCc1cc(-c2ccc(N(C)S(=O)(=O)c3ccccc3Cl)cc2C)cc2cnc(N[C@H]3CC[C@H](N)CC3)nc12] | N-(4-(2-(((1r,4r)-4-aminocyclohexyl)amino)-8-ethylquinazolin-6-yl)-3-methylphenyl)-2-chloro-N-methylbenzenesulfonamide | M + H⁺ = 564.2 | δ 8.98 (s, 1H), 8.51 (br s, 1H), 7.91 (d, J = 7.9 Hz, 1H), 7.65-7.55 (m, 2H), 7.49-7.39 (m, 3H), 7.19-7.14 (m, 2H), 7.12-7.07 (m, 1H), 3.98 (br t, J = 11.0 Hz, 1H), 3.42 (d, J = 1.8 Hz, 3H), 3.17 (br t, J = 11.4 Hz, 1H), 3.06 (q, J = 7.3 Hz, 2H), 2.32 (br d, J = 11.8 Hz, 2H), 2.20 (s, 3H), 2.15 (br d, J = 12.3 Hz, 2H), 1.69-1.43 (m, 4H), 1.37-1.28 (m, 3H). |
| 32 | 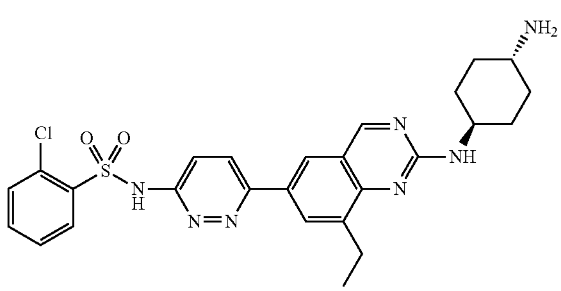 [SMILES: CCc1cc(-c2ccc(NS(=O)(=O)c3ccccc3Cl)nn2)cc2cnc(N[C@H]3CC[C@H](N)CC3)nc12] | N-(6-(2-(((1r,4r)-4-aminocyclohexyl)amino)-8-ethylquinazolin-6-yl)pyridazin-3-yl)-2-chlorobenzenesulfonamide | Calc'd for $C_{26}H_{29}ClN_7O_2S$: 538.2; Found: 538.2 | δ 9.03 (s, 1H), 8.53 (br s, 1H), 8.24-8.18 (m, 2H), 8.15 (d, J = 1.8 Hz, 1H), 8.10 (d, J = 2.2 Hz, 1H), 7.95 (d, J = 10.1 Hz, 1H), 7.56-7.43 (m, 3H), 4.03-3.91 (m, 1H), 3.23-3.11 (m, 1H), 3.06 (q, J = 7.5 Hz, 2H), 2.30 (br d, J = 10.1 Hz, 2H), 2.14 (br d, J = 11.8 Hz, 2H), 1.67-1.43 (m, 4H), 1.33 (t, J = 7.5 Hz, 3H) |

-continued

| Comp ID | Structure | Chemical Name | Mass (M + H+) | 1H NMR (CD3OD, 400 MHz) |
|---|---|---|---|---|
| 33 | 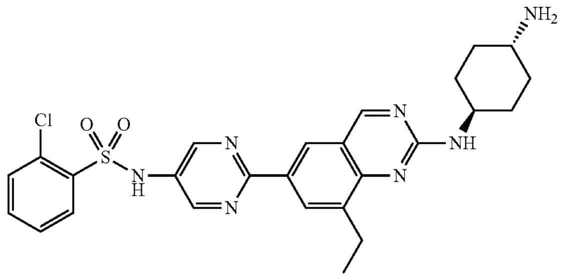 [SMILES: CCc1cc(-c2ncc(NS(=O)(=O)c3ccccc3Cl)cn2)cc2cnc(N[C@H]3CC[C@H](N)CC3)nc12] | N-(2-(2-(((1r,4r)-4-aminocyclohexyl)amino)-8-ethylquinazolin-6-yl)pyrimidin-5-yl)-2-chlorobenzenesulfonamide | Calc'd for $C_{26}H_{29}ClN_7O_2S$: 538.2; Found: 538.1 | δ 9.06 (s, 1H), 8.61 (s, 2H), 8.55-8.43 (m, 3H), 8.20-8.12 (m, 1H), 7.66-7.54 (m, 2H), 7.54-7.45 (m, 1H), 4.06-3.95 (m, 1H), 3.24-3.14 (m, 1H), 3.09 (q, J = 7.5 Hz, 2H), 2.33 (br d, J = 12.5 Hz, 2H), 2.16 (br d, J = 10.8 Hz, 2H), 1.72-1.42 (m, 4H), 1.36 (t, J = 7.5 Hz, 3H) |
| 34 | 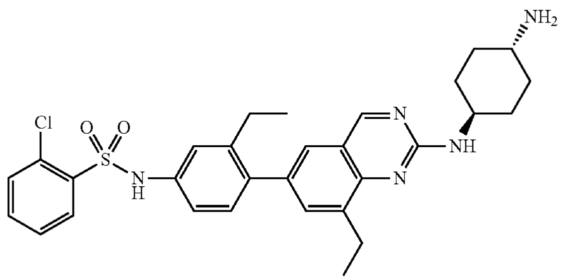 [SMILES: CCc1cc(NS(=O)(=O)c2ccccc2Cl)ccc1-c1cc(CC)c2nc(N[C@H]3CC[C@H](N)CC3)ncc2c1] | N-(4-(2-(((1r,4r)-4-aminocyclohexyl)amino)-8-ethylquinazolin-6-yl)-3-ethylphenyl)-2-chlorobenzenesulfonamide | M + H+ = 564.2 | δ 8.95 (s, 1H), 8.56 (br s, 1H), 8.14-8.06 (m, 1H), 7.60-7.52 (m, 2H), 7.45 (m, 1H), 7.40 (d, J = 2.9 Hz, 2H), 7.11 (d, J = 1.8 Hz, 1H), 7.08-6.99 (m, 2H), 4.03-3.85 (m, 1H), 3.16-2.97 (m, 3H), 2.51 (q, J = 7.5 Hz, 2H), 2.30 (br d, J = 10.6 Hz, 2H), 2.12 (br d, J = 12.1 Hz, 2H), 1.62-1.42 (m, 4H), 1.30 (t, J = 7.5 Hz, 3H), 0.98 (t, J = 7.5 Hz, 3H) |
| 35 | 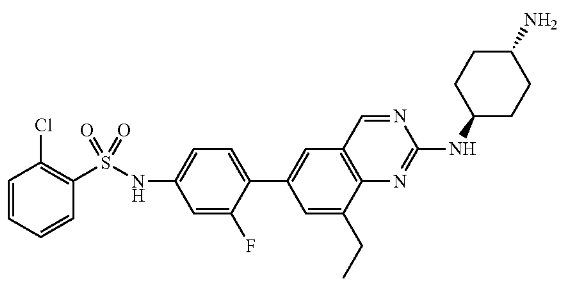 [SMILES: CCc1cc(-c2ccc(NS(=O)(=O)c3ccccc3Cl)cc2F)cc2cnc(N[C@H]3CC[C@H](N)CC3)nc12] | N-(4-(2-(((1r,4r)-4-aminocyclohexyl)amino)-8-ethylquinazolin-6-yl)-3-fluorophenyl)-2-chlorobenzenesulfonamide | Calc'd for $C_{28}H_{30}ClFN_5O_2S$: 554.2; Found: 554.1 | δ 8.97 (br d, J = 3.1 Hz, 1H), 8.55 (br s, 1H), 8.15 (br dd, J = 2.6, 7.5 Hz, 1H), 7.64 (br s, 2H), 7.57 (br d, J = 3.1 Hz, 2H), 7.51-7.43 (m, 1H), 7.37 (dt, J = 3.5, 8.6 Hz, 1H), 7.07-6.97 (m, 2H), 4.02-3.90 (m, 1H), 3.20-3.11 (m, 1H), 3.04 (br dd, J = 3.1, 7.3 Hz, 2H), 2.30 (br d, J = 11.2 Hz, 2H), 2.13 (br d, J = 11.2 Hz, 2H), 1.66-1.40 (m, 4H), 1.31 (dt, J = 3.6, 7.3 Hz, 3H) |
| 36 | 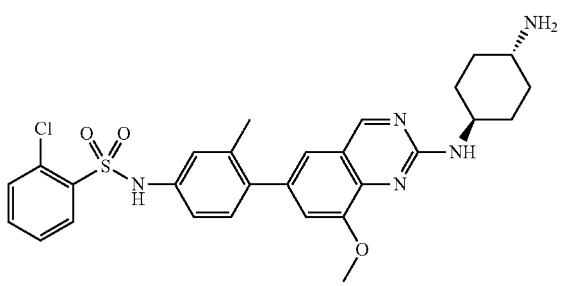 [SMILES: COc1cc(-c2ccc(NS(=O)(=O)c3ccccc3Cl)cc2C)cc2cnc(N[C@H]3CC[C@H](N)CC3)nc12] | N-(4-(2-(((1r,4r)-4-aminocyclohexyl)amino)-8-methoxyquinazolin-6-yl)-3-methylphenyl)-2-chlorobenzenesulfonamide | M + H+ = 552.1 | δ 8.98 (s, 1H), 8.47 (s, 1H), 8.15-8.04 (m, 1H), 7.58-7.52 (m, 2H), 7.44 (ddd, J = 2.6, 5.9, 8.1 Hz, 1H), 7.16 (d, J = 1.8 Hz, 1H), 7.12-7.03 (m, 4H), 4.05 (br t, J = 11.2 Hz, 1H), 3.95 (s, 3H), 3.14 (ddd, J = 3.9, 7.7, 11.6 Hz, 1H), 2.27-2.17 (m, 5H), 2.11 (br d, J = 11.4 Hz, 2H), 1.67-1.53 (m, 2H), 1.52-1.38 (m, 2H) |
| 37 | 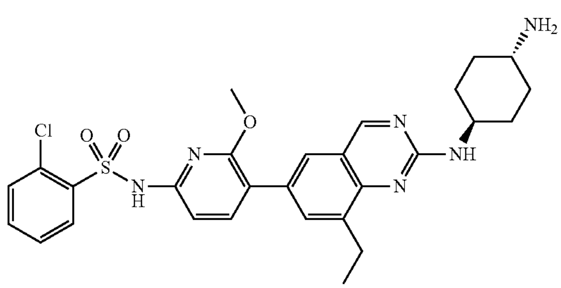 [SMILES: CCc1cc(-c2ccc(NS(=O)(=O)c3ccccc3Cl)nc2OC)cc2cnc(N[C@H]3CC[C@H](N)CC3)nc12] | N-(5-(2-(((1r,4r)-4-aminocyclohexyl)amino)-8-ethylquinazolin-6-yl)-6-methoxypyridin-2-yl)-2-chlorobenzenesulfonamide | M + H+ = 567.2 | δ 8.95 (s, 1 H), 8.54 (br s, 1 H), 8.31 (d, J = 7.72 Hz, 1 H), 7.65 (t, J = 7.50 Hz, 3 H), 7.56-7.60 (m, 2 H), 7.48-7.54 (m, 1 H), 6.63 (d, J = 7.94 Hz, 1 H), 3.91-4.01 (m, 1 H), 3.65 (s, 3 H), 3.10-3.21 (m, 1 H), 3.03 (q, J = 7.35 Hz, 2 H), 2.30 (br d, J = 12.13 Hz, 2 Hm), 2.13 (br d, J = 12.13 Hz, 2 H), 1.44- |

-continued

| Comp ID | Structure | Chemical Name | Mass (M + H⁺) | ¹H NMR (CD₃OD, 400 MHz) |
|---|---|---|---|---|
| | | | | 1.65 (m, 4 H), 1.30 (t, J = 7.50 Hz, 3 H) |
| 38 | 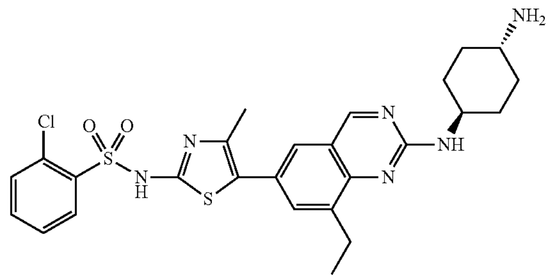 [SMILES: CCc1cc(-c2sc(NS(=O)(=O)c3ccccc3Cl)nc2C)cc2cnc(N[C@H]3CC[C@H](N)CC3)nc12] | N-(5-(2-(((1r,4r)-4-aminocyclohexyl)amino)-8-ethylquinazolin-6-yl)-4-methylthiazol-2-yl)-2-chlorobenzenesulfonamide | M + H⁺ = 557.2 | δ 9.02 (s, 1 H) 8.52 (br s, 1 H) 8.15 (d, J = 7.06 Hz, 1 H) 7.64 (s, 1 H) 7.51-7.59 (m, 3 H) 7.43-7.49 (m, 1 H) 3.92-4.04 (m, 1 H) 3.02-3.21 (m, 3 H) 2.30 (s, 5 H) 2.14 (br d, J = 12.13 Hz, 2 H) 1.44-1.64 (m, 4 H) 1.33 (t, J = 7.50 Hz, 3 H) |
| 39 | 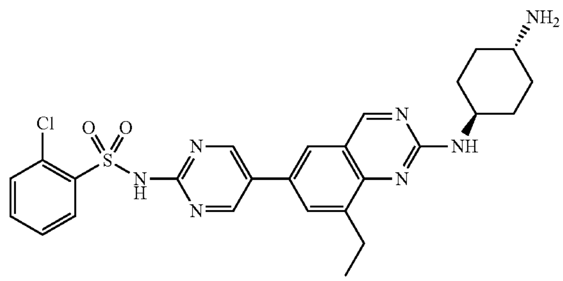 [SMILES: CCc1cc(-c2cnc(NS(=O)(=O)c3ccccc3Cl)nc2)cc2cnc(N[C@H]3CC[C@H](N)CC3)nc12] | N-(5-(2-(((1r,4r)-4-aminocyclohexyl)amino)-8-ethylquinazolin-6-yl)pyrimidin-2-yl)-2-chlorobenzenesulfonamide | M + H⁺ = 538.1 | δ 9.02 (br s, 1H), 8.51 (br s, 2H), 8.19 (s, 1H), 8.04 (br s, 1H), 7.78 (br d, J = 6.8 Hz, 2H), 7.36 (br s, 4H), 3.78 (br s, 1H), 3.03 (br s, 1H), 2.94 (q, J = 7.4 Hz, 2H), 2.09 (br s, 2H), 1.99 (br d, J = 10.8 Hz, 2H), 1.52 (br s, 2H), 1.42-1.30 (m, 2H), 1.23 (t, J = 7.4 Hz, 3H) |
| 40 | 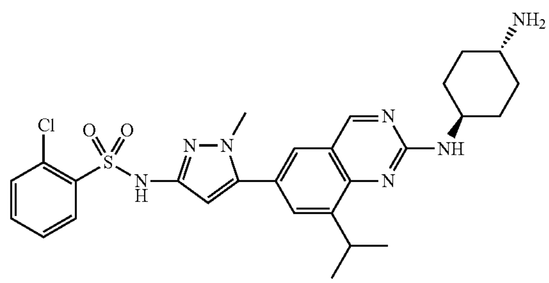 | N-(5-(2-(((1r,4r)-4-aminocyclohexyl)amino)-8-isopropylquinazolin-6-yl)-1-methyl-1H-pyrazol-3-yl)-2-chlorobenzenesulfonamide | M + H⁺ = 554.2 | δ 9.01 (s, 1H), 8.53 (br s, 1H), 8.12-8.07 (m, 1H), 7.60 (dd, J = 1.8, 10.5 Hz, 2H), 7.57-7.54 (m, 1H), 7.52 (d, J = 1.8 Hz, 1H), 7.47-7.41 (m, 1H), 6.09 (s, 1H), 4.03-3.87 (m, 2H), 3.71 (s, 3H), 3.17 (br t, J = 11.4 Hz, 1H), 2.30 (br d, J = 11.8 Hz, 2H), 2.14 (br d, J = 11.0 Hz, 2H), 1.68-1.41 (m, 5H), 1.34 (d, J = 7.0 Hz, 6H) |
| 41 | 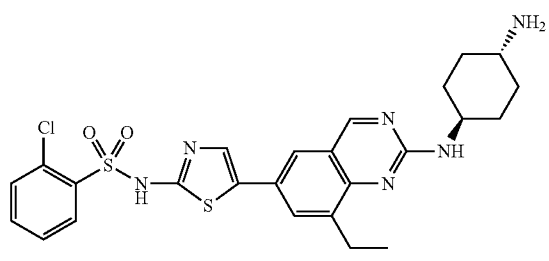 [SMILES: CCc1cc(-c2cnc(NS(=O)(=O)c3ccccc3Cl)s2)cc2cnc(N[C@H]3CC[C@H](N)CC3)nc12] | N-(5-(2-(((1r,4r)-4-aminocyclohexyl)amino)-8-ethylquinazolin-6-yl)thiazol-2-yl)-2-chlorobenzenesulfonamide | M + H⁺ = 543.1 | δ 8.98 (s, 1H), 8.51 (br s, 1H), 8.17 (d, J = 7.0 Hz, 1H), 7.73 (s, 1H), 7.65 (s, 1H), 7.58-7.40 (m, 4H), 4.01-3.89 (m, 1H), 3.19-2.98 (m, 3H), 2.30 (br d, J = 12.3 Hz, 2H), 2.13 (br d, J = 13.2 Hz, 2H), 1.66-1.41 (m, 4H), 1.33 (t, J = 7.5 Hz, 3H) |
| 42 | 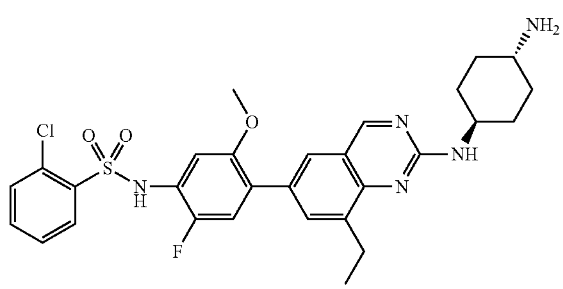 [SMILES: CCc1cc(-c2cc(F)c(NS(=O)(=O)c3ccccc3Cl)cc2OC)cc2cnc(N[C@H]3CC[C@H](N)CC3)nc12] | N-(4-(2-(((1r,4r)-4-aminocyclohexyl)amino)-8-ethylquinazolin-6-yl)-2-fluoro-5-methoxyphenyl)-2-chlorobenzenesulfonamide | M + H⁺ = 584.2 | δ 8.95 (s, 1 H), 8.55 (br s, 1 H), 8.09 (d, J = 7.28 Hz, 1 H), 7.54-7.67 (m, 4 H), 7.41-7.47 (m, 1 H), 7.05-7.11 (m, 2 H), 3.96 (br t, J = 11.36 Hz, 1 H), 3.70 (s, 3 H), 3.10-3.19 (m, 1 H), 3.03 (q, J = 7.72 Hz, 2 H), 2.30 (br d, J = 12.57 Hz, 2 H), 2.13 (br d, J = 11.47 Hz, 2 H), 1.42-1.65 (m, 4H), 1.31 (t, J = 7.39 Hz, 3 H) |

| Comp ID | Structure | Chemical Name | Mass (M + H⁺) | $^1$H NMR (CD$_3$OD, 400 MHz) |
|---|---|---|---|---|
| 43 | 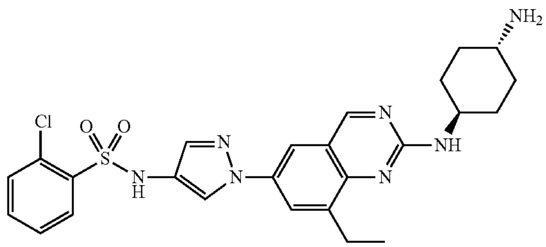 [SMILES: CCc1cc(-n2cc(NS(=O)(=O)c3ccccc3Cl)cn2)cc2cnc(N[C@H]3CC[C@H](N)CC3)nc12] | N-(1-(2-(((1r,4r)-4-aminocyclohexyl)amino)-8-ethylquinazolin-6-yl)-1H-pyrazol-4-yl)-2-chlorobenzenesulfonamide | M + H⁺ = 526.0 | δ 9.09 (br s, 1H), 8.40 (br s, 1H), 8.05 (s, 1H), 8.01-7.95 (m, 2H), 7.88 (d, J = 2.3 Hz, 1H), 7.65-7.47 (m, 2H), 7.44-7.34 (m, 2H), 3.77 (br s, 1H), 3.05-2.90 (m, 3H), 2.12-1.96 (m, 4H), 1.49-1.24 (m, 7H) |
| 44 | 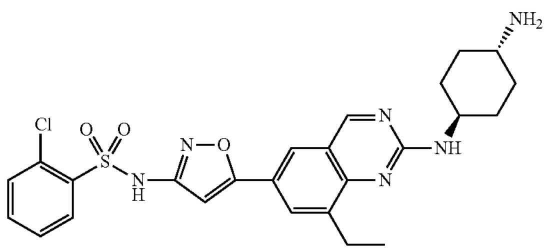 [SMILES: CCc1cc(-c2cc(NS(=O)(=O)c3ccccc3Cl)no2)cc2cnc(N[C@H]3CC[C@H](N)CC3)nc12] | N-(5-(2-(((1r,4r)-4-aminocyclohexyl)amino)-8-ethylquinazolin-6-yl)isoxazol-3-yl)-2-chlorobenzenesulfonamide | M + H⁺ = 527.1 | δ 9.13 (br s, 1H), 8.39 (br s, 1H), 8.06-7.90 (m, 2H), 7.79 (d, J = 1.6 Hz, 1H), 7.55 (br s, 1H), 7.46-7.40 (m, 1H), 7.39-7.29 (m, 2H), 6.53 (s, 1H), 3.80 (br s, 1H), 2.98 (q, J = 7.4 Hz, 3H), 2.17-1.94 (m, 3H), 4H), 1.53-1.32 (m, 4H), 1.31-1.22 (m, 3H). |
| 45 | 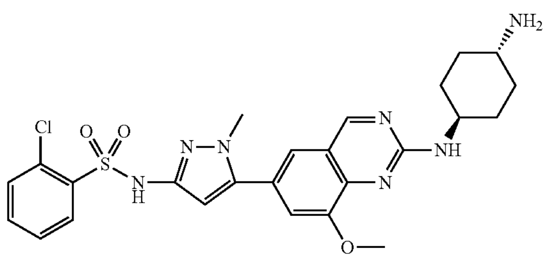 [SMILES: COc1cc(-c2cc(NS(=O)(=O)c3ccccc3Cl)nn2C)cc2cnc(N[C@H]3CC[C@H](N)CC3)nc12] | N-(5-(2-(((1r,4r)-4-aminocyclohexyl)amino)-8-methoxyquinazolin-6-yl)-1-methyl-1H-pyrazol-3-yl)-2-chlorobenzenesulfonamide | M + H⁺ = 542.2 | δ 9.05 (br s, 1H), 8.33 (br s, 2H), 8.02 (d, J = 7.7 Hz, 1H), 7.60-7.34 (m, 5H), 7.10 (br s, 1H), 6.02 (s, 1H), 3.89 (br s, 4H), 3.68 (s, 3H), 2.96 (br s, 1H), 1.97 (br s, 4H), 1.49-1.26 (m, 4H). |
| 46 | 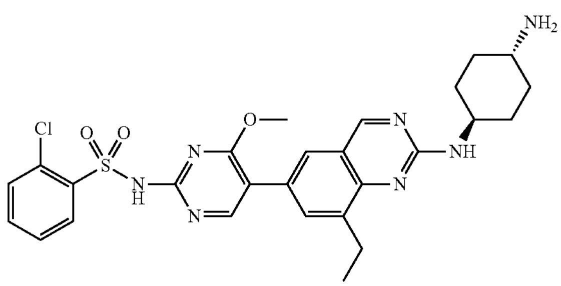 | N-(5-(2-(((1r,4r)-4-aminocyclohexyl)amino)-8-ethylquinazolin-6-yl)-4-methoxypyrimidin-2-yl)-2-chlorobenzenesulfonamide | M + H⁺ = 568.2 | δ 8.98 (s, 1 H), 8.50 (br s, 1 H), 8.33 (d, J = 7.94 Hz, 1 H), 8.14 (s, 1 H), 7.61-7.68 (m, 2 H), 7.48-7.58 (m, 3 H), 3.91-4.02 (m, 1 H), 3.71 (s, 3 H), 3.11-3.23 (m, 1 H), 3.04 (q, J = 7.72 Hz, 2 H), 2.31 (br d, J = 11.69 Hz, 2 H), 2.14 (br d, J = 11.47 Hz, 2 H), 1.43-1.66 (m, 4 H), 1.31 (t, J = 7.50 Hz, 3 H) |
| 47 | 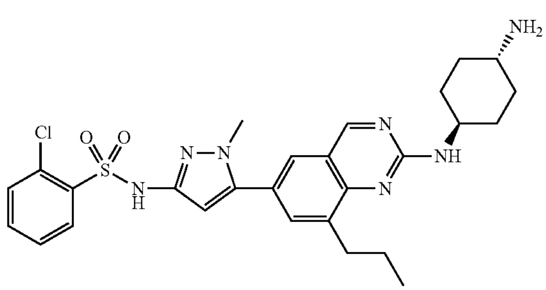 [SMILES: CCCc1cc(-c2cc(NS(=O)(=O)c3ccccc3Cl)nn2C)cc2cnc(N[C@H]3CC[C@H](N)CC3)nc12] | N-(5-(2-(((1r,4r)-4-aminocyclohexyl)amino)-8-propylquinazolin-6-yl)-1-methyl-1H-pyrazol-3-yl)-2-chlorobenzenesulfonamide | M + H⁺ = 554.2 | δ 9.02 (s, 1H), 8.48 (br s, 1H), 8.09 (dd, J = 1.3, 7.9 Hz, 1H), 7.62 (d, J = 2.0 Hz, 1H), 7.61-7.54 (m, 2H), 7.52 (d, J = 2.0 Hz, 1H), 7.44 (ddd, J = 1.9, 6.7, 8.1 Hz, 1H), 6.10 (s, 1H), 4.00-3.90 (m, 1H), 3.72 (s, 3H), 3.23-3.12 (m, 1H), 3.05-2.96 (m, 2H), 2.32 (br d, J = 11.7 Hz, 2H), 2.15 (br d, J = 11.2 Hz, 2H), 1.76 (qd, J = 7.4, 15.0 Hz, 2H), 1.67-1.41 (m, 4H), 1.01 (t, J = 7.3 Hz, 3H) |

-continued

| Comp ID | Structure | Chemical Name | Mass (M + H⁺) | ¹H NMR (CD₃OD, 400 MHz) |
|---|---|---|---|---|
| 48 | 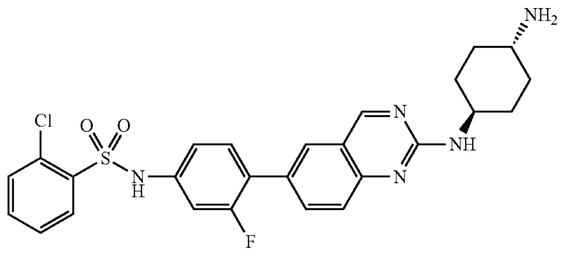 [SMILES: N[C@H]1CC[C@H](Nc2ncc3cc(-c4ccc(NS(=O)(=O)c5ccccc5Cl)cc4F)ccc3n2)CC1] | N-(4-(2-(((1r,4r)-4-aminocyclohexyl)amino)quinazolin-6-yl)-3-fluorophenyl)-2-chlorobenzenesulfonamide | M + H⁺ = 526.1 | δ 9.06 (s, 1H), 8.50 (br s, 1H), 8.18 (d, J = 7.6 Hz, 1H), 7.91-7.80 (m, 2H), 7.62-7.56 (m, 3H), 7.53-7.48 (m, 1H), 7.46-7.40 (m, 1H), 7.11-7.02 (m, 2H), 4.04-3.93 (m, 1H), 3.22-3.11 (m, 1H), 2.25 (br d, J = 13.0 Hz, 2H), 2.14 (br d, J = 11.9 Hz, 2H), 1.71-1.40 (m, 4H) |
| 49 | 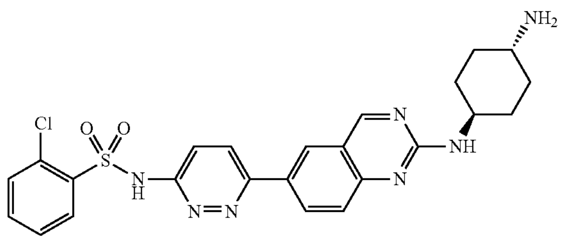 [SMILES: N[C@H]1CC[C@H](Nc2ncc3cc(-c4ccc(NS(=O)(=O)c5ccccc5Cl)nn4)ccc3n2)CC1] | N-(6-(2-(((1r,4r)-4-aminocyclohexyl)amino)quinazolin-6-yl)pyridazin-3-yl)-2-chlorobenzenesulfonamide | M + H⁺ = 510.1 | δ 9.13 (s, 1H), 8.42 (br s, 1H), 8.37-8.27 (m, 3H), 8.23 (d, J = 6.7 Hz, 1H), 8.07 (d, J = 10.0 Hz, 1H), 7.68-7.44 (m, 4H), 4.01 (br t, J = 11.2 Hz, 1H), 3.24-3.11 (m, 1H), 2.33-2.10 (m, 4H), 1.72-1.44 (m, 4H) |
| 50 | 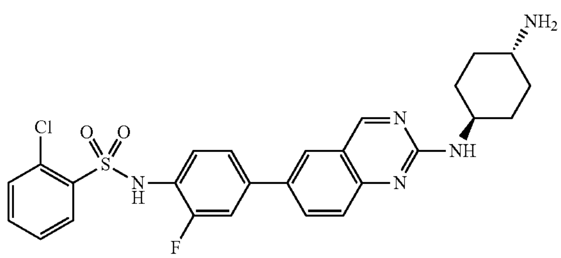 [SMILES: N[C@H]1CC[C@H](Nc2ncc3cc(-c4ccc(NS(=O)(=O)c5ccccc5Cl)c(F)c4)ccc3n2)CC1] | N-(4-(2-(((1r,4r)-4-aminocyclohexyl)amino)quinazolin-6-yl)-2-fluorophenyl)-2-chlorobenzenesulfonamide | M + H⁺ = 526.1 | δ 9.08 (br s, 1H), 8.25 (s, 1H), 8.00-7.91 (m, 3H), 7.50-7.29 (m, 5H), 7.24-7.12 (m, 2H), 3.81 (br d, J = 8.1 Hz, 1H), 3.03 (br d, J = 10.9 Hz, 1H), 2.11-1.92 (m, 4H), 1.53-1.29 (m, 4H) |
| 51 | 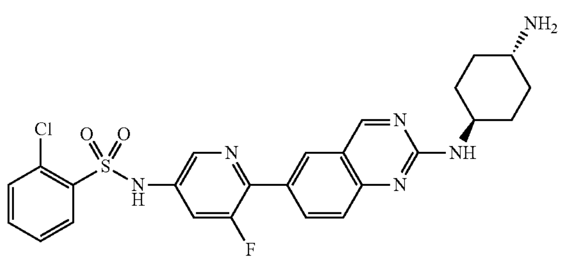 [SMILES: N[C@H]1CC[C@H](Nc2ncc3cc(-c4ncc(NS(=O)(=O)c5ccccc5Cl)cc4F)ccc3n2)CC1] | N-(6-(2-(((1r,4r)-4-aminocyclohexyl)amino)quinazolin-6-yl)-5-fluoropyridin-3-yl)-2-chlorobenzenesulfonamide | M + H⁺ = 527.1 | δ 9.08 (s, 1H), 8.45 (br s, 1H), 8.29 (s, 1H), 8.24-8.15 (m, 3H), 7.64-7.55 (m, 3H), 7.54-7.45 (m, 2H), 3.98 (br t, J = 11.4 Hz, 1H), 3.21-3.09 (m, 1H), 2.24 (br d, J = 11.7 Hz, 2H), 2.13 (br d, J = 11.7 Hz, 2H), 1.71-1.41 (m, 4H) |
| 52 | 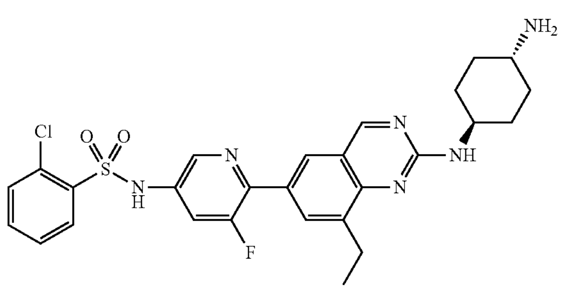 [SMILES: CCc1cc(-c2ncc(NS(=O)(=O)c3ccccc3Cl)cc2F)cc2cnc(N[C@H]3CC[C@H](N)CC3)nc12] | N-(6-(2-(((1r,4r)-4-aminocyclohexyl)amino)-8-ethylquinazolin-6-yl)-5-fluoropyridin-3-yl)-2-chlorobenzenesulfonamide | M + H⁺ = 555.2 | δ 9.02 (s, 1H), 8.51 (br s, 1H), 8.28 (s, 1H), 8.19 (d, J = 7.9 Hz, 1H), 8.05 (br d, J = 7.5 Hz, 2H), 7.64-7.56 (m, 2H), 7.54-7.42 (m, 2H), 3.99 (br t, J = 11.0 Hz, 1H), 3.18 (br t, J = 11.5 Hz, 1H), 3.08 (q, J = 7.5 Hz, 2H), 2.32 (br d, J = 11.2 Hz, 2H), 2.15 (br d, J = 11.2 Hz, 2H), 1.70-1.43 (m, 4H), 1.34 (t, J = 7.4 Hz, 3H). |

-continued

| Comp ID | Structure | Chemical Name | Mass (M + H⁺) | ¹H NMR (CD₃OD, 400 MHz) |
|---|---|---|---|---|
| 53 | 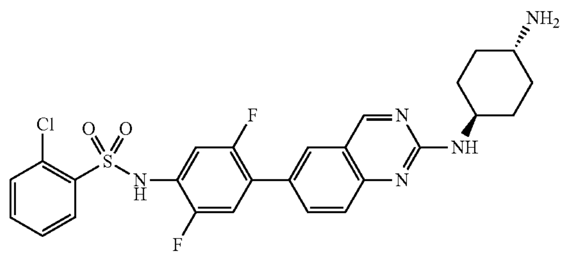 [SMILES: N[C@H]1CC[C@H](Nc2ncc3cc(-c4cc(F)c(NS(=O)(=O)c5ccccc5Cl)cc4F)ccc3n2)CC1] | N-(4-(2-(((1r,4r)-4-aminocyclohexyl)amino)quinazolin-6-yl)-2,5-difluorophenyl)-2-chlorobenzenesulfonamide | M + H⁺ = 544.1 | δ 9.10 (br s, 1 H), 8.17 (br s, 1 H), 7.97 (dd, J = 7.28, 1.98 Hz, 1 H), 7.85-7.89 (m, 1 H), 7.80 (br d, J = 8.82 Hz, 1 H), 7.36-7.47 (m, 4 H), 7.13-7.23 (m, 1 H), 6.98 (br dd, J = 14.33, 7.50 Hz, 1 H), 3.80 (br s, 1 H), 3.03 (br s, 1 H), 1.88-2.12 (m, 4 H), 1.22-1.57 (m, 4 H) |
| 54 | 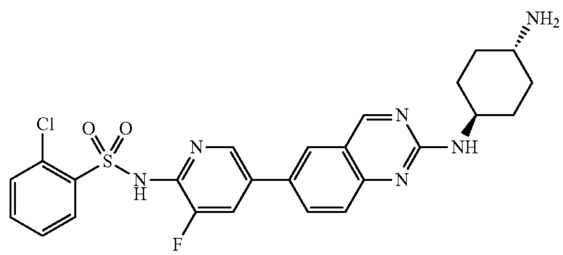 [SMILES: N[C@H]1CC[C@H](Nc2ncc3cc(-c4cnc(NS(=O)(=O)c5ccccc5Cl)c(F)c4)ccc3n2)CC1] | N-(5-(2-(((1r,4r)-4-aminocyclohexyl)amino)quinazolin-6-yl)-3-fluoropyridin-2-yl)-2-chlorobenzenesulfonamide | M + H⁺ = 527.1 | δ 9.10 (s, 1H), 8.29 (br dd, J = 2.1, 5.6 Hz, 3H), 8.23 (d, J = 1.8 Hz, 1H), 8.02-7.91 (m, 2H), 7.63-7.57 (m, 2H), 7.57-7.51 (m, 1H), 3.99 (br t, J = 11.2 Hz, 1H), 3.21-3.09 (m, 1H), 2.25 (br d, J = 12.3 Hz, 2H), 2.14 (br d, J = 12.0 Hz, 2H), 1.71-1.41 (m, 4H) |
| 55 | 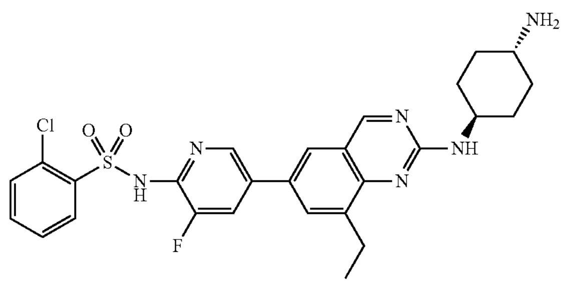 | N-(5-(2-(((1r,4r)-4-aminocyclohexyl)amino)-8-ethylquinazolin-6-yl)-3-fluoropyridin-2-yl)-2-chlorobenzenesulfonamide | M + H⁺ = 555.2 | ) δ 9.00 (s, 1H), 8.49 (br s, 1H), 8.25 (d, J = 8.1 Hz, 1H), 8.16 (s, 1H), 7.85 (br d, J = 11.6 Hz, 1H), 7.76 (br s, 2H), 7.57-7.51 (m, 2H), 7.51-7.44 (m, 1H), 4.01-3.87 (m, 1H), 3.22-3.12 (m, 1H), 3.06 (q, J = 7.5 Hz, 2H), 2.30 (br d, J = 11.5 Hz, 2H), 2.14 (br d, J = 12.2 Hz, 2H), 1.72-1.41 (m, 4H), 1.32 (t, J = 7.5 Hz, 3H) |
| 56 | 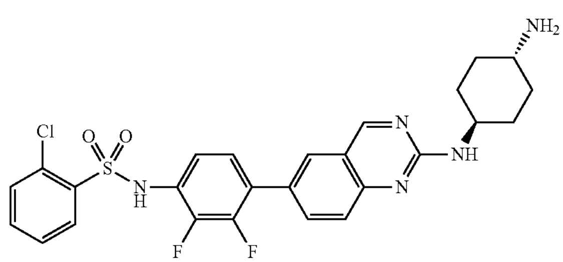 [SMILES: N[C@H]1CC[C@H](Nc2ncc3cc(-c4ccc(NS(=O)(=O)c5ccccc5Cl)c(F)c4F)ccc3n2)CC1] | N-(4-(2-(((1r,4r)-4-aminocyclohexyl)amino)quinazolin-6-yl)-2,3-difluorophenyl)-2-chlorobenzenesulfonamide | M + H⁺ = 544.1 | δ 9.06 (s, 1H), 8.42 (br s, 1H), 8.08-8.02 (m, 1H), 7.89 (s, 1H), 7.83 (br d, J = 9.0 Hz, 1H), 7.65-7.55 (m, 3H), 7.48-7.41 (m, 1H), 7.32-7.20 (m, 2H), 4.04-3.91 (m, 1H), 3.21-3.08 (m, 1H), 2.23 (br d, J = 11.2 Hz, 2H), 2.12 (br d, J = 12.3 Hz, 2H), 1.68-1.38 (m, 4H) |
| 57 | 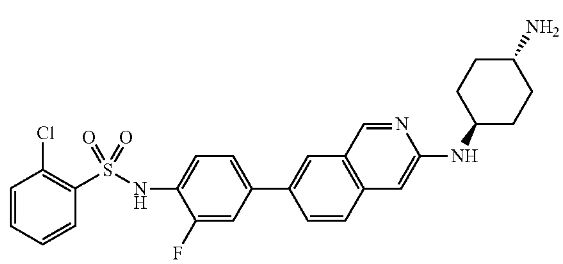 [SMILES: N[C@H]1CC[C@H](Nc2cc3ccc(-c4ccc(NS(=O)(=O)c5ccccc5Cl)c(F)c4)cc3cn2)CC1] | N-(4-(3-(((1r,4r)-4-aminocyclohexyl)amino)isoquinolin-7-yl)-2-fluorophenyl)-2-chlorobenzenesulfonamide | M + H⁺ = 525.1 | δ 8.83 (s, 1H), 8.46 (br s, 1H), 8.05-7.93 (m, 2H), 7.71 (dd, J = 1.9, 8.7 Hz, 1H), 7.62-7.53 (m, 3H), 7.50-7.44 (m, 1H), 7.44-7.37 (m, 3H), 6.68 (s, 1H), 3.68 (tt, J = 3.8, 11.2 Hz, 1H), 3.16 (tt, J = 3.9, 11.7 Hz, 1H), 2.29-2.18 (m, 2H), 2.12 (br d, J = 12.1 Hz, 2H), 1.61 (dq, J = 3.1, 12.6 Hz, 2H), 1.48-1.33 (m, 2H) |

-continued

| Comp ID | Structure | Chemical Name | Mass (M + H⁺) | ¹H NMR (CD₃OD, 400 MHz) |
|---|---|---|---|---|
| 58 | 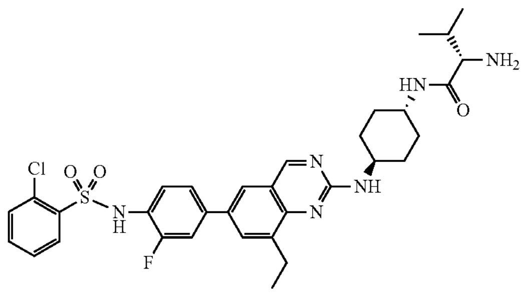 [SMILES: CCc1cc(-c2ccc(NS(=O)(=O)c3ccccc3Cl)c(F)c2)cc2cnc(N[C@H]3CC[C@H](NC(=O)[C@@H](N)C(C)C)CC3)nc12] | (S)-2-amino-N-((1r,4S)-4-((6-(4-((2-chlorophenyl)sulfonamido)-3-fluorophenyl)-8-ethylquinazolin-2-yl)amino)cyclohexyl)-3-methylbutanamide | M + H⁺ = 653.2 | δ 8.98 (s, 1H), 8.54 (br s, 1H), 8.02 (dd, J = 1.2, 7.9 Hz, 1H), 7.73 (br d, J = 4.3 Hz, 2H), 7.64-7.52 (m, 2H), 7.50-7.44 (m, 1H), 7.44-7.34 (m, 3H), 3.96 (br s, 1H), 3.80 (br s, 1H), 3.52 (br d, J = 6.0 Hz, 1H), 3.06 (q, J = 6.0 Hz, 2H), 2.24 (br s, 2H), 2.15 (br dd, J = 6.6, 13.2 Hz, 1H), 2.05 (br s, 2H), 1.50 (br d, J = 8.6 Hz, 4H), 1.33 (br t, J = 7.4 Hz, 3H), 1.07 (br dd, J = 4.0, 6.7 Hz, 6H). |
| 59 | 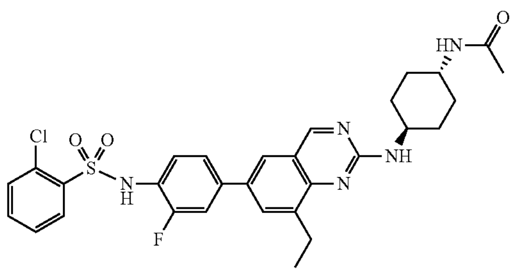 [SMILES: CCc1cc(-c2ccc(NS(=O)(=O)c3ccccc3Cl)c(F)c2)cc2cnc(N[C@H]3CC[C@H](NC(C)=O)CC3)nc12] | N-((1r,4r)-4-((6-(4-((2-chlorophenyl)-sulfonamido)-3-fluorophenyl)-8-ethylquinazolin-2-yl)amino)cyclohexyl)acetamide | M + H⁺ = 596.1 | δ 8.98 (s, 1H), 8.00 (dd, J = 1.5, 7.9 Hz, 1H), 7.75 (s, 2H), 7.63-7.52 (m, 2H), 7.50-7.44 (m, 1H), 7.43-7.36 (m, 3H), 3.98-3.88 (m, 1H), 3.68 (br d, J = 15.7 Hz, 1H), 3.06 (q, J = 7.4 Hz, 2H), 2.20 (br d, J = 11.7 Hz, 2H), 1.99 (br d, J = 9.3 Hz, 2H), 1.93 (s, 3H), 1.50-1.37 (m, 4H), 1.33 (t, J = 7.5 Hz, 3H). |
| 60 | 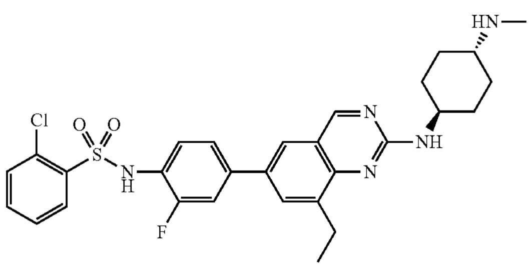 [SMILES: CCc1cc(-c2ccc(NS(=O)(=O)c3ccccc3Cl)c(F)c2)cc2cnc(N[C@H]3CC[C@H](NC)CC3)nc12] | 2-chloro-N-(4-(8-ethyl-2-(((1r,4r)-4-(methylamino)-cyclohexyl)amino)quinazolin-6-yl)-2-fluorophenyl)benzenesulfsulfonamide | M + H⁺ = 568.2 | δ 9.05 (br s, 1H), 8.25 (br s, 1H), 7.95 (dd, J = 2.0, 7.5 Hz, 1H), 7.80 (d, J = 1.3 Hz, 2H), 7.47-7.43 (m, 1H), 7.41-7.30 (m, 4H), 7.20-7.13 (m, 2H), 3.79 (br s, 1H), 2.98 (q, J = 7.6 Hz, 2H), 2.91 (br s, 1H), 2.55 (s, 3H), 2.09 (br d, J = 9.3 Hz, 4H), 1.46-1.33 (m, 4H), 1.28 (t, J = 7.4 Hz, 3H) |
| 61 | 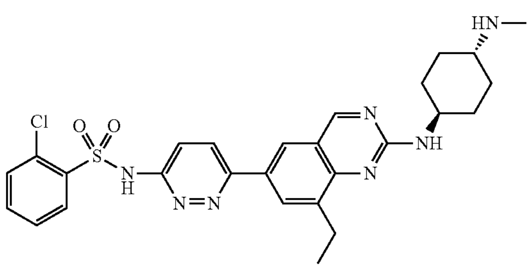 [SMILES: CCc1cc(-c2ccc(NS(=O)(=O)c3ccccc3Cl)nn2)cc2cnc(N[C@H]3CC[C@H](NC)CC3)nc12] | 2-chloro-N-(6-(8-ethyl-2-(((1r,4r)-4-(methylamino)cyclohexyl)amino)quinazolin-6-yl)pyridazin-3-yl)benzenesulfonamide | M + H⁺ = 552.2 | δ ppm 9.06 (s, 1H), 8.53 (br s, 1H), 8.58-8.47 (m, 1H), 8.29-8.13 (m, 4H), 7.99 (d, J = 9.8 Hz, 1H), 7.58-7.43 (m, 3H), 4.04-3.95 (m, 1H), 3.08 (q, J = 7.4 Hz, 3H), 2.73 (s, 3H), 2.39-2.20 (m, 4H), 1.64-1.42 (m, 4H), 1.34 (t, J = 7.5 Hz, 3H). |
| 62 | 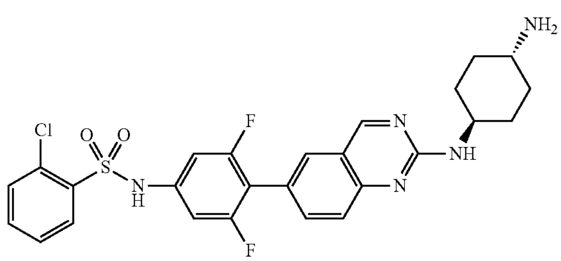 [SMILES: N[C@H]1CC[C@H](Nc2ncc3cc(-c4c(F)cc(NS(=O)(=O)c5ccccc5Cl)cc4F)ccc3n2)CC1] | N-(4-(2-(((1r,4r)-4-aminocyclohexyl)amino)quinazolin-6-yl)-3,5-difluorophenyl)-2-chlorobenzenesulfonamide | M + H⁺ = 544.1 | δ 8.93 (s, 1H), 8.42 (br s, 1H), 8.18-8.04 (m, 1H), 7.67 (s, 1H), 7.61-7.55 (m, 1H), 7.53-7.50 (m, 2H), 7.48-7.39 (m, 2H), 6.82-6.75 (m, 2H), 3.96-3.83 (m, 1H), 3.06 (tt, J = 3.9, 11.6 Hz, 1H), 2.15 (br d, J = 11.0 Hz, 2H), 2.03 (br d, J = 12.2 Hz, 2H), 1.59-1.46 (m, 2H), 1.44-1.31 (m, 2H). |

-continued

| Comp ID | Structure | Chemical Name | Mass (M + H⁺) | ¹H NMR (CD₃OD, 400 MHz) |
|---|---|---|---|---|
| 63 | 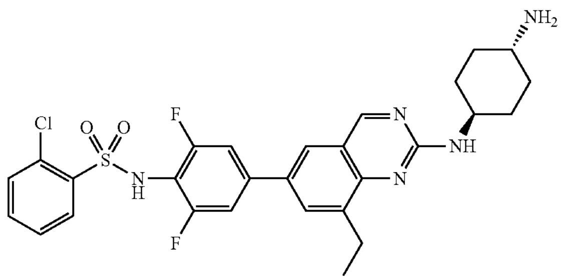 [SMILES: CCc1cc(-c2cc(F)c(NS(=O)(=O)c3ccccc3Cl)c(F)c2)cc2cnc(N[C@H]3CC[C@H](N)CC3)nc12] | N-(4-(2-(((1r,4r)-4-aminocyclohexyl)amino)-8-ethylquinazolin-6-yl)-2,6 difluorophenyl)-2-chlorobenzene-sulfonamide | M + H⁺ = 572.2 | δ 9.04 (br s, 1H), 8.43 (br s, 2H), 7.95 (br d, J = 7.8 Hz, 1H), 7.82 (br d, J = 15.6 Hz, 2H), 7.70-7.57 (m, 2H), 7.43 (br t, J = 7.4 Hz, 1H), 7.33 (br d, J = 8.9 Hz, 2H), 3.99 (br s, 1H), 3.25-3.03 (m, 3H), 2.33 (br d, J = 10.3 Hz, 2H), 2.17 (br d, J = 9.8 Hz, 2H), 1.70-1.46 (m, 4H), 1.36 (br t, J = 7.2 Hz, 3H). |
| 64 | 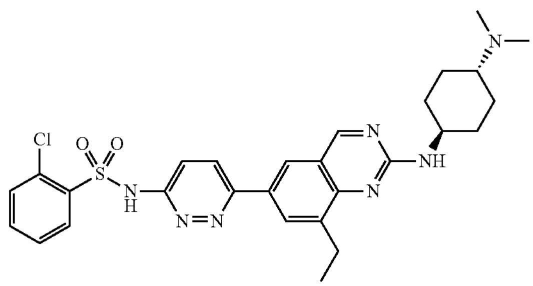 [SMILES: CCc1cc(-c2ccc(NS(=O)(=O)c3ccccc3Cl)nn2)cc2cnc(N[C@H]3CC[C@H](N(C)C)CC3)nc12] | 2-chloro-N-(6-(2-(((1r,4r)-4-(dimethylamino)cyclohexyl)amino)-8-ethylquinazolin-6-yl)pyridazin-3-yl)benzenesulfonamide | M + H⁺ = 566.2 | δ 9.06 (s, 1H), 8.53 (br s, 1H), 8.30-8.21 (m, 2H), 8.20-8.11 (m, 2H), 8.02 (d, J = 9.9 Hz, 1H), 7.60-7.47 (m, 3H), 4.06-3.96 (m, 1H), 3.30-3.22 (m, 1H), 3.10 (q, J = 7.5 Hz, 2H), 2.93-2.85 (m, 6H), 2.41 (br d, J = 11.0 Hz, 2H), 2.21 (br d, J = 12.2 Hz, 2H), 1.82-1.69 (m, 2H), 1.59-1.45 (m, 2H), 1.36 (t, J = 7.5 Hz, 3H). |
| 65 | 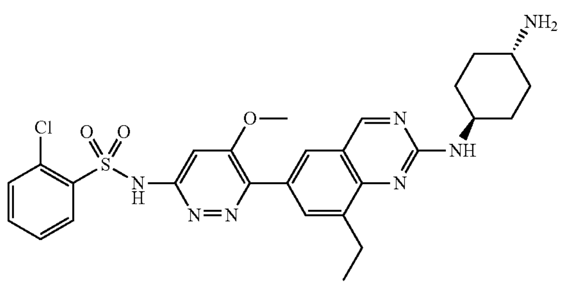 | N-(6-(2-(((1r,4r)-4-aminocyclohexyl)amino)-8-ethylquinazolin-6-yl)-5-methoxypyridazin-3-yl)-2-chlorobenzene-sulfonamide | M + H⁺ = 568.2 (LCMS) | δ 9.04 (s, 1H), 8.52 (br s, 1H), 8.24 (dd, J = 1.5, 7.7 Hz, 1H), 8.06 (d, J = 2.0 Hz, 1H), 7.98-7.91 (m, 1H), 7.61-7.45 (m, 3H), 7.34 (s, 1H), 4.05-3.95 (m, 4H), 3.19 (br t, J = 11.4 Hz, 1H), 3.07 (q, J = 7.5 Hz, 2H), 2.32 (br d, J = 11.1 Hz, 2H), 2.17 (br d, J = 11.4 Hz, 2H), 1.70-1.43 (m, 4H), 1.39-1.27 (m, 3H) |
| 66 | 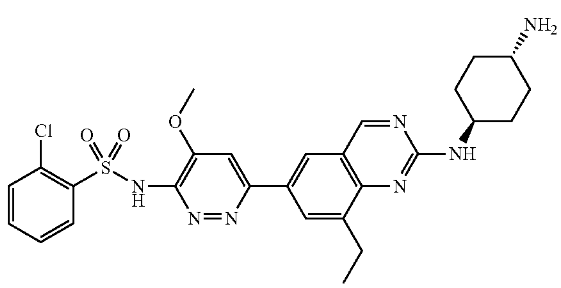 [SMILES: CCc1cc(-c2cc(OC)c(NS(=O)(=O)c3ccccc3Cl)nn2)cc2cnc(N[C@H]3CC[C@H](N)CC3)nc12] | N-(6-(2-(((1r,4r)-4-aminocyclohexyl)amino)-8-ethylquinazolin-6-yl)-4-methoxypyridazin-3-yl)-2-chlorobenzene-sulfonamide | M + H⁺ = 568.2 (LCMS) | δ 8.96 (s, 1H), 8.35 (br s, 1H), 8.19-8.05 (m, 3H), 7.52-7.32 (m, 4H), 4.03-3.79 (m, 4H), 3.14-2.93 (m, 3H), 2.21 (br d, J = 11.0 Hz, 2H), 2.05 (br d, J = 10.6 Hz, 2H), 1.61-1.33 (m, 4H), 1.25 (t, J = 7.5 Hz, 3H) |
| 67 | 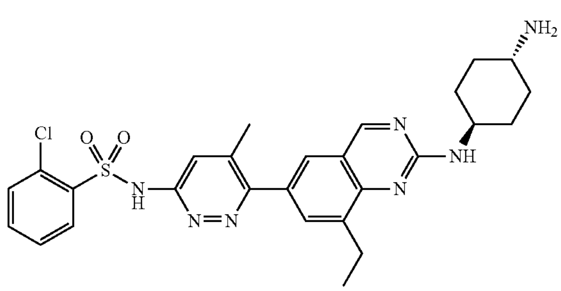 | N-(6-(2-(((1r,4r)-4-aminocyclohexyl)amino)-8-ethylquinazolin-6-yl)-5-methylpyridazin-3-yl)-2-chlorobenzene-sulfonamide | M + H⁺ = 552.1 (LCMS) | δ 9.04 (s, 1H), 8.56 (br s, 1H), 8.22 (br d, J = 7.3 Hz, 1H), 7.75 (s, 1H), 7.68 (br s, 2H), 7.57-7.41 (m, 3H), 3.98 (br t, J = 11.0 Hz, 1H), 3.22-3.01 (m, 3H), 2.41-2.25 (m, 5H), 2.14 (br d, J = 11.5 Hz, 2H), 1.70-1.42 (m, 4H), 1.33 (br t, J = 7.5 Hz, 3H) |

| Comp ID | Structure | Chemical Name | Mass (M + H+) | 1H NMR (CD3OD, 400 MHz) |
|---|---|---|---|---|
| 68 | 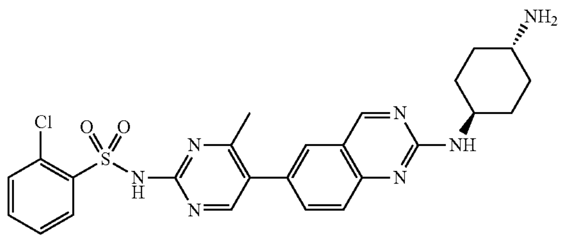 | N-(5-(2-(((1r,4r)-4-aminocyclohexyl)amino)quinazolin-6-yl)-4-methylpyrimidin-2-yl)-2-chlorobenzene-sulfonamide | M + H+ = 524 | δ 9.04 (s, 1H), 8.50 (br s, 1H), 8.31 (dd, J = 1.3, 7.7 Hz, 1H), 8.22 (s, 1H), 7.71-7.61 (m, 2H), 7.60-7.47 (m, 4H), 4.03-3.90 (m, 1H), 3.15 (tt, J = 3.9, 11.6 Hz, 1H), 2.29 (s, 3H), 2.23 (br d, J = 11.5 Hz, 2H), 2.12 (br d, J = 12.6 Hz, 2H), 1.66-1.40 (m, 4H). |
| 69 | 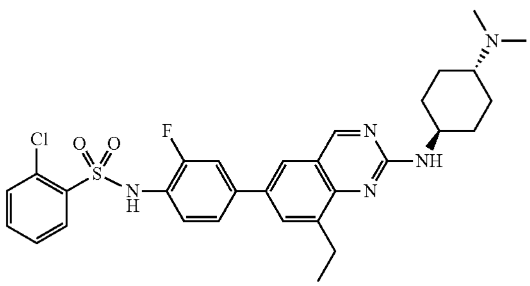 [SMILES: CCc1cc(-c2ccc(NS(=O)(=O)c3ccccc3Cl)c(F)c2)cc2cnc(N[C@H]3CC[C@H](N(C)C)CC3)nc12] | 2-chloro-N-(4-(2-(((1r,4r)-4-(dimethylamino)cyclohexyl)amino)-8-ethylquinazolin-6-yl)-2-fluorophenyl)ben-zenesulfsulfonamide | M + H+ = 582.2 (LCMS) | δ 9.01 (s, 1H), 8.56 (br s, 1H), 8.03 (d, J = 7.7 Hz, 1H), 7.77 (br s, 2H), 7.66-7.54 (m, 2H), 7.51-7.34 (m, 4H), 3.98 (br t, J = 11.6 Hz, 1H), 3.22-3.02 (m, 3H), 2.82 (s, 6H), 2.39 (br d, J = 12.0 Hz, 2H), 2.18 (br d, J = 12.1 Hz, 2H), 1.78-1.63 (m, 2H), 1.57-1.41 (m, 2H), 1.34 (t, J = 7.5 Hz, 2H) |
| 70 | 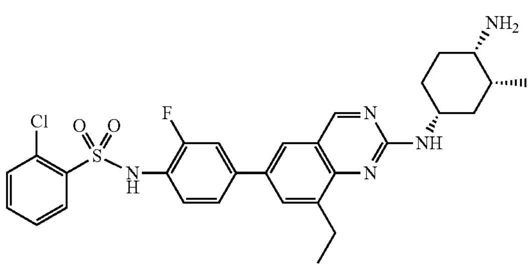 [SMILES: CCc1cc(-c2ccc(NS(=O)(=O)c3ccccc3Cl)c(F)c2)cc2cnc(N[C@@H]3CC[C@H](N)[C@H](C)C3)nc12] | N-(4-(2-(((1R,3R,4S)-4-amino-3-methylcyclohexyl)amino)-8-ethylquinazolin-6-yl)-2-fluorophenyl)-2-chlorobenzene-sulfonamide | M + H+ = 568.2 (LCMS) | δ 9.04 (s, 1H), 8.55 (br s, 1H), 8.03 (dd, J = 1.3, 7.9 Hz, 1H), 7.79 (s, 2H), 7.65-7.55 (m, 2H), 7.52-7.32 (m, 4H), 4.07 (ddd, J = 3.9, 7.6, 11.4 Hz, 1H), 3.46 (br s, 1H), 3.16-3.02 (m, 2H), 2.27-2.04 (m, 4H), 2.03-1.88 (m, 1H), 1.52-1.26 (m, 5H), 1.11 (d, J = 6.8 Hz, 3H) |
| 71 | 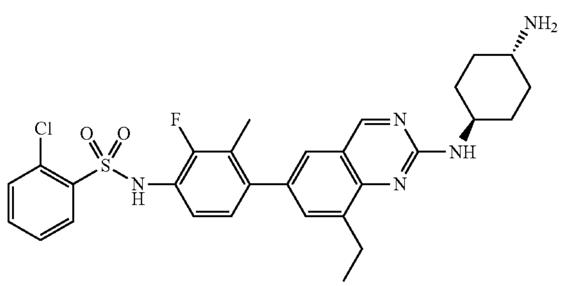 | N-(4-(2-(((1r,4r)-4-aminocyclohexyl)amino)-8-ethylquinazolin-6-yl)-2-fluoro-3-methylphenyl)-2-chlorobenzene-sulfonamide | M + H+ = 568.0 (LCMS) | δ 8.98 (s, 1H), 8.53 (br s, 1H), 8.03 (dd, J = 1.2, 8.0 Hz, 1H), 7.66-7.53 (m, 2H), 7.49-7.39 (m, 3H), 7.28 (t, J = 8.2 Hz, 1H), 6.97 (d, J = 8.4 Hz, 1H), 4.04-3.91 (m, 1H), 3.23-3.12 (m, 1H), 3.06 (q, J = 7.5 Hz, 2H), 2.32 (br d, J = 11.9 Hz, 2H), 2.20-2.05 (m, 5H), 1.67-1.42 (m, 4H), 1.31 (t, J = 7.4 Hz, 3H). |
| 72 | 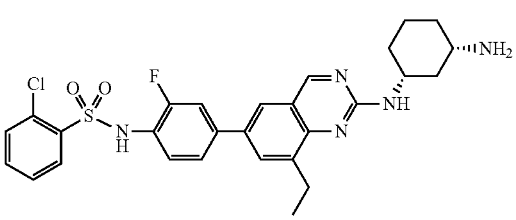 [SMILES: CCc1cc(-c2ccc(NS(=O)(=O)c3ccccc3Cl)c(F)c2)cc2cnc(N[C@@H]3CCC[C@H](N)C3)nc12] | N-(4-(2-(((1R,3S)-3-aminocyclohexyl)amino)-8-ethylquinazolin-6-yl)-2-fluorophenyl)-2-chlorobenzene-sulfonamide | M + H+ = 554.3 (LCMS) | δ 9.00 (s, 1H), 8.55 (br s, 1H), 8.02 (dd, J = 1.4, 8.0 Hz, 1H), 7.79-7.71 (m, 2H), 7.64-7.50 (m, 2H), 7.49-7.27 (m, 4H), 4.08 (ddd, J = 4.0, 7.7, 11.5 Hz, 1H), 3.23 (ddd, J = 3.9, 8.2, 11.8 Hz, 1H), 3.17-2.97 (m, 2H), 2.52 (br d, J = 11.2 Hz, 1H), 2.27-1.88 (m, 3H), 1.66-1.46 (m, 1H), 1.43-1.26 (m, 6H) |

-continued

| Comp ID | Structure | Chemical Name | Mass (M + H+) | 1H NMR (CD3OD, 400 MHz) |
|---|---|---|---|---|
| 73 | 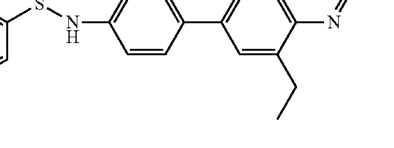 | (S)-2-chloro-N-(4-(8-ethyl-2-(piperidin-3-ylamino)quinazolin-6-yl)-2-fluorophenyl)benzenesulfsulfonamide | M + H+ = 540.2 (LCMS) | δ 9.08 (s, 1H), 8.51 (br s, 1H), 8.01 (dd, J = 1.3, 7.9 Hz, 1H), 7.81 (s, 2H), 7.66-7.34 (m, 6H), 4.45-4.24 (m, 1H), 3.66 (br dd, J = 3.3, 12.1 Hz, 1H), 3.20-2.97 (m, 4H), 2.24-2.06 (m, 2H), 1.97-1.76 (m, 2H), 1.34 (t, J = 7.5 Hz, 3H) |
| 74 | 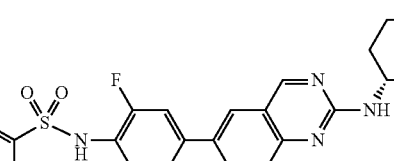 | N-(4-(2-(((1R,3R,4R)-4-amino-3-methylcyclohexyl)amino)-8-ethylquinazolin-6-yl)-2-fluorophenyl)-2-chlorobenzenesulfonamide | M + H+ = 568.2 (LCMS) | δ 9.04 (s, 1H), 8.56 (br s, 1H), 8.09-7.99 (m, 1H), 7.80 (s, 2H), 7.66-7.54 (m, 2H), 7.54-7.38 (m, 4H), 4.05 (br t, J = 11.6 Hz, 1H), 3.17-3.04 (m, 2H), 2.83 (dt, J = 3.9, 10.9 Hz, 1H), 2.37-2.25 (m, 2H), 2.16 (br dd, J = 3.5, 12.3 Hz, 1H), 1.76 (br s, 1H), 1.67-1.41 (m, 2H), 1.38-1.19 (m, 4H), 1.14 (d, J = 6.5 Hz, 3H). |
| 75 | 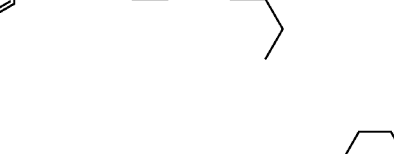 | N-(4-(2-(((1R,3S)-3-aminocyclohexyl)amino)quinazolin-6-yl)-2-fluorophenyl)-2-chlorobenzenesulfonamide | M + H+ = 526.1 (LCMS) | 1H NMR (400 MHz, DMSO-d6) δ 9.08 (s, 1H), 8.22 (br s, 1H), 7.98-7.88 (m, 3H), 7.46-7.28 (m, 5H), 7.18-7.11 (m, 2H), 3.93 (brs, 1H), 2.27 (br s, 1H), 1.91 (br s, 2H), 1.79 (br d, J = 12.8 Hz, 1H), 1.49-1.11 (m, 4H) |
| 76 | 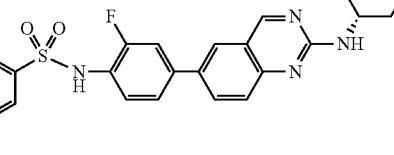 | (S)-2-chloro-N-(2-fluoro-4-(2-(piperidin-3-ylamino)quinazolin-6-yl)phenyl)benzenesulfsulfonamide | M + H+ = 512.1 (LCMS) | δ 9.11 (s, 1H), 8.56 (br s, 1H), 8.06-7.91 (m, 3H), 7.62-7.52 (m, 3H), 7.50-7.44 (m, 1H), 7.44-7.38 (m, 3H), 4.42-4.24 (m, 1H), 3.60 (br dd, J = 3.1, 12.1 Hz, 1H), 3.30 (br s, 1H), 3.04-2.94 (m, 2H), 2.24-2.01 (m, 2H), 1.95-1.67 (m, 2H). |
| 77 | 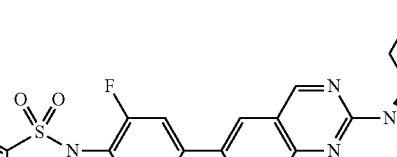 | N-(4-(2-(((1R,3R)-3-aminocyclopentyl)amino)quinazolin-6-yl)-2-fluorophenyl)-2-chlorobenzenesulfonamide | M + H+ = 512.1 (LCMS) | δ 9.05 (s, 1H), 8.52 (br s, 1H), 8.00 (dd, J = 1.3, 7.9 Hz, 1H), 7.95-7.88 (m, 2H), 7.61-7.51 (m, 3H), 7.50-7.43 (m, 1H), 7.43-7.34 (m, 3H), 4.66-4.56 (m, 1H), 3.81 (quin, J = 6.9 Hz, 1H), 2.40-2.25 (m, 2H), 2.15 (t, J = 6.9 Hz, 2H), 1.84-1.66 (m, 2H). |
| 78 | 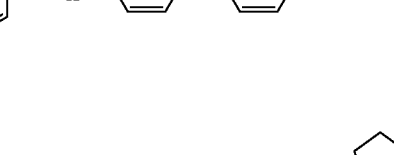 | N-(4-(2-(((1R,3R)-3-aminocyclopentyl)amino)-8-ethylquinazolin-6-yl)-2-fluorophenyl)-2-chlorobenzenesulfonamide | M + H+ = 540.1 (LCMS) | δ 9.00 (s, 1H), 8.48 (br s, 1H), 8.00 (dd, J = 1.3, 7.9 Hz, 1H), 7.75 (s, 2H), 7.61-7.51 (m, 2H), 7.49-7.34 (m, 4H), 4.60 (quin, J = 6.6 Hz, 1H), 3.80 (quin, J = 7.1 Hz, 1H), 3.08 (q, J = 7.4 Hz, 2H), 2.41-2.28 (m, 2H), 2.27-2.12 (m, 2H), 1.88-1.67 (m, 2H), 1.32 (t, J = 7.5 Hz, 3H) |

-continued

| Comp ID | Structure | Chemical Name | Mass (M + H+) | 1H NMR (CD3OD, 400 MHz) |
|---|---|---|---|---|
| 79 | 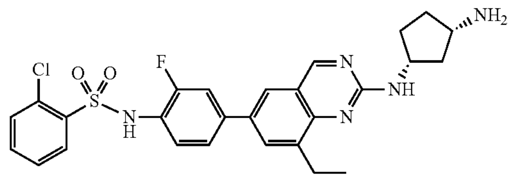 [SMILES: CCc1cc(-c2ccc(NS(=O)(=O)c3ccccc3Cl)c(F)c2)cc2cnc(N[C@@H]3CC[C@H](N)C3)nc12] | N-(4-(2-(((1R,3S)-3-aminocyclopentyl)amino)-8-ethylquinazolin-6-yl)-2-fluorophenyl)-2-chlorobenzenesulfonamide | M + H+ = 540.1 (LCMS) | δ 9.05 (s, 1H), 8.56 (br s, 1H), 8.03 (d, J = 7.9 Hz, 1H), 7.83-7.78 (m, 2H), 7.66-7.53 (m, 2H), 7.52-7.37 (m, 4H), 4.48 (quin, J = 7.0 Hz, 1H), 3.72 (quin, J = 7.2 Hz, 1H), 3.11 (q, J = 7.4 Hz, 2H), 2.85-2.71 (m, 1H), 2.33-2.14 (m, 2H), 2.01-1.81 (m, 2H), 1.76-1.64 (m, 1H), 1.39-1.31 (m, 3H) |
| 80 | 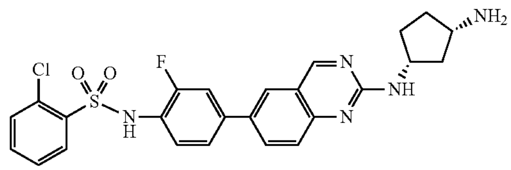 [SMILES: N[C@H]1CC[C@@H](Nc2ncc3cc(-c4ccc(NS(=O)(=O)c5ccccc5Cl)c(F)c4)ccc3n2)C1] | N-(4-(2-(((1R,3S)-3-aminocyclopentyl)amino)quinazolin-6-yl)-2-fluorophenyl)-2-chlorobenzenesulfonamide | M + H+ = 512.1 (LCMS) | δ 9.11 (s, 1H), 8.54 (br s, 1H), 8.08-7.95 (m, 3H), 7.67-7.37 (m, 7H), 4.55-4.39 (m, 1H), 3.80-3.66 (m, 1H), 2.77-2.61 (m, 1H), 2.29-2.11 (m, 2H), 2.05-1.83 (m, 2H), 1.77-1.63 (m, 1H) |
| 81 | 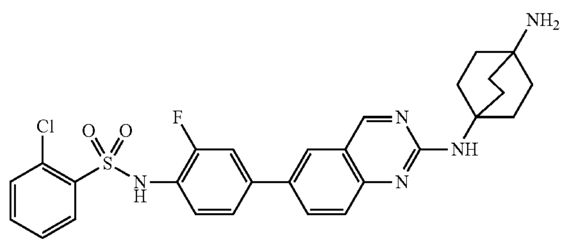 [SMILES: NC12CCC(Nc3ncc4cc(-c5ccc(NS(=O)(=O)c6ccccc6Cl)c(F)c5)ccc4n3)(CC1)CC2] | N-(4-(2-((4-aminobicyclo[2.2.2]octan-1-yl)amino)quinazolin-6-yl)-2-fluorophenyl)-2-chlorobenzenesulfonamide | M + H+ = 552.1 (LCMS) | δ 9.02 (s, 1H), 8.44 (br s, 1H), 8.00 (d, J = 7.9 Hz, 1H), 7.93 (br s, 2H), 7.62-7.52 (m, 3H), 7.51-7.44 (m, 1H), 7.41 (br d, J = 8.2 Hz, 3H), 2.35-2.27 (m, 6H), 1.99-1.92 (m, 6H) |
| 82 | 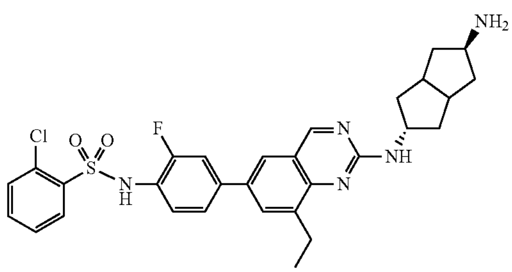 [SMILES: CCc1cc(-c2ccc(NS(=O)(=O)c3ccccc3Cl)c(F)c2)cc2cnc(N[C@H]3CC4C[C@H](N)CC4C3)nc12] | N-(4-(2-(((2r,5r)-5-aminooctahydropentalen-2-yl)amino)-8-ethylquinazolin-6-yl)-2-fluorophenyl)-2-chlorobenzenesulfonamide | M + H+ = 580.1 (LCMS) | δ 8.91 (s, 1H), 8.40 (br s, 1H), 7.91 (dd, J = 1.3, 7.9 Hz, 1H), 7.68 (s, 2H), 7.54-7.44 (m, 2H), 7.41-7.25 (m, 4H), 4.50-4.41 (m, 2H), 3.00 (q, J = 7.4 Hz, 2H), 2.68-2.55 (m, 2H), 2.36-2.22 (m, 2H), 1.97 (br dd, J = 5.9, 12.5 Hz, 2H), 1.66 (td, J = 9.0, 12.5 Hz, 2H), 1.38-1.21 (m, 5H) |
| 83 | 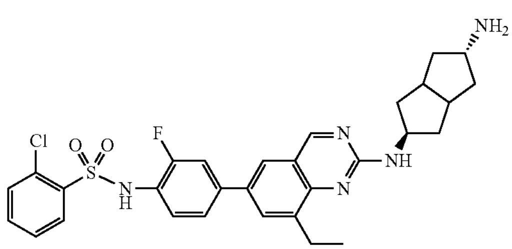 [SMILES: CCc1cc(-c2ccc(NS(=O)(=O)c3ccccc3Cl)c(F)c2)cc2cnc(N[C@H]3CC4C[C@H](N)CC4C3)nc12] | N-(4-(2-(((2r,5r)-5-aminooctahydropentalen-2-yl)amino)-8-ethylquinazolin-6-yl)-2-fluorophenyl)-2-chlorobenzenesulfonamide | M + H+ = 580.2 (LCMS) | δ 8.99 (s, 1H), 8.54 (br s, 1H), 8.00 (d, J = 7.9 Hz, 1H), 7.76 (s, 2H), 7.62-7.52 (m, 2H), 7.49-7.36 (m, 4H), 4.38-4.17 (m, 1H), 3.83-3.66 (m, 1H), 3.13-3.00 (m, 2H), 2.73 (br s, 2H), 2.55-2.46 (m, 2H), 1.94 (br dd, J = 6.4, 12.5 Hz, 2H), 1.85-1.74 (m, 2H), 1.32 (t, J = 7.5 Hz, 3H), 1.28-1.21 (m, 2H) |
| 84 | 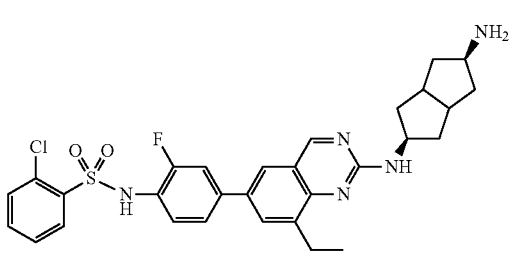 [SMILES: CCc1cc(-c2ccc(NS(=O)(=O)c3ccccc3Cl)c(F)c2)cc2cnc(N[C@H]3CC4C[C@@H](N)CC4C3)nc12] | N-(4-(2-(((2s,5s)-5-aminooctahydropentalen-2-yl)amino)-8-ethylquinazolin-6-yl)-2-fluorophenyl)-2-chlorobenzenesulfonamide | M + H+ = 580.1 (LCMS) | δ 8.99 (s, 1H), 8.48 (br s, 1H), 8.00 (dd, J = 1.3, 7.9 Hz, 1H), 7.75 (s, 2H), 7.62-7.52 (m, 2H), 7.50-7.36 (m, 4H), 4.50-4.38 (m, 1H), 3.57-3.45 (m, 1H), 3.06 (q, J = 7.6 Hz, 2H), 2.67-2.57 (m, 2H), 2.52 (br dd, J = 6.4, 12.5 Hz, 2H), 2.44- |

| Comp ID | Structure | Chemical Name | Mass (M + H⁺) | ¹H NMR (CD₃OD, 400 MHz) |
|---|---|---|---|---|
| | | | | 2.33 (m, 2H), 1.59-1.39 (m, 4H), 1.32 (t, J = 7.5 Hz, 3H) |
| 85 | 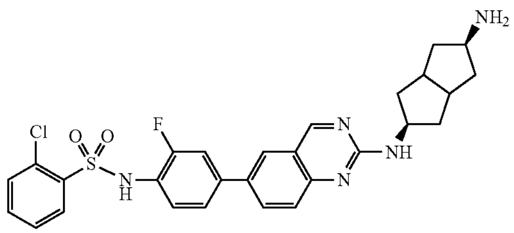 [SMILES: N[C@H]1CC2C[C@@H](Nc3ncc4cc(-c5ccc(NS(=O)(=O)c6ccccc6Cl)c(F)c5)ccc4n3)CC2C1] | N-(4-(2-(((2s,5s)-5-aminooctahydropentalen-2-yl)amino)quinazolin-6-yl)-2-fluorophenyl)-2-chlorobenzenesulfonamide | M + H⁺ = 552.1 (LCMS) | δ 9.06 (s, 1H), 8.47 (br s, 1H), 8.06-7.89 (m, 3H), 7.64-7.53 (m, 3H), 7.52-7.36 (m, 4H), 4.52-4.38 (m, 1H), 3.60-3.44 (m, 1H), 2.72-2.53 (m, 2H), 2.53-2.31 (m, 4H), 1.55-1.37 (m, 4H). |
| 86 | 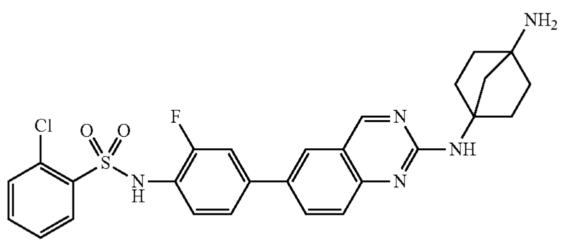 [SMILES: NC12CCC(Nc3ncc4cc(-c5ccc(NS(=O)(=O)c6ccccc6Cl)c(F)c5)ccc4n3)(CC1)C2] | N-(4-(2-((4-aminobicyclo[2.2.1]heptan-1-yl)amino)quinazolin-6-yl)-2-fluorophenyl)-2-chlorobenzenesulfonamide | M + H⁺ = 538.1 (LCMS) | δ 9.06 (s, 1H), 8.59-8.47 (m, 1H), 8.08-7.87 (m, 3H), 7.63-7.34 (m, 7H), 2.48-2.28 (m, 4H), 2.06-1.85 (m, 6H) |
| 87 | 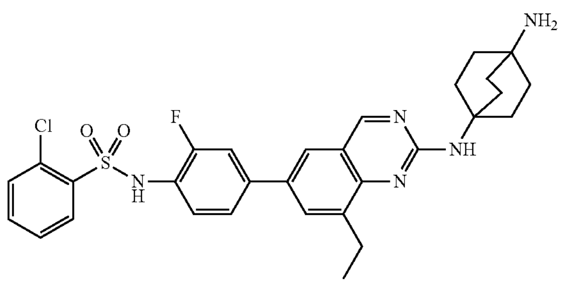 [SMILES: CCc1cc(-c2ccc(NS(=O)(=O)c3ccccc3Cl)c(F)c2)cc2cnc(NC34CCC(N)(CC3)CC4)nc12] | N-(4-(2-((4-aminobicyclo[2.2.2]octan-1-yl)amino)-8-ethylquinazolin-6-yl)-2-fluorophenyl)-2-chlorobenzenesulfonamide | M + H⁺ = 580.2 (LCMS) | δ 8.98 (s, 1H), 8.49 (br s, 1H), 8.02 (dd, J = 1.4, 7.9 Hz, 1H), 7.77 (dd, J = 1.9, 12.2 Hz, 2H), 7.63-7.55 (m, 2H), 7.51-7.38 (m, 4H), 3.10 (q, J = 7.5 Hz, 2H), 2.42-2.32 (m, 6H), 2.04-1.94 (m, 6H), 1.36 (t, J = 7.5 Hz, 3H) |
| 88 | 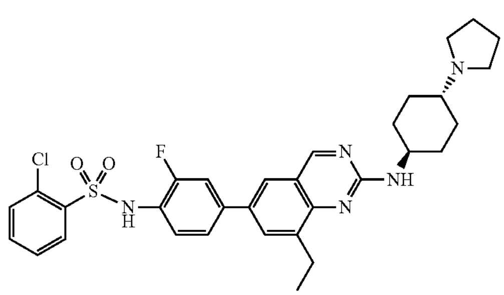 [SMILES: CCc1cc(-c2ccc(NS(=O)(=O)c3ccccc3Cl)c(F)c2)cc2cnc(N[C@H]3CC[C@H](N4CCCC4)CC3)nc12] | 2-chloro-N-(4-(8-ethyl-2-(((1r,4r)-4-(pyrrolidin-1-yl)cyclohexyl)amino)quinazolin-6-yl)-2-fluorophenyl)benzenesulfonamide | M + H⁺ = 608.3 (LCMS) | δ 9.02 (s, 1H), 8.57 (br s, 1H), 8.03 (d, J = 7.9 Hz, 1H), 7.79 (s, 2H), 7.64-7.54 (m, 2H), 7.51-7.39 (m, 4H), 3.98 (br t, J = 11.4 Hz, 1H), 3.33-3.29 (m, 4H), 3.12-3.01 (m, 3H), 2.44-2.24 (m, 4H), 2.07 (br s, 4H), 1.73-1.59 (m, 2H), 1.54-1.42 (m, 2H), 1.35 (t, J = 7.5 Hz, 3H) |
| 89 | 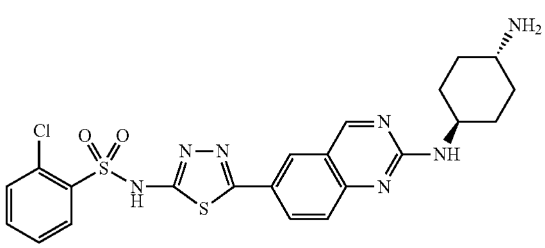 [SMILES: N[C@H]1CC[C@H](Nc2ncc3cc(-c4nnc(NS(=O)(=O)c5ccccc5Cl)s4)ccc3n2)CC1] | N-(5-(2-(((1r,4r)-4-aminocyclohexyl)amino)quinazolin-6-yl)-1,3,4-thiadiazol-2-yl)-2-chlorobenzenesulfonamide | M + H⁺ = 516.1 (LCMS) | δ 9.13 (br s, 1H), 8.19 (s, 1H), 8.10 (br d, J = 9.3 Hz, 1H), 8.02 (d, J = 2.0 Hz, 1H), 7.96 (dd, J = 1.9, 7.6 Hz, 1H), 7.50-7.31 (m, 5H), 3.80 (br d, J = 12.1 Hz, 1H), 2.98 (br s, 1H), 2.05-1.90 (m, 4H), 1.48-1.27 (m, 4H). |

| Comp ID | Structure | Chemical Name | Mass (M + H⁺) | ¹H NMR (CD₃OD, 400 MHz) |
|---|---|---|---|---|
| 90 | 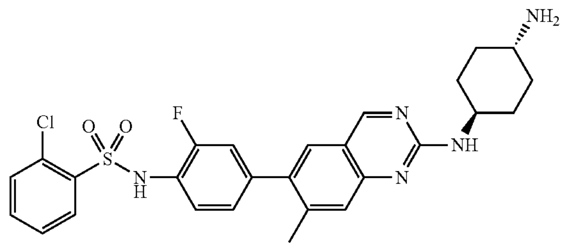 [SMILES: Cc1cc2nc(N[C@H]3CC[C@H](N)CC3)ncc2cc1-c1ccc(NS(=O)(=O)c2ccccc2Cl)c(F)c1] | N-(4-(2-(((1r,4r)-4-aminocyclohexyl)amino)-7-methylquinazolin-6-yl)-2-fluorophenyl)-2-chlorobenzenesulfonamide | M + H⁺ = 540.3 (LCMS) | δ 8.95 (s, 1H), 8.07 (dd, J = 1.6, 7.8 Hz, 1H), 7.60-7.47 (m, 3H), 7.43-7.32 (m, 3H), 7.07-6.94 (m, 2H), 4.00-3.89 (m, 1H), 3.04-2.93 (m, 1H), 2.34 (s, 3H), 2.23-2.16 (m, 2H), 2.12-2.03 (m, 2H), 1.59-1.41 (m, 4H) |
| 91 | 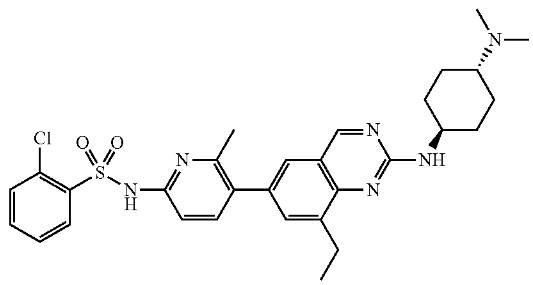 | 2-chloro-N-(5-(2-(((1r,4r)-4-(dimethylamino)cyclohexyl)amino)-8-ethylquinazolin-6-yl)-2-methylpyridin-2-yl)benzenesulfonamide | M + H⁺ = 567.1 (LCMS) | δ 8.99 (s, 1H), 8.40 (br s, 1H), 8.31-8.21 (m, 1H), 7.84 (s, 1H), 7.66-7.45 (m, 5H), 6.83 (s, 1H), 4.03-3.92 (m, 1H), 3.88 (s, 3H), 3.23-3.12 (m, 1H), 3.05 (q, J = 7.4 Hz, 2H), 2.31 (br d, J = 12.3 Hz, 2H), 2.14 (br d, J = 12.1 Hz, 2H), 1.68-1.42 (m, 4H), 1.31 (t, J = 7.5 Hz, 3H) |
| 92 | 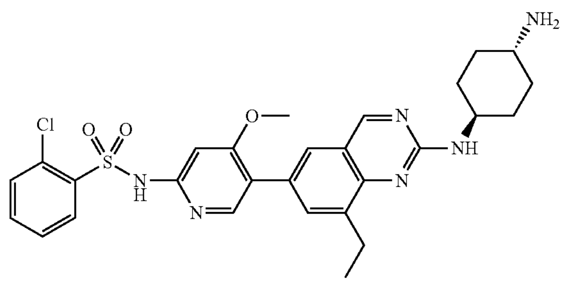 [SMILES: CCc1cc(-c2cnc(NS(=O)(=O)c3ccccc3Cl)cc2OC)cc2cnc(N[C@H]3CC[C@H](N)CC3)nc12] | N-(5-(2-(((1r,4r)-4-aminocyclohexyl)amino)-8-ethylquinazolin-6-yl)-4-methoxypyridin-2-yl)-2-chlorobenzenesulfonamide | M + H⁺ = 567.2 (LCMS) | δ 8.98 (s, 1H), 8.48 (br s, 1H), 8.20-8.12 (m, 1H), 8.06-7.91 (m, 3H), 7.64-7.54 (m, 2H), 7.49 (ddd, J = 2.6, 5.8, 8.0 Hz, 1H), 7.34 (d, J = 2.2 Hz, 1H), 4.02-3.92 (m, 1H), 3.84 (s, 3H), 3.24-3.12 (m, 1H), 3.05 (q, J = 7.6 Hz, 2H), 2.30 (br d, J = 11.0 Hz, 2H), 2.14 (br d, J = 11.9 Hz, 2H), 1.66-1.41 (m, 4H), 1.32 (t, J = 7.4 Hz, 3H) |
| 93 | 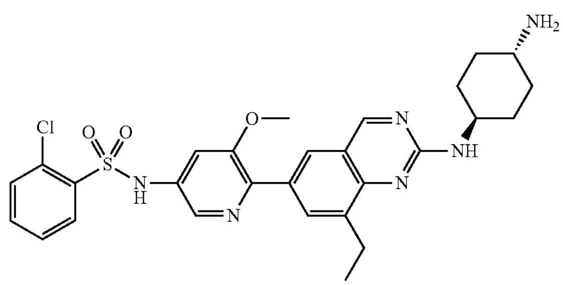 | N-(6-(2-(((1r,4r)-4-aminocyclohexyl)amino)-8-ethylquinazolin-6-yl)-5-methoxypyridin-3-yl)-2-chlorobenzenesulfonamide | M + H⁺ = 552.2 (LCMS) | δ 9.00 (s, 1H), 8.50 (br s, 1H), 8.30 (d, J = 7.3 Hz, 1H), 8.15 (s, 1H), 7.68 (s, 2H), 7.59-7.47 (m, 3H), 4.03-3.92 (m, 1H), 3.22-3.12 (m, 1H), 3.06 (q, J = 7.5 Hz, 2H), 2.37 (s, 3H), 2.30 (br d, J = 11.0 Hz, 2H), 2.14 (br d, J = 11.9 Hz, 2H), 1.66-1.42 (m, 4H), 1.31 (t, J = 7.5 Hz, 3H) |
| 94 | 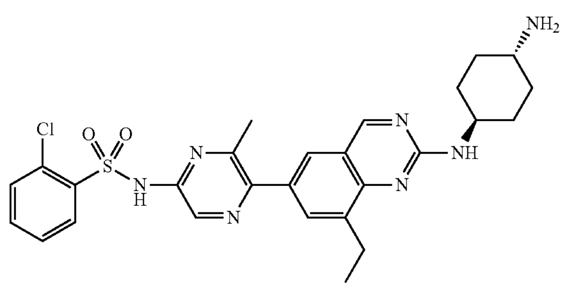 | N-(5-(2-(((1r,4r)-4-aminocyclohexyl)amino)-8-ethylquinazolin-6-yl)-6-methylpyrazin-2-yl)-2-chlorobenzenesulfonamide | M + H⁺ = 582.2 (LCMS) | δ 9.01 (s, 1H), 8.56 (br s, 1H), 8.03 (d, J = 7.7 Hz, 1H), 7.77 (br s, 2H), 7.66-7.54 (m, 2H), 7.51-7.34 (m, 4H), 3.98 (br t, J = 11.6 Hz, 1H), 3.22-3.02 (m, 3H), 2.82 (s, 6H), 2.39 (br d, J = 12.0 Hz, 2H), 2.18 (br d, J = 12.1 Hz, 2H), 1.78-1.63 (m, 2H), 1.57-1.41 (m, 2H), 1.34 (t, J = 7.5 Hz, 2H) |

Example 1: Synthesis of 2-chloro-N-(5-(2-(((1r,4r)-4-(dimethylamino)cyclohexyl)amino)-8-ethylquinazolin-6-yl)-6-methylpyridin-2-yl)benzenesulfonamide (91)

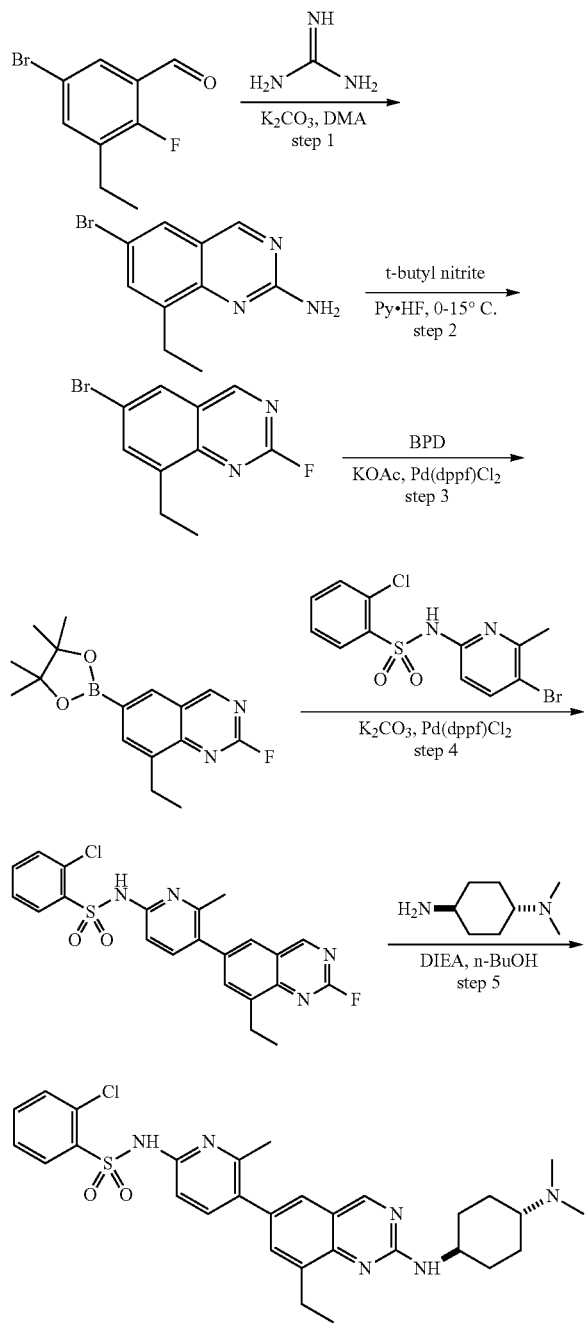

Step 1:

To a solution of guanidine (1.7 g, 13.8 mmol, $H_2CO_3$) and $K_2CO_3$ (5.7 g, 41.4 mmol) in DMA (60.0 mL) was dropwise added 5-bromo-3-ethyl-2-fluorobenzaldehyde (3.0 g, 13.8 mmol) in DMA (9.0 ml). The mixture was stirred at 160° C. for 1 h. The reaction mixture was concentrated under reduced pressure to give a residue. The residue was purified by column chromatography (SiO$_2$, Petroleum ether/Ethyl acetate=50/1 to 10/1) to give 6-bromo-8-ethylquinazolin-2-amine (1.4 g, 3.4 mmol, 24.7% yield). M+H$^+$=257.8 (LCMS).

Step 2:

To a solution of 6-bromo-8-ethylquinazolin-2-amine (10 g, 39.6 mmol) in pyridine (100.0 mL) was added pyridine hydrofluoride (220.0 g, 2.2 mol, 200.0 mL) at −40° C. The mixture was stirred at −40° C. for 15 min. Then tert-butyl nitrite (8.2 g, 79.3 mmol, 9.4 mL) was added. The mixture was stirred at 20° C. for 12 h. The mixture was poured into ice water and adjusted pH=7 with sat. NaHCO$_3$, extracted with ethyl acetate (500.0 mL×3). The combined organic layers were washed with brine (200.0 mL×3), dried over Na$_2$SO$_4$, filtered and concentrated under reduced pressure to give a residue. The residue was purified by column chromatography (SiO$_2$, Petroleum ether/Ethyl acetate=I/O to 10/1) to afford 6-bromo-8-ethyl-2-fluoroquinazoline (11.4 g, 43.9 mmol, 55.4% yield). M+H$^+$=257.0 (LCMS); $^1$H NMR (400 MHz, CHLOROFORM-d) δ 9.26 (d, J=2.6 Hz, 1H), 8.00 (d, J=2.2 Hz, 1H), 7.87 (d, J=1.1 Hz, 1H), 3.18 (q, J=7.5 Hz, 2H), 1.37 (t, J=7.5 Hz, 3H).

Step 3:

To a solution of 6-bromo-8-ethyl-2-fluoroquinazoline (6.0 g, 23.5 mmol) and KOAc (3.5 g, 35.3 mmol) in dioxane (100.0 mL) were added 4,4,4',4',5,5,5',5'-octamethyl-2,2'-bi(1,3,2-dioxaborolane) (7.2 g, 28.2 mmol) and Pd(dppf)Cl$_2$ (1.7 g, 2.3 mmol). The mixture was stirred at 90° for 12 h under N$_2$. The mixture was concentrated to get crude residue. The residue was purified by column chromatography (SiO$_2$, Petroleum ether/Ethyl acetate=I/O to 3/1) to give 8-ethyl-2-fluoro-6-(4,4,5,5-tetramethyl-1,3,2-dioxaborolan-2-yl)quinazoline (7.1 g, 23.5 mmol, 99.9% yield).

Step 4:

To a solution of 8-ethyl-2-fluoro-6-(4,4,5,5-tetramethyl-1,3,2-dioxaborolan-2-yl)quinazoline (7.1 g, 23.5 mmol) and K$_2$CO$_3$ (9.7 g, 70.4 mmol) in dioxane (150.0 mL) and H$_2$O (15.0 mL) were added N-(5-bromo-6-methylpyridin-2-yl)-2-chlorobenzenesulfonamide (10.2 g, 28.2 mmol) and Pd(dppf)Cl$_2$ (859 mg, 1.1 mmol). The mixture was stirred at 90° C. for 12 h under N$_2$. The mixture was concentrated to get a crude residue. The residue was purified by column chromatography (SiO$_2$, Petroleum ether/Ethyl acetate=1/0 to 0/1) to afford 2-chloro-N-(5-(8-ethyl-2-fluoroquinazolin-6-yl)-6-methylpyridin-2-yl)benzenesulfonamide (8.5 g, 15.3 mmol, 65.2% yield). M+H$^+$=457.1 (LCMS)

Step 5:

To a solution of 2-chloro-N-(5-(8-ethyl-2-fluoroquinazolin-6-yl)-6-methylpyridin-2-yl)benzenesulfonamide (8.5 g, 18.6 mmol) in n-BuOH (60.0 mL) was added (1r,4r)-N1,N1-dimethylcyclohexane-1,4-diamine(13.3 g, 74.4 mmol, HCl) and DIEA (16.8 g, 130.2 mmol, 22.6 mL). The mixture was stirred at 100° C. for 12 h. The mixture was concentrated to get crude residue. The residue was purified by prep-HPLC (FA condition) to afford 2-chloro-N-(5-(2-(((1r,4r)-4-(dimethylamino)cyclohexyl)amino)-8-ethylquinazolin-6-yl)-6-methylpyridin-2-yl)benzenesulfonamide (3.6 g, 5.7 mmol, 30.7% yield, formic acid salt (FA)). M+H$^+$=579.2 (LCMS); $^1$H NMR (400 MHz, METHANOL-d$_4$) δ 8.99 (s, 1H), 8.32 (s, 2H), 8.22 (d, J=7.5 Hz, 1H), 7.67 (d, J=8.9 Hz, 1H), 7.56-7.42 (m, 5H), 7.20 (d, J=8.9 Hz, 1H), 4.04-3.92 (m, 1H), 3.30-3.22 (m, 1H), 3.07 (q, J=7.4 Hz, 2H), 2.89 (s, 6H), 2.37 (s, 5H), 2.19 (br d, J=11.7 Hz, 2H), 1.81-1.66 (m, 2H), 1.56-1.41 (m, 2H), 1.31 (t, J=7.5 Hz, 3H).

Example 2: Synthesis of 2-chloro-N-(5-(2-(((1r,4r)-4-(dimethylamino)cyclohexyl)amino)-8-ethylquinazolin-6-yl)-3-fluoropyridin-2-yl)benzenesulfonamide (95)

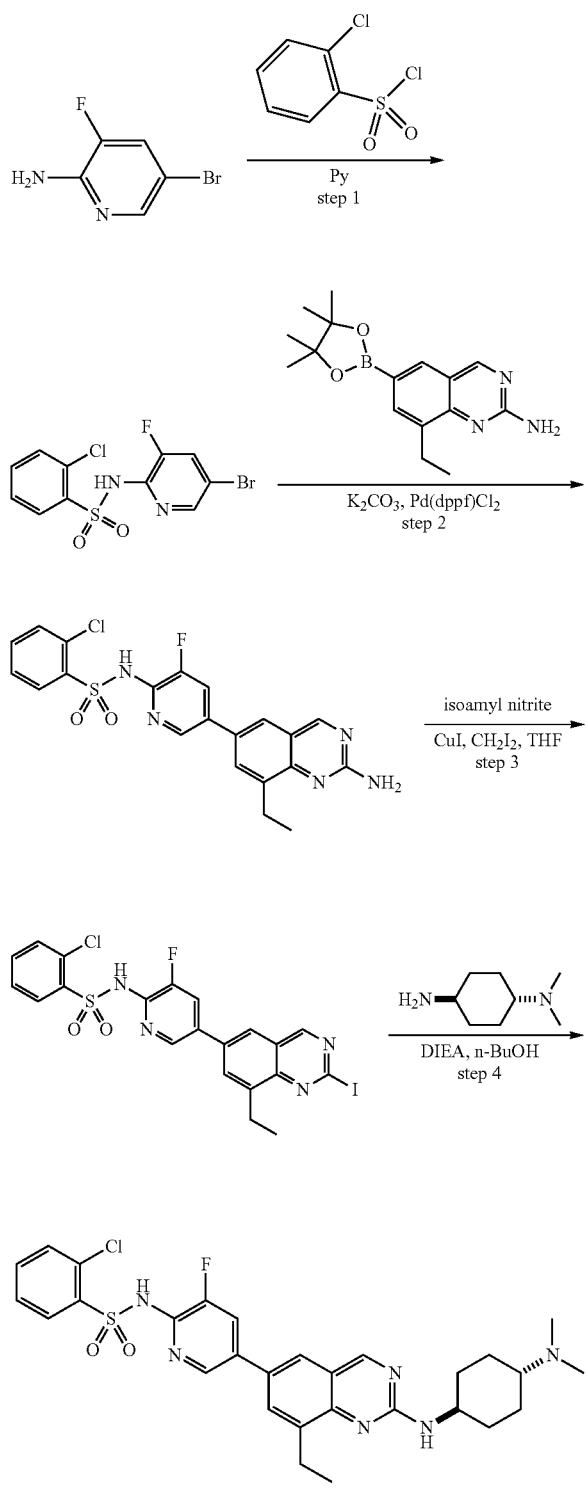

Step 1:

To a solution of 5-bromo-3-fluoropyridin-2-amine (815 mg, 4.2 mmol) in pyridine (20.0 mL) was added 2-chlorobenzene-1-sulfonyl chloride (1.4 g, 6.4 mmol, 871.5 uL). The mixture was stirred at 45° C. for 24 h. The mixture was concentrated under reduced pressure to give a residue. The residue was purified by column chromatography ($SiO_2$) to give N-(5-bromo-3-fluoropyridin-2-yl)-2-chlorobenzenesulfonamide (1.2 g, 2.0 mmol, 47.6% yield). $M+H^+$=366.8 (LCMS).

Step 2:

To a solution of N-(5-bromo-3-fluoropyridin-2-yl)-2-chlorobenzenesulfonamide (1.2 g, 3.2 mmol) and 8-ethyl-6-(4,4,5,5-tetramethyl-1,3,2-dioxaborolan-2-yl)quinazolin-2-amine (1.2 g, 3.8 mmol) in dioxane (30.0 mL) and $H_2O$ (3.0 mL) was added $K_2CO_3$ (1.3 g, 9.6 mmol) and Pd(dppf)$Cl_2$ (236 mg, 322.7 umol). The mixture was stirred at 90° C. for 12 h under $N_2$. The reaction mixture was concentrated in reduced pressure to give a residue. The residue was washed with $H_2O$ (20.0 mL×3) and ethyl acetate (20.0 mL×3). Then the residue was added MeOH (30.0 mL), THF (30.0 mL) and stirred at 25° C. for 12 h. Then the mixture was filtered. The filtrate was concentrated in reduced pressure to give a residue. The residue was purified by column chromatography ($SiO_2$) to give N-(5-(2-amino-8-ethylquinazolin-6-yl)-3-fluoropyridin-2-yl)-2-chlorobenzenesulfonamide (429 mg, crude). $M+H^+$=458.2 (LCMS).

Step 3:

To a solution of N-(5-(2-amino-8-ethylquinazolin-6-yl)-3-fluoropyridin-2-yl)-2-chlorobenzenesulfonamide (200 mg, 436.7 umol) and CuI (83 mg, 436.7 umol) in THF (5.0 mL) was added $CH_2I_2$ (584 mg, 2.1 mmol, 176.1 uL) and isopentyl nitrite (153 mg, 1.3 mmol, 176.4 uL). The mixture was stirred at 80° C. for 12 h. The reaction mixture was basified pH to 8-9 with $NH_3 \cdot H_2O$ (25% solution). Then the mixture was added water (20.0 mL) and extracted with ethyl acetate (40.0 mL×4). The combined organic phase was washed with brine (10.0 mL×3), dried with anhydrous $Na_2SO_4$, filtered and concentrated in vacuum to get a residue. The residue was purified by prep-HPLC (FA condition) to give 2-chloro-N-(5-(8-ethyl-2-iodoquinazolin-6-yl)-3-fluoropyridin-2-yl)benzeneesulfonamide (42 mg, 61.4 umol, 15.1% yield, FA). $M+H^+$=569.0 (LCMS).

Step 4:

To a solution of 2-chloro-N-(5-(8-ethyl-2-iodoquinazolin-6-yl)-3-fluoropyridin-2-yl)benzeneesulfonamide (37 mg, 65.0 umol) and (1r,4r)-N1,N1-dimethylcyclohexane-1,4-diamine (133 mg, 520.4 umol, TFA) in n-BuOH (2.0 mL) was basified pH to 8 with DIEA and added DIEA (25 mg, 195.1 umol, 33.9 uL). The mixture was taken up into a microwave tube. The sealed tube was heated at 150° C. for 6 h under microwave. The mixture was concentrated under reduced pressure to give a residue. The residue was purified by pre-HPLC (FA condition) to give 2-chloro-N-(5-(2-(((1r,4r)-4-(dimethylamino)cyclohexyl)amino)-8-ethylquinazolin-6-yl)-3-fluoropyridin-2-yl)benzenesulfonamide (5.2 mg, 7.6 umol, 11.7% yield, FA). $M+H^+$=583.2 (LCMS); $^1$H NMR (400 MHz, DMSO-$d_6$) δ 9.03 (br s, 1H), 8.17 (br s, 1H), 8.09-7.94 (m, 2H), 7.79 (s, 2H), 7.60 (br d, J=13.0 Hz, 1H), 7.41-7.23 (m, 4H), 3.79 (br s, 1H), 3.03-2.86 (m, 3H), 2.61 (s, 6H), 2.16 (br s, 2H), 2.00 (br d, J=10.4 Hz, 2H), 1.58-1.44 (m, 2H), 1.42-1.22 (m, 5H).

Example 3: Synthesis of N-(6-(2-(((1r,4r)-4-amino-cyclohexyl)amino)-8-ethylquinazolin-6-yl)-5-ethyl-pyridazin-3-yl)-2-chlorobenzenesulfonamide (96)

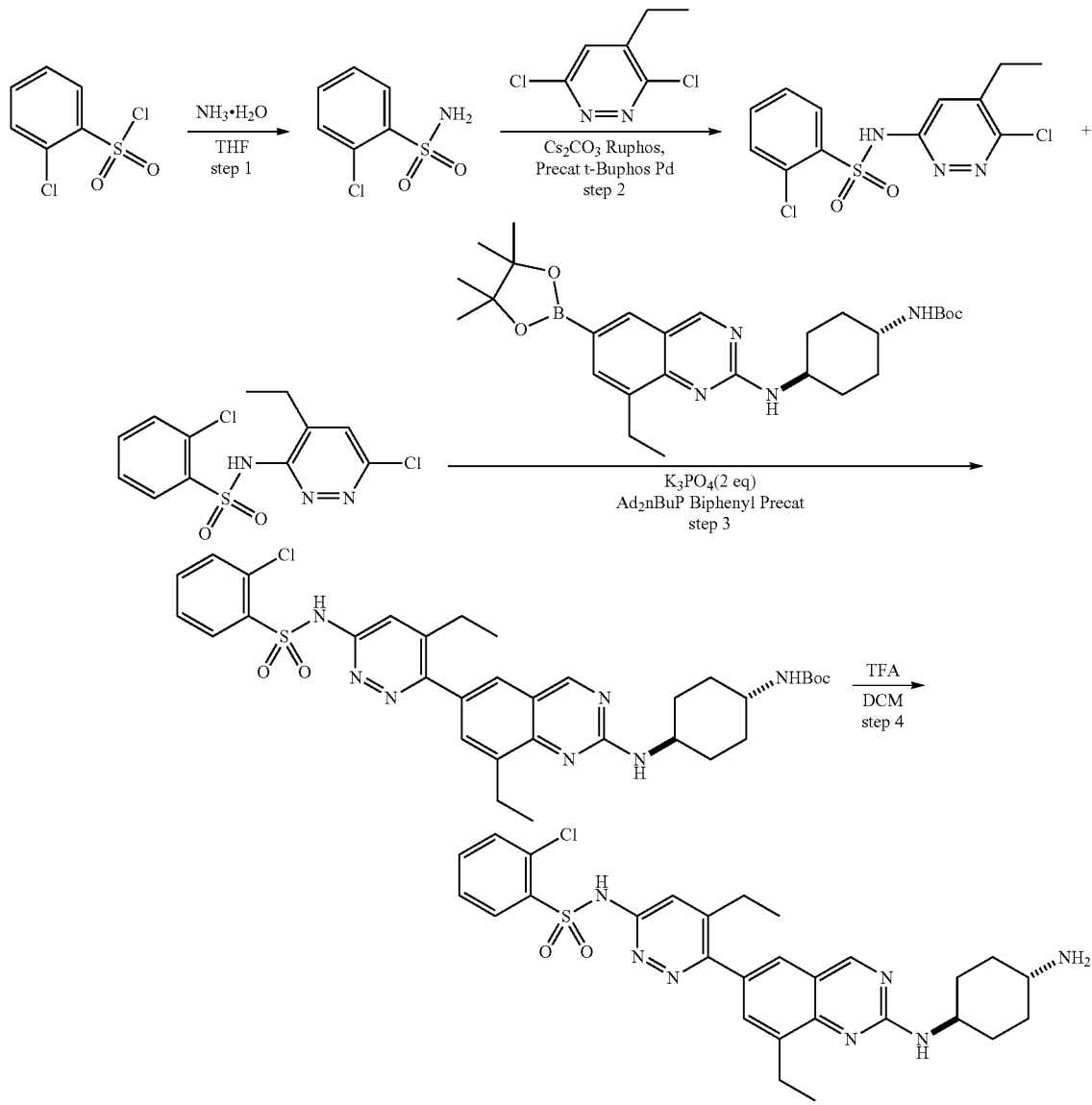

Step 1:

To a solution of 2-chlorobenzene-1-sulfonyl chloride (2.0 g, 9.5 mmol, 1.3 mL) in THF (20.0 mL) was added $NH_3 \cdot H_2O$ (3.3 g, 28.4 mmol, 3.7 mL, 25% solution) at 0° C. The mixture was stirred at 0° C. for 10 min and then warmed to 20° C. for 2 h. The reaction mixture was concentrated to afford 2-chlorobenzenesulfonamide (1.8 g, 9.4 mmol, 99.1% yield). 1H NMR (400 MHz, DMSO-d6) δ 7.96 (dd, J=1.4, 7.8 Hz, 1H), 7.65-7.55 (m, 2H), 7.54-7.34 (m, 7H).

Step 2:

A mixture of 3,6-dichloro-4-ethylpyridazine (500 mg, 2.8 mmol), 2-chlorobenzenesulfonamide (595 mg, 3.1 mmol), $Cs_2CO_3$ (2.7 g, 8.5 mmol), dicyclohexyl-[2-(2,6-diisopropoxyphenyl)phenyl]phosphane (132 mg, 282.4 umol) and [2-(2-aminoethyl)phenyl]-chloro-palladium; ditert-butyl-[2-(2,4,6-triisopropylphenyl)phenyl]phosphane (194 mg, 282.4 umol) in THF (30.0 mL) was degassed and purged with $N_2$ for 3 times, and then the mixture was stirred at 80° C. for 12 h under $N_2$ atmosphere. The reaction was concentrated to give a residue. The residue was purified by column chromatography ($SiO_2$) to give a crude product (280 mg). The crude product was purified by prep-HPLC (TFA condition) to afford 2-chloro-N-(6-chloro-5-ethylpyridazin-3-yl)benzenesulfonamide (20 mg, 54.2 umol, 1.9% yield). $^1$H NMR (400 MHz, METHANOL-$d_4$) δ 8.20 (d, J=7.7 Hz, 1H), 7.64 (br s, 1H), 7.57-7.53 (m, 2H), 7.52-7.46 (m, 1H), 2.71 (q, J=7.5 Hz, 2H), 1.23 (t, J=7.4 Hz, 3H); and 2-chloro-N-(6-chloro-4-ethylpyridazin-3-yl)benzenesulfonamide (100 mg, 270.9 umol, 10.7% yield). $^1$H NMR (400 MHz, METHANOL-$d_4$) δ 8.21 (d, J=7.6 Hz, 1H), 7.60-7.56 (m, 2H), 7.56-7.48 (m, 2H), 2.61 (br d, J=6.7 Hz, 2H), 1.18 (br t, J=7.2 Hz, 3H).

Step 3:

A mixture of 2-chloro-N-(6-chloro-4-ethylpyridazin-3-yl)benzenesulfonamide (54 mg, 161.1 umol), tert-butyl ((1r,4r)-4-((8-ethyl-6-(4,4,5,5-tetramethyl-1,3,2-dioxaborolan- 2-yl)quinazolin-2-yl)amino)cyclohexyl)carbamate (80 mg, 161.1 umol), K₃PO₄ (0.5 M, 644.6 uL) and [2-(2-aminophenyl)phenyl]-chloro-palladium; bis(1-adamantyl)-butylphosphane (11 mg, 16.1 umol) were degassed and purged with N₂ for 3 times and taken up into a microwave tube in 2-methyltetrahydrofuran (2.5 mL). The sealed tube was heated at 120° C. for 180 min under microwave. The reaction was concentrated to give a residue. The residue was purified by prep-TLC (SiO₂) to give tert-butyl ((1r,4r)-4-((6-(6-((2-chlorophenyl)sulfonamido)-4-ethylpyridazin-3-yl)-8-ethylquinazolin-2-yl)amino)cyclohexyl)carbamate (60 mg, crude). M+H⁺=666.3 (LCMS).

Step 4:

To a solution of tert-butyl ((1r,4r)-4-((6-(6-(2-chlorophenylsulfonamido)-4-ethylpyridazin-3-yl)-8-ethylquinazolin-2-yl)amino)cyclohexyl)carbamate (60 mg, 90.1 umol) in DCM (2.0 mL) was added TFA (1.0 mL). The mixture was stirred at 20° C. for 0.5 h. The reaction was concentrated to give a residue. The residue was dissolved in MeOH (1.0 mL) and basified pH to 7 with NH₃.H₂O (25% solution). The residue was purified by prep-HPLC (FA condition) to afford N-(6-(2-(((1r,4r)-4-aminocyclohexyl)amino)-8-ethylquinazolin-6-yl)-5-ethylpyridazin-3-yl)-2-chlorobenzenesulfonamide (5.1 mg, 7.9 umol, 8.8% yield, FA). M+H⁺=566.2 (LCMS); ¹H NMR (400 MHz, METHANOL-d₄) δ 9.08 (br s, 1H), 8.23 (br s, 1H), 8.03-7.38 (m, 7H), 3.99 (br s, 1H), 3.23-3.01 (m, 3H), 2.67 (br s, 2H), 2.31 (br d, J=10.1 Hz, 2H), 2.14 (br d, J=11.0 Hz, 2H), 1.66-1.44 (m, 4H), 1.33 (br t, J=7.4 Hz, 3H), 1.10 (br t, J=7.1 Hz, 3H).

Example 4: Synthesis of 2-chloro-N-(5-(2-(((1r,4r)-4-(dimethylamino)cyclohexyl)amino)-8-ethylquinazolin-6-yl)-3-fluoro-6-methylpyridin-2-yl)benzenesulfonamide (97)

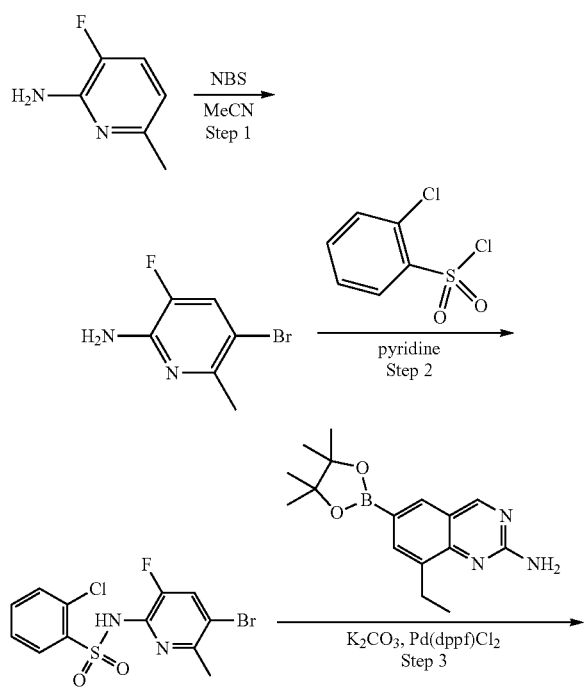

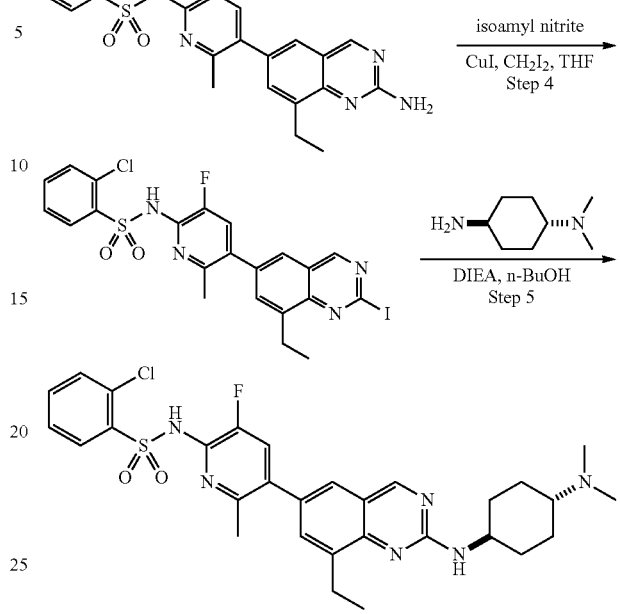

Step 1:

To a solution of 3-fluoro-6-methyl-pyridin-2-amine (500 mg, 3.9 mmol) in MeCN (15.0 mL) was added NBS (705 mg, 3.9 mmol) at 0° C. After addition, the resulting mixture was stirred at 25° C. for 2 h. The reaction mixture was concentrated under reduced pressure. The residue was purified by column chromatography (SiO₂) to afford 5-bromo-3-fluoro-6-methylpyridin-2-amine (750 mg, 3.1 mmol, 78.4% yield). ¹H NMR (CHLOROFORM-d, 400 MHz): δ 7.33 (d, J=9.5 Hz, 1H), 4.81-4.57 (m, 2H), 2.44 (d, J=1.1 Hz, 3H).

Step 2:

To a mixture of 5-bromo-3-fluoro-6-methylpyridin-2-amine (700 mg, 3.41 mmol), 2-chlorobenzenesulfonyl chloride (720 mg, 3.4 mmol, 464.9 uL) in pyridine (20.0 mL) was stirred at 45° C. for 12 h. The reaction mixture was concentrated under reduced pressure. The residue was purified by column chromatography (SiO₂) to afford N-(5-bromo-3-fluoro-6-methylpyridin-2-yl)-2-chlorobenzenesulfonamide (500 mg, 1.1 mmol, 34.7% yield). ¹H NMR (CHLOROFORM-d, 400 MHz): δ 8.27 (d, J=7.9 Hz, 1H), 7.53-7.33 (m, 4H), 2.24 (s, 3H).

Step 3:

A mixture of N-(5-bromo-3-fluoro-6-methylpyridin-2-yl)-2-chlorobenzenesulfonamide (200 mg, 526.8 umol), 8-ethyl-6-(4,4,5,5-tetramethyl-1,3,2-dioxaborolan-2-yl)quinazolin-2-amine (131 mg, 439.0 umol), K2CO3 (60 mg, 439.0 umol), Pd(dppf)Cl2 (32 mg, 43.9 umol) in dioxane (3.0 mL) and H2O (0.3 mL) was degassed and purged with N2 for 3 times, and then the mixture was stirred at 90° C. for 12 h under N2 atmosphere. The reaction mixture was concentrated under reduced pressure. The residue was purified by prep-TLC (SiO₂) to afford N-(5-(2-amino-8-ethylquinazolin-6-yl)-3-fluoro-6-methylpyridin-2-yl)-2-chlorobenzenesulfonamide (116 mg, 196.6 umol, 44.7% yield).

Step 4:

To a solution of N-(5-(2-amino-8-ethylquinazolin-6-yl)-3-fluoro-6-methylpyridin-2-yl)-2-chlorobenzenesulfonamide (116 mg, 245.8 umol), CuI (46 mg, 245.8 umol) in THF (5.0 mL) was added CH$_2$I$_2$(329 mg, 1.2 mmol, 99.1 uL) and isoamyl nitrite (86 mg, 737.3 umol, 99.2 uL). The mixture was stirred at 80° C. for 12 h. The reaction mixture was concentrated under reduced pressure. The residue was purified by prep-TLC (SiO$_2$) to afford 2-chloro-N-(5-(8-ethyl-2-iodoquinazolin-6-yl)-3-fluoro-6-methylpyridin-2-yl)benzenesulfonamide (46 mg, 62.5 umol, 25.4% yield). M+H$^+$=582.9 (LCMS).

Step 5:

To a solution of 2-chloro-N-(5-(8-ethyl-2-iodoquinazolin-6-yl)-3-fluoro-6-methylpyridin-2-yl)benzenesulfonamide (46 mg, 78.9 umol), (1r,4r)-N1,N1-dimethylcyclohexane-1,4-diamine (161 mg, 631.4 umol, TFA) in n-BuOH (2.0 mL) was adjusted pH to 8-9 with DIEA. Then DIEA (30 mg, 236.7 umol, 41.2 uL) was added. The mixture was stirred at 100° C. for 12 h. (1r,4r)-N1,N1-dimethylcyclohexane-1,4-diamine (161 mg) was added. The reaction stirred for another 12 h at 100° C. The reaction mixture was concentrated under reduced pressure. The residue was purified by prep-HPLC (FA condition) to afford 2-chloro-N-(5-(2-(((1r,4r)-4-(dimethylamino)cyclohexyl)amino)-8-ethylquinazolin-6-yl)-3-fluoro-6-methylpyridin-2-yl)benzenesulfonamide (2.1 mg, 3.1 umol, 4.0% yield, FA). M+H$^+$=597.2 (LCMS); $^1$H NMR (METHANOL-d$_4$, 400 MHz) δ 8.97 (s, 1H), 8.50 (s, 1H), 8.30 (d, J=7.5 Hz, 1H), 7.61-7.43 (m, 4H), 7.38 (d, J=10.8 Hz, 1H), 3.96 (br t, J=11.8 Hz, 1H), 3.18-3.09 (m, 1H), 3.07-3.00 (m, 2H), 2.81 (s, 6H), 2.37 (br d, J=13.2 Hz, 2H), 2.22-2.11 (m, 5H), 1.75-1.61 (m, 2H), 1.53-1.41 (m, 2H), 1.30 (t, J=7.5 Hz, 3H).

Example 5: Synthesis of 2-chloro-N-(5-(2-(((1r,4r)-4-(dimethylamino)cyclohexyl)amino)-8-ethylquinazolin-6-yl)-6-methoxypyridin-2-yl)benzenesulfonamide (99)

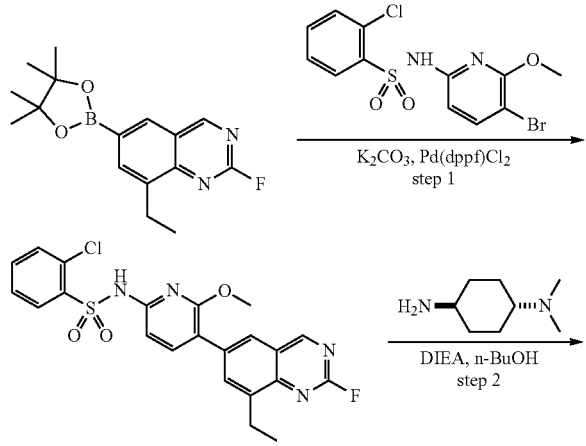

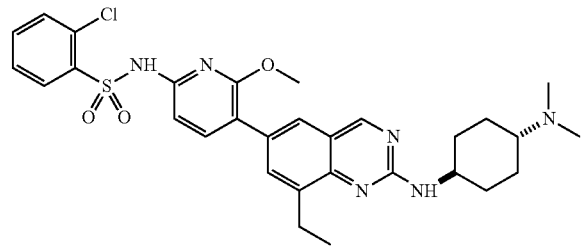

Step 1:

A mixture of N-(5-bromo-6-methoxy-2-pyridyl)-2-chloro-benzenesulfonamide (2.5 g, 6.6 mmol), 8-ethyl-2-fluoro-6-(4,4,5,5-tetramethyl-1,3,2-dioxaborolan-2-yl)quinazoline (2.0 g, 6.6 mmol), K$_2$CO$_3$ (2.7 g, 19.8 mmol), Pd(dppf)Cl$_2$ (484 mg, 661.9 umol) in H$_2$O (2.0 mL) and dioxane (20.0 mL) was degassed and purged with N$_2$ for 3 times, and then the mixture was stirred at 90° C. for 12 h under N$_2$ atmosphere. The reaction mixture was concentrated under reduced pressure to give a residue. The residue was purified by column chromatography (SiO$_2$, Petroleum ether/Ethyl acetate=10/1 to 0/1) to afford 2-chloro-N-(5-(8-ethyl-2-fluoroquinazolin-6-yl)-6-methoxypyridin-2-yl)benzenesulfonamide (2.0 g, 3.6 mmol, crude). M+H$^+$=473.1 (LCMS)

Step 2:

To a solution of 2-chloro-N-(5-(8-ethyl-2-fluoroquinazolin-6-yl)-6-methoxypyridin-2-yl)benzenesulfonamide (1.5 g, 3.1 mmol) in n-BuOH (30.0 mL) was added DIEA (2.9 g, 22.2 mmol, 3.9 mL) and (1r,4r)-N1,N1-dimethylcyclohexane-1,4-diamine (2.3 g, 12.7 mmol, HCl). The mixture was stirred at 100° C. for 24 h. The reaction mixture was concentrated under reduced pressure to give a residue. The residue was purified by prep-HPLC (FA condition) to afford 2-chloro-N-(5-(2-(((1r,4r)-4-(dimethylamino)cyclohexyl)amino)-8-ethylquinazolin-6-yl)-6-methoxypyridin-2-yl)benzenesulfonamide (1.13 g, 1.6 mmol, 52.1% yield, FA). M+H$^+$=595.2 (LCMS); $^1$H NMR (400 MHz, METHANOL-d$_4$) δ 8.96 (s, 1H), 8.41 (br s, 1H), 8.35-8.30 (m, 1H), 7.71-7.64 (m, 3H), 7.62-7.57 (m, 2H), 7.55-7.50 (m, 1H), 6.66 (d, J=7.9 Hz, 1H), 3.99 (tt, J=3.9, 11.6 Hz, 1H), 3.68 (s, 3H), 3.31-3.24 (m, 1H), 3.05 (q, J=7.4 Hz, 2H), 2.90 (s, 6H), 2.41 (br d, J=11.6 Hz, 2H), 2.20 (br d, J=12.1 Hz, 2H), 1.81-1.66 (m, 2H), 1.57-1.44 (m, 2H), 1.32 (t, J=7.5 Hz, 3H).

Example 6: Synthesis of 2-chloro-N-(5-(2-(((1r,4r)-4-(dimethylamino)cyclohexyl)amino)-7-methylquinazolin-6-yl)-6-methoxypyridin-2-yl)benzenesulfonamide (108)

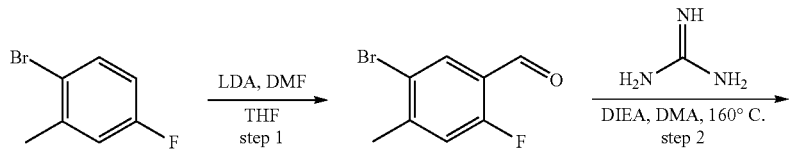

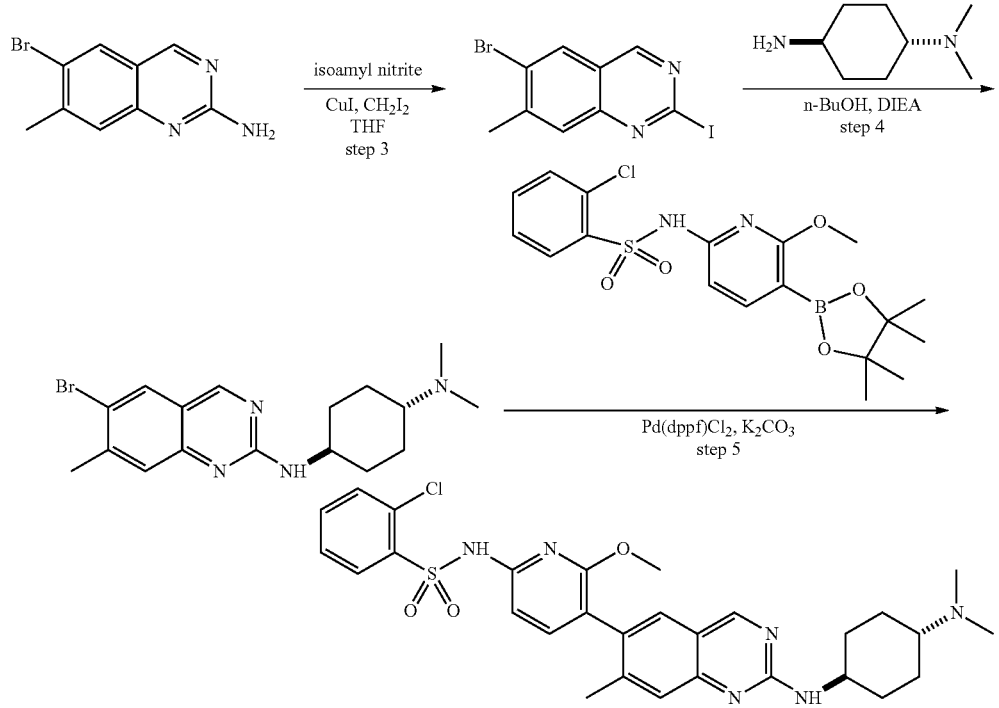

The title compound was synthesized according to the synthetic procedure reported for the preparation of N-(5-(2-(((1r,4r)-4-aminocyclohexyl)amino)-7-ethylquinazolin-6-yl)-6-methoxypyridin-2-yl)-2-chlorobenzenesulfonamide (7.5 mg, 11.2 umol, 4.5% yield, FA). M+H$^+$=581.2 (LCMS); $^1$H NMR (400 MHz, METHANOL-d$_4$) δ 8.93 (s, 1H), 8.57 (br s, 1H), 8.33 (d, J=7.3 Hz, 1H), 7.63-7.58 (m, 2H), 7.52 (ddd, J=3.1, 5.4, 8.1 Hz, 1H), 7.46-7.41 (m, 2H), 7.37 (s, 1H), 6.64 (d, J=7.8 Hz, 1H), 4.04-3.89 (m, 1H), 3.59 (s, 3H), 3.19-3.08 (m, 1H), 2.89-2.65 (m, 6H), 2.30 (br d, J=12.1 Hz, 2H), 2.23-2.09 (m, 5H), 1.79-1.62 (m, 2H), 1.57-1.39 (m, 2H).

Example 7: Synthesis of 2-chloro-N-(5-(2-(((1r,4r)-4-(dimethylamino)cyclohexyl)amino)-8-ethylquinazolin-6-yl)-6-ethylpyridin-2-yl)benzenesulfonamide (117)

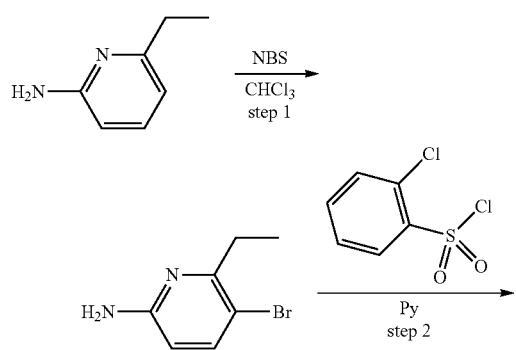

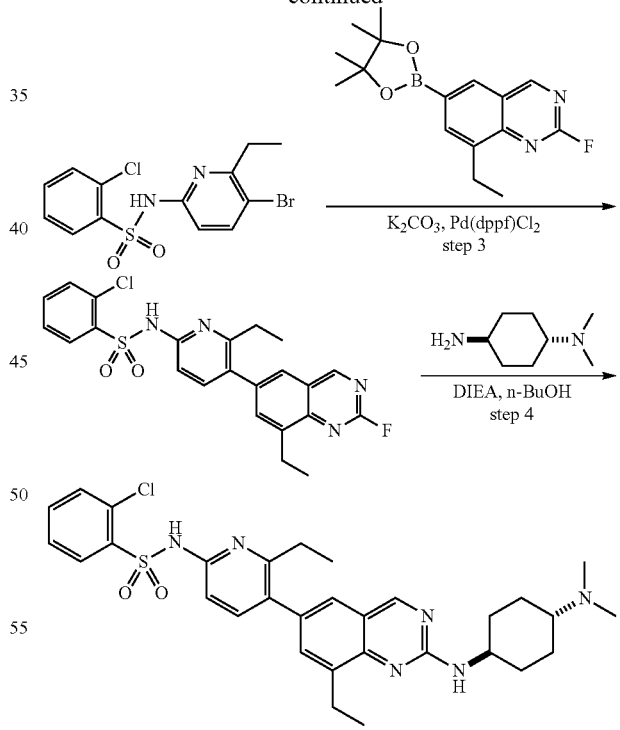

Step 1:
To a solution of 6-ethylpyridin-2-amine (1.8 g, 15.1 mmol) in CHCl$_3$ (50.0 mL) was added NBS (2.7 g, 15.1 mmol) at 0° C. The mixture was stirred at 25° C. for 0.5 h. The reaction mixture was concentrated under reduced pressure. The residue was purified by column chromatography (SiO$_2$) to give 5-bromo-6-ethylpyridin-2-amine (3 g, 14.7 mmol, 97.5% yield). M+H⁺=201.0 (LCMS); ¹H NMR (400 MHz, DMSO-d₆) δ 7.43 (d, J=8.6 Hz, 1H), 6.22 (d, J=8.6 Hz, 1H), 6.03 (s, 2H), 2.62 (q, J=7.6 Hz, 2H), 1.15-1.08 (m, 3H).

Step 2:

To a solution of 5-bromo-6-ethylpyridin-2-amine (1.0 g, 5.0 mmol) in pyridine (20.0 mL) was added 2-chlorobenzene-1-sulfonyl chloride (1.3 g, 5.9 mmol, 812.7 uL). The mixture was stirred at 45° C. for 12 h. The reaction mixture was concentrated under reduced pressure. The residue was purified by column chromatography (SiO₂) to give N-(5-bromo-6-ethylpyridin-2-yl)-2-chlorobenzenesulfonamide (1.0 g, 2.3 mmol, 47.5% yield). M+H⁺=375.0 (LCMS).

Step 3:

A mixture of N-(5-bromo-6-ethylpyridin-2-yl)-2-chlorobenzenesulfonamide (149 mg, 397.1 umol), 8-ethyl-2-fluoro-6-(4,4,5,5-tetramethyl-1,3,2-dioxaborolan-2-yl)quinazoline (100 mg, 330.9 umol), K₂CO₃ (137.2 mg, 992.9 umol), Pd(dppf)Cl₂ (24 mg, 33.1 umol) in dioxane (4.0 mL) and H₂O (0.4 mL) was degassed and purged with N₂ for 3 times, and then the mixture was stirred at 90° C. for 12 h under N₂ atmosphere. The reaction mixture was concentrated under reduced pressure. The residue was purified by column chromatography (SiO₂) to afford 2-chloro-N-(6-ethyl-5-(8-ethyl-2-fluoroquinazolin-6-yl)pyridin-2-yl)benzenesulfonamide (110 mg, 217.2 umol, 65.6% yield). M+H⁺=471.2 (LCMS).

Step 4:

To a solution of 2-chloro-N-(6-ethyl-5-(8-ethyl-2-fluoroquinazolin-6-yl)pyridin-2-yl)benzenesulfonamide (110 mg, 233.6 umol) in n-BuOH (4.0 mL) was added DIEA (242 mg, 1.9 mmol, 325.5 uL) and (1r,4r)-N1,N1-dimethylcyclohexane-1,4-diamine (133 mg, 934.3 umol, HCl). The mixture was stirred at 100° C. for 12 h. The reaction mixture was concentrated under reduced pressure. The residue was purified by prep-HPLC (FA condition) to afford 2-chloro-N-(5-(2-(((1r,4r)-4-(dimethylamino)cyclohexyl)amino)-8-ethylquinazolin-6-yl)-6-ethylpyridin-2-yl)benzenesulfonamide (27.1 mg, 42.2 umol, 18.1% yield, FA). M+H⁺=593.2 (LCMS); ¹H NMR (400 MHz, METHANOL-d₄) δ 9.01 (s, 1H), 8.42 (br s, 1H), 8.26 (d, J=7.6 Hz, 1H), 7.63 (d, J=8.8 Hz, 1H), 7.56 (d, J=3.9 Hz, 2H), 7.54-7.46 (m, 3H), 7.12 (d, J=8.8 Hz, 1H), 4.06-3.95 (m, 1H), 3.31-3.25 (m, 1H), 3.09 (q, J=7.3 Hz, 2H), 2.91 (s, 6H), 2.66 (q, J=7.5 Hz, 2H), 2.41 (br d, J=11.6 Hz, 2H), 2.21 (br d, J=11.5 Hz, 2H), 1.84-1.67 (m, 2H), 1.60-1.44 (m, 2H), 1.33 (t, J=7.5 Hz, 3H), 1.11 (t, J=7.5 Hz, 3H).

Example 8: Synthesis of N-(5-(8-ethyl-2-(((1r,4r)-4-(methylamino)cyclohexyl)amino)quinazolin-6-yl)-6-methoxypyridin-2-yl)-2-methylbenzenesulfonamide (118)

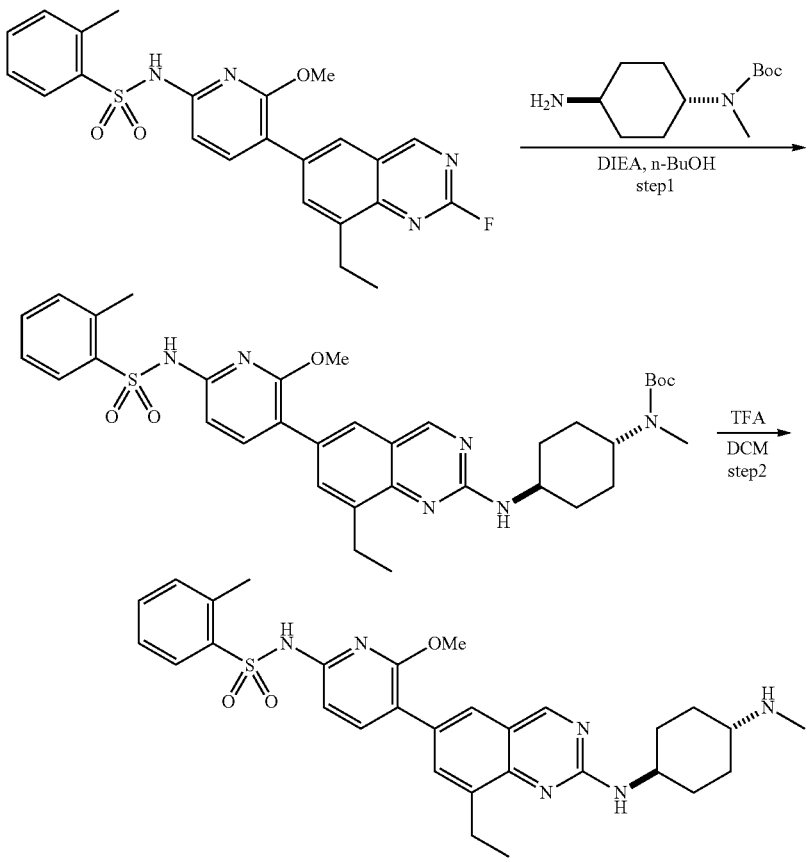

Step 1:

To a solution of N-(5-(8-ethyl-2-fluoroquinazolin-6-yl)-6-methoxypyridin-2-yl)-2-methylbenzenesulfonamide (0.4 g, 883.9 umol) in n-BuOH (5.0 mL) was added DIEA (799 mg, 6.1 mmol, 1.0 mL) and (1r,4r)-N1,N1-dimethylcyclohexane-1,4-diamine (403 mg, 1.7 mmol). The mixture was stirred at 100° C. for 12 h. The reaction mixture was concentrated under reduced pressure. The residue was purified by column chromatography (SiO₂) to afford tert-butyl (((1r,4r)-4-((8-ethyl-6-(2-methoxy-6-(2-methylphenylsulfonamido)pyridin-3-yl)quinazolin-2-yl)amino)cyclohexyl)(methyl)carbamate (260 mg, 330.5 umol, 37.3% yield). M+H+=661.3 (LCMS).

Step 2:

To a solution of tert-butyl (((1r,4r)-4-((8-ethyl-6-(2-methoxy-6-(2-methylphenylsulfonamido)pyridin-3-yl)quinazolin-2-yl)amino)cyclohexyl)(methyl)carbamate (260 mg, 393.4 umol) in DCM (5.0 mL) was added TFA (2.0 mL). The mixture was stirred at 25° C. for 10 min. The reaction mixture was concentrated under reduced pressure. The residue was added dichloromethane (2.0 mL) and NH$_3$.H$_2$O (25% solution) to pH 7, concentrated under reduced pressure again. The residue was purified by prep-HPLC (FA condition) to afford N-(5-(8-ethyl-2-(((1r,4r)-4-(methylamino)cyclohexyl)amino)quinazolin-6-yl)-6-methoxypyridin-2-yl)-2-methylbenzenesulfonamide (116.8 mg, 185.5 umol, 47.1% yield, FA). M+H+=561.2 (LCMS); $^1$H NMR (400 MHz, METHANOL-d$_4$) δ 8.93 (s, 1H), 8.49 (br s, 1H), 8.15 (d, J=7.7 Hz, 1H), 7.62 (dd, J=9.0, 11.7 Hz, 3H), 7.52-7.45 (m, 1H), 7.39-7.32 (m, 2H), 6.64 (d, J=7.9 Hz, 1H), 4.01-3.88 (m, 1H), 3.70 (s, 3H), 3.15-2.96 (m, 3H), 2.71 (d, J=10.6 Hz, 6H), 2.33 (br d, J=11.9 Hz, 2H), 2.23 (br d, J=12.1 Hz, 2H), 1.66-1.38 (m, 4H), 1.29 (t, J=7.4 Hz, 3H).

Example 9: Synthesis N-(5-(2-(((1r,4r)-4-(dimethylamino)cyclohexyl)amino)-8-ethylquinazolin-6-yl)-6-methoxypyridin-2-yl)-2-methylbenzenesulfonamide (119)

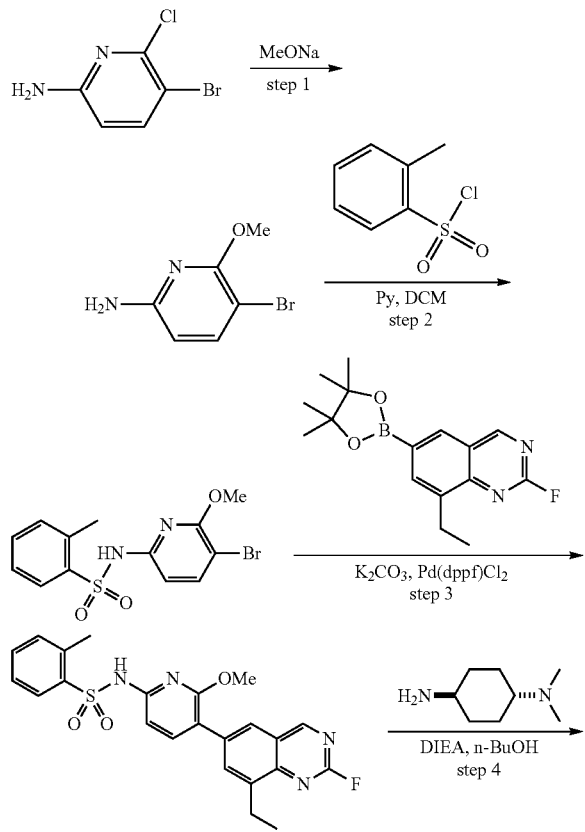

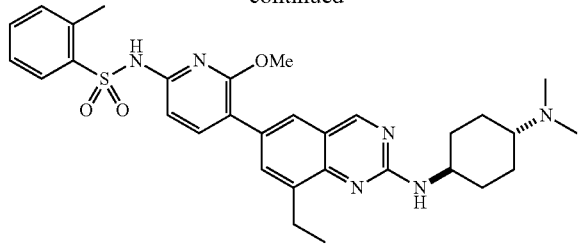

Step 1:

To a solution of 5-bromo-6-chloro-pyridin-2-amine (500 mg, 2.4 mmol) in NaOMe (7.0 mL, 30% solution) was stirred at 70° C. for 12 h. The residue was added water (25.0 mL) and extracted with ethyl acetate (30.0 mL×3). The combined organic phase was washed with brine (15.0 mL×2), dried with anhydrous Na$_2$SO$_4$, filtered and concentrated in vacuum to afford 5-bromo-6-methoxypyridin-2-amine (480 mg, crude).

Step 2:

To a solution of 5-bromo-6-methoxypyridin-2-amine (1.0 g, 4.9 mmol) in DCM (20.0 mL) was added 2-methylbenzenesulfonyl chloride (1.1 g, 5.9 mmol, 853.6 uL) and pyridine (1.2 g, 14.8 mmol, 1.2 mL). The mixture was stirred at 45° C. for 12 h. The reaction mixture was concentrated under reduced pressure. The residue was purified by column chromatography (SiO$_2$, Petroleum ether/Ethyl acetate=100/1 to 50/1) to afford N-(5-bromo-6-methoxypyridin-2-yl)-2-methylbenzenesulfonamide (1.0 g, 2.5 mmol, 52.2% yield). M+H+=357.0 (LCMS).

Step 3:

A mixture of 8-ethyl-2-fluoro-6-(4,4,5,5-tetramethyl-1,3,2-dioxaborolan-2-yl)quinazoline (0.5 g, 1.6 mmol), N-(5-bromo-6-methoxypyridin-2-yl)-2-methylbenzenesulfonamide (591 mg, 1.6 mmol), K$_2$CO$_3$ (686 mg, 4.9 mmol), Pd(dppf)Cl$_2$ (121 mg, 165.4 umol) in H$_2$O (1.0 mL) and dioxane (10.0 mL) was degassed and purged with N$_2$ for 3 times, and then the mixture was stirred at 90° C. for 12 h under N$_2$ atmosphere. The reaction mixture was concentrated under reduced pressure. The residue was purified by column chromatography (SiO$_2$, Petroleum ether/Ethyl acetate=10/1 to 0/1) to afford N-(5-(8-ethyl-2-fluoroquinazolin-6-yl)-6-methoxypyridin-2-yl)-2-methylbenzenesulfonamide (0.6 g, 464.0 umol, 28.0% yield). M+H+=452.9 (LCMS).

Step 4:

To a solution of N-(5-(8-ethyl-2-fluoroquinazolin-6-yl)-6-methoxypyridin-2-yl)-2-methylbenzenesulfonamide (200 mg, 441.9 umol) in n-BuOH (5.0 mL) was added DIEA (399 mg, 3.0 mmol, 538.8 uL) and (1r,4r)-N1,N1-dimethylcyclohexane-1,4-diamine (315 mg, 1.7 mmol, HCl). The mixture was stirred at 100° C. for 12 h. The reaction mixture was concentrated under reduced pressure. The residue was purified by prep-HPLC (FA condition) to give N-(5-(2-(((1r,4r)-4-(dimethylamino)cyclohexyl)amino)-8-ethylquinazolin-6-yl)-6-methoxypyridin-2-yl)-2-methylbenzenesulfonamide (46.4 mg, 72.3 umol, 16.3% yield, FA). M+H+=575.3 (LCMS); $^1$H NMR (400 MHz, METHANOL-d$_4$) δ 8.93 (s, 1H), 8.49-8.29 (m, 1H), 8.15 (d, J=7.7 Hz, 1H), 7.71-7.58 (m, 3H), 7.52-7.43 (m, 1H), 7.42-7.27 (m, 2H), 6.64 (d, J=7.9 Hz, 1H), 4.02-3.90 (m, 1H), 3.70 (s, 3H), 3.28-3.20 (m, 1H), 3.07-2.96 (m, 2H), 2.88 (s, 6H), 2.69 (s, 3H), 2.39 (br d, J=14.3 Hz, 2H), 2.18 (br d, J=11.9 Hz, 2H), 1.81-1.63 (m, 2H), 1.55-1.39 (m, 2H), 1.29 (t, J=7.5 Hz, 3H).

Example 10: Synthesis of 2-chloro-N-(5-(8-ethyl-2-(((1r,4r)-4-(methylamino)cyclohexyl)amino)quinazolin-6-yl)-6-methylpyridin-2-yl)benzenesulfonamide (122)

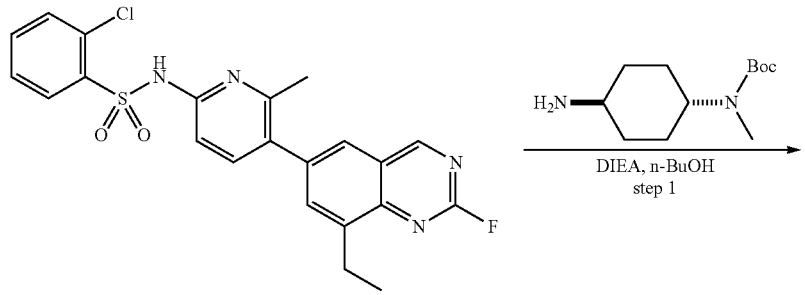

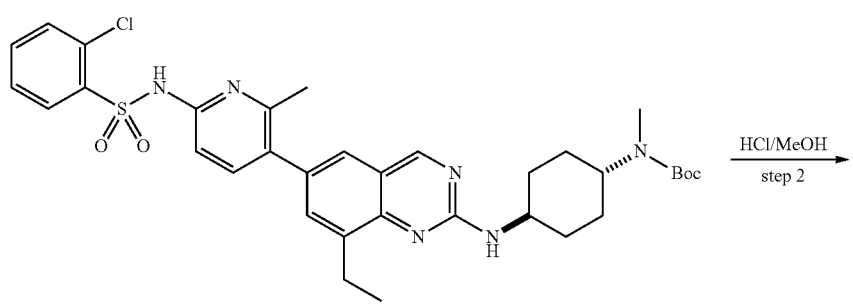

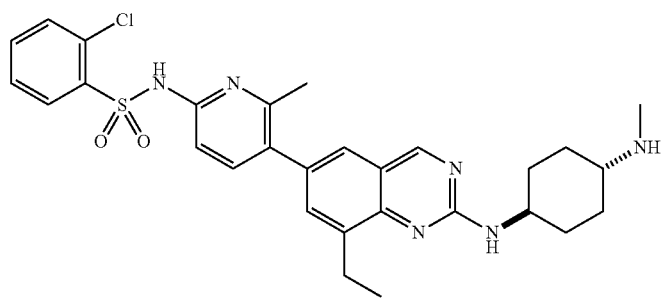

Step 1:

To a solution of 2-chloro-N-(5-(8-ethyl-2-fluoroquinazolin-6-yl)-6-methylpyridin-2-yl)benzenesulfonamide (0.6 g, 1.3 mmol) in n-BuOH (15.0 mL) was added DIEA (509 mg, 3.9 mmol, 686.0 uL) and tert-butyl ((1r,4r)-4-aminocyclohexyl)(methyl)carbamate (600 mg, 2.6 mmol). The mixture was stirred at 100° C. for 12 h. The reaction was concentrated to give a residue. The residue was purified by flash silica gel chromatography (SiO$_2$) to afford tert-butyl ((1r,4r)-4-((6-(6-(2-chlorophenylsulfonamido)-2-methylpyridin-3-yl)-8-ethylquinazolin-2-yl)amino)cyclohexyl)(methyl)carbamate (700 mg, 1.1 mmol, 80.1% yield).

Step 2:

The mixture of tert-butyl ((1r,4r)-4-((6-(6-(2-chlorophenylsulfonamido)-2-methylpyridin-3-yl)-8-ethylquinazolin-2-yl)amino)cyclohexyl)(methyl)carbamate (700 mg, 1.1 mmol) in HCl/MeOH (4M, 15.0 mL) was stirred at 20° C. for 0.5 h. The reaction was concentrated to give a residue. The residue (30 mg) was dissolved in MeOH (2.0 mL), basified pH to 7 with NH$_3$.H$_2$O (25% solution) and then was purified by prep-HPLC (FA condition) to afford 2-chloro-N-(5-(8-ethyl-2-(((1r,4r)-4-(methylamino)cyclohexyl)amino)quinazolin-6-yl)-6-methylpyridin-2-yl)benzenesulfonamide (19 mg, 31.2 umol, FA). M+H$^+$=565.2 (LCMS); $^1$H NMR (400 MHz, METHANOL-d$_4$) δ 9.00 (s, 1H), 8.56 (br s, 1H), 8.28-8.20 (m, 1H), 7.68 (d, J=8.9 Hz, 1H), 7.58-7.44 (m, 5H), 7.22 (d, J=8.9 Hz, 1H), 4.06-3.93 (m, 1H), 3.17-3.00 (m, 3H), 2.74 (s, 3H), 2.39 (m, 5H), 2.26 (br d, J=12.2 Hz, 2H), 1.67-1.42 (m, 4H), 1.33 (t, J=7.5 Hz, 3H). The residue (500 mg) was dissolved in MeOH (10.0 mL), basified pH to 7 with NH$_3$.H$_2$O (25% solution) and then was purified by prep-HPLC (FA condition) to afford 2-chloro-N-(5-(8-ethyl-2-(((1r,4r)-4-(methylamino)cyclohexyl)amino)quinazolin-6-yl)-6-methylpyridin-2-yl)benzenesulfonamide (270 mg, 397.61 umol, 37.79% yield, FA).

Example 11: 2-chloro-N-(5-(8-ethyl-2-(((1r,4r)-4-(ethyl(methyl)amino)cyclohexyl)amino)quinazolin-6-yl)-6-methylpyridin-2-yl)benzenesulfonamide (125)

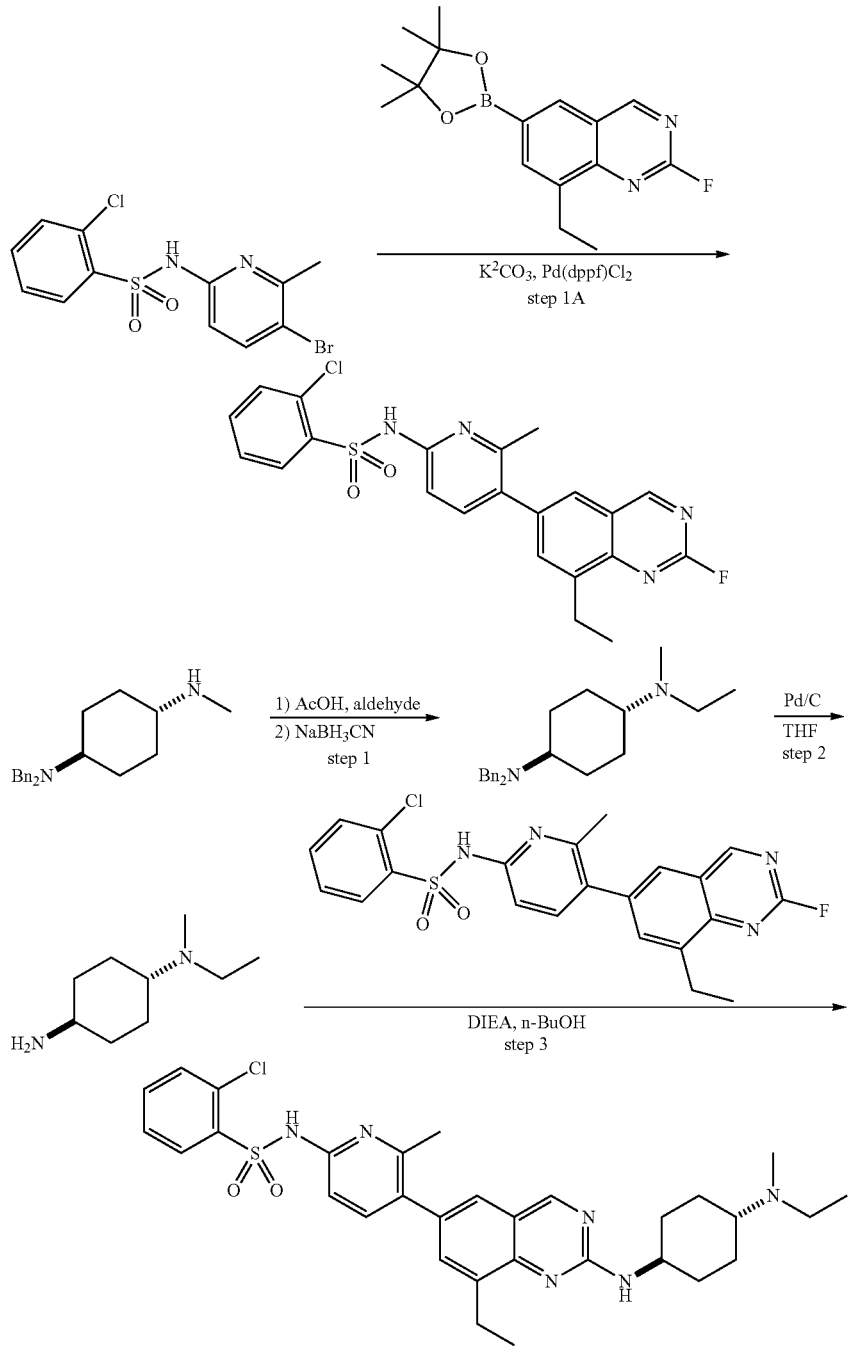

Step 1A:

A mixture of 8-ethyl-2-fluoro-6-(4,4,5,5-tetramethyl-1,3,2-dioxaborolan-2-yl)quinazoline (2.0 g, 6.6 mmol), N-(5-bromo-6-methylpyridin-2-yl)-2-chlorobenzenesulfonamide (2.8 g, 7.9 mmol), K$_2$CO$_3$ (2.7 g, 19.86 mmol), Pd(dppf)Cl$_2$ (484 mg, 661.9 umol) in dioxane (45.0 mL) and H$_2$O (4.5 mL) was degassed and purged with N$_2$ for 3 times, and then the mixture was stirred at 90° C. for 12 h under N$_2$ atmosphere. The reaction mixture was concentrated under reduced pressure. The residue was purified by column chromatography (SiO$_2$) to afford 2-chloro-N-(5-(8-ethyl-2-fluoroquinazolin-6-yl)-6-methylpyridin-2-yl)benzene sulfonamide (1.2 g, 1.8 mmol, 27.7% yield). M+H$^+$=457.1 (LCMS).

Step 1:

To a solution of (1r,4r)-N1,N1-dibenzyl-N4-methylcyclohexane-1,4-diamine (447 mg, 1.4 mmol, HCl) in MeOH (15.0 mL) was adjusted pH=7 by adding TEA (146 mg, 1.4 mmol, 201.7 uL) and adjusted pH=5 by adding CH$_3$COOH (87 mg, 1.4 mmol, 82.9 uL), and then added acetaldehyde (798 mg, 7.2 mmol, 1.0 mL, 40% in H₂O), the mixture was stirred at 30° C. for 1 h. And then added NaBH₃CN (455 mg, 7.2 mmol), the mixture was stirred at 30° C. for 12 h. The reaction mixture was concentrated under reduced pressure. The residue was diluted with NaHCO₃ (10.0 mL) and extracted with ethyl acetate (5.0 mL×3). The combined organic layers were concentrated under reduced pressure to give a residue to give crude (1r,4r)-N1,N1-dibenzyl-N4-ethyl-N4-methylcyclohexane-1,4-diamine (440 mg, crude).

Step 2:

To a solution of (1r,4r)-N1,N1-dibenzyl-N4-ethyl-N4-methylcyclohexane-1,4-diamine (440 mg, 1.3 mmol) in THF (10.0 mL) was added Pd/C (0.4 g, 10% Pd basis) under N₂ atmosphere. The suspension was degassed and purged with H₂ (50 psi) for 3 times. The mixture was stirred at 60° C. for 24 h. The reaction mixture was filtrated with methanol (60.0 mL), and the filter liquor concentrated under reduced pressure to afford crude (1r,4r)-N1-ethyl-N1-methylcyclohexane-1,4-diamine (200 mg, crude).

Step 3:

To a solution of (1r,4r)-N1-ethyl-N1-methylcyclohexane-1,4-diamine (51 mg, 328.2 umol) in n-BuOH (2.0 mL) was added DIEA (42 mg, 328.2 umol, 57.1 uL) and 2-chloro-N-(5-(8-ethyl-2-fluoroquinazolin-6-yl)-6-methylpyridin-2-yl)benzene sulfonamide (50 mg, 109.4 umol). The mixture was stirred at 100° C. for 12 h. The reaction mixture was concentrated under reduced pressure. The residue was purified by prep-HPLC (FA condition) to afford 2-chloro-N-(5-(8-ethyl-2-(((1r,4r)-4-(ethyl(methyl)amino)cyclohexyl)amino)quinazolin-6-yl)-6-methylpyridin-2-yl)benzenesulfonamide (16.1 mg, 25.2 umol, 23.0% yield, FA). M+H⁺=593.2 (LCMS); ¹H NMR (400 MHz, METHANOL-d₄) δ 8.98 (s, 1H), 8.54 (s, 1H), 8.26-8.18 (m, 1H), 7.66 (d, J=8.8 Hz, 1H), 7.56-7.42 (m, 5H), 7.20 (d, J=9.0 Hz, 1H), 4.04-3.90 (m, 1H), 3.34 (br d, J=2.9 Hz, 1H), 3.23 (q, J=7.2 Hz, 2H), 3.13-2.99 (m, 2H), 2.81 (s, 3H), 2.37 (s, 5H), 2.14 (br d, J=11.7 Hz, 2H), 1.83-1.69 (m, 2H), 1.58-1.38 (m, 2H), 1.33 (td, J=7.4, 17.4 Hz, 6H).

Example 12: Synthesis of 2-chloro-N-(5-(8-ethyl-2-(((1r,4r)-4-(methyl(2,2,2-trifluoroethyl)amino)cyclohexyl)amino)quinazolin-6-yl)-6-methylpyridin-2-yl)benzenesulfonamide (126)

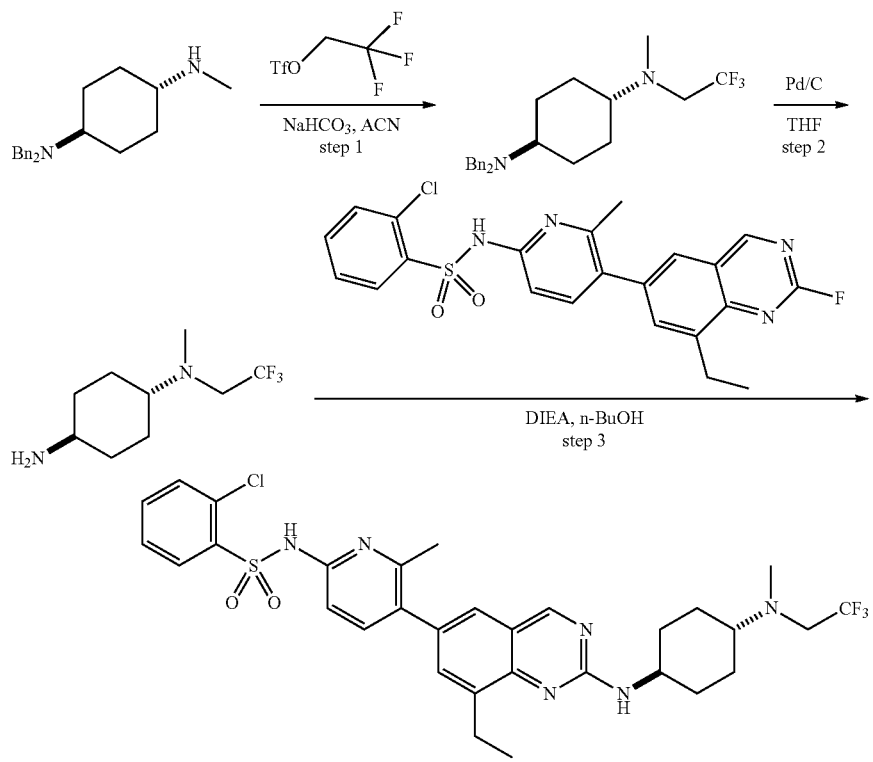

Step 1:

To a solution of (1r,4r)-N1,N1-dibenzyl-N4-methylcyclohexane-1,4-diamine (0.7 g, 2.3 mmol, HCl) in MeCN (20.0 mL) was added NaHCO₃ (763 mg, 9.1 mmol, 353.1 uL) and 2,2,2-trifluoroethyl trifluoromethanesulfonate (790 mg, 3.4 mmol). The mixture was stirred at 70° C. for 12 h. The reaction was filtered and concentrated to give a residue. The residue was purified by column chromatography (SiO₂) to afford (1r,4r)-N1,N1-dibenzyl-N4-methyl-N4-(2,2,2-trifluoroethyl)cyclohexane-1,4-diamine (800 mg, 1.1 mmol, 47.0% yield). M+H⁺=391.3 (LCMS).

Step 2:

To a solution of (1r,4r)-N1,N1-dibenzyl-N4-methyl-N4-(2,2,2-trifluoroethyl)cyclohexane-1,4-diamine (0.8 g, 2.1 mmol) in THF (15.0 mL) was added Pd/C (0.8 g, 10% Pd basis) under N₂ atmosphere. The suspension was degassed and purged with H₂ for 3 times. The mixture was stirred under H₂ (50 Psi) at 60° C. for 24 h. The reaction was filtered and concentrated to give (1r,4r)-N1-methyl-N1-(2,2,2-trifluoroethyl)cyclohexane-1,4-diamine (350 mg, crude).

Step 3:

To a solution of (1r,4r)-N1-methyl-N1-(2,2,2-trifluoroethyl)cyclohexane-1,4-diamine (69 mg, 328.3 umol) in n-BuOH (4.0 mL) was added 2-chloro-N-(5-(8-ethyl-2-fluororoquinazolin-6-yl)-6-methylpyridin-2-yl)benzenesulfonamide (50 mg, 109.4 umol) and DIEA (42 mg, 328.3 umol, 57.2 uL). The mixture was stirred at 90° C. for 12 h. The reaction was concentrated to give a residue. The residue was purified by prep-HPLC (FA condition) to afford 2-chloro-N-(5-(8-ethyl-2-(((1r,4r)-4-(methyl(2,2,2-trifluoroethyl)amino)cyclohexyl)amino)quinazolin-6-yl)-6-methylpyridin-2-yl)benzenesulfonamide (29.8 mg, 42.4 umol, 38.8% yield, FA). M+H$^+$=647.2 (LCMS); $^1$H NMR (400 MHz, METHANOL-d$_4$) δ 8.96 (s, 1H), 8.22 (d, J=7.5 Hz, 1H), 7.68 (br d, J=9.0 Hz, 1H), 7.57-7.42 (m, 5H), 7.21 (br s, 1H), 3.89 (br t, J=11.1 Hz, 1H), 3.16-3.02 (m, 4H), 2.57 (br t, J=11.0 Hz, 1H), 2.47 (s, 3H), 2.37 (s, 3H), 2.25 (br d, J=11.9 Hz, 2H), 1.92 (br d, J=11.9 Hz, 2H), 1.52-1.35 (m, 4H), 1.31 (t, J=7.5 Hz, 3H).

Example 13: Synthesis of 2-chloro-N-(5-(8-ethyl-2-(((1r,4r)-4-(methylamino)cyclohexyl)amino)quinazolin-6-yl)-3-fluoro-6-methoxypyridin-2-yl)benzenesulfonamide (127)

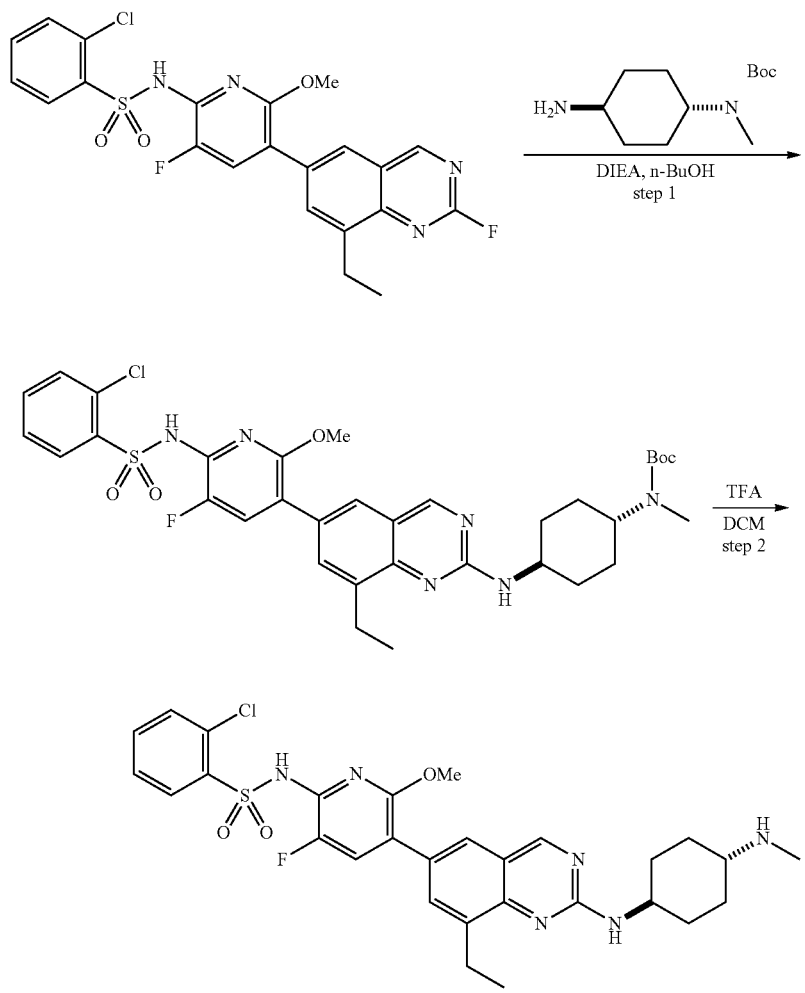

Step 1:
To a solution of 2-chloro-N-(5-(8-ethyl-2-fluoroquinazolin-6-yl)-3-fluoro-6-methoxypyridin-2-yl)benzenesulfonamide (130 mg, 264.8 umol) in n-BuOH (6.0 mL) was added tert-butyl ((1r,4r)-4-aminocyclohexyl)(methyl)carbamate (181 mg, 794.4 umol) and DIEA (103 mg, 794.4 umol, 138.4 uL). The mixture was stirred at 90° C. for 12 h. The reaction was concentrated to give a residue. The residue was purified by column chromatography (SiO$_2$) to afford tert-butyl ((1r,4r)-4-((6-(6-(2-chlorophenylsulfonamido)-5-fluoro-2-methoxypyridin-3-yl)-8-ethylquinazolin-2-yl)amino)cyclohexyl)(methyl)carbamate (170 mg, 243.12 umol, 91.81% yield).

Step 2:
To a solution of tert-butyl ((1r,4r)-4-((6-(6-(2-chlorophenylsulfonamido)-5-fluoro-2-methoxypyridin-3-yl)-8-ethylquinazolin-2-yl)amino)cyclohexyl)(methyl)carbamate (170 mg, 243.1 umol) in DCM (3.0 mL) was added TFA (1.5 mL). The mixture was stirred at 20° C. for 0.5 h. The reaction was concentrated to give a residue. The residue was dissolved in MeOH (2.0 mL) and basified pH to 7 with NH$_3$.H$_2$O (25% solution). The residue was purified by prep-HPLC (FA condition) to afford 2-chloro-N-(5-(8-ethyl-2-(((1r,4r)-4-(methylamino)cyclohexyl)amino)quinazolin-6-yl)-3-fluoro-6-methoxypyridin-2-yl)benzenesulfonamide (26.8 mg, 40.3 umol, 16.6% yield, FA). M+H$^+$=599.2 (LCMS); $^1$H NMR (400 MHz, DMSO-d$_6$) δ 8.99 (br s, 1H), 8.19-8.07 (m, 2H), 7.64 (s, 2H), 7.39-7.31 (m, 4H), 7.26 (br s, 1H), 3.77 (br s, 1H), 3.20 (s, 3H), 3.03-2.86 (m, 3H), 2.57 (s, 3H), 2.09 (br d, J=11.0 Hz, 4H), 1.47-1.27 (m, 4H), 1.22 (br t, J=7.4 Hz, 3H).

Example 14: Synthesis of 2-chloro-N-(5-(2-(((1r,4r)-4-(dimethylamino)cyclohexyl)amino)-8-ethylquinazolin-6-yl)-3-fluoro-6-methoxypyridin-2-yl)benzenesulfonamide (128)

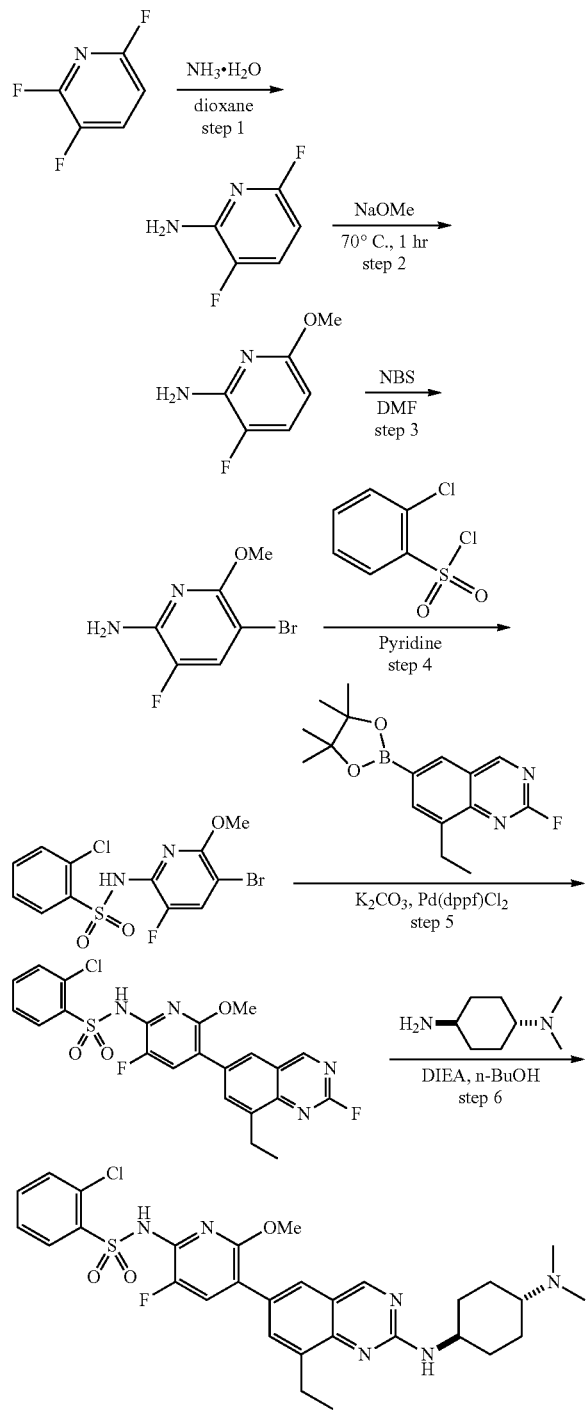

Step 1:

To a solution of 2,3,6-trifluoropyridine (2.4 g, 18.0 mmol) in dioxane (12.0 mL) was added NH$_3$·H$_2$O (12.0 mL, 25% solution). The mixture was stirred at 100° C. for 12 h. The reaction was extracted with ethyl acetate (15.0 mL×3). The combined organic phase was washed with brine (15.0 mL×3), dried over anhydrous Na$_2$SO$_4$, filtered and concentrated to give 3,6-difluoropyridin-2-amine (2.0 g, 15.4 mmol, 85.2% yield).

Step 2:

The mixture of 3,6-difluoropyridin-2-amine (2.0 g, 15.4 mmol) in NaOMe (30.0 mL, 30% solution) was stirred at 70° C. for 1 h. Water (30.0 mL) was added to the reaction mixture and extracted with ethyl acetate (30 mL×3). The combined organic phase was washed with brine (30 mL×3), dried over anhydrous Na$_2$SO$_4$, filtered and concentrated to give a residue. The residue was purified by prep-HPLC (neutral condition) to give 3-fluoro-6-methoxypyridin-2-amine (0.8 g, 5.1 mmol, 33% yield). $^1$H NMR (400 MHz, CHLOROFORM-d) δ 7.17 (dd, J=8.7, 9.6 Hz, 1H), 6.01 (dd, J=2.1, 8.4 Hz, 1H), 4.42 (br s, 2H), 3.82 (s, 3H).

Step 3:

To a solution of 3-fluoro-6-methoxypyridin-2-amine (300 mg, 2.1 mmol) in DMF (12.0 mL) was added NBS (376 mg, 2.1 mmol) at 0° C. The mixture was stirred at 0° C. for 2 h. Cold H$_2$O (10.0 mL) was added to the reaction mixture and extracted with ethyl acetate (10.0 mL×3). The combined organic phase was washed with brine (10.0 mL×3), dried over anhydrous Na$_2$SO$_4$, filtered and concentrated to give residue. The residue was purified by column chromatography (SiO$_2$) to afford 5-bromo-3-fluoro-6-methoxypyridin-2-amine (420 mg, 1.7 mmol, 81.0% yield). $^1$H NMR (400 MHz, CHLOROFORM-d) δ 7.41 (d, J=9.0 Hz, 1H), 4.45 (br s, 2H), 3.90 (s, 3H).

Step 4:

To a solution of 5-bromo-3-fluoro-6-methoxypyridin-2-amine (400 mg, 1.8 mmol) in pyridine (10.0 mL) was added 2-chlorobenzenesulfonyl chloride (420 mg, 2.0 mmol, 271.1 uL). The mixture was stirred at 45° C. for 12 h. The reaction was concentrated to give a residue. The residue was purified by column chromatography (SiO$_2$) to give N-(5-bromo-3-fluoro-6-methoxypyridin-2-yl)-2-chlorobenzenesulfonamide (680 mg). M+H$^+$=396.9 (LCMS).

Step 5:

A mixture of 8-ethyl-2-fluoro-6-(4,4,5,5-tetramethyl-1,3,2-dioxaborolan-2-yl)quinazoline (300 mg, 992.9 umol), N-(5-bromo-3-fluoro-6-methoxypyridin-2-yl)-2-chlorobenzenesulfonamide (471 mg, 1.2 mmol), K$_2$CO$_3$ (206 mg, 1.5 mmol) and Pd(dppf)Cl$_2$ (73 mg, 99.3 umol) in dioxane (15.0 mL) and H$_2$O (1.5 mL) was degassed and purged with N$_2$ for 3 times, and then the mixture was stirred at 90° C. for 12 h under N$_2$ atmosphere. The reaction was concentrated to give a residue. The residue was purified by flash silica gel chromatography (SiO$_2$) to afford 2-chloro-N-(5-(8-ethyl-2-fluoroquinazolin-6-yl)-3-fluoro-6-methoxypyridin-2-yl)benzenesulfonamide (230 mg, 364.2 umol, 36.7% yield). M+H$^+$=491.2 (LCMS).

Step 6:

To a solution of 2-chloro-N-(5-(8-ethyl-2-fluoroquinazolin-6-yl)-3-fluoro-6-methoxypyridin-2-yl)benzenesulfonamide (100 mg, 203.7 umol) in n-BuOH (4.0 mL) was added (1r,4r)-N1,N1-dimethylcyclohexane-1,4-diamine (109 mg, 611.1 umol, HCl) and DIEA (210.6 mg, 1.6 mmol, 283.9 uL). The mixture was stirred at 90° C. for 12 h. The reaction was concentrated to give a residue. The residue was purified by prep-HPLC (FA condition) to afford 2-chloro-N-(5-(2-(((1r,4r)-4-(dimethylamino)cyclohexyl)amino)-8-ethylquinazolin-6-yl)-3-fluoro-6-methoxypyridin-2-yl)benzenesulfonamide (37.2 mg, 54.6 umol, 26.8% yield, FA). M+H$^+$=613.2 (LCMS); $^1$H NMR (400 MHz, METHANOL-d$_4$) δ 8.93 (br s, 1H), 8.32 (br d, J=7.5 Hz, 3H), 7.71-7.43 (m, 6H), 3.95 (br s, 1H), 3.47 (s, 3H), 3.27-3.19 (m, 1H), 3.01 (br d, J=7.1 Hz, 2H), 2.88 (br s, 6H), 2.37 (br d, J=9.8 Hz, 2H), 2.18 (br d, J=8.7 Hz, 2H), 1.72 (br d, J=10.5 Hz, 2H), 1.47 (br d, J=12.3 Hz, 2H), 1.28 (br t, J=7.0 Hz, 3H), 1.20 (s, 1H).

Example 15: Synthesis of 2-chloro-N-(5-(2-(((1r,4r)-4-((cyclobutylmethyl)(methyl)amino)cyclohexyl)amino)-8-ethylquinazolin-6-yl)-6-methylpyridin-2-yl)benzenesulfonamide (130)

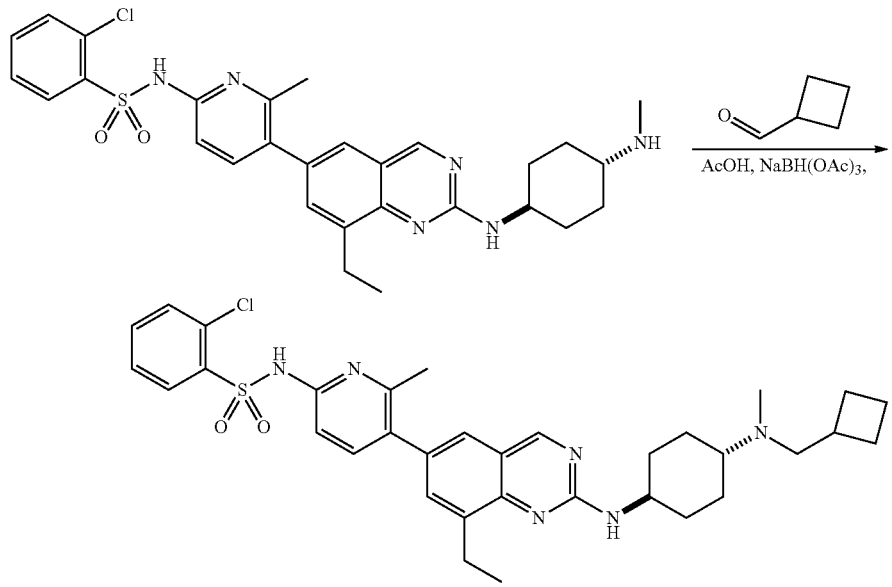

To a solution of 2-chloro-N-(5-(8-ethyl-2-(((1r,4r)-4-(methylamino)cyclohexyl)amino)quinazolin-6-yl)-6-methylpyridin-2-yl)benzenesulfonamide (60 mg, 98.2 umol, FA) in DCE (2.0 mL) and DCM (2.0 mL) was added TEA to basify pH to 7 and then cyclobutanecarbaldehyde (33 mg, 294.5 umol, 128.6 uL) was added. AcOH (0.05 mL) was added to above mixture to adjusted pH to 5 and the mixture was stirred at 30° C. for 2h. NaBH(OAc)$_3$ (104 mg, 490.9 umol) was added to the mixture and the reaction was stirred at 30° C. for 12 h. The reaction was concentrated to give a residue. The residue was purified by prep-HPLC (FA condition) to afford 2-chloro-N-(5-(2-(((1r,4r)-4-((cyclobutylmethyl)(methyl)amino)cyclohexyl)amino)-8-ethylquinazolin-6-yl)-6-methylpyridin-2-yl)benzenesulfonamide (34.8 mg, 51.2 umol, 52.1% yield, FA). M+H$^+$=633.2 (LCMS); $^1$H NMR (400 MHz, METHANOL-d$_4$) δ 8.98 (s, 1H), 8.50 (br s, 1H), 8.22 (d, J=7.7 Hz, 1H), 7.66 (d, J=8.8 Hz, 1H), 7.56-7.41 (m, 5H), 7.20 (br d, J=8.6 Hz, 1H), 3.98 (br t, J=11.4 Hz, 1H), 3.23 (br d, J=7.1 Hz, 3H), 3.06 (q, J=7.4 Hz, 2H), 2.79 (m, 4H), 2.43-2.32 (m, 5H), 2.26-2.09 (m, 4H), 2.08-1.97 (m, 1H), 1.96-1.84 (m, 3H), 1.77 (q, J=12.4 Hz, 2H), 1.55-1.42 (m, 2H), 1.31 (t, J=7.4 Hz, 3H).

Example 16: Synthesis of 2-chloro-N-(5-(8-(1,1-difluoroethyl)-2-(((1r,4r)-4-(dimethylamino)cyclohexyl)amino)quinazolin-6-yl)-6-methylpyridin-2-yl)benzenenesulfonamide (131)

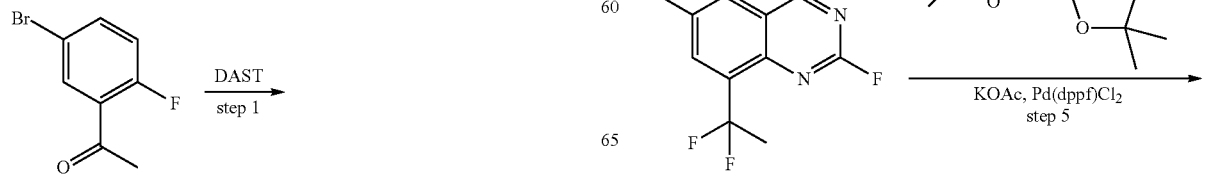

-continued

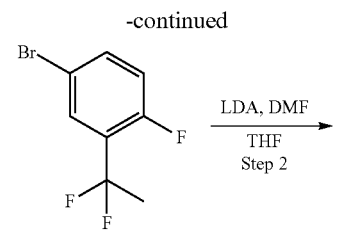

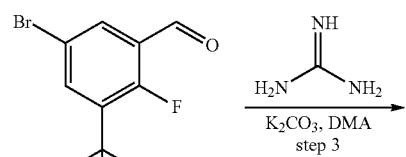

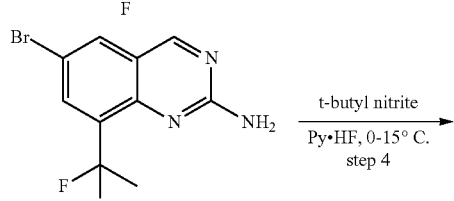

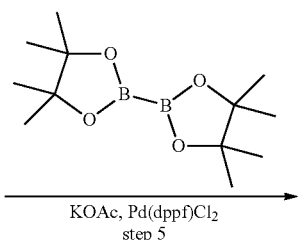

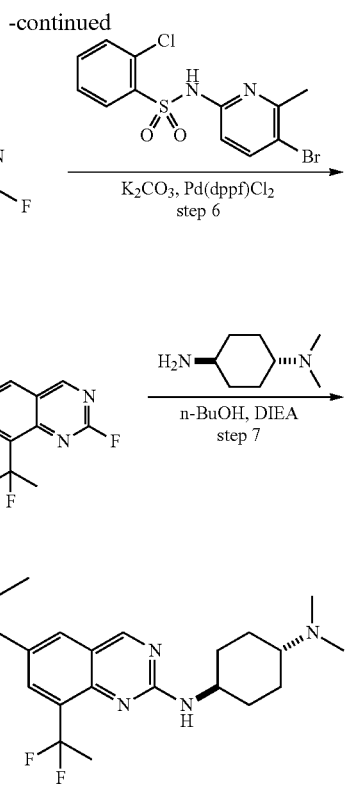

Step 1:

To a solution of 1-(5-bromo-2-fluoro-phenyl)ethanone (1.0 g, 4.6 mmol) in DAST (12.2 g, 75.6 mmol, 10.0 mL) was stirred at 45° C. for 12 h. The mixture was poured into ice Sat. NaHCO₃ (100.0 mL) and extracted with ethyl acetate (10.0 mL×3). The combined organic layers were washed with brine (10.0 mL×3), dried over Na₂SO₄, filtered and concentrated under reduced pressure to give a residue. The residue was purified by column chromatography (SiO₂) to afford 4-bromo-2-(1,1-difluoroethyl)-1-fluorobenzene (1.0 g, 4.1 mmol, 90.8% yield). ¹H NMR (CHLOROFORM-d, 400 MHz): δ 7.68 (dd, J=2.4, 6.6 Hz, 1H), 7.57-7.50 (m, 1H), 7.07-6.98 (m, 1H), 1.99 (dt, J=1.1, 18.5 Hz, 3H).

Step 2:

To a solution of 4-bromo-2-(1,1-difluoroethyl)-1-fluorobenzene (450 mg, 1.8 mmol) in THF (10.0 mL) was added LDA (2 M, 1.2 mL) at −78° C. The mixture was stirred at −78° C. for 1 h. Then DMF (165 mg, 2.2 mmol, 173.8 uL) was added and stirred for 1 h at −78° C. The mixture was poured into Sat NH₄Cl (10.0 mL) and extracted with ethyl acetate (10.0 mL×3). The combined organic layers were washed with brine (10.0 mL×3), dried over Na₂SO₄, filtered and concentrated under reduced pressure to give a residue. The residue was purified by column chromatography (SiO₂) to afford 5-bromo-3-(1,1-difluoroethyl)-2-fluorobenzaldehyde (0.4 g, 1.5 mmol, 79.5% yield). ¹H NMR (CHLOROFORM-d, 400 MHz): δ 10.33 (s, 1H), 8.07 (dd, J=2.4, 5.5 Hz, 1H), 7.92 (dd, J=2.4, 6.4 Hz, 1H), 2.05 (t, J=18.6 Hz, 3H).

Step 3:

To a solution of guanidine (181 mg, 1.5 mmol, H₂CO₃) and K₂CO₃ (621 mg, 4.4 mmol, 4.8 mL) in DMA (10.0 mL) was added a solution of 5-bromo-3-(1,1-difluoroethyl)-2-fluorobenzaldehyde (0.4 g, 1.5 mmol) in DMA (1.5 mL). Then the mixture was stirred at 160° C. for 1 h. The mixture was concentrated to get crude residue add H₂O (30.0 mL) and extracted with Ethyl acetate (30.0 mL×3). The combined organic layers were washed with brine (20.0 mL×3), dried over Na₂SO₄, filtered and concentrated under reduced pressure to give a residue. The residue was purified by column chromatography (SiO₂) to afford 6-bromo-8-(1,1-difluoroethyl)quinazolin-2-amine (0.4 g, 1.39 mmol, 92.69% yield).

Step 4:

To a solution of 6-bromo-8-(1,1-difluoroethyl)quinazolin-2-amine (0.4 g, 1.3 mmol) in pyridine (3.5 mL) was added pyridine; hydrofluoride (7.7 g, 77.7 mmol, 7.00 mL) at −40° C. The mixture was stirred at −40° C. for 15 min. Then tert-butyl nitrite (286 mg, 2.7 mmol, 330.2 uL) was added. The mixture was stirred at 20° C. for 12 h. The mixture was poured into ice water and adjusted pH=7 with sat NaHCO₃ extracted with ethyl acetate (50.0 mL×3). The combined organic layers were washed with brine (20.0 mL×3), dried over Na₂SO₄, filtered and concentrated under reduced pressure to give a residue. The residue was purified by column chromatography (SiO₂) to afford 6-bromo-8-(1,1-difluoroethyl)-2-fluoroquinazoline (0.3 g, 1.0 mmol, 74.2% yield). ¹H NMR (CHLOROFORM-d, 400 MHz): δ 9.35 (d, J=2.4 Hz, 1H), 8.31 (s, 1H), 8.25 (d, J=2.1 Hz, 1H), 2.30 (t, J=19.0 Hz, 3H).

Step 5:

To a solution of 6-bromo-8-(1,1-difluoroethyl)-2-fluoroquinazoline (0.3 g, 1.03 mmol) and KOAc (151 mg, 1.5 mmol) in dioxane (6.0 mL) were added 4,4,4',4',5,5,5',5'-octamethyl-2,2'-bi(1,3,2-dioxaborolane) (314 mg, 1.2 mmol) and Pd(dppf)Cl₂ (75 mg, 103.0 umol). The mixture was stirred at 90° C. for 12 h under N₂. The mixture was concentrated to get crude residue. The residue was purified by column chromatography (SiO₂) to afford 8-(1,1-difluoroethyl)-2-fluoro-6-(4,4,5,5-tetramethyl-1,3,2-dioxaborolan-2-yl)quinazoline (0.3 g, crude).

Step 6:

To a solution of 8-(1,1-difluoroethyl)-2-fluoro-6-(4,4,5,5-tetramethyl-1,3,2-dioxaborolan-2-yl)quinazoline (150 mg, 443.6 umol) and K₂CO₃ (183 mg, 1.3 mmol) in dioxane (2.0 mL) and H₂O (0.2 mL) were added N-(5-bromo-6-methylpyridin-2-yl)-2-chlorobenzenesulfonamide (192 mg, 532.3 umol) and Pd(dppf)Cl₂ (32 mg, 44.3 umol). The mixture was stirred at 90° C. for 12 h under N₂. The mixture was concentrated to get crude residue. The residue was purified by column chromatography (SiO₂) to afford 2-chloro-N-(5-(8-(1,1-difluoroethyl)-2-fluoroquinazolin-6-yl)-6-methylpyridin-2-yl)benzenesulfonamide (90 mg, crude).

Step 7:

To a solution of 2-chloro-N-(5-(8-(1,1-difluoroethyl)-2-fluoroquinazolin-6-yl)-6-methylpyridin-2-yl)benzenesulfonamide (90 mg, 182.5 umol) in n-BuOH (2.0 mL) was added (1r,4r)-N1,N1-dimethylcyclohexane-1,4-diamine (103 mg, 730.3 umol, HCl) and DIEA (188 mg, 1.4 mmol, 254.4 uL). The mixture was stirred at 100° C. for 12 h. The mixture was concentrated to get crude residue. The residue was purified by prep-HPLC (FA condition) to afford 2-chloro-N-(5-(8-(1,1-difluoroethyl)-2-(((1r,4r)-4-(dimethylamino)cyclohexyl)amino)quinazolin-6-yl)-6-methylpyridin-2-yl)benzenesulfonamide (6.8 mg, 10.4 umol, 5.7% yield, FA). M+H⁺= 615.2 (LCMS); ¹H NMR (DMSO-d₆, 400 MHz) δ 9.13 (s, 1H), 8.24 (s, 1H), 8.17-8.08 (m, 1H), 7.87 (s, 1H), 7.79 (s, 1H), 7.74-7.62 (m, 2H), 7.59-7.45 (m, 3H), 7.06 (br d, J=9.0 Hz, 1H), 3.69 (br s, 1H), 2.38-2.22 (m, 13H), 2.17-2.05 (m, 2H), 1.91 (br s, 2H), 1.33 (br d, J=6.4 Hz, 4H).

Example 17: Synthesis of 2-chloro-N-(5-(8-(1,1-difluoroethyl)-2-(((1r,4r)-4-(dimethylamino)cyclohexyl)amino)quinazolin-6-yl)-6-methoxypyridin-2-yl)benzenesulfonamide (124)

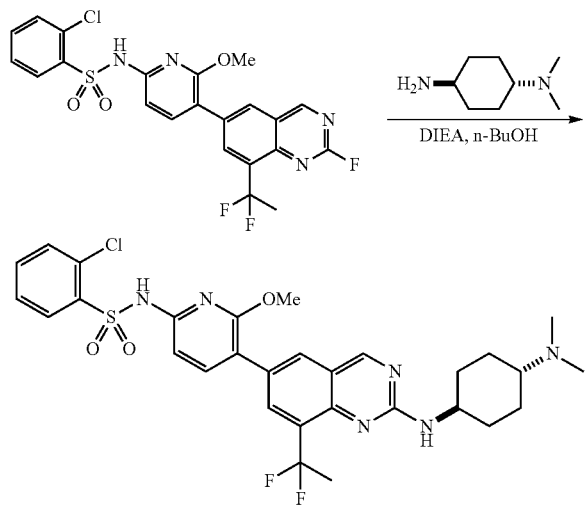

The title compound was synthesized according to the synthetic procedure reported for the preparation of 2-chloro-N-(5-(8-(1,1-difluoroethyl)-2-(((1r,4r)-4-(dimethylamino)cyclohexyl)amino)quinazolin-6-yl)-6-methylpyridin-2-yl)benzenesulfonamide. (5.4 mg, 7.7 umol, 7.8% yield, FA). M+H$^+$=631.2 (LCMS); $^1$H NMR (400 MHz, METHANOL-d$_4$) δ 9.02 (s, 1H), 8.47 (br s, 1H), 8.31 (d, J=7.7 Hz, 1H), 8.04 (s, 1H), 7.89 (d, J=1.5 Hz, 1H), 7.67 (d, J=7.9 Hz, 1H), 7.63-7.55 (m, 2H), 7.55-7.49 (m, 1H), 6.65 (d, J=7.9 Hz, 1H), 3.90 (br s, 1H), 3.67 (s, 3H), 3.29-3.21 (m, 1H), 2.88 (s, 6H), 2.39 (br d, J=10.6 Hz, 2H), 2.32-2.12 (m, 5H), 1.77-1.60 (m, 2H), 1.57-1.41 (m, 2H).

Example 18: Synthesis of 2-chloro-N-(5-(8-ethyl-2-(((1r,4r)-4-((2-methoxyethyl)(methyl)amino)cyclohexyl)amino)quinazolin-6-yl)-6-methylpyridin-2-yl)benzenesulfonamide (132)

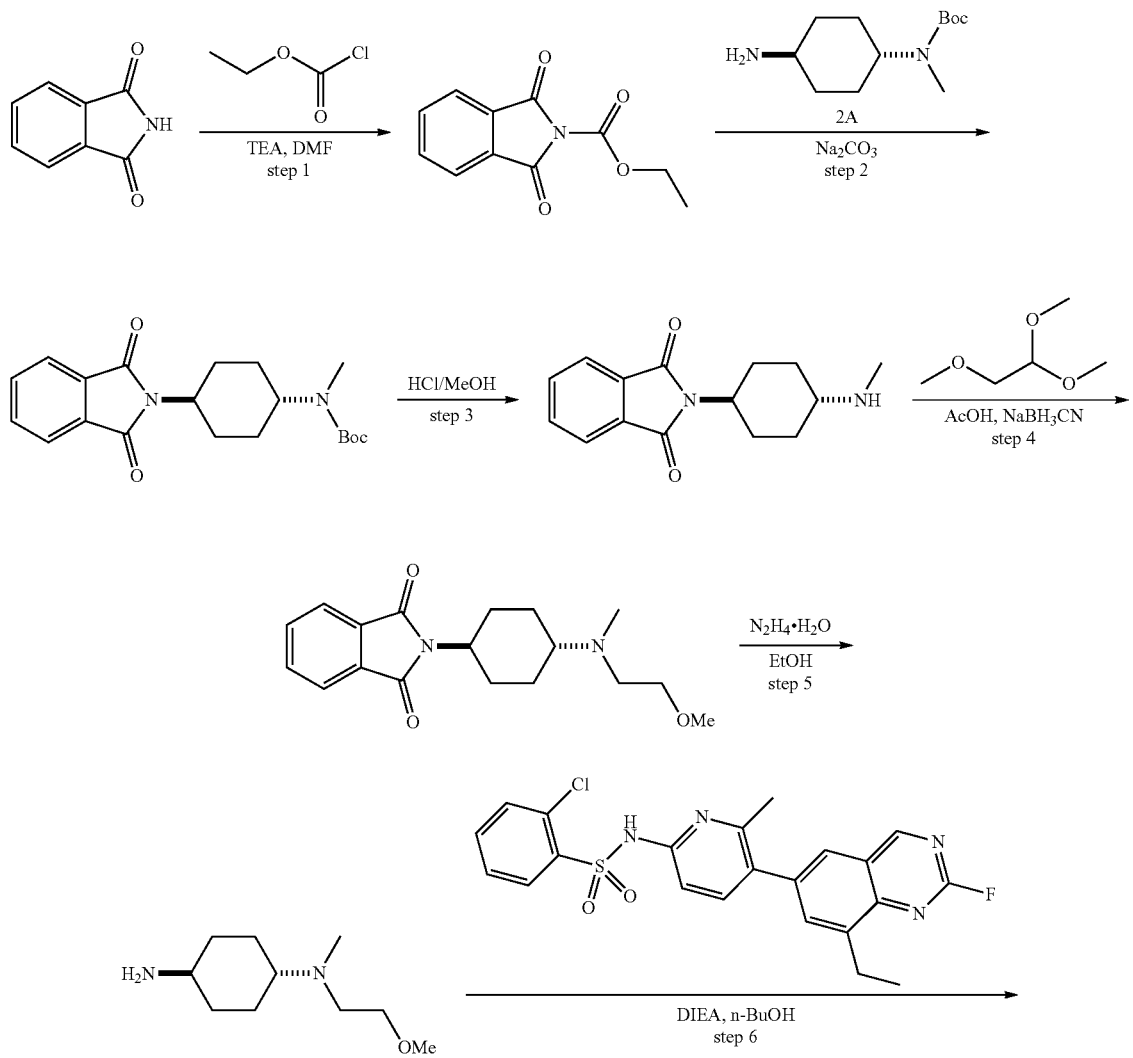

-continued

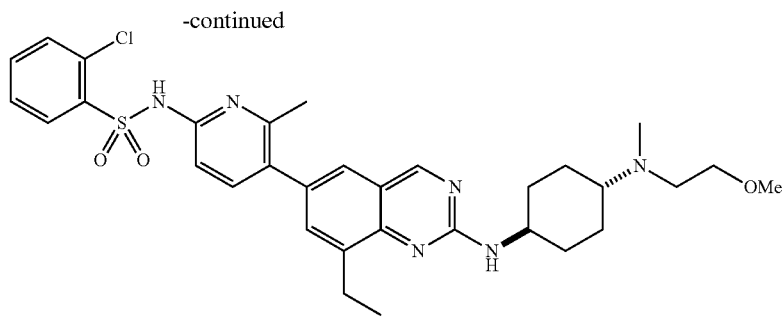

Step 1:

To a solution of isoindoline-1,3-dione (10.0 g, 67.9 mmol), TEA (8.9 g, 88.3 mmol, 12.3 mL) in DMF (60.0 mL) was added ethyl carbonochloridate (8.8 g, 81.5 mmol, 7.7 mL). The mixture was stirred at 25° C. for 12 h. The reaction mixture was filtered to give ethyl 1,3-dioxoisoindoline-2-carboxylate (700 mg, crude). $^1$H NMR (400 MHz, CHLOROFORM-d) δ 8.03-7.93 (m, 2H), 7.88-7.78 (m, 2H), 4.50 (q, J=7.2 Hz, 2H), 1.45 (t, J=7.2 Hz, 3H).

Step 2:

To a solution of ethyl 1,3-dioxoisoindoline-2-carboxylate (700 mg, 3.1 mmol), tert-butyl ((1r,4r)-4-aminocyclohexyl)(methyl)carbamate (875 mg, 3.8 mmol) in H$_2$O (20.0 mL) was added Na$_2$CO$_3$ (406 mg, 3.8 mmol). The mixture was stirred at 15° C. for 12 h. The reaction mixture was filtered to get a cake, the cake was washed by MeOH (20.0 mL×3) to give tert-butyl ((1r,4r)-4-(1,3-dioxoisoindolin-2-yl)cyclohexyl)(methyl)carbamate (800 mg, crude). $^1$H NMR (400 MHz, DMSO-d$_6$) δ 7.91-7.76 (m, 4H), 4.10-3.94 (m, 1H), 2.70 (s, 3H), 2.19 (br s, 2H), 1.77 (br d, J=12.1 Hz, 2H), 1.65 (br s, 4H), 1.41 (s, 9H), 1.38 (s, 1H).

Step 3:

To a solution of tert-butyl ((1r,4r)-4-(1,3-dioxoisoindolin-2-yl)cyclohexyl)(methyl)carbamate (767 mg, 2.1 mmol) in HCl/MeOH (40.0 mL, 4M) was stirred at 25° C. for 30 min. The reaction mixture was concentrated under reduced pressure to give 2-((1r,4r)-4-(methylamino)cyclohexyl)isoindoline-1,3-dione (600 mg, crude, HCl). $^1$H NMR (400 MHz, DMSO-d$_6$) δ 7.88-7.78 (m, 4H), 4.04-3.90 (m, 1H), 3.57 (br s, 2H), 3.16 (s, 2H), 3.08-2.93 (m, 1H), 2.24-2.13 (m, 3H), 2.13-2.05 (m, 1H), 1.83 (br d, J=10.8 Hz, 2H), 1.59-1.42 (m, 2H).

Step 4:

To a solution of 1,1,2-trimethoxyethane (4.9 g, 40.8 mmol, 5.2 mL) in H$_2$O (40.0 mL) and HCl (1.0 mL, 1M) was stirred at 60° C. for 2 h. Then the reaction mixture was extracted with dichloromethane (30.0 mL×3). The combined organic layers were washed with brine (30.0 mL×3), dried over Na$_2$SO$_4$, filtered to give a filtrate. To the filtrate was added the solution of 2-((1r,4r)-4-(methylamino)cyclohexyl)isoindoline-1,3-dione (600 mg, 2.0 mmol, HCl) which was added TEA to adjust pH=7 in MeOH (100.0 mL). Then CH$_3$COOH (183 mg, 3.0 mmol, 175.0 uL) was added to adjust pH=5. And then NaBH$_3$CN (256 mg, 4.0 mmol) was added to above reaction mixture. The mixture was stirred at 45° C. for 12 h. The reaction mixture was extracted with dichloromethane (30.0 mL×3). The combined organic layers were washed with brine (30.0 mL×3), dried over Na$_2$SO$_4$, filtered and concentrated under reduced pressure to give 2-((1r,4r)-4-((2-methoxyethyl)(methyl)amino)cyclohexyl)isoindoline-1,3-dione (800 mg, crude). $^1$H NMR (400 MHz, CHLOROFORM-d) δ 7.84-7.78 (m, 2H), 7.74-7.69 (m, 2H), 4.14 (tt, J=4.1, 12.1 Hz, 1H), 3.94-3.86 (m, 2H), 3.70-3.63 (m, 1H), 3.48 (s, 3H), 3.31-3.21 (m, 2H), 2.81 (s, 3H), 2.48-2.32 (m, 4H), 1.94 (br d, J=10.8 Hz, 2H), 1.74-1.58 (m, 2H).

Step 5:

To a solution of 2-((1r,4r)-4-((2-methoxyethyl)(methyl)amino)cyclohexyl)isoindoline-1,3-dione (400 mg, 1.2 mmol) in EtOH (5.0 mL) was added N$_2$H4.H$_2$O (645 mg, 12.6 mmol, 626.9 uL). The mixture was stirred at 80° C. for 2 h. The reaction mixture was concentrated under reduced pressure. The residue was washed with DCM (50.0 mL×3). The combined organic layers was concentrated under reduced pressure to give (1r,4r)-N1-(2-methoxyethyl)-N1-methylcyclohexane-1,4-diamine (150 mg, crude).

Step 6:

To a solution of 2-chloro-N-(5-(8-ethyl-2-fluoroquinazolin-6-yl)-6-methylpyridin-2-yl)benzenesulfonamide (50 mg, 109.4 umol) in n-BuOH (2.0 mL) was added DIEA (42 mg, 328.2 umol, 57.1 uL) and (1r,4r)-N1-(2-methoxyethyl)-N1-methylcyclohexane-1,4-diamine (40.7 mg, 218.8 umol). The mixture was stirred at 100° C. for 12 h. The mixture was concentrated under reduced pressure to give a residue. The residue was purified by pre-HPLC (FA condition) to afford 2-chloro-N-(5-(8-ethyl-2-(((1r,4r)-4-((2-methoxyethyl)(methyl)amino)cyclohexyl)amino)quinazolin-6-yl)-6-methylpyridin-2-yl)benzenesulfonamide (6.5 mg, 9.6 umol, 8.8% yield, FA). M+H$^+$=623.2 (LCMS); $^1$H NMR (400 MHz, METHANOL-d$_4$) δ 8.99 (s, 1H), 8.53 (br s, 1H), 8.28-8.17 (m, 1H), 7.67 (d, J=8.8 Hz, 1H), 7.58-7.42 (m, 5H), 7.20 (d, J=8.8 Hz, 1H), 3.98 (tt, J=4.0, 11.4 Hz, 1H), 3.71 (t, J=5.0 Hz, 2H), 3.44 (s, 3H), 3.36-3.32 (m, 3H), 3.13-3.02 (m, 2H), 2.85 (s, 3H), 2.37 (s, 5H), 2.14 (br d, J=12.1 Hz, 2H), 1.84-1.67 (m, 2H), 1.57-1.42 (m, 2H), 1.32 (t, J=7.5 Hz, 3H).

Example 19: Synthesis 2-chloro-N-(5-(2-(((1r,4r)-4-(dimethylamino)cyclohexyl)amino)-8-methylquinazolin-6-yl)-6-methoxypyridin-2-yl)benzenesulfonamide (133)

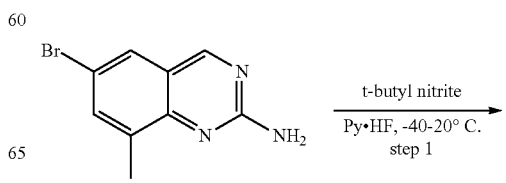

-continued

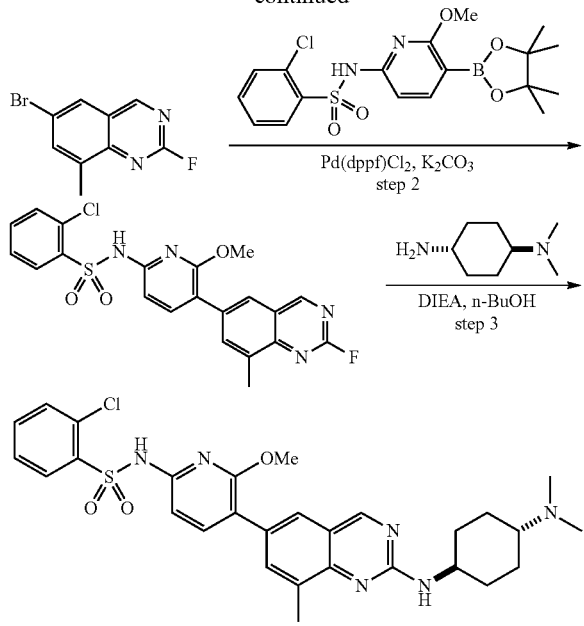

Step 1:

To a solution of 6-bromo-8-methylquinazolin-2-amine (0.5 g, 2.1 mmol) in pyridine (5.0 mL) was added pyridine; hydrofluoride (11.0 g, 110.9 mmol, 10.0 mL) at −40° C. The mixture was stirred at −40° C. for 15 min. Then tert-butyl nitrite (866 mg, 8.4 mmol, 999.1 uL) was added. The mixture was stirred at 20° C. for 4 h. The reaction mixture was quenched by addition NaHCO$_3$ (50.0 mL) to pH 7, and then diluted with ethyl acetate (20.0 mL×3). The combined organic layers were washed with brine (20.0 mL×3), dried over Na$_2$SO$_4$, filtered and concentrated under reduced pressure to give a residue. The residue was purified by column chromatography (SiO$_2$) to afford 6-bromo-2-fluoro-8-methylquinazoline (130 mg, 534.5 umol, 25.4% yield). M+H$^+$= 243.1 (LCMS)

Step 2:

A mixture of 6-bromo-2-fluoro-8-methylquinazoline (130 mg, 539.2 umol), 2-chloro-N-(6-methoxy-5-(4,4,5,5-tetramethyl-1,3,2-dioxaborolan-2-yl)pyridin-2-yl)benzenesulfonamide (229 mg, 539.2 umol), K$_2$CO$_3$ (223 mg, 1.6 mmol), Pd(dppf)Cl$_2$ (39 mg, 53.9 umol) in dioxane (4.0 mL) and H$_2$O (0.4 mL) was degassed and purged with N$_2$ for 3 times, and then the mixture was stirred at 90° C. for 12 h under N$_2$ atmosphere. The reaction mixture was concentrated under reduced pressure. The residue was purified by column chromatography (SiO$_2$) to afford 2-chloro-N-(5-(2-fluoro-8-methylquinazolin-6-yl)-6-methoxypyridin-2-yl) benzenesulfonamide (130 mg, 181.3 umol, 33.6% yield). M+ H$^+$=458.9 (LCMS).

Step 3:

To a solution of 2-chloro-N-(5-(2-fluoro-8-methylquinazolin-6-yl)-6-methoxypyridin-2-yl) benzenesulfonamide (130 mg, 283.2 umol) in n-BuOH (2.0 mL) was added DIEA (292 mg, 2.2 mmol, 394.7 uL), (1r,4r)-N1,N1-dimethylcyclohexane-1,4-diamine (253 mg, 1.4 mmol, HCl). The mixture was stirred at 100° C. for 12 h. The reaction mixture was concentrated under reduced pressure. The residue was purified by prep-HPLC (FA condition) to afford 2-chloro-N-(5-(2-(((1r,4r)-4-(dimethylamino)cyclohexyl)amino)-8-methylquinazolin-6-yl)-6-methoxypyridin-2-yl) benzenesulfonamide (25.7 mg, 39.9 umol, 14.1% yield, FA). M+H$^+$=581.2 (LCMS); $^1$H NMR (400 MHz, METHANOL-d$_4$) δ 8.96 (s, 1H), 8.50 (br s, 1H), 8.37-8.31 (m, 1H), 7.73-7.58 (m, 5H), 7.57-7.51 (m, 1H), 6.65 (d, J=7.9 Hz, 1H), 4.01 (br t, J=11.7 Hz, 1H), 3.67 (s, 3H), 3.28-3.20 (m, 1H), 2.89 (s, 6H), 2.55 (s, 3H), 2.40 (br d, J=12.1 Hz, 2H), 2.19 (br d, J=11.6 Hz, 2H), 1.86-1.66 (m, 2H), 1.60-1.43 (m, 2H).

Example 20: Synthesis of 2-chloro-N-(5-(2-(((1r,4r)-4-(dimethylamino)cyclohexyl)amino)-8-(trifluoromethyl)quinazolin-6-yl)-6-methoxypyridin-2-yl) benzenesulfonamide (135)

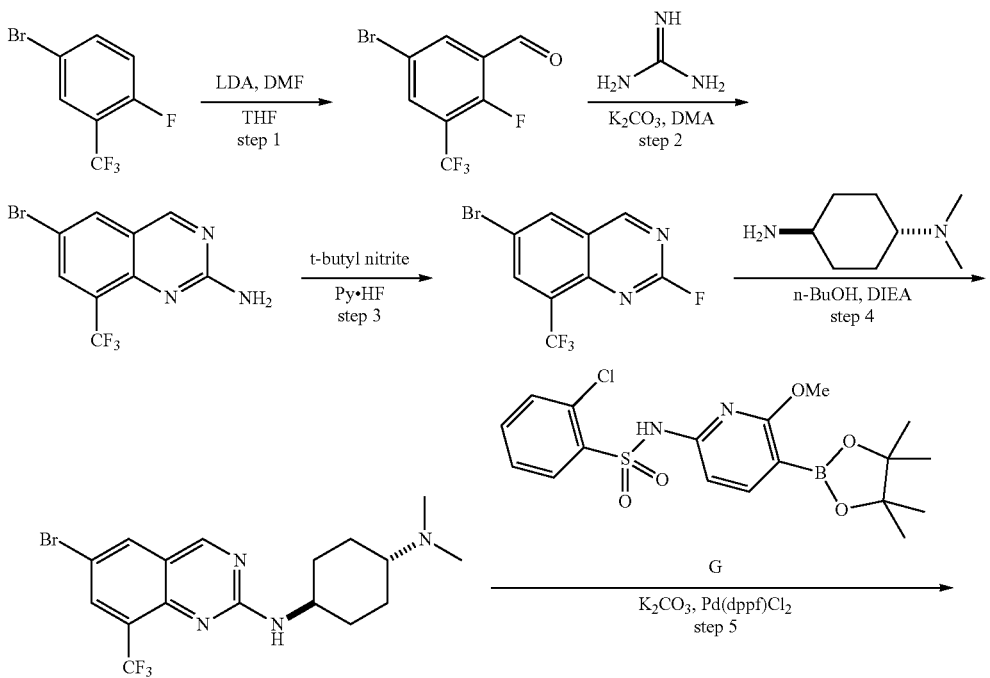

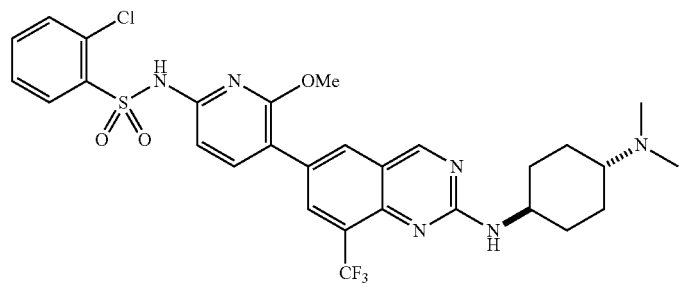

Step 1:

To a solution of 4-bromo-1-fluoro-2-(trifluoromethyl)benzene (5.0 g, 20.5 mmol, 2.9 mL) in THF (50.0 mL) was added LDA (2 M, 13.3 mL) at −78° C. The mixture was stirred at −78° C. for 1 hr. Then DMF (1.8 g, 24.6 mmol, 1.9 mL) was added and stirred for 1 h at −78° C. The mixture was poured into Sat NH$_4$Cl (20.0 mL) and extracted with ethyl acetate (20.0 mL×3). The combined organic layers were washed with brine (20.0 mL×3), dried over Na$_2$SO$_4$, filtered and concentrated under reduced pressure to give a residue. The residue was purified by column chromatography (SiO$_2$) to afford 5-bromo-2-fluoro-3-(trifluoromethyl)benzaldehyde (4 g, 14.7 mmol, 71.7% yield). $^1$H NMR (CHLOROFORM-d, 400 MHz): δ 10.35 (s, 1H), 8.19 (dd, J=2.5, 5.4 Hz, 1H), 7.98 (dd, J=2.1, 6.1 Hz, 1H)

Step 2:

To a solution of guanidine (1.3 g, 11.0 mmol, H$_2$CO$_3$) and K$_2$CO$_3$ (4.5 g, 33.2 mmol) in DMA (60.0 mL) was added a solution of 5-bromo-2-fluoro-3-(trifluoromethyl)benzaldehyde (3.0 g, 11.0 mmol) in DMA (9.0 mL). Then the mixture was stirred at 160° C. for 1 h. The mixture was concentrated to get crude residue add H$_2$O (30.0 mL) and extracted with ethyl acetate (30.0 mL×3). The combined organic layers were washed with brine (20.0 mL×3), dried over Na$_2$SO$_4$, filtered and concentrated under reduced pressure to give a residue. The residue was purified by column chromatography (SiO$_2$) to afford 6-bromo-8-(trifluoromethyl)quinazolin-2-amine (1.6 g, 4.6 mmol, 42.0% yield). $^1$H NMR (DMSO-d$_6$, 400 MHz) δ 9.19 (s, 1H), 8.34 (d, J=2.2 Hz, 1H), 8.12 (d, J=2.0 Hz, 1H), 7.42 (s, 2H).

Step 3:

To a solution of 6-bromo-8-(trifluoromethyl)quinazolin-2-amine (1.5 g, 5.1 mmol) in pyridine (13.0 mL) was added pyridine; hydrofluoride (28.6 g, 288.5 mmol, 26.0 mL) at −40° C. The mixture was stirred at −40° C. for 15 min. Then tert-butyl nitrite (1.0 g, 10.2 mmol, 1.2 mL) was added. The mixture was stirred at 20° C. for 12 h. The mixture was poured into ice water and adjusted pH=7 with sat NaHCO$_3$ extracted with ethyl acetate (50.0 mL×3). The combined organic layers were washed with brine (20.0 mL×3), dried over Na$_2$SO$_4$, filtered and concentrated under reduced pressure to give a residue. The residue was purified by column chromatography (SiO$_2$) to afford 6-bromo-2-fluoro-8-(trifluoromethyl)quinazoline (1.0 g, 3.3 mmol, 64.9% yield). M+H$^+$=294.9 (LCMS);

Step 4:

To a solution of 6-bromo-2-fluoro-8-(trifluoromethyl)quinazoline (0.5 g, 1.69 mmol) in n-BuOH (20.0 mL) were added (1r,4r)-N1,N1-dimethylcyclohexane-1,4-diamine (363 mg, 2.0 mmol, HCl). DIEA (1.1 g, 8.4 mmol, 1.4 mL). The mixture was stirred at 100° C. for 4 h. The mixture was concentrated to get crude residue and added MTBE (20.0 mL). The mixture was stirred at 25° C. for 1 h. Then the mixture was filtered to afford (1r,4r)-N1-(6-bromo-8-(trifluoromethyl)quinazolin-2-yl)-N4,N4-dimethylcyclohexane-1,4-diamine (0.4 g, crude).

Step 5:

To a solution of (1r,4r)-N1-(6-bromo-8-(trifluoromethyl)quinazolin-2-yl)-N4,N4-dimethylcyclohexane-1,4-diamine (0.2 g, 479.3 umol) and K$_2$CO$_3$ (198 mg, 1.4 mmol) in dioxane (2.0 mL) and H$_2$O (0.2 mL) were added 2-chloro-N-(6-methoxy-5-(4,4,5,5-tetramethyl-1,3,2-dioxaborolan-2-yl)pyridin-2-yl)benzenesulfonamide (244 mg, 575.1 umol) and Pd(dppf)Cl$_2$ (35 mg, 47.9 umol). The mixture was stirred at 90° C. for 12 h under N$_2$. The mixture was concentrated to get crude residue. The residue was purified by prep-HPLC (FA condition) to afford 2-chloro-N-(5-(2-(((1r,4r)-4-(dimethylamino)cyclohexyl)amino)-8-(trifluoromethyl)quinazolin-6-yl)-6-methoxypyridin-2-yl)benzenesulfonamide (144 mg, 207.0 umol, 43.2% yield, FA). M+H$^+$=635.2 (LCMS); $^1$H NMR (METHANOL-d$_4$, 400 MHz) δ 9.07 (br s, 1H), 8.55 (s, 1H), 8.36-8.29 (m, 1H), 8.15 (d, J=1.3 Hz, 1H), 8.02 (s, 1H), 7.70 (d, J=8.1 Hz, 1H), 7.64-7.56 (m, 2H), 7.56-7.49 (m, 1H), 6.66 (d, J=7.9 Hz, 1H), 3.91 (br s, 1H), 3.68 (s, 3H), 3.26-3.08 (m, 1H), 2.82 (br s, 6H), 2.39 (br s, 2H), 2.18 (br d, J=8.3 Hz, 2H), 1.80-1.59 (m, 2H), 1.56-1.39 (m, 2H).

Example 21: Synthesis of 2-chloro-N-(5-(8-ethyl-2-(((1r,4r)-4-(methylamino)cyclohexyl)amino)quinazolin-6-yl)-6-methoxypyridin-2-yl)benzenesulfonamide (116)

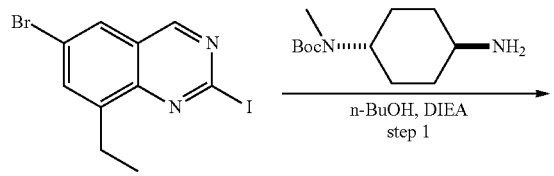

-continued

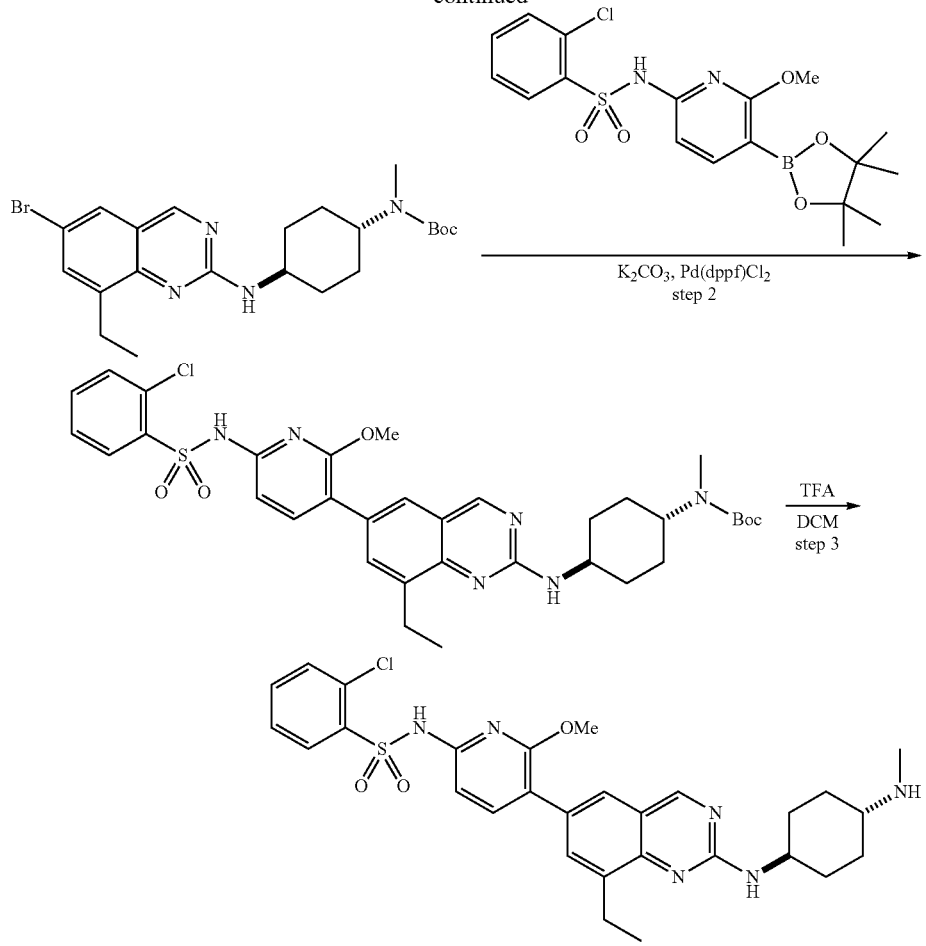

The title compound was synthesized according to the synthetic procedure reported for the preparation of 2-chloro-N-(5-(2-(((1r,4r)-4-(dimethylamino)cyclohexyl)amino)-8-(trifluoromethyl)quinazolin-6-yl)-6-methoxypyridin-2-yl)benzenesulfonamide (114 mg, FA). M+H$^+$=581.2 (LCMS); $^1$H NMR (400 MHz, METHANOL-d$_4$) δ 8.96 (s, 1H), 8.54 (s, 1H), 8.33 (d, J=7.3 Hz, 1H), 7.70-7.63 (m, 3H), 7.62-7.56 (m, 2H), 7.56-7.49 (m, 1H), 6.65 (d, J=7.9 Hz, 1H), 4.06-3.91 (m, 1H), 3.67 (s, 3H), 3.18-2.99 (m, 3H), 2.74 (s, 3H), 2.45-2.16 (m, 4H), 1.64-1.43 (m, 4H), 1.32 (t, J=7.5 Hz, 3H).

Example 21A: Synthesis of (1r,4r)-N1,N1-dimethylcyclohexane-1,4-diamine

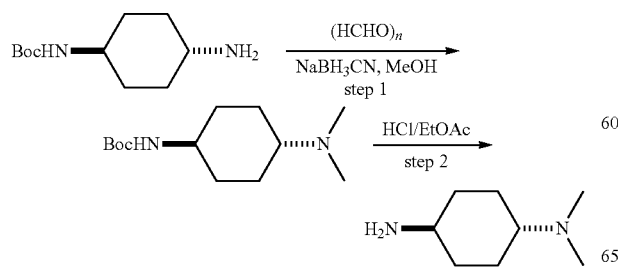

The title compound was synthesized according to the synthetic procedure reported for the preparation of N1,N1-dimethylbicyclo[2.2.2]octane-1,4-diamine (8.3 g, 46.4 mmol, 99.6% yield, HCl). $^1$H NMR (400 MHz, DMSO-d$_6$) δ 11.02 (br s, 1H), 8.31 (br s, 3H), 3.62-3.36 (m, 1H), 3.15-3.03 (m, 1H), 2.96 (br d, J=4.0 Hz, 1H), 2.65 (d, J=4.9 Hz, 6H), 2.09 (br s, 4H), 1.65-1.31 (m, 4H).

Example 21B: Synthesis of (1s,4s)-N1,N1-dimethylcyclohexane-1,4-diamine

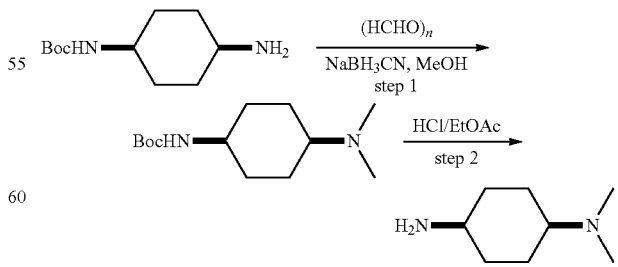

The title compound was synthesized according to the synthetic procedure reported for the preparation of N1,N1-dimethylbicyclo[2.2.2]octane-1,4-diamine (1.7 g, crude, HCl). ¹H NMR (400 MHz, METHANOL-d₄) δ 3.53 (br s, 1H), 3.41-3.33 (m, 1H), 2.89 (s, 6H), 2.13-1.88 (m, 9H).

Example 22: Synthesis 2-chloro-N-(5-(2-(((1r,4r)-4-(dimethylamino)cyclohexyl)amino)-8-(methoxymethyl)quinazolin-6-yl)-6-methoxypyridin-2-yl)benzenesulfonamide (137)

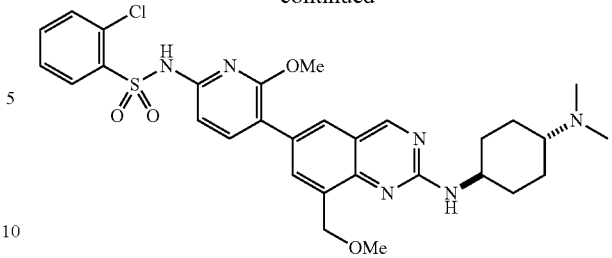

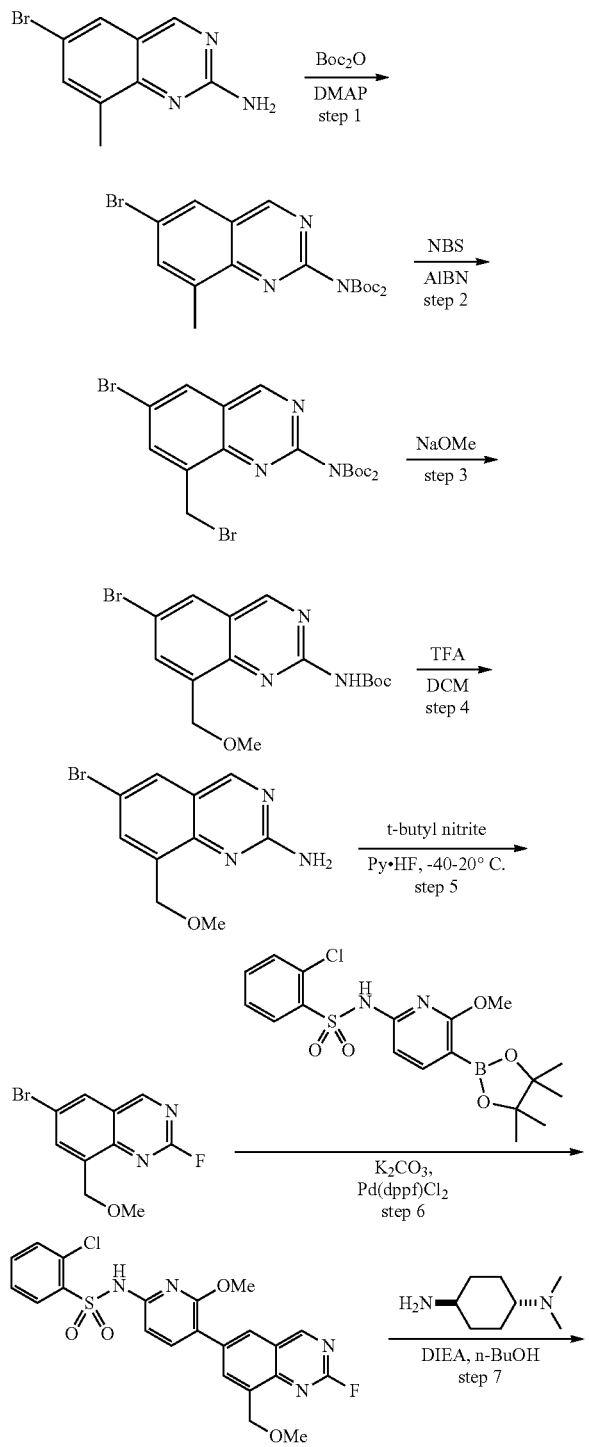

Step 1:
To a solution of 6-bromo-8-methylquinazolin-2-amine (6.6 g, 27.8 mmol) in Boc₂O (100.0 mL) was added DMAP (3.4 g, 27.8 mmol). The mixture was stirred at 100° C. for 12 h. The reaction mixture was concentrated under reduced pressure to give a residue. The residue was purified by column chromatography (SiO₂) to afford tert-butyl N-(6-bromo-8-methyl-quinazolin-2-yl)-N-tert-butoxycarbonyl-carbamate (4.1 g, 6.6 mmol, 24.0% yield). ¹H NMR (400 MHz, DMSO-d₆) δ 9.59 (s, 1H), 8.33 (d, J=1.8 Hz, 1H), 8.12-8.06 (m, 1H), 2.63 (s, 3H), 1.39 (s, 22H).

Step 2:
To a solution of tert-butyl N-(6-bromo-8-methyl-quinazolin-2-yl)-N-tert-butoxycarbonyl-carbamate (3.5 g, 8.1 mmol) and NBS (4.3 g, 24.5 mmol) in ACN (90.0 mL) was added AIBN (1.3 g, 8.1 mmol). The mixture was stirred at 90° C. for 12 h. The reaction mixture was concentrated under reduced pressure to give a residue. The residue was purified by column chromatography (SiO₂) to afford tert-butyl N-[6-bromo-8-(bromomethyl)quinazolin-2-yl]-N-tert-butoxycarbonyl-carbamate (2.3 g, 3.1 mmol, 38.1% yield).

Step 3:
To a solution of tert-butyl N-[6-bromo-8-(bromomethyl)quinazolin-2-yl]-N-tert-butoxycarbonyl-carbamate (0.5 g, 966.7 umol) in NaOMe (10.0 mL, 30% solution) was stirred at 30° C. for 12 h. The reaction mixture was added into H₂O (10 mL), then was filtered and the solid was desired tert-butyl N-[6-bromo-8-(methoxymethyl)quinazolin-2-yl]carbamate (0.3 g, crude).

Step 4:
To a solution of tert-butyl N-[6-bromo-8-(methoxymethyl)quinazolin-2-yl]carbamate (0.3 g, 814.7 umol) in HCl/EtOAc (10.0 mL, 4M) was stirred at 25° C. for 0.5 h. The reaction mixture was concentrated under reduced pressure. The residue was added DCM (10.0 mL) and TFA (4.0 mL). The mixture was stirred at 25° C. for 4 h. The reaction mixture was concentrated under reduced pressure. The reaction mixture was quenched by addition NaHCO₃ (9.0 mL), and then extracted with ethyl acetate (3.0 mL×3). The combined organic layers were washed with brine (3.0 mL×3), dried over Na₂SO₄, filtered and concentrated under reduced pressure to give 6-bromo-8-(methoxymethyl)quinazolin-2-amine (200 mg, crude).

Step 5:
To a solution of 6-bromo-8-(methoxymethyl)quinazolin-2-amine (170 mg, 634.0 umol) in pyridine (2.0 mL) was added pyridine; hydrofluoride (4.4 g, 44.4 mmol, 4.0 mL) at −40 OC. The mixture was stirred at −40° C. for 15 min. Then tert-butyl nitrite (261 mg, 2.5 mmol, 301.6 uL) was added. The mixture was stirred at 20° C. for 1 h. The reaction mixture was quenched by addition NaHCO₃ (5.0 mL) to pH 7, and then diluted with ethyl acetate (3.0 mL×3). The combined organic layers were washed with brine (3.0 mL×3), dried over Na₂SO₄, filtered and concentrated under reduced pressure to give a residue. The residue was purified by column chromatography (SiO$_2$) to afford 6-bromo-2-fluoro-8-(methoxymethyl)quinazoline (100 mg). M+H$^+$=271.0 (LCMS).

Step 6:

A mixture of 6-bromo-2-fluoro-8-(methoxymethyl)quinazoline (100 mg, 368.8 umol), 2-chloro-N-(6-methoxy-5-(4,4,5,5-tetramethyl-1,3,2-dioxaborolan-2-yl)pyridin-2-yl)benzenesulfonamide (172 mg, 405.7 umol), K$_2$CO$_3$ (152 mg, 1.1 mmol), Pd(dppf)Cl$_2$ (26 mg, 36.8 umol) in dioxane (2.0 mL) and H$_2$O (0.2 mL) was degassed and purged with N$_2$ for 3 times, and then the mixture was stirred at 90° C. for 12 h under N$_2$ atmosphere. The reaction mixture was concentrated under reduced pressure. The residue was purified by prep-TLC (SiO$_2$) to afford 2-chloro-N-(5-(2-fluoro-8-(methoxymethyl)quinazolin-6-yl)-6-methoxypyridin-2-yl)benzenesulfonamide (0.1 g, 188.1 umol, 51.0% yield). M+H$^+$=489.0 (LCMS).

Step 7:

To a solution of 2-chloro-N-(5-(2-fluoro-8-(methoxymethyl)quinazolin-6-yl)-6-methoxypyridin-2-yl)benzenesulfonamide (100 mg, 204.5 umol) in n-BuOH (2.0 mL) was added DIEA (158 mg, 1.2 mmol, 213.7 uL) and (1r,4r)-N1,N1-dimethylcyclohexane-1,4-diamine (73 mg, 409.0 umol, HCl). The mixture was stirred at 100° C. for 12 h. The reaction mixture was concentrated under reduced pressure. The residue was purified by prep-HPLC (FA condition) to afford 2-chloro-N-(5-(2-(((1r,4r)-4-(dimethylamino)cyclohexyl)amino)-8-(methoxymethyl)quinazolin-6-yl)-6-methoxypyridin-2-yl)benzenesulfonamide (33.3 mg, 44.8 umol, 21.9% yield, FA). M+H$^+$=611.2 (LCMS); $^1$H NMR (400 MHz, METHANOL-d$_4$) δ 8.95 (s, 1H), 8.43 (br s, 1H), 8.34-8.23 (m, 1H), 7.84 (d, J=2.0 Hz, 1H), 7.72 (d, J=2.0 Hz, 1H), 7.63 (d, J=7.9 Hz, 1H), 7.59-7.54 (m, 2H), 7.53-7.45 (m, 1H), 6.63 (d, J=7.9 Hz, 1H), 3.94 (tt, J=3.8, 11.5 Hz, 1H), 3.64 (s, 3H), 3.46 (s, 3H), 3.29-3.19 (m, 1H), 2.87 (s, 5H), 2.36 (br d, J=12.1 Hz, 2H), 2.23-2.12 (m, 2H), 1.81-1.62 (m, 2H), 1.55-1.36 (m, 2H); $^1$H NMR (400 MHz, DMSO-d$_6$) δ 9.06 (br s, 1H), 8.29-8.15 (m, 2H), 7.75 (dd, J=2.0, 9.7 Hz, 2H), 7.64-7.47 (m, 4H), 7.37 (br s, 1H), 6.53 (br d, J=7.9 Hz, 1H), 4.80 (s, 2H), 3.76 (br s, 1H), 3.48 (s, 3H), 3.39 (s, 3H), 2.74-2.62 (m, 1H), 2.48 (br s, 6H), 2.14 (br s, 2H), 1.96 (br d, J=8.9 Hz, 2H), 1.56-1.20 (m, 4H).

Example 23: Synthesis of 2-chloro-N-(5-(2-(((1r,4r)-4-(dimethylamino)cyclohexyl)amino)-8-methylquinazolin-6-yl)-3-fluoro-6-methoxypyridin-2-yl)benzenesulfonamide (145)

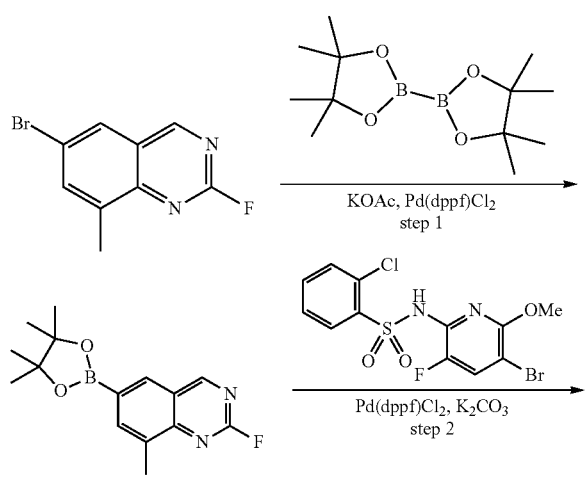

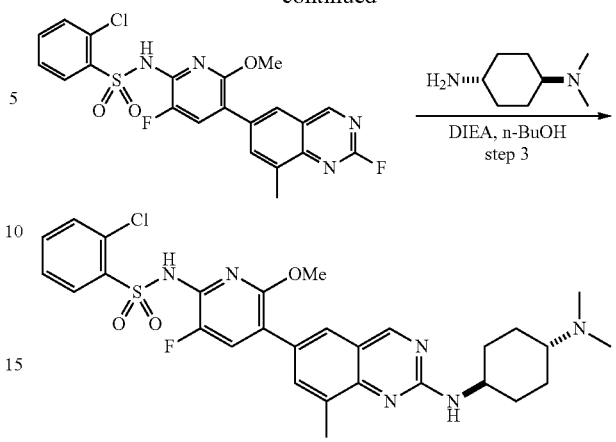

Step 1:

A mixture of 6-bromo-2-fluoro-8-methylquinazoline (500 mg, 2.0 mmol), 4,4,4',4',5,5,5',5'-octamethyl-2,2'-bi(1,3,2-dioxaborolane) (632 mg, 2.4 mmol), KOAc (610 mg, 6.22 mmol), Pd(dppf)Cl$_2$ (151 mg, 207.4 umol) in dioxane (20.0 mL) was degassed and purged with N$_2$ for 3 times, and then the mixture was stirred at 90° C. for 12 h under N$_2$ atmosphere. The reaction mixture was concentrated under reduced pressure. The residue was purified by column chromatography (SiO$_2$) to afford 2-fluoro-8-methyl-6-(4,4,5,5-tetramethyl-1,3,2-dioxaborolan-2-yl)quinazoline (590 mg, 1.9 mmol, 95.7% yield). M+H$^+$=289.2 (LCMS).

Step 2:

A mixture of 2-fluoro-8-methyl-6-(4,4,5,5-tetramethyl-1,3,2-dioxaborolan-2-yl)quinazoline (349 mg, 1.2 mmol), N-(5-bromo-3-fluoro-6-methoxypyridin-2-yl)-2-chlorobenzenesulfonamide (400 mg, 1.0 mmol), K$_2$CO$_3$ (419 mg, 3.0 mmol), Pd(dppf)Cl$_2$ (73 mg, 101 umol) in dioxane (15.0 mL) and H$_2$O (1.5 mL) was degassed and purged with N$_2$ for 3 times, and then the mixture was stirred at 90° C. for 12 h under N$_2$ atmosphere. The reaction mixture was concentrated under reduced pressure. The residue was purified by column chromatography (SiO$_2$) to afford 2-chloro-N-(3-fluoro-5-(2-fluoro-8-methylquinazolin-6-yl)-6-methoxypyridin-2-yl)benzenesulfonamide (450 mg, 802 umol, 79.3% yield). M+H$^+$=477.2 (LCMS).

Step 3:

To a solution of (1r,4r)-N1,N1-dimethylcyclohexane-1,4-diamine (281 mg, 1.5 mmol, HCl) in n-BuOH (7.0 mL) was added DIEA (325 mg, 2.5 mmol, 438.3 uL) and 2-chloro-N-(3-fluoro-5-(2-fluoro-8-methylquinazolin-6-yl)-6-methoxypyridin-2-yl)benzenesulfonamide (150 mg, 314.5 umol). The mixture was stirred at 100° C. for 24 h. The reaction mixture was concentrated under reduced pressure. The residue was purified by prep-HPLC (FA condition) to afford 2-chloro-N-(5-(2-(((1r,4r)-4-(dimethylamino)cyclohexyl)amino)-8-methylquinazolin-6-yl)-3-fluoro-6-methoxypyridin-2-yl)benzenesulfonamide (54.9 mg, 82.9 umol, 26.3% yield, FA). M+H$^+$=599.2 (LCMS); $^1$H NMR (400 MHz, DMSO-d$_6$) δ 9.00 (br s, 1H), 8.19-8.09 (m, 2H), 7.67 (br d, J=7.7 Hz, 2H), 7.36 (br d, J=7.6 Hz, 4H), 7.27 (br s, 1H), 3.82 (br s, 1H), 3.22 (s, 3H), 3.09 (br s, 1H), 2.70 (s, 6H), 2.46 (s, 3H), 2.19 (br s, 2H), 2.01 (br d, J=11.7 Hz, 2H), 1.64-1.47 (m, 2H), 1.36 (q, J=11.5 Hz, 2H).

Example 24: Synthesis of 2-chloro-N-(5-(2-(((1s, 4s)-4-(dimethylamino)cyclohexyl)amino)-8-methylquinazolin-6-yl)-6-methoxypyridin-2-yl)benzenesulfonamide (139)

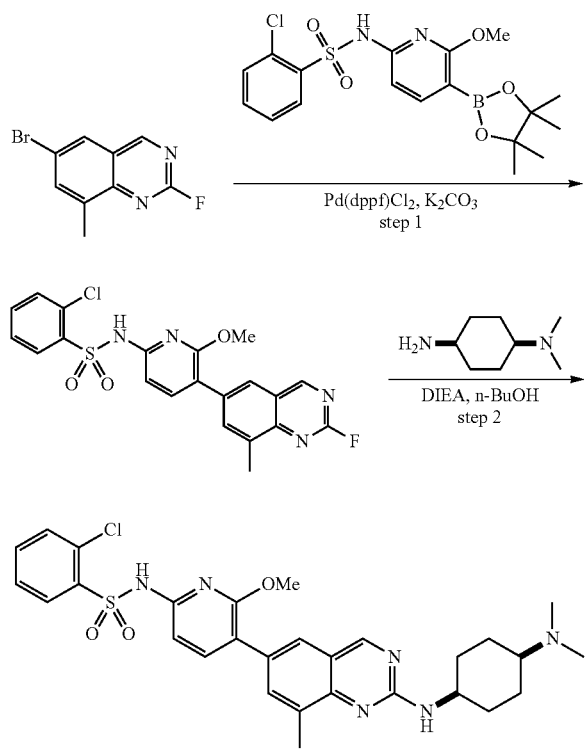

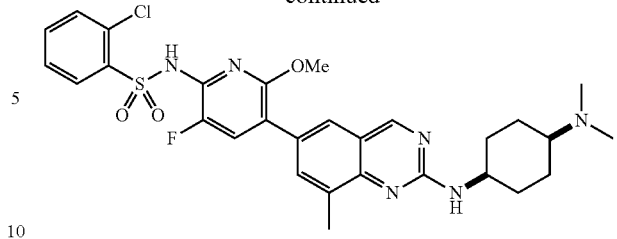

The title compound was synthesized according to the synthetic procedure reported for the preparation of 2-chloro-N-(5-(2-(((1r,4r)-4-(dimethylamino)cyclohexyl)amino)-8-methylquinazolin-6-yl)-3-fluoro-6-methoxypyridin-2-yl)benzenesulfonamide (72.4 mg, 111.1 umol, 35.3% yield, FA). M+H$^+$=599.1 (LCMS); $^1$H NMR (400 MHz, DMSO-d$_6$) δ 9.03 (s, 1H), 8.18-8.11 (m, 2H), 7.68 (s, 2H), 7.43-7.37 (m, 3H), 7.36 (br d, J=2.6 Hz, 1H), 4.21 (br s, 1H), 3.22 (s, 3H), 3.11 (br s, 1H), 2.77-2.62 (m, 6H), 2.46 (s, 3H), 2.07 (br d, J=12.1 Hz, 2H), 1.94-1.54 (m, 6H).

Example 26: Synthesis of 2-chloro-N-(5-(2-(((1s, 4s)-4-(dimethylamino)cyclohexyl)amino)-8-ethylquinazolin-6-yl)-3-fluoro-6-methoxypyridin-2-yl)benzenesulfonamide (142)

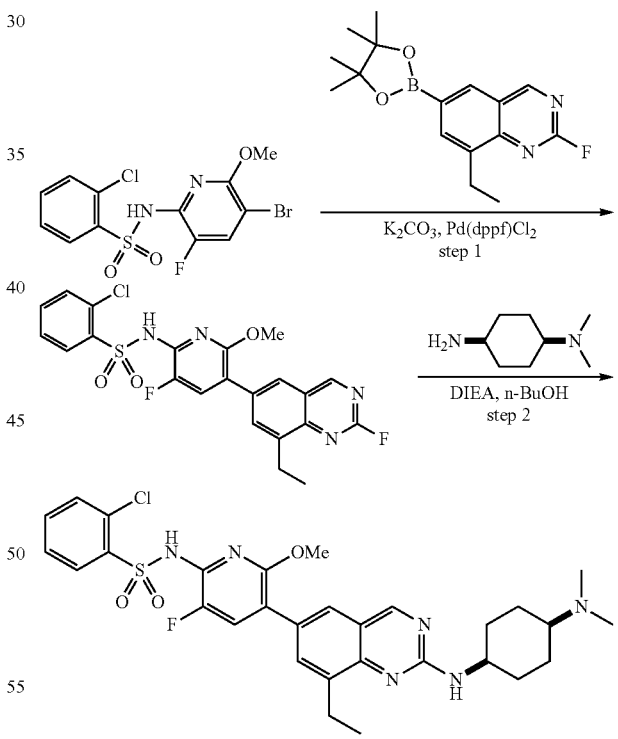

The title compound was synthesized according to the synthetic procedure reported for the preparation of 2-chloro-N-(5-(2-(((1r,4r)-4-(dimethylamino)cyclohexyl)amino)-8-methylquinazolin-6-yl)-3-fluoro-6-methoxypyridin-2-yl)benzenesulfonamide (64.6 mg, 100.7 umol, 29.6% yield, FA). M+H$^+$=581.1 (LCMS); $^1$H NMR (400 MHz, METHANOL-d$_4$) δ 8.95 (s, 1H), 8.55 (br s, 1H), 8.30 (d, J=7.6 Hz, 1H), 7.71-7.53 (m, 5H), 7.53-7.44 (m, 1H), 6.61 (d, J=7.9 Hz, 1H), 4.28 (br s, 1H), 3.63 (s, 3H), 3.25-3.10 (m, 1H), 2.82 (s, 6H), 2.51 (s, 3H), 2.28 (br d, J=12.8 Hz, 2H), 2.00-1.67 (m, 6H).

Example 25: Synthesis of 2-chloro-N-(5-(2-(((1s, 4s)-4-(dimethylamino)cyclohexyl)amino)-8-methylquinazolin-6-yl)-3-fluoro-6-methoxypyridin-2-yl)benzenesulfonamide (147)

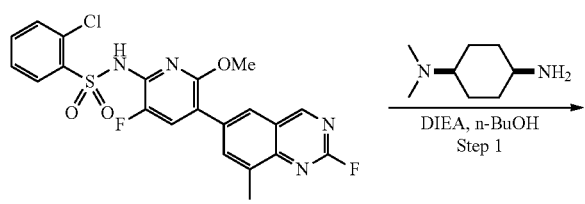

Step 1:

A mixture of 8-ethyl-2-fluoro-6-(4,4,5,5-tetramethyl-1,3,2-dioxaborolan-2-yl)quinazoline (100 mg, 331 umol), N-(5-bromo-3-fluoro-6-methoxypyridin-2-yl)-2-chlorobenzenesulfonamide (131 mg, 331 umol), K$_2$CO$_3$ (69 mg, 496.4 umol) and Pd(dppf)Cl$_2$ (24 mg, 33.1 umol) in dioxane (15.0 mL) and H$_2$O (1.5 mL) was degassed and purged with N$_2$ for 3 times, and then the mixture was stirred at 90° C. for 12 h under N$_2$ atmosphere. The reaction was concentrated to give a residue. The residue was purified by prep-TLC (SiO$_2$) to afford 2-chloro-N-(5-(8-ethyl-2-fluoroquinazolin-6-yl)-3-fluoro-6-methoxypyridin-2-yl)benzenesulfonamide (90 mg, 47.7 umol, 14.4% yield). M+H$^+$=491.0 (LCMS).

Step 2:

To a solution of 2-chloro-N-(5-(8-ethyl-2-fluoroquinazolin-6-yl)-3-fluoro-6-methoxypyridin-2-yl)benzenesulfonamide (90 mg, 183.3 umol) in n-BuOH (4.0 mL) was added DIEA (190 mg, 1.5 mmol, 255.5 uL) and (1s,4s)-N1,N1-dimethylcyclohexane-1,4-diamine (131 mg, 733.3 umol, HCl). The mixture was stirred at 120° C. for 12 h. The reaction was concentrated to give a residue. The residue was purified by prep-HPLC (FA condition) to afford 2-chloro-N-(5-(2-(((1s,4s)-4-(dimethylamino)cyclohexyl)amino)-8-ethylquinazolin-6-yl)-3-fluoro-6-methoxypyridin-2-yl)benzenesulfonamide (60.3 mg, 85.3 umol, 46.5% yield, FA). M+H$^+$=613.2 (LCMS); $^1$H NMR (400 MHz, DMSO-d$_6$) δ 9.04 (s, 1H), 8.19-8.12 (m, 1H), 7.68 (d, J=2.9 Hz, 2H), 7.44-7.33 (m, 5H), 4.18 (br s, 1H), 3.23 (s, 3H), 3.10 (br s, 1H), 2.95 (q, J=7.4 Hz, 2H), 2.74-2.65 (m, 6H), 2.08 (br d, J=13.1 Hz, 2H), 1.92-1.58 (m, 6H), 1.24 (t, J=7.5 Hz, 3H).

Example 27: Synthesis of 2-chloro-N-(5-(2-(((1s, 4s)-4-(dimethylamino)cyclohexyl)amino)-8-ethylquinazolin-6-yl)-6-methoxypyridin-2-yl)benzenesulfonamide (141)

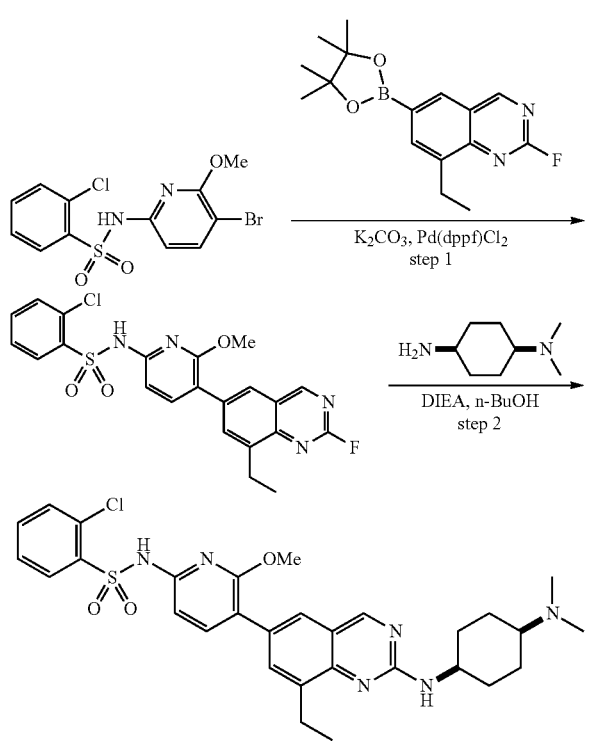

The title compound was synthesized according to the synthetic procedure reported for the preparation of 2-chloro-N-(5-(2-(((1s,4s)-4-(dimethylamino)cyclohexyl)amino)-8-ethylquinazolin-6-yl)-3-fluoro-6-methoxypyridin-2-yl)benzenesulfonamide. (51.8 mg, 74.5 umol, 17.6% yield, FA). M+H$^+$=595.1 (LCMS); $^1$H NMR (400 MHz, METHANOL-d$_4$) δ 8.97 (s, 1H), 8.42 (s, 1H), 8.34-8.27 (m, 1H), 7.70-7.46 (m, 6H), 6.63 (d, J=7.9 Hz, 1H), 4.28 (br t, J=2.9 Hz, 1H), 3.65 (s, 3H), 3.33 (t, 1H), 3.02 (q, J=7.5 Hz, 2H), 2.87 (s, 6H), 2.30 (br d, J=13.0 Hz, 2H), 2.02-1.71 (m, 6H), 1.28 (t, J=7.4 Hz, 3H).

Example 28: Synthesis of 2-chloro-N-(5-(2-(((1s, 4s)-4-(dimethylamino)-4-methylcyclohexyl)amino)-8-ethylquinazolin-6-yl)-3-fluoro-6-methoxypyridin-2-yl)benzenesulfonamide (144)

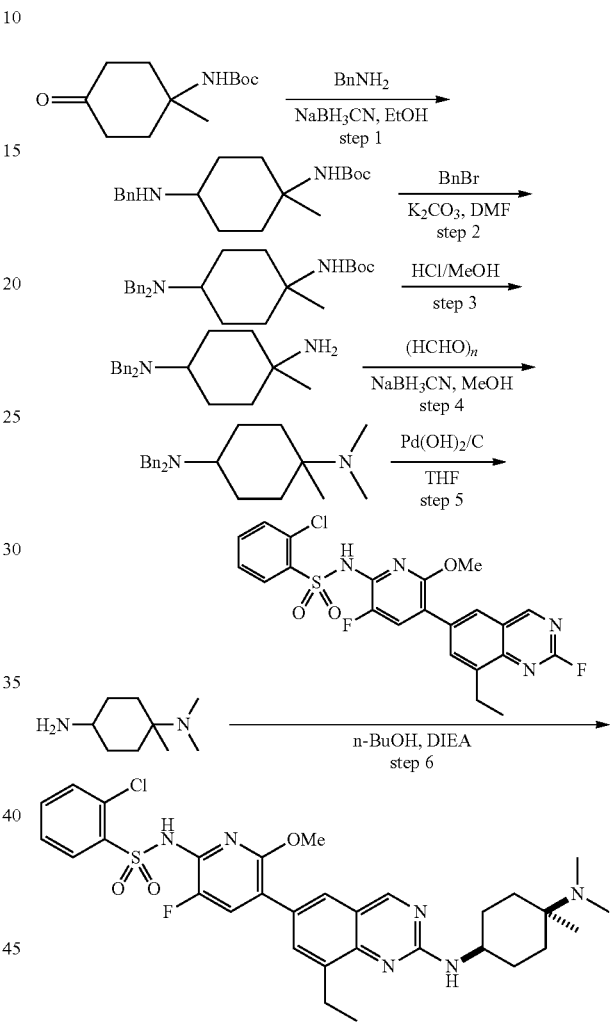

Step 1:

To a solution of tert-butyl (1-methyl-4-oxocyclohexyl)carbamate (900 mg, 4 mmol) in EtOH (20.0 mL) was added phenylmethanamine (509 mg, 4.7 mmol, 517.9 uL) and AcOH (238 mg, 4 mmol, 226.5 uL) at 0° C. The resulting mixture was stirred at 0° C. for 15 min. Follow by successive addition of NaBH$_3$CN (498 mg, 7.9 mmol), the mixture was stirred at 20° C. for 12 h. The reaction was concentrated to give a residue. The residue was dissolved in saturated aqueous NaHCO$_3$ (20.0 mL) and extracted with ethyl acetate (20.0 mL×3). The combined organic phase was dried over anhydrous Na$_2$SO$_4$, filtered and concentrated to give tert-butyl (4-(benzylamino)-1-methylcyclohexyl)carbamate (1.3 g, crude).

Step 2:

To a solution of tert-butyl (4-(benzylamino)-1-methylcyclohexyl)carbamate (1.2 g, 3.7 mmol) in DMF (20.0 mL) was added K$_2$CO$_3$ (1.6 g, 11.3 mmol) and bromomethylbenzene (773 mg, 4.5 mmol, 537.1 uL). The mixture was stirred at 40° C. for 12 h. The reaction was quenched with H₂O (30.0 mL) and extracted with ethyl acetate (20 mL×3). The combined organic was washed with brine (20 mL×3), dried over anhydrous Na₂SO₄, filtered and concentrated to give a residue. The residue was purified by flash silica gel chromatography (SiO₂) to afford tert-butyl (4-(dibenzylamino)-1-methylcyclohexyl)carbamate (1.5 g, 3.4 mmol, 90% yield). ¹H NMR (400 MHz, CHLOROFORM-d) δ 7.42-7.35 (m, 4H), 7.34-7.29 (m, 4H), 7.26-7.19 (m, 2H), 3.69-3.63 (m, 4H), 2.60-2.46 (m, 1H), 2.13 (br d, J=11.9 Hz, 1H), 1.94 (br d, J=9.3 Hz, 1H), 1.84-1.66 (m, 2H), 1.61-1.50 (m, 3H), 1.47-1.39 (m, 9H), 1.36-1.24 (m, 4H).

Step 3:

The mixture of tert-butyl (4-(dibenzylamino)-1-methylcyclohexyl)carbamate (500 mg, 1.2 mmol) in HCl/MeOH (4M, 10.0 mL) was stirred at 20° C. for 1 h. The reaction was concentrated to give N¹,N¹-dibenzyl-4-methylcyclohexane-1,4-diamine (400 mg, crude, HCl).

Step 4:

To a solution of N¹,N¹-dibenzyl-4-methylcyclohexane-1,4-diamine (350 mg, 1 mmol, HCl) in MeOH (10.0 mL) was added TEA to basify pH to 7 and then (HCHO)n (274 mg, 3 mmol) was added. AcOH (61 mg, 1 mmol, 58 uL,) was added to adjust pH to 5 and then the mixture was stirred at 60° C. for 2 h. NaBH₃CN (255 mg, 4.1 mmol) was added and the mixture was stirred at 60° C. for 12 h. The reaction was concentrated to give a residue. The residue was dissolved in saturated NaHCO₃ (10.0 mL) and extracted with ethyl acetate (10.0 mL×3). The combined organic phase was dried over anhydrous Na₂SO₄, filtered and concentrated to give N⁴,N⁴-dibenzyl-N¹,N¹,1-trimethylcyclohexane-1,4-diamine (330 mg, crude).

Step 5:

To a solution of N⁴,N⁴-dibenzyl-N¹,N¹,1-trimethylcyclohexane-1,4-diamine (330 mg, 980.6 umol) in THF (10.0 mL) and AcOH (0.1 mL) was added Pd(OH)₂/C (400 mg, 980.6 umol, 10% Pd basis) under N₂ atmosphere. The suspension was degassed and purged with H₂ for 3 times. The mixture was stirred under H₂ (50 Psi) at 50° C. for 12 h. The reaction was filtered and concentrated to give N¹,N¹,1-trimethylcyclohexane-1,4-diamine (150 mg, crude).

Step 6:

To a solution of 2-chloro-N-(5-(8-ethyl-2-fluoroquinazolin-6-yl)-3-fluoro-6-methoxypyridin-2-yl)benzenesulfonamide (30 mg, 61.1 umol) in n-BuOH (3.0 mL) was added DIEA (63 mg, 488.9 umol, 85.2 uL) and N¹,N¹,1-trimethylcyclohexane-1,4-diamine (38 mg, 244.4 umol). The mixture was stirred at 120° C. for 12 h. The reaction was concentrated to give a residue. The residue was purified by prep-HPLC (FA condition) to afford 2-chloro-N-(5-(2-(((1s,4s)-4-(dimethylamino)-4-methylcyclohexyl)amino)-8-ethylquinazolin-6-yl)-3-fluoro-6-methoxypyridin-2-yl)benzenesulfonamide (3.7 mg, 5.4 umol, 8.9% yield, FA). M+H⁺= 627.3 (LCMS); ¹H NMR (400 MHz, METHANOL-d₄) δ 8.98 (br s, 1H), 8.53 (br s, 1H), 8.32 (br d, J=7.8 Hz, 1H), 7.69 (s, 2H), 7.62-7.47 (m, 4H), 4.16 (br s, 1H), 3.46 (s, 3H), 3.03 (q, J=7.4 Hz, 2H), 2.85 (s, 6H), 2.13-1.92 (m, 6H), 1.86 (br d, J=5.7 Hz, 2H), 1.41 (s, 3H), 1.29 (br t, J=7.4 Hz, 3H); ¹H NMR (400 MHz, DMSO-d₆) δ 8.98 (s, 1H), 8.18-8.12 (m, 1H), 7.66 (s, 2H), 7.44-7.32 (m, 4H), 3.99 (br s, 1H), 3.31 (s, 3H), 2.96 (q, J=7.5 Hz, 2H), 2.51 (br s, 6H), 2.01-1.75 (m, 6H), 1.58-1.47 (m, 2H), 1.24 (t, J=7.5 Hz, 3H), 1.13 (s, 3H).

Example 29: Synthesis of 2-chloro-N-(5-(2-(((1s,4s)-4-(dimethylamino)-4-methylcyclohexyl)amino)-8-ethylquinazolin-6-yl)-6-methoxypyridin-2-yl)benzenesulfonamide (143)

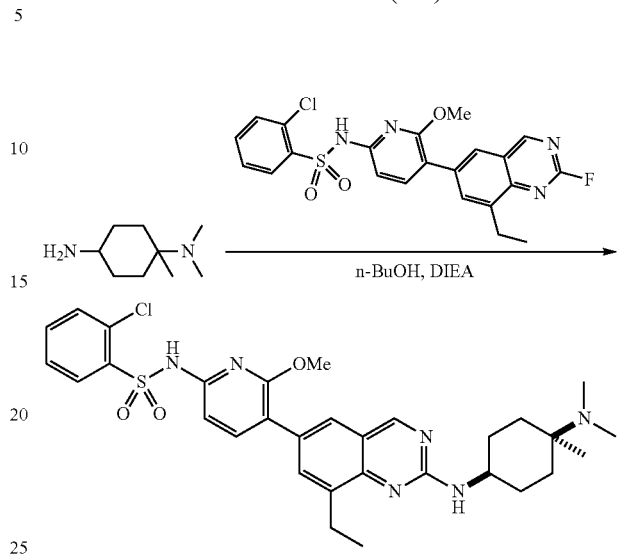

The title compound was synthesized according to the synthetic procedure reported for the preparation of 2-chloro-N-(5-(2-(((1s,4s)-4-(dimethylamino)-4-methylcyclohexyl)amino)-8-ethylquinazolin-6-yl)-3-fluoro-6-methoxypyridin-2-yl)benzenesulfonamide (6.4 mg, 9.4% yield). M+H⁺= 609.3 (LCMS); ¹H NMR (400 MHz, METHANOL-d₄) δ 8.94 (s, 1H), 8.33-8.27 (m, 1H), 7.64 (dd, J=1.9, 13.4 Hz, 2H), 7.60 (d, J=8.1 Hz, 1H), 7.58-7.54 (m, 2H), 7.52-7.46 (m, 1H), 6.60 (d, J=7.9 Hz, 1H), 4.10 (br t, J=5.3 Hz, 1H), 3.62 (s, 3H), 3.02 (q, J=7.5 Hz, 2H), 2.68-2.59 (m, 6H), 2.06-1.89 (m, 6H), 1.73-1.62 (m, 2H), 1.31-1.22 (m, 6H).

Example 30: Synthesis of 2-chloro-N-(5-(2-(((1r,4r)-4-(dimethylamino)cyclohexyl)amino)-8-fluoroquinazolin-6-yl)-6-methoxypyridin-2-yl)benzenesulfonamide (148)

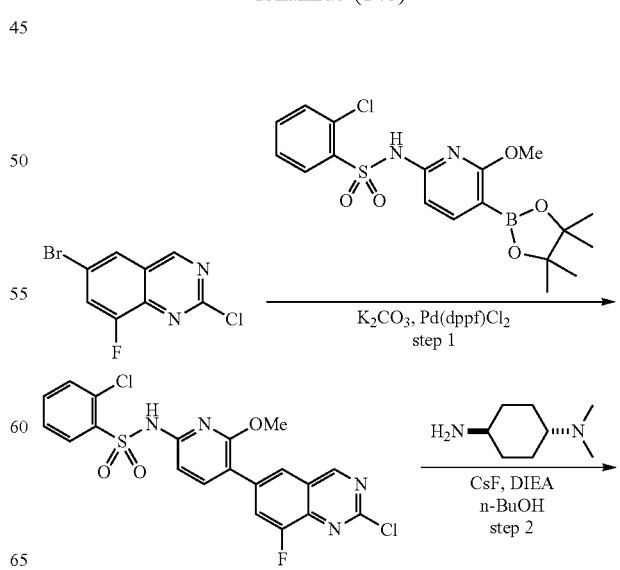

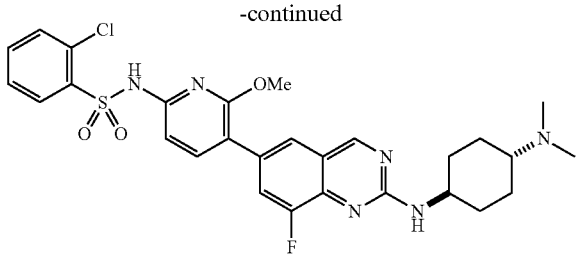

Step 1:

A mixture of 6-bromo-2-chloro-8-fluoroquinazoline (90 mg, 344.2 umol), 2-chloro-N-(6-methoxy-5-(4,4,5,5-tetramethyl-1,3,2-dioxaborolan-2-yl)pyridin-2-yl)benzenesulfonamide (146 mg, 344.2 umol), $K_2CO_3$ (142 mg, 1.0 mmol, Pd(dppf)Cl$_2$ (25 mg, 34.4 umol) in dioxane (4.0 mL) and H$_2$O (0.4 mL) was degassed and purged with N$_2$ for 3 times, and then the mixture was stirred at 90° C. for 12 h under N$_2$ atmosphere. The reaction mixture was concentrated under reduced pressure to give a residue. The residue was purified by prep-TLC (SiO$_2$) to afford 2-chloro-N-(5-(2-chloro-8-fluoroquinazolin-6-yl)-6-methoxypyridin-2-yl)benzenesulfonamide (95 mg, 29.9% yield) as a yellow solid. M+H$^+$=479.1.

Step 2:

To a solution of (1r,4r)-N1,N1-dimethylcyclohexane-1,4-diamine (55 mg, 312.9 umol, HCl) in n-BuOH (3.0 mL) were added DIEA (60 mg, 469.4 umol, 81.7 uL), 2-chloro-N-(5-(2-chloro-8-fluoroquinazolin-6-yl)-6-methoxypyridin-2-yl)benzenesulfonamide (75 mg, 156.4 umol) and CsF (23 mg, 156.4 umol, 5.7 uL). The reaction vessel was sealed and heated under microwave at 140° C. for 2 h. The reaction mixture was concentrated under reduced pressure to give a residue. The residue was purified by prep-HPLC (FA condition) to afford 2-chloro-N-(5-(2-(((1r,4r)-4-(dimethylamino)cyclohexyl)amino)-8-fluoroquinazolin-6-yl)-6-methoxypyridin-2-yl)benzenesulfonamide (13.2 mg, 13.1% yield, FA) as a yellow solid. M+H$^+$=585.1; $^1$H NMR (400 MHz, METHANOL-d$_4$) δ 9.03 (br s, 1H), 8.55 (br s, 1H), 8.33-8.28 (m, 1H), 7.71-7.54 (m, 5H), 7.54-7.46 (m, 1H), 6.63 (d, J=7.9 Hz, 1H), 4.07-3.95 (m, 1H), 3.67 (s, 3H), 3.09 (br t, J=12.1 Hz, 1H), 2.77 (s, 6H), 2.29 (br d, J=10.8 Hz, 2H), 2.13 (br d, J=11.2 Hz, 2H), 1.76-1.61 (m, 2H), 1.53-1.39 (m, 2H).

Example 31: Synthesis of 2-chloro-N-(3-fluoro-6-methoxy-5-(2-(((1r,4r)-4-(methylamino)cyclohexyl)amino)quinazolin-6-yl)pyridin-2-yl)benzenesulfonamide (150)

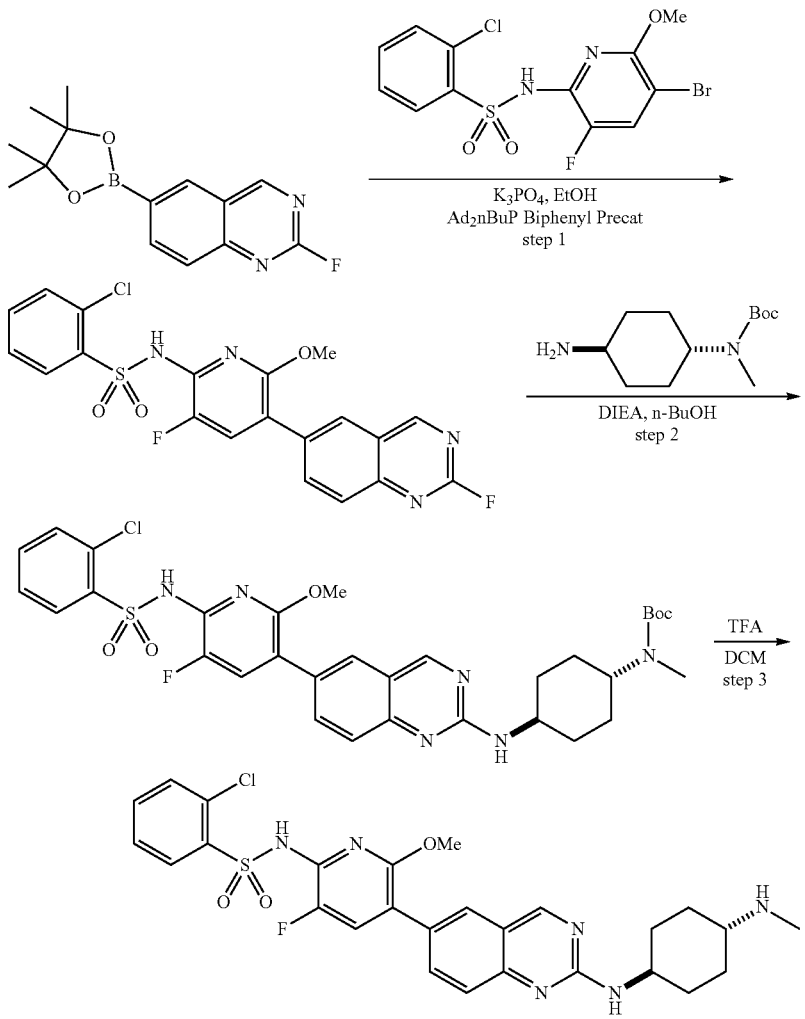

Step 1:

To a solution of compound 2-fluoro-6-(4,4,5,5-tetramethyl-1,3,2-dioxaborolan-2-yl)quinazoline (200 mg, 729.6 umol) and $K_3PO_4$ (0.5 M, 2.9 mL) in EtOH (12.0 mL) were added N-(5-bromo-3-fluoro-6-methoxypyridin-2-yl)-2-chlorobenzenesulfonamide (317 mg, 802.6 umol) and [2-(2-aminophenyl)phenyl]-chloro-palladium; bis(1-adamantyl)-butyl-phosphane (48 mg, 72.9 umol). The mixture was stirred at 80° C. for 12 h under $N_2$. The mixture was concentrated to afford 2-chloro-N-(3-fluoro-5-(2-fluoroquinazolin-6-yl)-6-methoxypyridin-2-yl)benzenesulfonamide (200 mg, crude) as a yellow oil.

Step 2:

To a solution of compound 2-chloro-N-(3-fluoro-5-(2-fluoroquinazolin-6-yl)-6-methoxypyridin-2-yl)benzenesulfonamide (150 mg, 324.0 umol) in n-BuOH (4.0 mL) was added DIEA (209 mg, 1.6 mmol, 282.2 uL) and compound 2A (147 mg, 648.1 umol). The mixture was stirred at 100° C. for 12 h. The mixture was concentrated and the residue was purified by flash silica gel chromatography to afford compound tert-butyl ((1r,4r)-4-((6-(6-((2-chlorophenyl)sulfonamido)-5-fluoro-2-methoxypyridin-3-yl)quinazolin-2-yl)amino)cyclohexyl)(methyl)carbamate (50 mg, 22.9% yield) as a yellow oil.

Step 3:

A solution of tert-butyl ((1r,4r)-4-((6-(6-((2-chlorophenyl)sulfonamido)-5-fluoro-2-methoxypyridin-3-yl)quinazolin-2-yl)amino)cyclohexyl)(methyl)carbamate (50 mg, 74.5 umol) in DCM (2.0 mL) and TFA (1.0 mL) was stirred at 25° C. for 10 min. The mixture was concentrated to give a residue. The residue was dissolved in MeOH (2.0 mL) and basified pH to 8 with $NH_3.H_2O$ (25% purity), concentrated to give a residue. The residue was purified by prep-HPLC (FA condition) to afford 2-chloro-N-(3-fluoro-6-methoxy-5-(2-(((1r,4r)-4-(methylamino)cyclohexyl)amino)quinazolin-6-yl)pyridin-2-yl)benzenesulfonamide (31.5 mg, 68.5% yield, FA) as a yellow solid. M+H$^+$=571.2 (LCMS); $^1$H NMR (400 MHz, DMSO-$d_6$) δ 9.04 (s, 1H), 8.18-8.12 (m, 2H), 7.85-7.79 (m, 2H), 7.42-7.32 (m, 5H), 7.29 (br d, J=8.1 Hz, 1H), 3.82 (br s, 1H), 3.23 (s, 3H), 2.98 (br s, 1H), 2.58 (s, 3H), 2.08 (br d, J=9.9 Hz, 4H), 1.53-1.25 (m, 4H).

Example 32: Synthesis of 2-chloro-N-(5-(2-(((1r,4r)-4-(dimethylamino)cyclohexyl)amino)quinazolin-6-yl)-3-fluoro-6-methoxypyridin-2-yl)benzenesulfonamide (149)

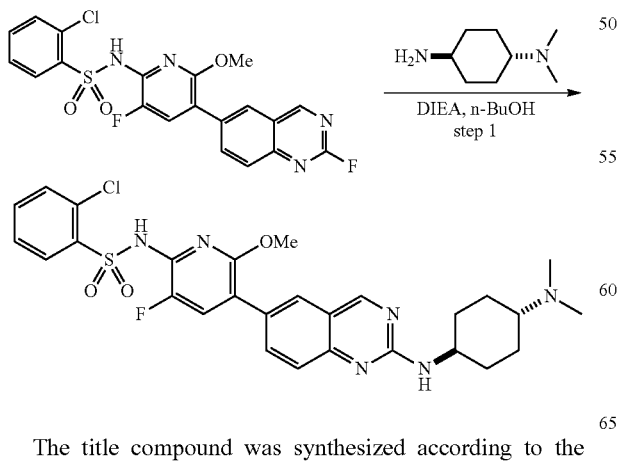

The title compound was synthesized according to the synthetic procedure described in Example 31 to afford 2-chloro-N-(5-(2-(((1r,4r)-4-(dimethylamino)cyclohexyl)amino)quinazolin-6-yl)-3-fluoro-6-methoxypyridin-2-yl)benzenesulfonamide (12.6 mg, 19.9 umol, 18.4% yield, FA) as a yellow solid. M+H$^+$=585.2 (LCMS); $^1$H NMR (400 MHz, DMSO-$d_6$) δ 9.04 (s, 1H), 8.17-8.10 (m, 2H), 7.81 (qd, J=2.2, 4.6 Hz, 2H), 7.42-7.32 (m, 5H), 7.29 (br d, J=7.9 Hz, 1H), 3.92-3.78 (m, 1H), 3.23 (s, 3H), 3.13-3.01 (m, 1H), 2.69 (s, 6H), 2.10 (br d, J=10.4 Hz, 2H), 1.99 (br d, J=11.5 Hz, 2H), 1.57 (q, J=12.1 Hz, 2H), 1.35 (q, J=11.5 Hz, 2H).

Example 33: Synthesis of 2-chloro-N-(5-(2-(((1R,2S,4R)-4-(dimethylamino)-2-fluorocyclohexyl)amino)-8-ethylquinazolin-6-yl)-6-methylpyridin-2-yl)benzenesulfonamide (151)

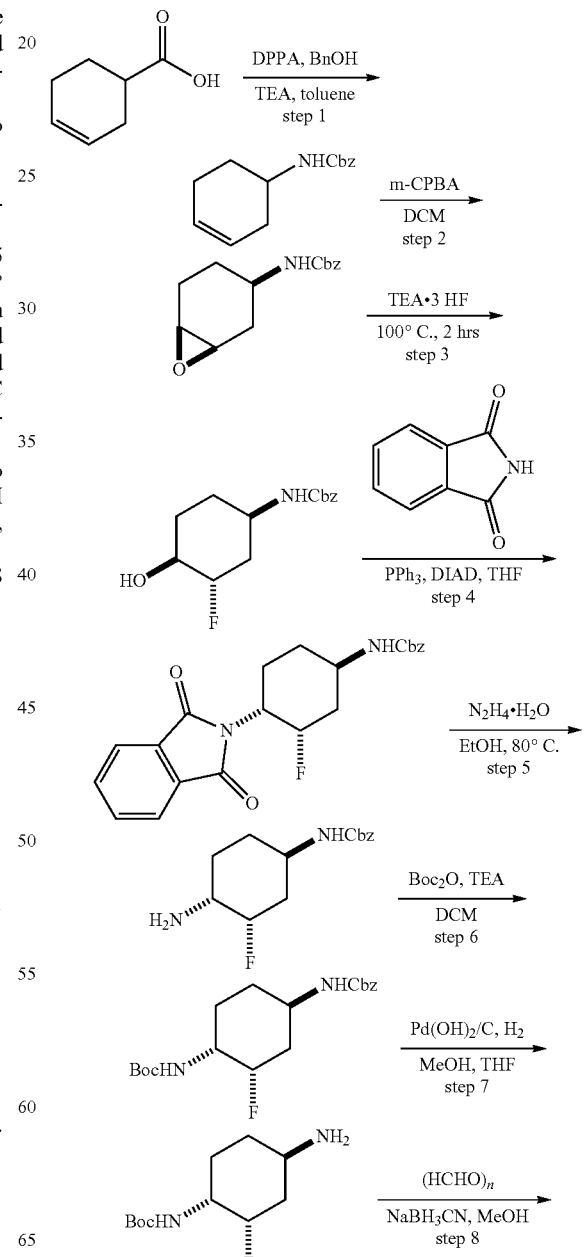

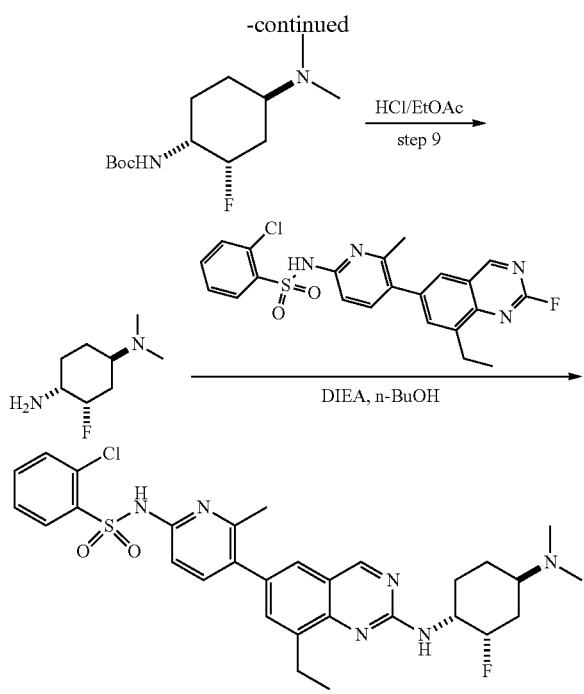

Step 1:

To a solution of cyclohex-3-enecarboxylic acid (20.0 g, 158.5 mmol) in toluene (360.0 mL) was added TEA (17.6 g, 174.3 mmol, 24.2 mL) and DPPA (45.8 g, 166.4 mmol, 36.0 mL). The mixture was degassed and purged with $N_2$ for 3 times, it was stirred at 25° C. for 1.5 h under $N_2$ atmosphere. Then it was warmed to 110° C. and stirred for another 2.5 h. BnOH (18.8 g, 174.3 mmol, 18.1 mL) was added to the mixture and the resulting mixture was stirred at 110° C. for 12 h. The reaction was concentrated under reduced pressure to give a residue. The residue was purified by flash silica gel chromatography to afford benzyl cyclohex-3-en-1-ylcarbamate (33.0 g, 81.0% yield) as a white solid. $^1$H NMR (400 MHz, CHLOROFORM-d) δ 7.44-7.29 (m, 5H), 5.73-5.65 (m, 1H), 5.63-5.56 (m, 1H), 5.11 (s, 2H), 4.81 (br s, 1H), 3.88 (br s, 1H), 2.41 (br d, J=17.2 Hz, 1H), 2.19-2.09 (m, 2H), 1.96-1.84 (m, 2H), 1.66-1.52 (m, 1H).

Step 2:

To a solution of benzyl cyclohex-3-en-1-ylcarbamate (15.0 g, 64.8 mmol) in DCM (180.0 mL) was added m-CPBA (18.1 g, 84.3 mmol, 80% purity) portion wise at 25° C. The mixture was stirred at 25° C. for 3 h. The reaction mixture was filtered and the filtrated was washed with $Na_2SO_3$ (100 mL×2) aqueous solution, and then the organic phase washed with saturated $NaHCO_3$ (100 mL×2) aqueous solution, dried over $Na_2SO_4$, filtered and concentrated to give a residue. The residue was purified by flash silica gel chromatography to afford benzyl ((1R,3R,6S)-7-oxabicyclo[4.1.0]heptan-3-yl)carbamate (10.6 g, 52.8% yield) as a white solid. $^1$H NMR (400 MHz, CHLOROFORM-d) δ 7.39-7.29 (m, 5H), 5.18-5.03 (m, 3H), 3.74 (br s, 1H), 3.18 (br s, 2H), 2.30-2.18 (m, 1H), 2.04-1.81 (m, 2H), 1.58-1.43 (m, 2H)

Step 3:

A mixture of benzyl ((1R,3R,6S)-7-oxabicyclo[4.1.0]heptan-3-yl)carbamate (10.6 g, 42.8 mmol) and N,N-diethylethanamine; trihydrofluoride (34.5 g, 214.3 mmol, 34.9 mL) was stirred at 100° C. for 2 h. The reaction mixture was cooled to 20° C. and slowly poured into $K_2CO_3$ (29.6 g, 214.3 mmol) in $H_2O$ (600.0 ml). Then the mixture was extracted with ethyl acetate (50 ml×3). The combined organic layer was washed with saturated brine (50 ml×2), dried over $Na_2SO_4$, filtered and concentrated to give a residue. The residue was purified by HPLC (TFA condition) to afford benzyl ((1R,3S,4S)-3-fluoro-4-hydroxycyclohexyl)carbamate (3 g) as a pale yellow oil.

Step 4:

To a solution of isoindoline-1,3-dione (1.6 g, 11.2 mmol), benzyl ((1R,3S,4S)-3-fluoro-4-hydroxycyclohexyl)carbamate (3.0 g, 11.2 mmol) and $PPh_3$ (3.8 g, 14.5 mmol) in THF (100.0 mL) was added DIAD (2.9 g, 14.5 mmol, 2.8 mL) under $N_2$ atmosphere. The mixture was stirred at 45° C. for 12 h. The reaction was concentrated under reduced pressure to give a residue. MeCN (50 mL) was added to the residue. The resulting mixture was filtered and the filter cake was washed with MeCN (20 mL×3), dried in vacuum to give benzyl ((1R,3S,4R)-4-(1,3-dioxoisoindolin-2-yl)-3-fluorocyclohexyl)carbamate (2.3 g, crude) as a white solid. M+Na$^+$=419.1 (LCMS); $^1$HNMR (400 MHz, DMSO-d$_6$) δ 7.94-7.79 (m, 4H), 7.42-7.29 (m, 5H), 5.02 (s, 2H), 4.96-4.76 (m, 1H), 4.23-4.03 (m, 1H), 3.75-3.58 (m, 1H), 3.01-2.82 (m, 1H), 2.18 (br s, 1H), 1.98 (br d, J=12.3 Hz, 1H), 1.84-1.54 (m, 2H), 1.48-1.32 (m, 1H).

Step 5:

To a solution of benzyl ((1R,3S,4R)-4-(1,3-dioxoisoindolin-2-yl)-3-fluorocyclohexyl)carbamate (0.8 g, 2.0 mmol) in EtOH (10.0 mL) was added $N_2H_4.H_2O$ (2.5 mL, purity 98%). The mixture was stirred at 80° C. for 3 h. The reaction was concentrated under reduced pressure to give a residue. DCM (30.0 mL) was added to the residue. The resulting mixture was filtered and the filter cake was washed with DCM (10 mL×3). The combined organic layers were concentrated to give benzyl ((1R,3S,4R)-4-amino-3-fluorocyclohexyl)carbamate (530 mg, crude) as a white solid. $^1$H NMR (400 MHz, METHANOL-d$_4$) δ 7.38-7.25 (m, 5H), 5.06 (s, 2H), 4.81-4.65 (m, 1H), 3.76-3.65 (m, 1H), 2.76-2.60 (m, 1H), 2.31-2.19 (m, 1H), 1.98-1.89 (m, 1H), 1.81-1.71 (m, 1H), 1.66-1.41 (m, 2H), 1.33 (dq, J=3.7, 12.4 Hz, 1H).

Step 6:

To a solution of benzyl ((1R,3S,4R)-4-amino-3-fluorocyclohexyl)carbamate (430 mg, 1.61 mmol) in DCM (15 mL) was added $Boc_2O$ (704 mg, 3.2 mmol, 741.8 uL) and TEA (490 mg, 4.8 mmol, 674.2 uL). The mixture was stirred at 25° C. for 3 h. The reaction was concentrated under reduced pressure to give a residue. The residue was purified by flash silica gel chromatography to afford benzyl tert-butyl ((1R,2S,4R)-2-fluorocyclohexane-1,4-diyl)dicarbamate (530 mg, 1.1 mmol, 71.6% yield) as a white solid. $^1$H NMR (400 MHz, METHANOL-d$_4$) δ 7.48-7.22 (m, 5H), 5.06 (s, 2H), 4.71 (br s, 1H), 3.72 (tt, J=4.1, 12.0 Hz, 1H), 3.58-3.39 (m, 1H), 2.31-2.19 (m, 1H), 2.01-1.89 (m, 1H), 1.76-1.66 (m, 2H), 1.63-1.34 (m, 11H).

Step 7:

To a solution of benzyl tert-butyl ((1R,2S,4R)-2-fluorocyclohexane-1,4-diyl)dicarbamate (530 mg, 1.4 mmol) in MeOH (10.0 mL) and THF (10.0 mL) was added $Pd(OH)_2/C$ (400 mg, 20% purity) under $N_2$ atmosphere. The suspension was degassed and purged with $H_2$ for 3 times. The mixture was stirred under $H_2$ (15 Psi) at 25° C. for 4 h. The suspension was filtered through a pad of Celite and filter cake was washed with MeOH (20.0 mL×3). The combined filtrates were concentrated to dryness to give benzyl tert-butyl ((1R,2S,4R)-2-fluorocyclohexane-1,4-diyl)dicarbamate (330 mg, crude) as a yellow oil.

Step 8:
To a solution of benzyl tert-butyl ((1R,2S,4R)-2-fluoro-cyclohexane-1,4-diyl)dicarbamate (330 mg, 1.4 mmol) in MeOH (15.0 mL) was added (HCHO)n (570 mg, 6.3 mmol) and AcOH (8 mg, 142.0 umol, 8.1 uL) at 25° C. for 1 h. NaBH₃CN (446 mg, 7.1 mmol) was then added and the mixture was stirred at 45° C. for 12 h. The reaction mixture was concentrated under reduced pressure. The residue was diluted with saturated aqueous NaHCO₃ (20.0 mL) and extracted with DCM (10×3). The combined organic solution was dried over Na₂SO₄, filtered and concentrated under reduced pressure to give tert-butyl ((1R,2S,4R)-4-(dimethylamino)-2-fluorocyclohexyl)carbamate (300 mg, crude) as a white solid. ¹H NMR (400 MHz, METHANOL-d₄) δ 4.89 (br s, 0.5H), 4.77 (br s, 0.5H), 3.55-3.39 (m, 1H), 2.68-2.58 (m, 1H), 2.27 (s, 6H), 2.22 (td, J=4.2, 8.8 Hz, 1H), 1.98-1.89 (m, 1H), 1.84-1.73 (m, 1H), 1.63 (dq, J=3.9, 12.7 Hz, 2H), 1.56-1.31 (m, 10H).

Step 9:
A solution of tert-butyl ((1R,2S,4R)-4-(dimethylamino)-2-fluorocyclohexyl)carbamate (300 mg, 1.1 mmol) in HCl/EtOAc (5.0 mL, 4 M) was stirred at 25° C. for 1 h. The reaction mixture was concentrated under reduced pressure to give (1R,3 S,4R)-3-fluoro-N1,N1-dimethylcyclohexane-1,4-diamine (226 mg, crude, HCl) as a white solid.

Step 10:
To a solution of (1R,3 S,4R)-3-fluoro-N1,N1-dimethyl-cyclohexane-1,4-diamine (50 mg, 254.2 umol, HCl) in n-BuOH (3.0 mL) was added DIEA (98 mg, 762.6 umol, 132.8 uL) and 2-chloro-N-(5-(8-ethyl-2-fluoroquinazolin-6-yl)-6-methylpyridin-2-yl)benzenesulfonamide (116 mg, 254.2 umol). The mixture was stirred at 100° C. for 12 h. The reaction was concentrated under reduced pressure to give a residue. The residue was purified by prep-HPLC (FA condition) to afford 2-chloro-N-(5-(2-(((1R,2S,4R)-4-(dimethylamino)-2-fluorocyclohexyl)amino)-8-ethylquinazolin-6-yl)-6-methylpyridin-2-yl)benzenesulfonamide (37.7 mg, 55.8 umol, 21.9% yield, FA) as a white solid. M+H⁺=597.2 (LCMS); ¹H NMR (400 MHz, METHANOL-d₄) δ 9.03 (s, 1H), 8.43 (br s, 1H), 8.25-8.20 (m, 1H), 7.66 (d, J=8.9 Hz, 1H), 7.56-7.43 (m, 5H), 7.20 (d, J=8.8 Hz, 1H), 5.38-5.17 (m, 1H), 4.34-4.18 (m, 1H), 3.62-3.51 (m, 1H), 3.07 (q, J=7.5 Hz, 2H), 2.88 (s, 6H), 2.55 (dt, J=3.9, 8.5 Hz, 1H), 2.37 (s, 3H), 2.27-2.14 (m, 2H), 2.13-1.75 (m, 3H), 1.31 (t, J=7.5 Hz, 3H).

Example 34: Synthesis of 2-chloro-N-(5-(2-(((1r,4r)-4-(dimethylamino)cyclohexyl)amino)-8-ethylquinazolin-6-yl)-6-methylpyridin-2-yl)-3-fluorobenzenesulfonamide (158)

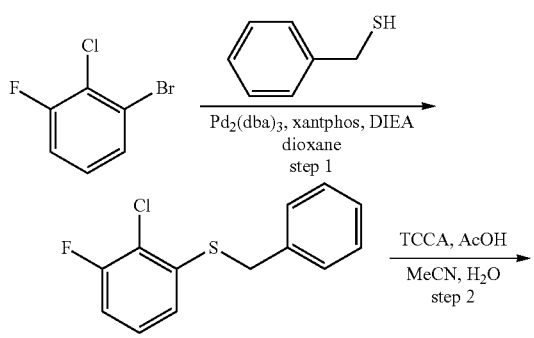

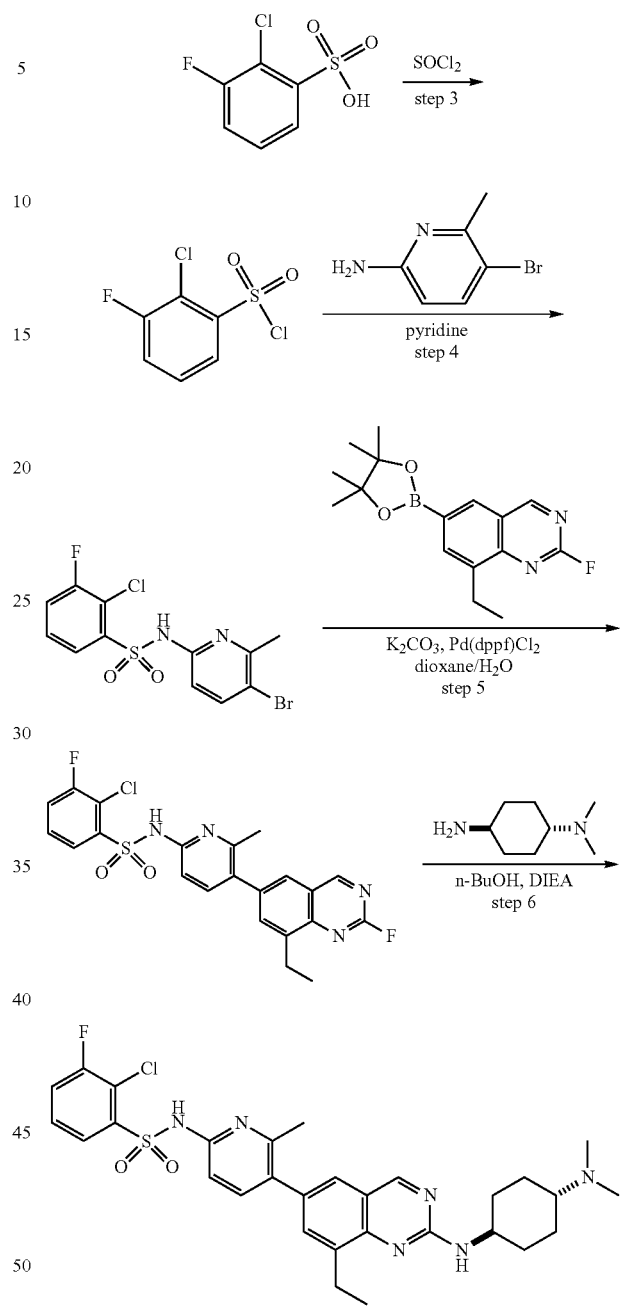

Step 1:
A mixture of 1-bromo-2-chloro-3-fluoro-benzene (1 g, 4.7 mmol), phenylmethanethiol (712 mg, 5.7 mmol), Pd₂(dba)₃ (875 mg, 954.9 umol), DIEA (1.9 g, 14.3 mmol) and Xantphos (552.5 mg, 954.9 umol,) in dioxane (20.0 mL) was degassed and purged with N₂ for 3 times, and then the mixture was stirred at 100° C. for 12 h under N₂ atmosphere. The reaction mixture was concentrated under reduced pressure. The residue was purified by column chromatography (SiO₂) to give benzyl(2-chloro-3-fluorophenyl)sulfane (800 mg, 46.4% yield) as a yellow oil. ¹H NMR (400 MHz, CHLOROFORM-d) δ 7.28-7.16 (m, 5H), 7.06-7.01 (m, 1H), 6.95-6.93 (m, 1H), 6.87 (dt, J=1.3, 8.4 Hz, 1H), 4.08 (s, 2H).

Step 2:

To a solution of benzyl(2-chloro-3-fluorophenyl)sulfane (550 mg, 2.2 mmol) in MeCN (10.0 mL) was added TCCA (505 mg, 2.2 mmol) and AcOH (13 mg, 217.6 umol), H₂O (7 mg, 435.2 umol). The mixture was stirred at 0° C. for 1 h. The reaction mixture was diluted with H₂O (10.0 mL) and extracted with ethyl acetate (10.0 mL×3). The combined organic layers were washed with brine (5.0 mL×2), dried over Na₂SO₄, filtered and concentrated under reduced pressure to give a residue. The residue was purified by column chromatography (SiO₂) to afford 2-chloro-3-fluorobenzenesulfonic acid (300 mg, 30.1% yield) as a colorless oil. M−H⁺=208.9 (LCMS).

Step 3:

A solution of 2-chloro-3-fluorobenzenesulfonic acid (400 mg, 1.9 mmol) in SOCl₂ (5.0 mL) was stirred at 60° C. for 12 h. The reaction mixture was concentrated under reduced pressure to afford 2-chloro-3-fluorobenzenesulfonyl chloride (360 mg, crude) as a brown oil.

Step 4:

To a solution of 2-chloro-3-fluorobenzenesulfonyl chloride (100 mg, 436.6 umol) in pyridine (2.0 mL) was added 5-bromo-6-methyl-pyridin-2-amine (81 mg, 436.6 umol). The mixture was stirred at 45° C. for 12 h. The reaction mixture was concentrated under reduced pressure to give a residue. The residue was purified by column chromatography (SiO₂) to give N-(5-bromo-6-methylpyridin-2-yl)-2-chloro-3-fluorobenzenesulfonamide (50 mg, 24.8% yield) as a yellow oil. M+H⁺=381.0 (LCMS).

Step 5:

A mixture of N-(5-bromo-6-methylpyridin-2-yl)-2-chloro-3-fluorobenzenesulfonamide (50 mg, 65.9 umol), 8-ethyl-2-fluoro-6-(4,4,5,5-tetramethyl-1,3,2-dioxaborolan-2-yl)quinazoline (29.9 mg, 988 umol), K₂CO₃ (27 mg, 197.6 umol), Pd(dppf)Cl₂ (4.8 mg, 6.6 umol) and H₂O (0.2 mL) in dioxane (2.0 mL) was degassed and purged with N₂ for 3 times, and then the mixture was stirred at 90° C. for 12 h under N₂ atmosphere. The reaction mixture was concentrated under reduced pressure to give a residue. The residue was purified by prep-TLC (SiO₂) to give 2-chloro-N-(5-(8-ethyl-2-fluoroquinazolin-6-yl)-6-methylpyridin-2-yl)-3-fluorobenzenesulfonamide as a pale yellow solid (50 mg). M+H⁺=475.1 (LCMS).

Step 6:

To a solution of 2-chloro-N-(5-(8-ethyl-2-fluoroquinazolin-6-yl)-6-methylpyridin-2-yl)-3-fluorobenzenesulfonamide (50 mg, 105.3 umol) in n-BuOH (2.0 mL) was added DIEA (68.0 mg, 526.4 umol) and (1r,4r)-N1,N1-dimethylcyclohexane-1,4-diamine (37 mg, 210.6 umol, HCl). The mixture was stirred at 100° C. for 12 h. The reaction mixture was concentrated under reduced pressure to give a residue. The residue was purified by prep-HPLC (FA condition) to afford 2-chloro-N-(5-(2-(((r,4r)-4-(dimethylamino)cyclohexyl)amino)-8-ethylquinazolin-6-yl)-6-methylpyridin-2-yl)-3-fluorobenzenesulfonamide (9.9 mg, 14.7% yield, FA) as a white solid. M+H⁺=597.2 (LCMS); ¹H NMR (400 MHz, METHANOL-d₄) δ 9.01 (s, 1H), 8.57 (s, 1H), 8.06 (d, J=7.5 Hz, 1H), 7.73 (d, J=8.9 Hz, 1H), 7.57-7.43 (m, 4H), 7.27 (d, J=9.0 Hz, 1H), 4.04-3.92 (m, 1H), 3.16-3.04 (m, 2H), 2.94 (br t, J=11.6 Hz, 1H), 2.70 (s, 6H), 2.41 (s, 3H), 2.37 (br d, J=11.7 Hz, 2H), 2.15 (br d, J=11.7 Hz, 2H), 1.71-1.58 (m, 2H), 1.54-1.42 (m, 2H), 1.34 (t, J=7.5 Hz, 3H).

Example 35: Synthesis of 2,3-dichloro-N-(5-(2-(((1r,4r)-4-(dimethylamino)cyclohexyl)amino)-8-ethylquinazolin-6-yl)-6-methylpyridin-2-yl)benzenesulfonamide (152)

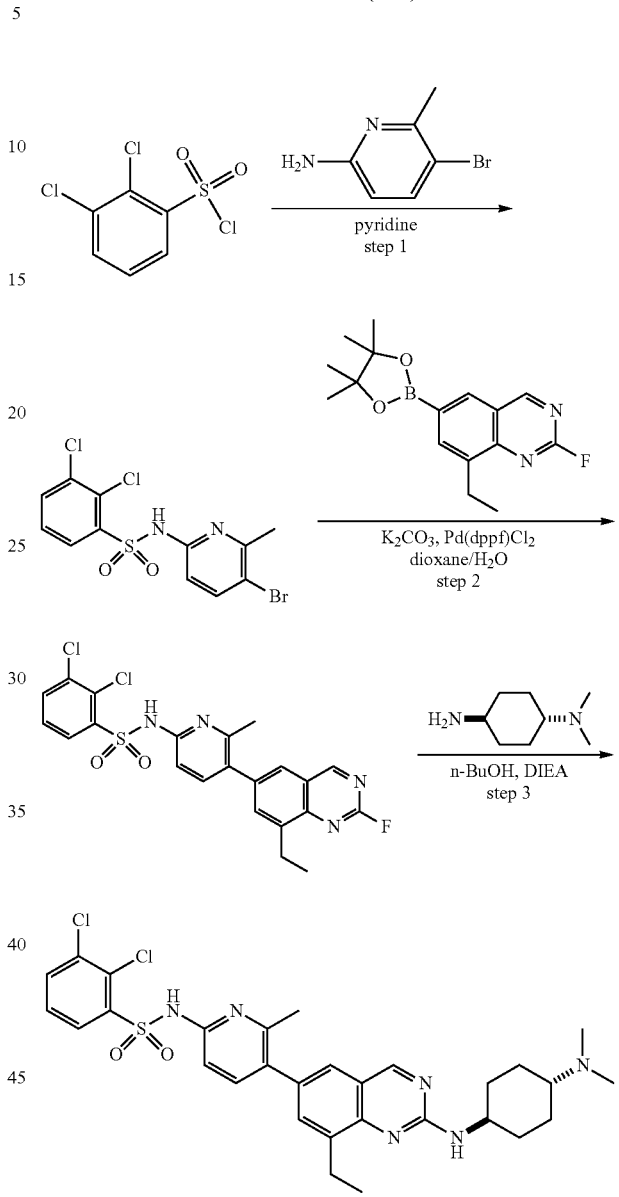

The title compound was synthesized according to the synthetic procedure described in Example 34 to afford 2,3-dichloro-N-(5-(2-(((1r,4r)-4-(dimethylamino)cyclohexyl)amino)-8-ethylquinazolin-6-yl)-6-methylpyridin-2-yl)benzenesulfonamide (37.7 mg, 31.1% yield, FA) as a pale yellow solid. M+H⁺=613.2 (LCMS); ¹H NMR (400 MHz, METHANOL-d₄) δ 8.99 (s, 1H), 8.37 (br s, 1H), 8.18 (dd, J=1.3, 7.9 Hz, 1H), 7.77-7.69 (m, 2H), 7.55-7.48 (m, 2H), 7.45 (t, J=7.9 Hz, 1H), 7.25 (d, J=9.0 Hz, 1H), 4.03-3.93 (m, 1H), 3.29-3.23 (m, 1H), 3.07 (q, J=7.4 Hz, 2H), 2.89 (s, 6H) 2.39 (s, 5H), 2.19 (br d, J=12.1 Hz, 2H), 1.80-1.66 (m, 2H), 1.55-1.43 (m, 2H), 1.31 (t, J=7.5 Hz, 3H).

Example 36: Synthesis of 2-chloro-N-(5-(2-(((1r,4r)-4-(dimethylamino)cyclohexyl)amino)quinazolin-6-yl)-3-fluoro-6-methylpyridin-2-yl)benzenesulfonamide (153)

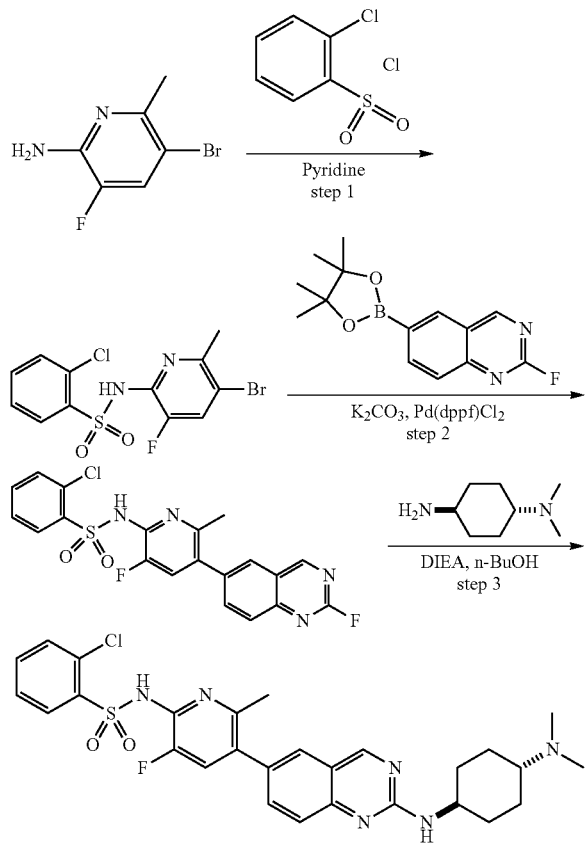

The title compound was synthesized according to the synthetic procedure described in Example 34 to afford 2-chloro-N-(5-(2-(((1r,4r)-4-(dimethylamino)cyclohexyl)amino)quinazolin-6-yl)-3-fluoro-6-methylpyridin-2-yl)benzenesulfonamide (18.9 mg, 16.9% yield, FA) as a pale yellow solid. M+H$^+$=569.2 (LCMS). $^1$H NMR (400 MHz, METHANOL-d$_4$) δ 9.05 (s, 1H), 8.55 (br s, 1H), 8.33 (dd, J=1.4, 7.6 Hz, 1H), 7.75-7.62 (m, 2H), 7.61-7.50 (m, 4H), 7.43 (d, J=10.6 Hz, 1H), 4.10-3.91 (m, 1H), 3.28-3.15 (m, 1H), 2.87 (s, 6H), 2.38-2.26 (m, 2H), 2.23-2.15 (m, 5H), 1.80-1.67 (m, 2H), 1.57-1.43 (m, 2H).

Example 37: Synthesis of 2-chloro-N-(5-(2-(((1r,4r)-4-(dimethylamino)cyclohexyl)amino)-8-ethylquinazolin-6-yl)-4-methoxypyrimidin-2-yl)benzenesulfonamide (154)

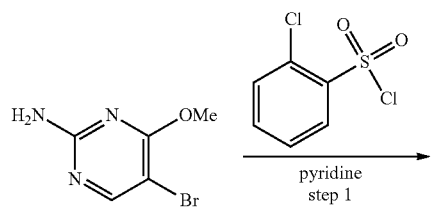

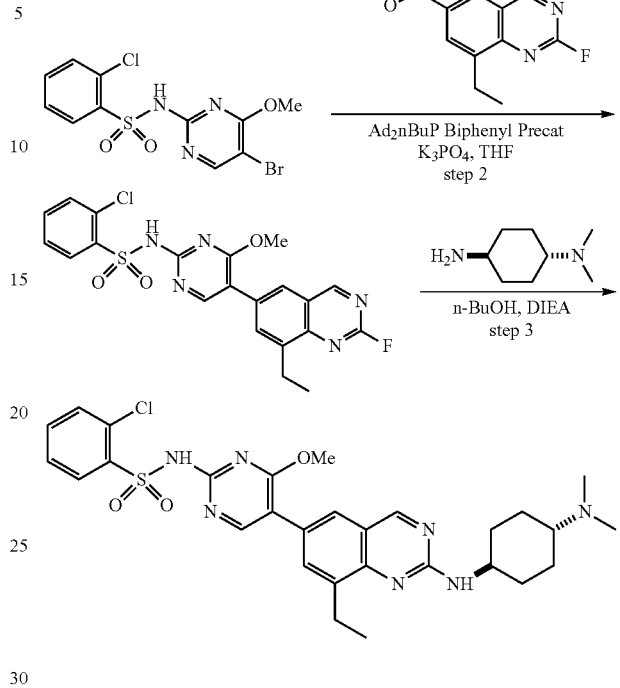

Step 1:

To a solution of 5-bromo-4-methoxypyrimidin-2-amine (400 mg, 1.9 mmol) in pyridine (6.0 mL) was added 2-chlorobenzenesulfonyl chloride (620 mg, 2.9 mmol, 400.4 uL). The mixture was stirred at 45° C. for 16 h. Additional 2-chlorobenzenesulfonyl chloride (827 mg, 3.9 mmol, 533.9 uL) was added and the mixture was stirred at 45° C. for 5 h. The reaction mixture was concentrated under reduced pressure. The crude product was triturated with MTBE (5.0 mL), ethyl acetate (5.0 mL), and methanol (2.0 mL) at 25° C. for 15 min. Then the mixture was filtered to give N-(5-bromo-4-methoxypyrimidin-2-yl)-2-chlorobenzenesulfonamide (170 mg, 17.7% yield) as a yellow solid. M+H$^+$=379.8 (LCMS).

Step 2:

A mixture of N-(5-bromo-4-methoxypyrimidin-2-yl)-2-chlorobenzenesulfonamide (90 mg, 237.7 umol), 8-ethyl-2-fluoro-6-(4,4,5,5-tetramethyl-1,3,2-dioxaborolan-2-yl)quinazoline (71 mg, 237.7 umol), K$_3$PO$_4$ (0.5 M, 1.4 mL), and [2-(2-aminophenyl)phenyl]-chloro-palladium; bis(1-adamantyl)-butyl-phosphane (15 mg, 23.7 umol) in THF (5.0 mL) was degassed and purged with N$_2$ for 3 times, and then the mixture was stirred at 80° C. for 12 h under N$_2$ atmosphere. The reaction mixture was concentrated under reduced pressure. The residue was purified by prep-TLC (SiO$_2$) to afford 2-chloro-N-(5-(8-ethyl-2-fluoroquinazolin-6-yl)-4-methoxypyrimidin-2-yl)benzenesulfonamide (104 mg, 28.2% yield) as a yellow solid. M+H$^+$=474.3 (LCMS).

Step 3:

A mixture of (1r,4r)-N1,N1-dimethylcyclohexane-1,4-diamine (62 mg, 438.9 umol, HCl), 2-chloro-N-(5-(8-ethyl-2-fluoroquinazolin-6-yl)-4-methoxypyrimidin-2-yl)benzenesulfonamide (104 mg, 219.4 umol), DIEA (141.8 mg, 1.1 mmol, 191.1 uL) in n-BuOH (2.0 mL), and then the mixture was stirred at 100° C. for 12 h. The reaction mixture was concentrated under reduced pressure. The residue was purified by prep-HPLC (FA condition) to afford 2-chloro-N-(5-

(2-(((1r,4r)-4-(dimethylamino)cyclohexyl)amino)-8-ethylquinazolin-6-yl)-4-methoxypyrimidin-2-yl)benzenesulfonamide (10.2 mg, 7.1% yield, FA) as a pale yellow solid. M+H+=596.2; $^1$H NMR (400 MHz, METHANOL-$d_4$) δ 8.94 (s, 1H), 8.53 (br s, 1H), 8.30 (d, J=7.7 Hz, 1H), 8.12 (s, 1H), 7.62 (d, J=8.2 Hz, 2H), 7.55-7.44 (m, 3H), 4.02-3.88 (m, 1H), 3.67 (s, 3H), 3.15 (br d, J=6.0 Hz, 1H), 3.02 (q, J=7.4 Hz, 2H), 2.87-2.77 (m, 6H), 2.36 (br d, J=10.8 Hz, 2H), 2.16 (br d, J=11.9 Hz, 2H), 1.76-1.62 (m, 2H), 1.54-1.40 (m, 2H), 1.32-1.24 (m, 3H).

Example 38: Synthesis of 2-chloro-N-(5-(2-(((1r,4r)-4-(dimethylamino)cyclohexyl)amino)-8-fluoroquinazolin-6-yl)-3-fluoro-6-methylpyridin-2-yl)benzenesulfonamide (156)

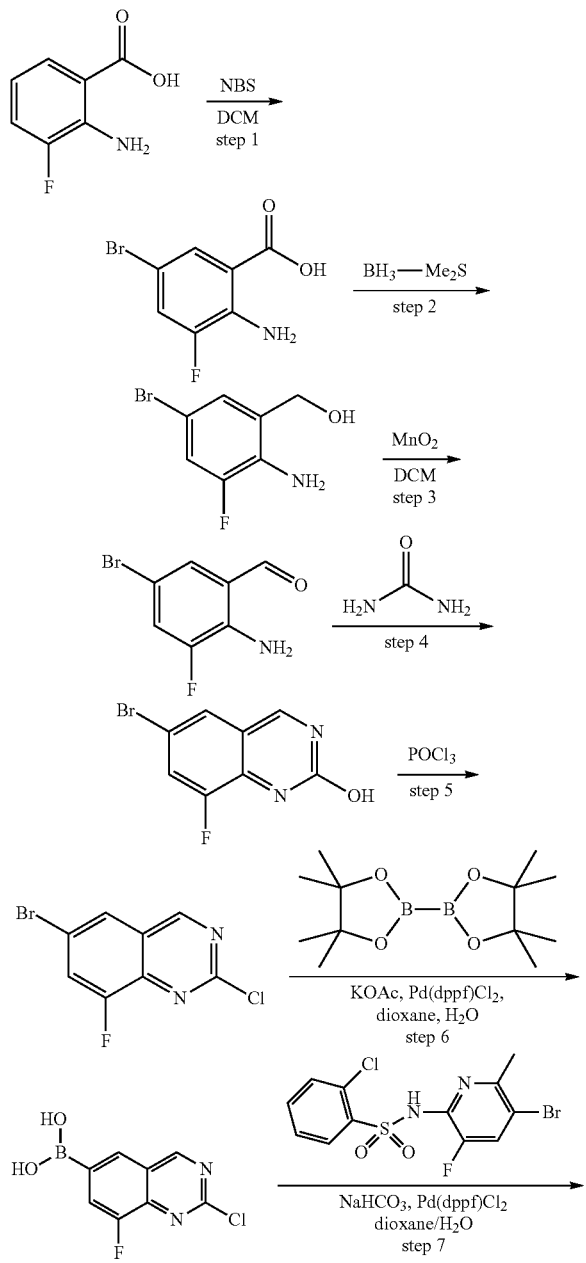

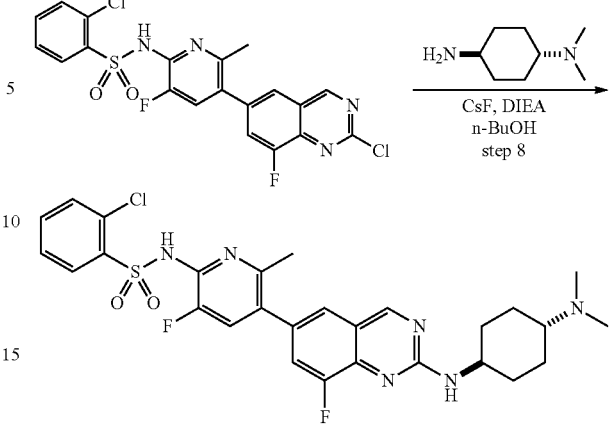

Step 1:

To a solution of 2-amino-3-fluoro-benzoic acid (10.0 g, 64.4 mmol) in DCM (100.0 mL) was added NBS (11.4 g, 64.4 mmol) in small portions at 20° C. The resulting mixture was stirred at 20° C. for 3 h. The reaction mixture was filtered. The cake was collected and dried to give 2-amino-5-bromo-3-fluorobenzoic acid (14.9 g, crude) as a yellow solid. $^1$H NMR (400 MHz, DMSO-$d_6$) δ 11.07 (br s, 1H), 7.66-7.60 (m, 1H), 7.52 (dd, J=2.4, 10.7 Hz, 1H).

Step 2:

To a solution of 2-amino-5-bromo-3-fluorobenzoic acid (1.0 g, 4.2 mmol) in THF (10.0 mL) was added BH$_3$-Me$_2$S (10 M, 10.0 mL) at 0° C. The reaction mixture was stirred at 20° C. for 4 h. The reaction mixture was quenched with MeOH (100.0 mL) and then the mixture was concentrated under reduced pressure. The residue was diluted with aqueous sodium bicarbonate (25.0 mL) and extracted with ethyl acetate (30.0 mL×3). The combined organic layers were washed with brine (30.0 mL×3), dried over Na$_2$SO$_4$, and concentrated under reduced pressure to give a residue. The residue was purified by column chromatography (SiO$_2$) to give (2-amino-5-bromo-3-fluorophenyl)methanol (740 mg) as a white solid. $^1$H NMR (400 MHz, DMSO-$d_6$) δ 7.18 (dd, J=2.3, 10.6 Hz, 1H), 7.12 (s, 1H), 5.26 (t, J=5.6 Hz, 1H), 5.06 (s, 2H), 4.40 (d, J=5.5 Hz, 2H).

Step 3:

To a solution of (2-amino-5-bromo-3-fluorophenyl)methanol (740 mg, 3.3 mmol) in DCM (50.0 mL) was added MnO$_2$ (2.9 g, 33.6 mmol). The mixture was stirred at 20° C. for 12 h. The reaction mixture was filtered. The filtrate was concentrated under reduced pressure. The residue was purified by column chromatography (SiO$_2$) to afford 2-amino-5-bromo-3-fluorobenzaldehyde (585 mg, 71.8% yield) as a yellow solid. $^1$H NMR (400 MHz, CHLOROFORM-d) δ 9.84 (d, J=2.0 Hz, 1H), 7.49-7.43 (m, 1H), 7.30 (dd, J=2.1, 10.5 Hz, 1H), 6.50-5.84 (m, 2H).

Step 4:

A mixture of 2-amino-5-bromo-3-fluorobenzaldehyde (585 mg, 2.68 mmol) and urea (2.4 g, 40.2 mmol, 2.1 mL) was heated 180° C. for 4 h. The reaction mixture was poured into H$_2$O (30.0 mL) and the resulting mixture was filtered. The cake was washed with H$_2$O (10.0 mL×3) to give 6-bromo-8-fluoroquinazolin-2-ol (650 mg, crude) as a yellow solid.

Step 5:

A solution of 6-bromo-8-fluoroquinazolin-2-ol (650 mg, 2.6 mmol) in POCl₃ (7.0 mL) was stirred at 110° C. for 2 h. The reaction mixture was concentrated under reduced pressure. The residue was diluted with NaHCO₃ (20.0 mL) and extracted with ethyl acetate (15.0 mL×3). The combined organic layers were washed with brine (15.0 mL×3), dried over Na₂SO₄, filtered, and concentrated under reduced pressure to give a residue. The residue was purified by flash silica gel chromatography to give 6-bromo-2-chloro-8-fluoroquinazoline (370 mg, 51.3% yield) as a pale yellow solid. M+H⁺=262.8 (LCMS).

Step 6:

A mixture of 6-bromo-2-chloro-8-fluoroquinazoline (350 mg, 1.3 mmol), 4,4,4',4',5,5,5',5'-octamethyl-2,2'-bi(1,3,2-dioxaborolane) (373 mg, 1.4 mmol), Pd(dppf)Cl₂ (97 mg, 133.8 umol), KOAc (394 mg, 4.0 mmol) in dioxane (12.0 mL) was degassed and purged with N₂ for 3 times, and then the mixture was stirred at 90° C. for 12 h under N₂ atmosphere. The reaction mixture was concentrated under reduced pressure to give a residue. EtOAc (20.0 mL) was added to the residue. The resulting mixture was filtered and the filtrate was concentrated to give a residue. The residue was purified by flash silica gel chromatography to give (2-chloro-8-fluoroquinazolin-6-yl)boronic acid (300 mg, 88.1% yield) as a yellow solid. M+H⁺=227.2 (LCMS).

Step 7:

A mixture of (2-chloro-8-fluoroquinazolin-6-yl)boronic acid (120 mg, 530.0 umol), N-(5-bromo-3-fluoro-6-methylpyridin-2-yl)-2-chlorobenzenesulfonamide (201 mg, 530.0 umol), Pd(dppf)Cl₂ (38 mg, 53.0 umol), and NaHCO₃ (133 mg, 1.5 mmol, 61.8 uL) in dioxane (4.0 mL) and H₂O (0.4 mL) was degassed and purged with N₂ 3 times. The reaction mixture was stirred at 80° C. for 12 h under N₂ atmosphere. The reaction mixture was concentrated under reduced pressure to give a residue. Ethyl acetate (10.0 mL) was added to the residue. The resulting mixture was filtered and the filtrate was concentrated to give a residue. The residue was purified by flash silica gel chromatography to give 2-chloro-N-(5-(2-chloro-8-fluoroquinazolin-6-yl)-3-fluoro-6-methylpyridin-2-yl)benzenesulfonamide (56 mg, 14.7% yield) as a yellow solid. M+H⁺=481.2 (LCMS).

Step 8:

To a solution of (1r,4r)-N1,N1-dimethylcyclohexane-1,4-diamine (41 mg, 232.7 umol, HCl) in n-BuOH (3.0 mL) was added DIEA (45 mg, 349.0 umol, 60.8 uL), 2-chloro-N-(5-(2-chloro-8-fluoroquinazolin-6-yl)-3-fluoro-6-methylpyridin-2-yl)benzenesulfonamide (56 mg, 116.3 umol), and CsF (17 mg, 116.3 umol). The reaction vessel was sealed and heated under microwave at 140° C. for 4 h. The reaction mixture was concentrated under reduced pressure to give a residue. The residue was purified by prep-HPLC (FA condition) to give 2-chloro-N-(5-(2-(((1r,4r)-4-(dimethylamino)cyclohexyl)amino)-8-fluoroquinazolin-6-yl)-3-fluoro-6-methylpyridin-2-yl)benzenesulfonamide (12.9 mg, 17.7% yield) as a yellow solid. M+H⁺=587.2 (LCMS); ¹H NMR (400 MHz, METHANOL-d₄) δ 9.03 (br s, 1H), 8.52 (br s, 1H), 8.31 (d, J=7.7 Hz, 1H), 7.58-7.44 (m, 4H), 7.41 (d, J=10.8 Hz, 2H), 4.02 (tt, J=3.9, 11.5 Hz, 1H), 3.23 (br t, J=12.0 Hz, 1H), 2.86 (s, 6H), 2.30 (br d, J=11.0 Hz, 2H), 2.21-2.12 (m, 5H), 1.79-1.65 (m, 2H), 1.54-1.39 (m, 2H).

Example 39: Synthesis of 2-chloro-N-(5-(2-(((1r,4r)-4-(dimethylamino)cyclohexyl)amino)-8-fluoroquinazolin-6-yl)-3-fluoro-6-methoxypyridin-2-yl)benzenesulfonamide (155)

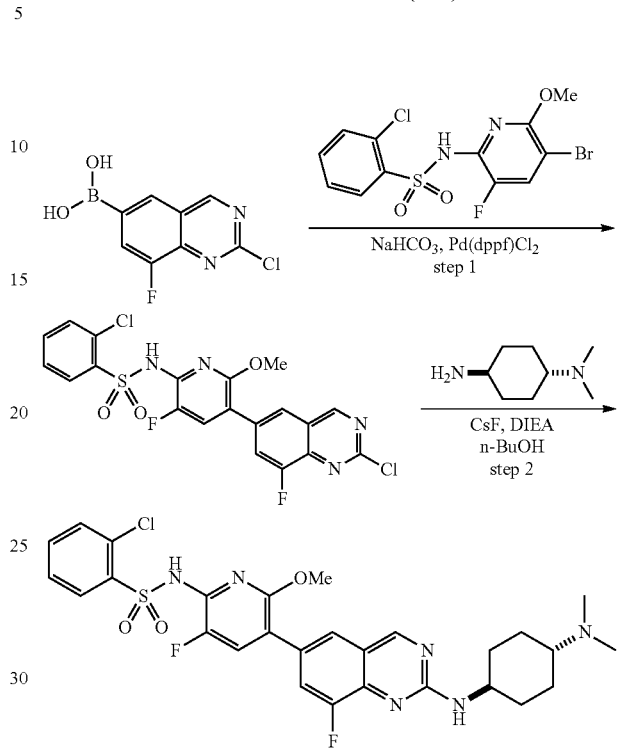

The title compound was synthesized according to the synthetic procedure described in Example 38 to afford 2-chloro-N-(5-(2-(((1r,4r)-4-(dimethylamino)cyclohexyl)amino)-8-fluoroquinazolin-6-yl)-3-fluoro-6-methoxypyridin-2-yl)benzenesulfonamide (2.1 mg, 5.0% yield, FA) as a yellow solid. M+H⁺=603.1; ¹H NMR (400 MHz, METHANOL-d₄) δ 9.04 (s, 1H), 8.32 (d, J=7.7 Hz, 1H), 7.70-7.65 (m, 2H), 7.65-7.62 (m, 1H), 7.59-7.55 (m, 2H), 7.53-7.46 (m, 1H), 4.09-3.97 (m, 1H), 3.49 (s, 3H), 3.28-3.19 (m, 1H), 2.87 (s, 6H), 2.32 (br d, J=10.6 Hz, 2H), 2.16 (br d, J=11.9 Hz, 2H), 1.81-1.63 (m, 2H), 1.57-1.37 (m, 2H).

Example 40: Synthesis of 2-chloro-N-(5-(2-(((1r,4r)-4-(dimethylamino)cyclohexyl)amino)-8-ethylquinazolin-6-yl)-6-methoxypyrazin-2-yl)benzenesulfonamide (157)

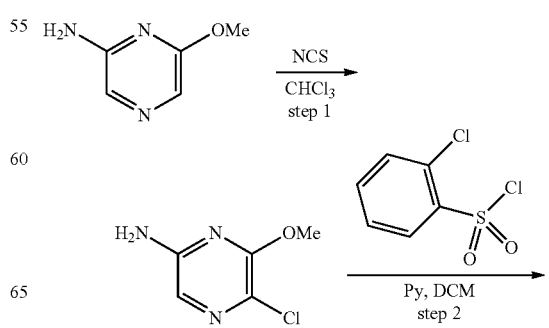

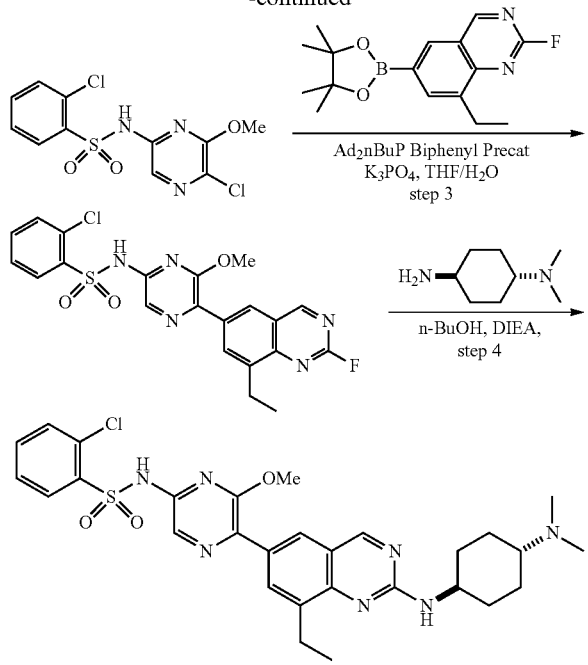

Step 1:

To a solution of 6-methoxypyrazin-2-amine (0.5 g, 4.0 mmol) in $CHCl_3$ (25 mL) was added NCS (533 mg, 4.0 mmol). The reaction mixture was stirred at 40° C. for 12 h. The mixture was concentrated to give a residue. The residue was purified by column chromatography ($SiO_2$) to give 5-chloro-6-methoxypyrazin-2-amine (95 mg, 14.9% yield) as a yellow solid. $^1H$ NMR (400 MHz, CHLOROFORM-d) δ 7.32 (s, 1H), 4.42 (s, 2H), 3.96 (s, 3H).

Step 2:

To a solution of 5-chloro-6-methoxypyrazin-2-amine (95 mg, 595.3 umol) in DCM (8.0 mL) was added pyridine (141 mg, 1.7 mmol) and 2-chlorobenzenesulfonyl chloride (188 mg, 893.0 umol). The reaction mixture was stirred at 45° C. for 12 h. TLC indicated 5-chloro-6-methoxypyrazin-2-amine was remained, so 2-chlorobenzenesulfonyl chloride (62 mg, 293.7 umol) was added and the mixture was stirred at 45° C. for 12 h. The reaction mixture was concentrated to give a residue. The residue was purified by column chromatography ($SiO_2$) to give 2-chloro-N-(5-chloro-6-methoxypyrazin-2-yl)benzenesulfonamide (131 mg, 59.4% yield) as a yellow solid. $M+H^+=333.9$ (LCMS).

Step 3:

A mixture of 2-chloro-N-(5-chloro-6-methoxypyrazin-2-yl)benzenesulfonamide (50 mg, 149.6 umol), 8-ethyl-2-fluoro-6-(4,4,5,5-tetramethyl-1,3,2-dioxaborolan-2-yl)quinazoline (45 mg, 149.6 umol), $K_3PO_4$ (0.5 M, 598.4 uL), and [2-(2-aminophenyl)phenyl]-chloro-palladium; bis(1-adamantyl)-butyl-phosphane (10 mg, 14.9 umol) in THF (2.0 mL) was degassed and purged with $N_2$ 3 times. The mixture was stirred at 80° C. for 12 h under $N_2$ atmosphere. The reaction mixture was concentrated to give a residue. The residue was purified by prep-TLC ($SiO_2$) to give 2-chloro-N-(5-(8-ethyl-2-fluoroquinazolin-6-yl)-6-methoxypyrazin-2-yl)benzenesulfonamide (44 mg, crude) as a yellow solid.

Step 4:

To a solution of 2-chloro-N-(5-(8-ethyl-2-fluoroquinazolin-6-yl)-6-methoxypyrazin-2-yl)benzenesulfonamide (44 mg, 92.8 umol) in n-BuOH (3.0 mL) was added (1r,4r)-N1,N1-dimethylcyclohexane-1,4-diamine (26 mg, 185.7 umol, HCl) and DIEA (60 mg, 464.2 umol). The reaction mixture was stirred at 100° C. for 12 h. Additional (1r,4r)-N1,N1-dimethylcyclohexane-1,4-diamine (26 mg, 185.7 umol, HCl) and DIEA (60 mg, 464.2 umol) were added. The reaction mixture was stirred at 100° C. for another 20 h. The reaction mixture was concentrated under reduced pressure to give a residue. The residue was purified by prep-HPLC (FA condition) to give 2-chloro-N-(5-(2-(((1r,4r)-4-(dimethylamino)cyclohexyl)amino)-8-ethylquinazolin-6-yl)-6-methoxypyrazin-2-yl)benzenesulfonamide (5.1 mg, 7.8% yield, FA) as a pale yellow solid. $M+H^+=596.2$ (LCMS); $^1$HNMR (400 MHz, METHANOL-$d_4$) δ 8.98 (s, 1H), 8.56-8.44 (m, 1H), 8.33 (d, J=7.9 Hz, 1H), 8.14 (s, 2H), 7.86 (s, 1H), 7.61-7.48 (m, 3H), 4.03-3.92 (m, 1H), 3.73 (s, 3H), 3.27-3.17 (m, 1H), 3.10-3.02 (m, 2H), 2.88 (s, 6H), 2.44-2.34 (m, 2H), 2.18 (br dd, J=1.7, 12.7 Hz, 2H), 1.81-1.66 (m, 2H), 1.57-1.41 (m, 2H), 1.33 (t, J=7.5 Hz, 3H).

Example 41: Synthesis of 2-chloro-N-(6-(2-(((1r,4r)-4-(dimethylamino)cyclohexyl)amino)-8-ethylquinazolin-6-yl)-5-methoxypyridazin-3-yl)benzenesulfonamide (159)

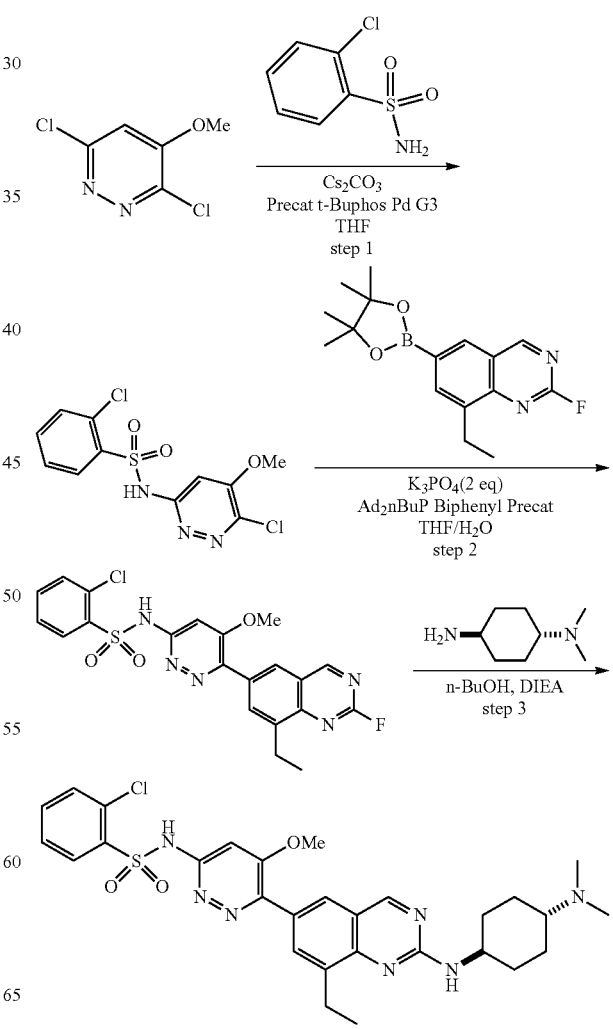

Step 1:

To a solution of 2-chlorobenzenesulfonamide (1.0 g, 5.4 mmol) in THF (40.0 mL) was added 3,6-dichloro-4-methoxypyridazine (0.6 g, 3.6 mmol), [2-(2-aminophenyl)phenyl]-methylsulfonyloxy-palladium; ditert-butyl-[2-(2,4,6-triisopropylphenyl)phenyl]phosphane (288 mg, 363.1 umol), and Cs$_2$CO$_3$ (2.3 g, 7.2 mmol). The reaction mixture was stirred at 80° C. for 12 h. The reaction mixture was concentrated to give a residue. The residue was diluted with H$_2$O (20.0 mL) and extracted with EtOAc (20.0 mL×3). The combined organic layers were washed with brine (20.0 mL×3), dried over Na$_2$SO$_4$, filtered, and concentrated under reduced pressure to give a residue. The residue was purified by prep-HPLC (TFA condition) to give 2-chloro-N-(6-chloro-5-methoxypyridazin-3-yl)benzenesulfonamide (75 mg, 6.1% yield) as a red solid. $^1$H NMR (400 MHz, DMSO-d$_6$) δ 8.13 (d, J=7.3 Hz, 1H), 7.61-7.57 (m, 2H), 7.57-7.48 (m, 1H), 7.24 (br d, J=7.7 Hz, 1H), 3.95 (s, 3H).

Step 2:

A mixture of 2-chloro-N-(6-chloro-5-methoxypyridazin-3-yl)benzenesulfonamide (50 mg, 149.6 umol), 8-ethyl-2-fluoro-6-(4,4,5,5-tetramethyl-1,3,2-dioxaborolan-2-yl)quinazoline (54 mg, 179.5 umol), K$_3$PO$_4$ (0.5 M, 598.4 uL), and [2-(2-aminophenyl)phenyl]-chloro-palladium; bis(1-adamantyl)-butyl-phosphane (10 mg, 14.9 umol) in THF (2.0 mL) was taken up into a microwave tube, then degassed and purged with N$_2$ for 3 times. The sealed tube was heated at 120° C. for 4 h under microwave. The reaction mixture was concentrated under reduced pressure to give a residue. The residue was purified by prep-TLC (SiO$_2$) to afford 2-chloro-N-(6-(8-ethyl-2-fluoroquinazolin-6-yl)-5-methoxy-pyridazin-3-yl)benzenesulfonamide (14 mg, 16.6% yield) as a yellow solid. M+H$^+$=474.1 (LCMS).

Step 3:

To a solution of 2-chloro-N-(6-(8-ethyl-2-fluoroquinazolin-6-yl)-5-methoxypyridazin-3-yl)benzenesulfonamide (21 mg, 44.3 umol) in n-BuOH (1.0 mL) was added (1r,4r)-N1,N1-dimethylcyclohexane-1,4-diamine (15 mg, 88.6 umol, HCl) and DIEA (28 mg, 221.5 umol). The reaction mixture was stirred at 100° C. for 12 h. The reaction mixture was concentrated under reduced pressure to give a residue. The residue was purified by prep-HPLC (FA condition) to give 2-chloro-N-(6-(2-(((1r,4r)-4-(dimethylamino)cyclohexyl)amino)-8-ethylquinazolin-6-yl)-5-methoxypyridazin-3-yl)benzenesulfonamide (3.8 mg, 12.8% yield, FA) as a pale yellow solid. M+H$^+$=596.2 (LCMS); $^1$HNMR (400 MHz, METHANOL-d$_4$) δ 9.03 (s, 1H), 8.59-8.50 (m, 1H), 8.27-8.18 (m, 1H), 8.06 (d, J=1.1 Hz, 1H), 7.94 (s, 1H), 7.63-7.44 (m, 3H), 7.33 (s, 1H), 4.01 (s, 3H), 3.99-3.94 (m, 1H), 3.15-3.01 (m, 3H), 2.77 (s, 6H), 2.37 (br dd, J=1.9, 11.1 Hz, 2H), 2.20-2.10 (m, 2H), 1.82-1.60 (m, 2H), 1.57-1.42 (m, 2H), 1.33 (t, J=7.5 Hz, 3H).

Example 42: Synthesis of 2-chloro-N-(5-(2-(((1r,4r)-4-(dimethylamino)cyclohexyl)amino)-8-ethylquinazolin-6-yl)-6-methylpyridin-2-yl)-3-methyl-benzenesulfonamide (160)

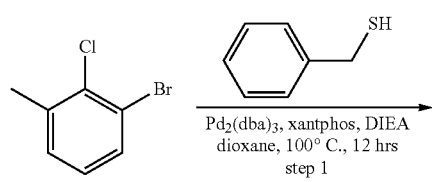

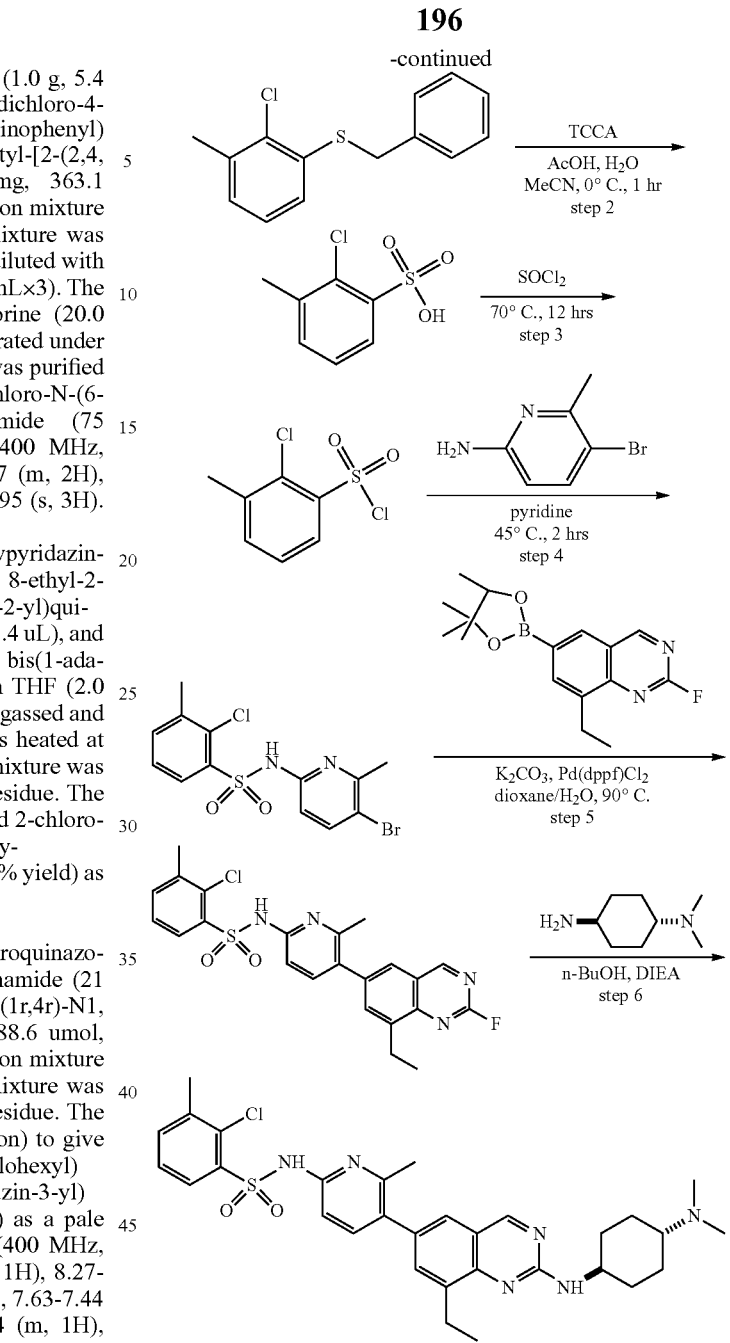

Step 1:

A mixture of 1-bromo-2-chloro-3-methyl-benzene (3.0 g, 14.6 mmol), phenylmethanethiol (2.1 g, 17.5 mmol, 2.0 mL), (1E,4E)-1,5-diphenylpenta-1,4-dien-3-one; palladium (2.6 g, 2.9 mmol), DIEA (5.6 g, 43.8 mmol, 7.6 mL), and (5-diphenylphosphanyl-9,9-dimethyl-xanthen-4-yl)-diphenyl-phosphane (1.6 g, 2.9 mmol) in dioxane (60.0 mL) was degassed and purged with N$_2$ for 3 times, and then the mixture was stirred at 100° C. for 12 h under N$_2$ atmosphere. The reaction mixture was concentrated under reduced pressure. The residue was purified by column chromatography (SiO$_2$) to afford benzyl(2-chloro-3-methylphenyl)sulfane (2.6 g, 53.6% yield) as a yellow solid. $^1$HNMR (400 MHz, CHLOROFORM-d) δ 7.44-7.37 (m, 2H), 7.36-7.23 (m, 3H), 7.16-7.03 (m, 3H), 4.42-3.93 (m, 2H), 2.73-2.22 (m, 3H).

Step 2:

To a solution of benzyl(2-chloro-3-methylphenyl)sulfane (0.5 g, 2.0 mmol) in MeCN (5.0 mL) was added H$_2$O (7 mg, 401.9 umol, 7.2 uL) and AcOH (12 mg, 200.9 umol, 11.4 uL) then added trichloroisocyanuric acid (TCCA) (467 mg, 2.0 mmol) at 0° C. The reaction mixture was stirred at 0° C. for 1 h. The reaction mixture was concentrated under reduced pressure. The residue was purified by prep-HPLC (basic condition) to afford 2-chloro-3-methylbenzenesulfonic acid (70 mg, 16.8% yield) as a white solid.

Step 3:

A solution of 2-chloro-3-methylbenzenesulfonic acid (100 mg, 483.9 umol) in SOCl$_2$ (4.0 mL) and DMF (0.1 mL) was stirred at 70° C. for 12 h. The reaction mixture was concentrated under reduced pressure to afford 2-chloro-3-methylbenzenesulfonyl chloride (100 mg, crude) as yellow oil.

Step 4:

To a solution of 5-bromo-6-methyl-pyridin-2-amine (80 mg, 427.7 umol) in pyridine (2.0 mL) was added 2-chloro-3-methylbenzenesulfonyl chloride (96 mg, 427.7 umol). The reaction mixture was stirred at 45° C. for 2 h. The reaction mixture was concentrated under reduced pressure. The residue was purified by prep-HPLC (FA condition) to give N-(5-bromo-6-methylpyridin-2-yl)-2-chloro-3-methylbenzenesulfonamide (16 mg, 8.8% yield, FA) as a white solid.

Step 5:

A mixture of N-(5-bromo-6-methylpyridin-2-yl)-2-chloro-3-methylbenzenesulfonamide (6 mg, 14.2 umol FA), 8-ethyl-2-fluoro-6-(4,4,5,5-tetramethyl-1,3,2-dioxaborolan-2-yl)quinazoline (4 mg, 14.2 umol), K$_2$CO$_3$ (5 mg, 42.6 umol), and Pd(dppf)Cl$_2$ (1 mg, 1.4 umol) in dioxane (2.0 mL) and H$_2$O (0.2 mL) was degassed and purged with N$_2$ for 3 times, and then the mixture was stirred at 90° C. for 12 h under N$_2$ atmosphere. The reaction mixture was concentrated under reduced pressure. The residue was combined with another 10 mg batch and purified by prep-TLC (SiO$_2$) to afford 2-chloro-N-(5-(8-ethyl-2-fluoroquinazolin-6-yl)-6-methylpyridin-2-yl)-3-methylbenzenesulfonamide (20 mg) as a white solid. M+H$^+$=471.2 (LCMS).

Step 6:

To a solution of 2-chloro-N-(5-(8-ethyl-2-fluoroquinazolin-6-yl)-6-methylpyridin-2-yl)-3-methylbenzenesulfonamide (20 mg, 42.4 umol) in n-BuOH (2.0 mL) was added DIEA (27 mg, 212.3 umol, 36.9 uL) and (1r,4r)-N1,N1-dimethylcyclohexane-1,4-diamine (15 mg, 84.9 umol, HCl). The reaction mixture was stirred at 100° C. for 12 h. The reaction mixture was concentrated under reduced pressure. The residue was purified by prep-HPLC (FA condition) to give 2-chloro-N-(5-(2-(((1r,4r)-4-(dimethylamino)cyclohexyl)amino)-8-ethylquinazolin-6-yl)-6-methylpyridin-2-yl)-3-methylbenzenesulfonamide (4.7 mg, 16.6% yield, FA) as a pale yellow solid. M+H$^+$=593.2 (LCMS); $^1$H NMR (400 MHz, METHANOL-d$_4$) δ 9.00 (s, 1H), 8.58 (br s, 1H), 8.11 (d, J=7.6 Hz, 1H), 7.67 (d, J=8.9 Hz, 1H), 7.55-7.47 (m, 3H), 7.41-7.33 (m, 1H), 7.19 (d, J=8.8 Hz, 1H), 3.98 (ddd, J=4.0, 7.8, 11.5 Hz, 1H), 3.13-3.06 (m, 2H), 3.00 (br t, J=11.7 Hz, 1H), 2.73 (s, 6H), 2.44 (s, 3H), 2.41-2.31 (m, 5H), 2.16 (br d, J=12.0 Hz, 2H), 1.75-1.57 (m, 2H), 1.54-1.40 (m, 2H), 1.33 (t, J=7.5 Hz, 3H).

Example 43: Synthesis of 2-chloro-N-(5-(2-(((1r,4r)-4-(dimethylamino)cyclohexyl)amino)-8-ethyl-7-fluoroquinazolin-6-yl)-3-fluoro-6-methoxypyridin-2-yl)benzenesulfonamide (163)

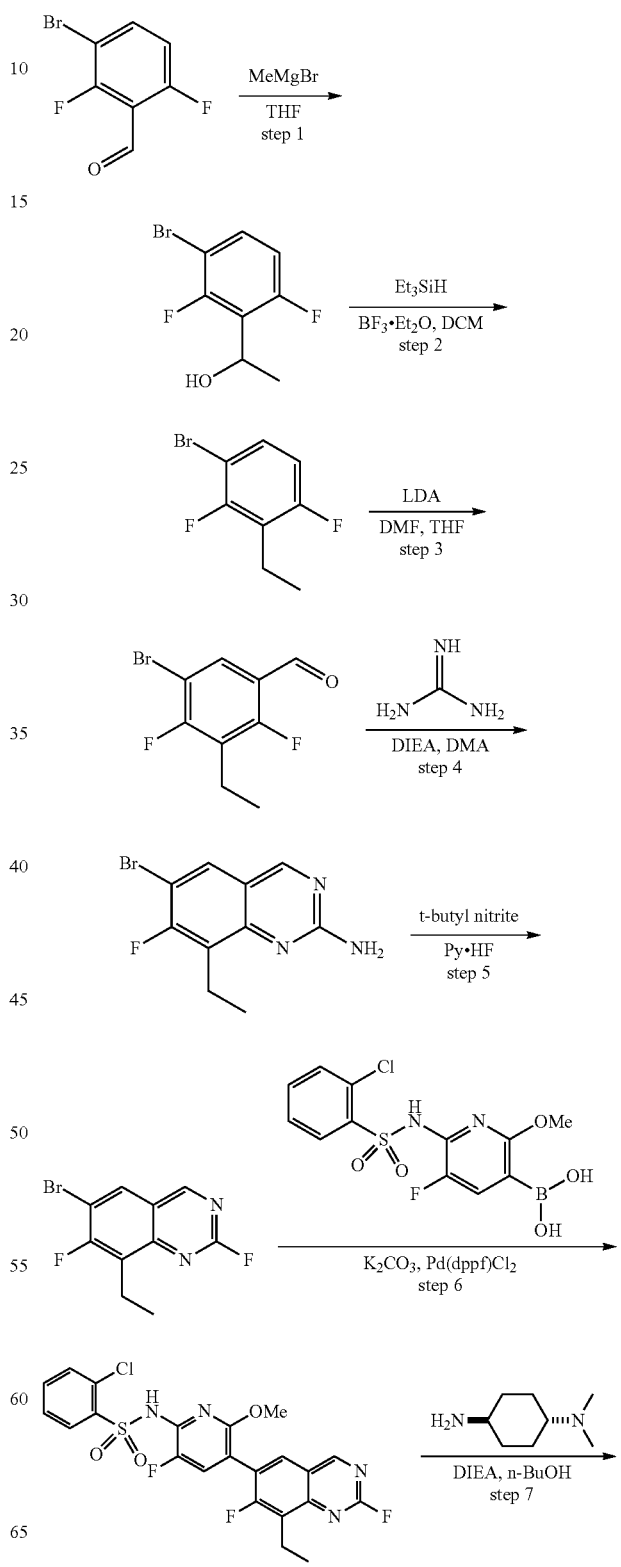

-continued

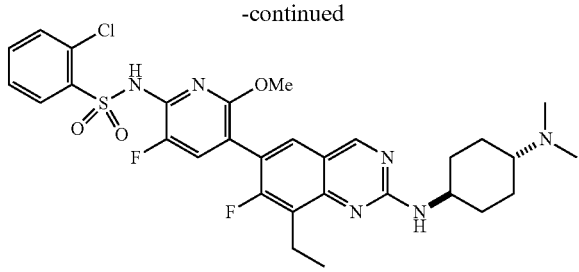

Step 1:
To a solution of 3-bromo-2,6-difluoro-benzaldehyde (20 g, 90.5 mmol) in THF (320.0 mL) at −78° C. was added MeMgBr (3 M, 42.2 mL) dropwise under $N_2$ atmosphere. The reaction mixture was stirred at −78° C. for 30 minutes, then at 0° C. for 1.5 h. The reaction mixture was quenched by addition of saturated $NH_4Cl$ (300.0 mL) aqueous solution and extracted with ethyl acetate (80.0 mL×3). The combined organic layers were washed with brine (80.0 mL×3), dried over $Na_2SO_4$, filtered, and concentrated under reduced pressure to give a residue. The residue was purified by flash silica gel chromatography to afford 1-(3-bromo-2,6-difluorophenyl)ethan-1-ol (21.0 g, 78.3% yield) as a yellow oil. $^1$H NMR (400 MHz, CHLOROFORM-d) δ 7.39 (ddd, J=5.8, 7.8, 8.8 Hz, 1H), 6.77 (dt, J=1.7, 9.3 Hz, 1H), 5.30-5.14 (m, 1H), 2.79 (br d, J=3.1 Hz, 1H), 1.58 (d, J=6.8 Hz, 3H).

Step 2:
To a solution of 1-(3-bromo-2,6-difluorophenyl)ethan-1-ol (21.0 g, 88.5 mmol) and $Et_3SiH$ (20.6 g, 177.1 mmol, 28.3 mL) in DCM (800.0 mL) was added $BF_3.Et_2O$ (44.9 g, 310.0 mmol, 39.0 mL, 98% purity) at 0° C. under $N_2$ atmosphere. The reaction mixture was stirred at 35° C. for 72 h. The reaction mixture was quenched by addition saturated $NaHCO_3$ (500.0 mL) aqueous solution at 0° C. and extracted with DCM (100.0 mL×3). The combined organic layers were washed with brine (100.0 mL×3), dried over $Na_2SO_4$, filtered, and concentrated under reduced pressure to give a residue. The residue was purified by flash silica gel chromatography to give 1-bromo-3-ethyl-2,4-difluorobenzene (9.8 g, 40.0% yield) as a colorless oil. $^1$H NMR (400 MHz, CHLOROFORM-d) δ 7.35 (ddd, J=5.9, 7.9, 8.9 Hz, 1H), 6.78 (dt, J=1.7, 8.8 Hz, 1H), 2.73 (tq, J=1.3, 7.5 Hz, 2H), 1.21 (t, J=7.6 Hz, 3H).

Step 3:
To a solution of 1-bromo-3-ethyl-2,4-difluorobenzene (9.8 g, 44.3 mmol) in THF (100.0 mL) was added dropwise LDA (2 M, 26.6 mL) at −78° C. After addition, the mixture was stirred at this temperature for 1 h, and then DMF (4.2 g, 57.6 mmol, 4.4 mL) was added dropwise at −78° C. The resulting mixture was stirred at −78° C. for 1 h. The reaction mixture was quenched by addition saturated $NH_4Cl$ (100.0 mL) aqueous solution and extracted with ethyl acetate (50.0 mL×3). The combined organic layers were washed with brine (50.0 mL×3), dried over $Na_2SO_4$, filtered, and concentrated under reduced pressure to give a residue. The residue was purified by flash silica gel chromatography to afford 5-bromo-3-ethyl-2,4-difluorobenzaldehyde (3.3 g, 20.9% yield) as a yellow oil. $^1$H NMR (400 MHz, CHLOROFORM-d) δ 10.24 (s, 1H), 7.95 (t, J=7.5 Hz, 1H), 2.79 (tq, J=1.4, 7.6 Hz, 2H), 1.29-1.21 (m, 3H).

Step 4:
To a solution of 5-bromo-3-ethyl-2,4-difluorobenzaldehyde (3.3 g, 13.2 mmol) in DMA (65.0 mL) was added guanidine (1.6 g, 13.2 mmol, $H_2CO_3$) and DIEA (1.7 g, 13.2 mmol, 2.3 mL). The mixture was stirred at 160° C. for 1 h. The reaction mixture was quenched by addition $H_2O$ (200.0 mL) and extracted with ethyl acetate (30.0 mL×3). The combined organic layers were washed with brine (30.0 mL×3), dried over $Na_2SO_4$, filtered, and concentrated under reduced pressure to give a residue. The residue was purified by flash silica gel chromatography to afford 6-bromo-8-ethyl-7-fluoroquinazolin-2-amine (318 mg, 7.1% yield) as a yellow oil. $^1$HNMR (400 MHz, CHLOROFORM-d) δ 8.89 (s, 1H), 7.78 (d, J=7.5 Hz, 1H), 5.24 (br s, 2H), 3.09 (dq, J=2.2, 7.5 Hz, 2H), 1.25 (t, J=7.5 Hz, 3H).

Step 5:
To a solution of 6-bromo-8-ethyl-7-fluoroquinazolin-2-amine (318 mg, 1.1 mmol) in pyridine (3.0 mL) was added pyridine; hydrofluoride (6.6 g, 66.6 mmol, 6.0 mL) at −40° C. The mixture was stirred at −40° C. for 15 min. Then tert-butyl nitrite (242 mg, 2.3 mmol, 280.0 uL) was added. The mixture was stirred at 25° C. for 1 h. The reaction mixture was quenched by addition saturated $NaHCO_3$ (400.0 mL) and extracted with EtOAc (50.0 mL×3). The combined organic layers were washed with brine (50.0 mL×3), dried over $Na_2SO_4$, filtered, and concentrated under reduced pressure. The residue was purified by flash silica gel chromatography to afford 6-bromo-8-ethyl-2,7-difluoroquinazoline (180 mg, 54.3% yield) as a yellow solid. $^1$HNMR (400 MHz, CHLOROFORM-d) δ 9.25 (d, J=2.4 Hz, 1H), 8.12 (d, J=7.1 Hz, 1H), 3.22 (dq, J=2.1, 7.5 Hz, 2H), 1.30 (t, J=7.5 Hz, 3H).

Step 6:
A mixture of 6-bromo-8-ethyl-2,7-difluoroquinazoline (40 mg, 146.4 umol), (6-((2-chlorophenyl)sulfonamido)-5-fluoro-2-methoxypyridin-3-yl)boronic acid (105 mg, 292.9 umol), $K_2CO_3$ (60 mg, 439.4 umol), $Pd(dppf)Cl_2$ (10 mg, 14.6 umol), and $H_2O$ (0.1 mL) in dioxane (1.0 mL) was degassed and purged with $N_2$ for 3 times. The reaction mixture was stirred at 90° C. for 12 h under $N_2$ atmosphere. The reaction mixture was concentrated under reduced pressure. The residue was purified by prep-TLC ($SiO_2$) to afford 2-chloro-N-(5-(8-ethyl-2,7-difluoroquinazolin-6-yl)-3-fluoro-6-methoxypyridin-2-yl)benzenesulfonamide (27 mg, 21.2% yield) as yellow oil. M+H$^+$=509.1 (LCMS).

Step 7:
To a solution of 2-chloro-N-(5-(8-ethyl-2,7-difluoroquinazolin-6-yl)-3-fluoro-6-methoxypyridin-2-yl)benzenesulfonamide (27 mg, 53.0 umol) in n-BuOH (2.0 mL) was added DIEA (34 mg, 265.2 umol, 46.2 uL) and (1r,4r)-N1,N1-dimethylcyclohexane-1,4-diamine (18 mg, 106.1 umol, HCl). The reaction mixture was stirred at 100° C. for 12 h. The reaction mixture was concentrated under reduced pressure. The residue was purified by prep-HPLC (FA condition) to give 2-chloro-N-(5-(2-(((1r,4r)-4-(dimethylamino)cyclohexyl)amino)-8-ethyl-7-fluoroquinazolin-6-yl)-3-fluoro-6-methoxypyridin-2-yl)benzenesulfonamide (3.0 mg, 7.8% yield, FA) as a yellow solid. M+H$^+$=631.2 (LCMS); $^1$H NMR (400 MHz, METHANOL-d$_4$) δ 8.87 (br s, 1H), 8.30 (br d, J=7.9 Hz, 1H), 7.53-7.47 (m, 3H), 7.45 (br s, 1H), 7.37 (br d, J=9.7 Hz, 1H), 3.93 (br s, 1H), 3.36 (s, 3H), 3.15 (br d, J=12.8 Hz, 1H), 3.01 (br d, J=6.6 Hz, 2H), 2.83 (s, 6H), 2.34 (br d, J=10.8 Hz, 2H), 2.15 (br d, J=10.4 Hz, 2H), 1.75-1.58 (m, 2H), 1.53-1.37 (m, 2H), 1.19 (br t, J=6.5 Hz, 3H).

Example 44: Synthesis of 2-chloro-N-(5-(2-(((1r,4r)-4-(dimethylamino)cyclohexyl)amino)-8-ethyl-7-fluoroquinazolin-6-yl)-6-methylpyridin-2-yl)benzenesulfonamide (161)

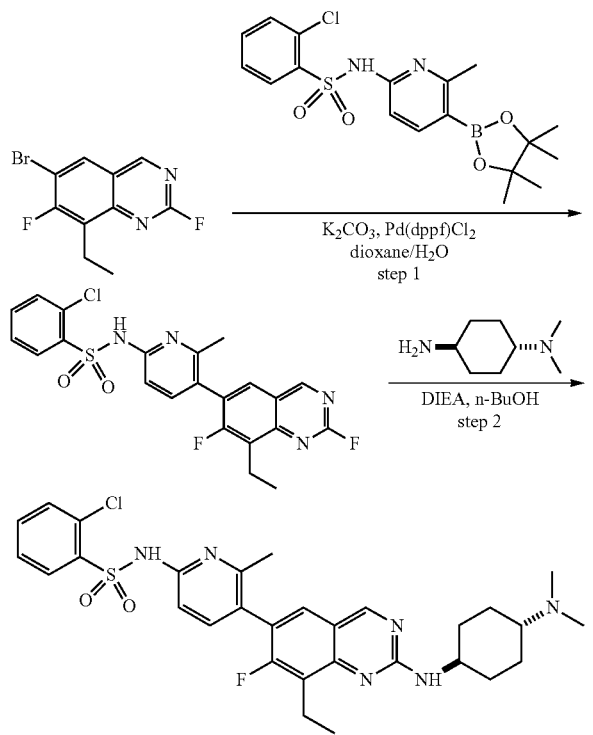

The title compound was synthesized according to the synthetic procedure described in Example 43 to afford 2-chloro-N-(5-(2-(((1r,4r)-4-(dimethylamino)cyclohexyl)amino)-8-ethyl-7-fluoroquinazolin-6-yl)-6-methylpyridin-2-yl)benzenesulfonamide (7.9 mg, 12.6% yield, FA) as a pale yellow solid. M+H$^+$=597.3 (LCMS); $^1$H NMR (400 MHz, METHANOL-d$_4$) δ 8.95 (s, 1H), 8.52 (br s, 1H), 8.23 (d, J=8.4 Hz, 1H), 7.61 (d, J=8.8 Hz, 1H), 7.57-7.51 (m, 3H), 7.51-7.45 (m, 1H), 7.17 (br d, J=8.6 Hz, 1H), 4.04-3.93 (m, 1H), 3.23 (br t, J=10.8 Hz, 1H), 3.08 (q, J=7.5 Hz, 2H), 2.86 (s, 6H), 2.38 (br d, J=10.4 Hz, 2H), 2.25 (s, 3H), 2.19 (br d, J=11.7 Hz, 2H), 1.79-1.65 (m, 2H), 1.58-1.42 (m, 2H), 1.25 (t, J=7.4 Hz, 3H).

Example 45: Synthesis of 2-chloro-N-(5-(2-(((1r,4r)-4-(dimethylamino)cyclohexyl)amino)-8-ethyl-7-fluoroquinazolin-6-yl)-3-fluoro-6-methylpyridin-2-yl)benzenesulfonamide (162)

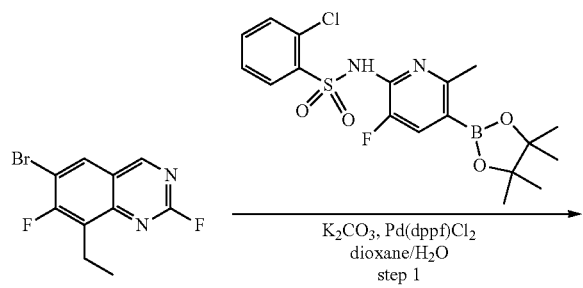

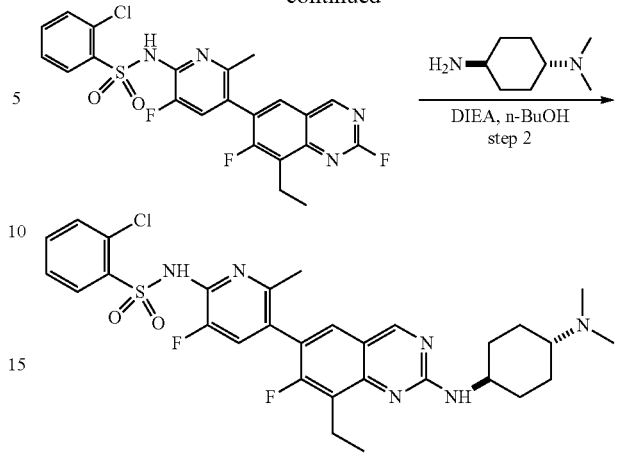

The title compound was synthesized according to the synthetic procedure described in Example 43 to afford 2-chloro-N-(5-(2-(((1r,4r)-4-(dimethylamino)cyclohexyl)amino)-8-ethyl-7-fluoroquinazolin-6-yl)-3-fluoro-6-methylpyridin-2-yl)benzenesulfonamide (3.4 mg, 6.4% yield, FA) as a white solid. M+H$^+$=615.3 (LCMS); $^1$H NMR (400 MHz, METHANOL-d$_4$) δ 8.94 (br s, 1H), 8.55 (br s, 1H), 8.31 (br d, J=7.7 Hz, 1H), 7.60-7.46 (m, 4H), 7.38 (br d, J=10.4 Hz, 1H), 3.98 (br s, 1H), 3.23 (br s, 1H), 3.07 (br d, J=7.1 Hz, 2H), 2.86 (s, 6H), 2.38 (br d, J=9.3 Hz, 2H), 2.18 (br d, J=10.8 Hz, 2H), 2.03 (s, 3H), 1.80-1.63 (m, 2H), 1.57-1.38 (m, 2H), 1.23 (br t, J=7.0 Hz, 3H).

II. Biological Evaluation

Example 1: In Vitro FRET Assay

In vitro FRET assay was performed to evaluate the ability of select compounds to inhibit IRE1, the results of which are summarized in Table 3. To perform the in vitro FRET assay, 1× complete assay buffer (CAB; 1M DTT, 50 mM sodium citrate pH 7.15, 1 mM magnesium acetate, 0.02% tween 20) was used to dilute SignalChem IRE1a protein to a final concentration of 2 nM. Selected compounds were serially diluted with DMSO in a non-binding black 384-well plate for a total of 15 ul in each well. 2 ul of the serially diluted compound or DMSO control were then added to new wells containing 98 ul of 1×CAB, for a total volume of 100 ul, 10 ul of which were then transferred to wells of a new plate. 5 ul of the diluted IRE1a was then added to each well. 5 ul of a 400 mM XBP1 RNA probe was then added to each well. Fluorescence was then read over 30 minutes in kinetic mode (485/515 nm).

Two RNA probes were used, XBP1 wildtype (SEQ ID NO: 2) which is able to be spliced by active IRE1a or XBP1 mutant (SEQ ID NO: 3) which is unable to be spliced. Each probe contained a 5' 6-FAM modification and a 3' IOWA Black FQ modification.

A second FRET assay was performed to assess ATP-mediated inhibition. In this case, compounds and IRE1a were prepared and combined as discussed above, with the addition of ATP up to 1 mM final concentration. This mixture was incubated at room temperature for 60 minutes and then 5 ul of 400 nM XBP1 wildtype or mutant RNA probe was added. Plates were then read over 30 minutes in kinetic mode (485/515 nm).

TABLE 3

| Compound Ref. No. | Mean $IC_{50}$ |
|---|---|
| 23; Formic Acid Salt | A |
| 24; Formic Acid Salt | A |
| 25; Formic Acid Salt | A |
| 26; Formic Acid Salt | A |
| 27; Formic Acid Salt | A |
| 28; Formic Acid Salt | A |
| 29; Formic Acid Salt | A |
| 30; Formic Acid Salt | C |
| 31; Formic Acid Salt | D |
| 32; Formic Acid Salt | A |
| 33; Formic Acid Salt | A |
| 34; Formic Acid Salt | A |
| 35; Formic Acid Salt | A |
| 36; Formic Acid Salt | A |
| 37; HCl Salt | A |
| 38; Formic Acid Salt | A |
| 39; Formic Acid Salt | A |
| 40; Formic Acid Salt | A |
| 41; Formic Acid Salt | A |
| 42; Formic Acid Salt | A |
| 43; Formic Acid Salt | A |
| 44; Formic Acid Salt | A |
| 45; Formic Acid Salt | C |
| 46; Formic Acid Salt | A |
| 47; Formic Acid Salt | A |
| 48; Formic Acid Salt | A |
| 49; Formic Acid Salt | A |
| 50; Formic Acid Salt | A |
| 51; Formic Acid Salt | A |
| 52; Formic Acid Salt | A |
| 53; Formic Acid Salt | A |
| 54; Formic Acid Salt | A |
| 55; Formic Acid Salt | A |
| 56; Formic Acid Salt | A |
| 57; Formic Acid Salt | A |
| 58; Formic Acid Salt | B |
| 59; Formic Acid Salt | B |
| 60; Formic Acid Salt | A |
| 61; Formic Acid Salt | A |
| 62; Formic Acid Salt | A |
| 63; Formic Acid Salt | A |
| 64; Formic Acid Salt | A |
| 65; Formic Acid Salt | A |
| 66; Formic Acid Salt | A |
| 67; Formic Acid Salt | A |
| 68; Formic Acid Salt | A |
| 69; Formic Acid Salt | A |
| 70; Formic Acid Salt | A |
| 71; Formic Acid Salt | A |
| 72; Formic Acid Salt | A |
| 73; Formic Acid Salt | A |
| 74; Formic Acid Salt | A |
| 75; Formic Acid Salt | A |
| 76; Formic Acid Salt | A |
| 77; Formic Acid Salt | A |
| 78; Formic Acid Salt | A |
| 79; Formic Acid Salt | A |
| 80; Formic Acid Salt | A |
| 81; Formic Acid Salt | A |
| 82; Formic Acid Salt | A |
| 83; Formic Acid Salt | B |
| 84; Formic Acid Salt | A |
| 85; Formic Acid Salt | A |
| 86; Formic Acid Salt | A |
| 87; Formic Acid Salt | A |
| 88; Formic Acid Salt | A |
| 89; Formic Acid Salt | A |
| 90; Formic Acid Salt | A |
| 91; Formic Acid Salt | A |
| 92; Formic Acid Salt | A |
| 93; Formic Acid Salt | A |
| 94; Formic Acid Salt | A |
| 95; Formic Acid Salt | A |
| 96; Formic Acid Salt | A |
| 97; Formic Acid Salt | A |
| 98; Formic Acid Salt | A |
| 99; Formic Acid Salt | A |
| 108; Formic Acid Salt | A |
| 116; Formic Acid Salt | A |
| 117; Formic Acid Salt | A |
| 118; Formic Acid Salt | A |
| 119; Formic Acid Salt | A |
| 122; Formic Acid Salt | A |
| 124; Formic Acid Salt | A |
| 125; Formic Acid Salt | A |
| 126; Formic Acid Salt | C |
| 127; Formic Acid Salt | A |
| 128; Formic Acid Salt | A |
| 130; Formic Acid Salt | A |
| 131; Formic Acid Salt | A |
| 132; Formic Acid Salt | A |
| 133; Formic Acid Salt | A |
| 135; Formic Acid Salt | A |
| 137; Formic Acid Salt | A |
| 139; Formic Acid Salt | B |
| 141; Formic Acid Salt | A |
| 142; Formic Acid Salt | B |
| 143; Formic Acid Salt | B |
| 144; Formic Acid Salt | C |
| 145; Formic Acid Salt | A |
| 147; Formic Acid Salt | B |
| 148; Formic Acid Salt | A |
| 149; Formic Acid Salt | A |
| 150; Formic Acid Salt | A |
| 151; Formic Acid Salt | A |
| 152; Formic Acid Salt | A |
| 153; Formic Acid Salt | A |
| 154; Formic Acid Salt | A |
| 155; Formic Acid Salt | A |
| 156; Formic Acid Salt | D |
| 157; Formic Acid Salt | A |
| 158; Formic Acid Salt | A |
| 159; Formic Acid Salt | A |
| 160; Formic Acid Salt | A |
| 161; Formic Acid Salt | A |
| 162; Formic Acid Salt | A |
| 163; Formic Acid Salt | A |

Note:
Biochemical assay Mean $IC_{50}$ data are designated within the following ranges:
A: ≤5 nM; B: >5 nM to ≤50 nM; C: >50 nM to ≤100 nM; and D: >100 nM to ≤10 uM.

Example 2: In Vitro Luciferase Assay

Compounds disclosed herein were assessed for disruption of IRE1 signaling using a IRE1a Endoribonuclease Nano-luciferase Assay. Briefly, 2.5×10$^6$ 293T cells were seeded in a 10 cm$^2$ tissue culture plate. About 24 hours later, the cells were transfected with Effectene. In a 15 mL tube, the following was added: 2 ug XBP1 luciferase reporter plasmid (PGK-Luc2-P2A-XBP1u-Nanoluciferase-PEST); 300 ul EC buffer; and 16 ul Enhancer, followed by incubation at room temp for 5 minutes. Next, 60 ul Effectene (Qiagen 301427) was added, followed by incubation at room temperature for 10 minutes. 2.6 mL cDMEM media was added. Old media was aspirated from the cells, followed by addition of 7 mL fresh media. Full transfection mixture was added dropwise to cells. Cells were incubated for 6 hours, followed by trypsinization, centrifugation and resuspension in 11 mL fresh cDMEM media. 100 uL of cells were plated per a well in a 96 well plate. A day later, ER stressors of choice+/− inhibitors were added. To harvest, media was aspirated from cells completely, then 50 uL 1× passive lysis buffer (Promega: E1941) was added per well and put on shaker (300 rpm) for 30 minutes at room temperature. Cells were centrifuged, and 15 uL sample per well was added to a new, opaque white 384 well plate (Corning 3570). 15 uL OneGlo (nanoluciferase kit, Promega N1630) was added. Plates were spun down, placed on shaker (300 rpm) for 10 minutes.

Plates were read on luminometer, 1000 ms integration time per well. 15 uL Stop and Glo (nanoluciferase kit) was added. Plates were spun down, placed on shaker (300 rpm) for 10 minutes. Plates were read on luminometer, 1000 ms second integration time per well. Recordings are provided below in Table 4.

TABLE 4

| Compound Ref. No. | Mean $EC_{50}$ |
|---|---|
| 23; Formic Acid Salt | A |
| 24; Formic Acid Salt | A |
| 25; Formic Acid Salt | A |
| 26; Formic Acid Salt | A |
| 27; Formic Acid Salt | A |
| 28; Formic Acid Salt | A |
| 29; Formic Acid Salt | D |
| 32; Formic Acid Salt | A |
| 33; Formic Acid Salt | A |
| 34; Formic Acid Salt | B |
| 35; Formic Acid Salt | A |
| 37; HCl Salt | A |
| 44; Formic Acid Salt | A |
| 46; Formic Acid Salt | A |
| 47; Formic Acid Salt | B |
| 48; Formic Acid Salt | B |
| 51; Formic Acid Salt | C |
| 52; Formic Acid Salt | A |
| 53; Formic Acid Salt | A |
| 54; Formic Acid Salt | B |
| 55; Formic Acid Salt | A |
| 56; Formic Acid Salt | A |
| 57; Formic Acid Salt | A |
| 58; Formic Acid Salt | A |
| 59; Formic Acid Salt | C |
| 60; Formic Acid Salt | A |
| 61; Formic Acid Salt | A |
| 62; Formic Acid Salt | B |
| 64; Formic Acid Salt | A |
| 65; Formic Acid Salt | B |
| 66; Formic Acid Salt | C |
| 67; Formic Acid Salt | B |
| 68; Formic Acid Salt | C |
| 69; Formic Acid Salt | A |
| 70; Formic Acid Salt | A |
| 71; Formic Acid Salt | A |
| 72; Formic Acid Salt | D |
| 73; Formic Acid Salt | A |
| 74; Formic Acid Salt | A |
| 75; Formic Acid Salt | D |
| 76; Formic Acid Salt | B |
| 77; Formic Acid Salt | B |
| 78; Formic Acid Salt | A |
| 79; Formic Acid Salt | B |
| 80; Formic Acid Salt | D |
| 81; Formic Acid Salt | A |
| 82; Formic Acid Salt | B |
| 83; Formic Acid Salt | C |
| 84; Formic Acid Salt | B |
| 85; Formic Acid Salt | D |
| 86; Formic Acid Salt | C |
| 87; Formic Acid Salt | A |
| 88; Formic Acid Salt | A |
| 89; Formic Acid Salt | D |
| 90; Formic Acid Salt | B |
| 91; Formic Acid Salt | A |
| 92; Formic Acid Salt | D |
| 93; Formic Acid Salt | A |
| 94; Formic Acid Salt | A |
| 95; Formic Acid Salt | A |
| 97; Formic Acid Salt | A |
| 98; Formic Acid Salt | A |
| 99; Formic Acid Salt | A |
| 108; Formic Acid Salt | A |
| 116; Formic Acid Salt | A |
| 117; Formic Acid Salt | A |
| 118; Formic Acid Salt | A |
| 119; Formic Acid Salt | A |
| 122; Formic Acid Salt | A |
| 124; Formic Acid Salt | A |
| 125; Formic Acid Salt | A |
| 127; Formic Acid Salt | A |
| 128; Formic Acid Salt | A |
| 130; Formic Acid Salt | A |
| 131; Formic Acid Salt | A |
| 132; Formic Acid Salt | A |
| 133; Formic Acid Salt | A |
| 135; Formic Acid Salt | A |
| 137; Formic Acid Salt | A |
| 141; Formic Acid Salt | D |
| 145; Formic Acid Salt | A |
| 148; Formic Acid Salt | A |
| 149; Formic Acid Salt | B |
| 150; Formic Acid Salt | B |
| 151; Formic Acid Salt | A |
| 152; Formic Acid Salt | A |
| 153; Formic Acid Salt | B |
| 154; Formic Acid Salt | A |
| 155; Formic Acid Salt | C |
| 157; Formic Acid Salt | A |
| 158; Formic Acid Salt | A |
| 159; Formic Acid Salt | B |
| 160; Formic Acid Salt | A |
| 161; Formic Acid Salt | A |
| 162; Formic Acid Salt | A |
| 163; Formic Acid Salt | A |

Note:
Biochemical assay Mean $EC_{50}$ data are designated within the following ranges:
A: ≤5 nM; B: >5 nM to ≤50 nM; C: >50 nM to ≤100 nM; and D: >100 nM to ≤10 uM.

Example 3: Growth Assay

A growth assay was performed to evaluate the compounds disclosed herein for cytotoxicity. Briefly, 5,000,000 293T cells were resuspended in 18 mL of cDMEM for a final concentration of 277,777 cells/mL. 180 uL (50,000 cells) cDMEM was seeded per well in a 96 well flat bottom plate as shown in Table 5, with "media" wells left unfilled. In a separate 96 well dilution plate, 199 uL cDMEM and 1 uL of DMSO or any one of the compounds disclosed herein (shown as Test Compound 1, 2, 3, 4, 5, or 6 below) were added to wells A4, A8, $C_4$, $C_8$, E4, E8, G4, and G8. 133.3 uL cDMEM was added to wells 1, 2, 3, 5, 6, and 7 in rows A, C, E and G of the dilution plate. Compounds were serially diluted leftwards in threefold dilutions (66.7 uL into 133.3 uL cDMEM). 20 uL of each dilution was transferred in duplicate (duplicates in vertical paired wells) to the cells plated in the 96-well plate shown in Table 5, to the total concentrations shown below. 200 uL cDMEM was added to media wells (wells G5-H8). The plate was then placed in a humidified chamber for a 2 day incubation, and then photographed (media was more yellow in wells with potent cell growth). Absorbance was then measured at ~535 nM (lower for more acidic media) and ~450 nM (higher for more acidic media). The results of the growth assay as shown in Table 6.

TABLE 5

|   | 1 | 2 | 3 | 4 | 5 | 6 | 7 | 8 |
|---|---|---|---|---|---|---|---|---|
| A |   |   |   | Test Compound 1 |   |   |   | Test Compound 5 |
| B |   |   |   |   |   |   |   |   |
| C |   |   |   | Test Compound 2 |   |   |   | Test Compound 6 |
| D |   |   |   |   |   |   |   |   |
| E |   |   |   | Test Compound 3 |   |   |   | DMSO |
| F |   |   |   |   |   |   |   |   |
| G |   |   |   | Test Compound 4 |   |   |   | media only |
| H |   |   |   |   |   |   |   |   |
| Conc (uM) | 0.185 | 0.556 | 1.667 | 5 | 0.185 | 0.5556 | 1.667 | 5 |

TABLE 6

| Compound Ref. No. | % Growth at 0.185 uM | % Growth at 0.5556 uM | % Growth at 1.667 uM | % Growth at 5 uM |
|---|---|---|---|---|
| 23; Formic Acid Salt | D | C | C | D |
| 24; Formic Acid Salt | D | D | C | C |
| 25; Formic Acid Salt | D | D | D | D |
| 27; Formic Acid Salt | D | D | C | B |
| 28; Formic Acid Salt | D | D | C | B |
| 29; Formic Acid Salt | D | D | D | D |
| 32; Formic Acid Salt | D | D | C | B |
| 33; Formic Acid Salt | D | D | D | C |
| 34; Formic Acid Salt | D | D | D | A |
| 35; Formic Acid Salt | D | D | C | B |
| 37; HCl Salt | n/a | D | C | B |
| 46; Formic Acid Salt | D | D | D | D |
| 52; Formic Acid Salt | D | D | D | C |
| 55; Formic Acid Salt | D | D | D | D |
| 65; Formic Acid Salt | D | D | D | C |
| 67; Formic Acid Salt | D | D | C | C |
| 69; Formic Acid Salt | n/a | D | C | C |
| 71; Formic Acid Salt | D | D | C | B |

Note:
% Growth data are designated within the following ranges:
A: ≤25%; B: >25% to ≤50%; C: >50% to ≤75%; D: >75% to ≤100%;

Example 4: ELISA Assay

Total human or mouse CD4 T cells are isolated by negative selection with Miltenyi MACS beads. Mouse CD4 T cells are isolated from mouse spleen while human CD4 T cells were isolated from human PBMCs. CD4 T cells are washed and then mixed with CD3/CD28 activator Dynabeads at 8 pm. After a 36 hour incubation, select IRE1a inhibitor compounds or IRE1a inhibitor controls are added and incubated for 2 hours.

After the two hour incubation, mouse or human cell-free malignant ascites supernatants or cRPMI control are added. After a 10 hour incubation, supernatants are isolated and used in an IFN-g ELISA assay. Trizol is added to each ELISA well containing T Cells for isolating RNA. ELISA assay is performed with the eBioscience Ready-Set-Go IFN-g ELISA kit according to the manufacturer's recommended protocol.

Example 5: T Cell Metabolism Assay

Total human or mouse CD4 T cells are isolated by negative selection with Miltenyi MACS beads. Mouse CD4 T cells are isolated from mouse spleen while human CD4 T cells are isolated from human PBMCs. One and a half million CD4 T cells are washed and then mixed with CD3/CD28 activator Dynabeads at a 1:1 bead:cell ratio and plated in complete RPMI in a 6 well plate. After a 24 hour incubation, select IRE1a inhibitor compounds or IRE1a inhibitor control compounds are added and incubated for 2 hours. After the two hour incubation, mouse or human cell-free malignant ascites supernatants or cRPMI control are added. After a 16 hour incubation, the dynabeads are removed by magnetic separation and mitochondrial oxygen consumption rate (OCR) and glycolytic extracellular acidification rate (ECAR) is measured with the Seahorse XFe96 Analyzer (Agilent). Samples are assayed in triplicate with 150,000 viable cells plated in each well of the assay plate. Supernatants are additionally isolated and used in downstream IFN-g ELISA assays. IRE1a activity is also measured by quantifying XBP1 splicing with quantitative PCR or by intracellular flow cytometric staining with an XBP1s-specific monoclonal antibody (clone: Q3-695; BD Pharmingen).

Example 6: Inflammatory Cytokine Production Assay

Approximately $3 \times 10^6$ mouse bone marrow cells (after RBC lysis) are seeded in 10 mL cRPMI with 20 ng/mL GM-CSF in a petri dish. On culture day 3, 10 mL of cRPMI+20 ng/mL GM-CSF is added. On culture day 6, non-adherent cells from each plate are collected and resuspended in 20 mL of fresh cRPMI+20 ng/mL GM-CSF. On culture day 7, suspension cells are harvested, counted, and the resuspended at 500,000 cells per 180 microliters in fresh cRPMI+20 ng/mL GM-CSF+110% final concentration of IRE1a inhibitor compounds or DMSO as a control. 180 microliters of cell suspension are added to each well of a 96 well flat bottom TC-treated plate and incubated for 2 hours. 20 ul of 10×LPS (1 ug/mL) prepared in cRPMI+20 ng/mL GM-CSF is added to indicated wells and incubated for another 6 hours. Cells are spun down and supernatant was stored in a new 96-well V-bottom plate. 200 microliters of trizol is added to pelleted cells for subsequent RNA analysis.

Example 7: Xbp1 Activation in ID8 Mouse Model

A syngeneic mouse model for metastatic, orthotopic ovarian cancer is used to analyze the in vivo effects of compounds described herein. In a first analysis, IRE1a/XBP1 activation is assessed in the ID8 mouse model for ovarian cancer.

Parental ID8 or aggressive ID8-Defb29/Vegf-A intraperitoneal ovarian tumors are generated. About $1-2 \times 10^6$ tumor cells are injected into wild type female C57BL/6 mice. After 3 weeks, a first group of 3-5 tumor bearing mice (parental ID8 and ID8-Defb29/Vegf-A mice) and tumor-free naïve mice are injected intraperitoneally with a compound from Table 1. Additional groups of 3-5 tumor bearing mice and naïve mice are injected with vehicle (PBS) as a control. Tumors are resected and ascites drained from the mice 12-24 hours after the compound administration for analyzing IRE1a pathway activation in the tumor microenvironment.

Fluorescently activated cell sorting (FACS) is then performed to purify cells from the tumors and ascites. Tumor dendritic cells (tDCs) ($CD45^+CD11c^+CD11b^+MHC-II^+CD8\alpha^{low}$), tumor cells ($CD45-SSC^{hi}$), CD4+ T cells ($CD45^+CD3^+CD4^+$) and CD8+ T cells ($CD45^+CD3^+CD8^+$) are isolated from tumors and ascites of parental ID8 mice and ID8-Defb29/Vegf-A mice. Control splenic dendritic cells (sDCs) ($CD45^+CD11c^+CD11b^+MHC-II^+CD8\alpha^-$) or splenic T cells ($CD45^+CD3^+CD4^+$ or $CD45^+CD3^+CD8^+$) are isolated from spleens of naïve mice or ID8 mice and ID8-Defb29/Vegf-A mice. During sorting, viable cells are identified using the LIVE/DEAD Fixable Yellow Dead Cell Stain Kit (Life Technologies).

Total Xbp1 mRNA expression and spliced Xbp1 (Xbp1s) are quantified in splenic DCs and T cells from naïve mice, splenic DCs and T cells from parental ID8 mice and ID8-Defb29/Vegf-A mice, and tDCs, tumor cells, and tumor-infiltrating T cells from parental ID8 mice and ID8-Defb29/Vegf-A mice administered either vehicle or a compound from Table 1. Briefly, RNA from sorted cells are isolated using the Trizol reagent. 0.1-1 ug of RNA are used to generate cDNA using the High Capacity cDNA Reverse Transcription Kit (Life Technologies). Mouse Xbp1 splicing assays are performed using conventional Reverse Transcription PCR (RT-PCR) and primers shown in Table 8. Gene expression analysis is also performed via Reverse Transcription quantitative PCR (RT-qPCR) using a Stratagene Mx3005 instrument and SYBR green I (Life Technologies). Gene expression is measured of Xbp1 target genes including ERdj4, Sec24d, and Sec61a1 and general ER stress response markers Hspa5 (BiP) and Ddit3 (CHOP). Murine Xbp1s transcript expression is analyzed using a primer that spans the splicing junction site.

TABLE 8

| Species | Gene | Oligo name | Sequence 5'-3' | SEQ ID NO | Purpose |
|---|---|---|---|---|---|
| Mouse | Xbp1 | Xbp1-SA-F | ACACGTTTGGGAATGGACAC | | Splicing Assay |
| | | Xbp1-SA-R | CCATGGGAAGATGTTCTGGG | | |
| Mouse | Actb | actb1083 | CTCAGGAGGAGCAATGATCTTGAT | | RT-qPCR |
| | | actb987 | TACCACCATGTACCCAGGCA | | |
| Mouse | Xbp1 | Xbp1.total-F | GACAGAGAGTCAAACTAACGT | | RT-qPCR |
| | | Xbp1.total-R | GTCCAGCAGGCAAGAAGGT | | |
| Mouse | Xbp1s | XBPsA406F | AAGAACACGCTTGGGAATGG | | RT-qPCR |
| | | XBPsAa518R | CTGCACCTGCTGCGGAC | | |
| Mouse | Dnajb9/Erdj4 | ERdj4-F | TAAAAGCCCTGATGCTGAAGC | | RT-qPCR |
| | | ERdj4-R | TCCGACTATTGGCATCCGA | | |
| Mouse | Sec61a1 | Sec61a1-F | CTATTTCCAGGGCTTCCGAGT | | RT-qPCR |
| | | Sec61a1-R | AGGTGTTGTACTGGCCTCGGT | | |
| Mouse | Sec24d | Sec24d-F | TCCACTCTCCCCATGGTTTA | | RT-qPCR |
| | | Sec24d-R | GCTATATCCGCTGCACTACG | | |
| Mouse | Hspa5/BiP | BiP-F | TCATCGGACGCACTTGGAA | | RT-qPCR |
| | | BiP 78-R | CAACCACCTTGAATGGCAAGA | | |
| Mouse | Ddit3/CHOP | CHOP-F | GTCCCTAGCTTGGCTGACAGA | | RT-qPCR |
| | | CHOP-R | TGGAGAGCGAGGGCTTTG | | |
| Mouse | Agpat6 | Agpat6-F | AGCTTGATTGTCAACCTCCTG | | RT-qPCR |

Protein analysis of XBP1S is performed by Western blot or intracellular flow cytometric analysis of splenic DCs and T cells from naïve mice, splenic DCs and T cells from parental ID8 mice and ID8-Defb29/Vegf-A mice, and tDCs, tumor cells and tumor-infiltrating T cells from parental ID8 mice and ID8-Defb29/Vegf-A mice administered either vehicle or a compound from Table 1. Briefly, for Western blotting 5×10$^6$ sDCs, tumor cells, T cells, or tDCs are washed twice in 1× cold PBS and nuclear proteins are purified using the Nuclear Extraction Kit (Life Technologies). Proteins are quantified using the BCA method (Pierce) and 15-20 ug of nuclear proteins are separated via SDS-PAGE and are transferred onto nitrocellulose membranes. Anti-mouse XBP1s (Biolegend, clone 9D11A43) is raised in mouse using a partial mouse XBP1s recombinant protein (162-267 aa)corresponding to the XBP1s C-terminus, and is used at a 1:500 dilution for immunoblotting. Rabbit anti-mouse Lamin B (Cell Signaling, #12586) is used at 1:1000. HRP-conjugated secondary antibodies to rabbit and mouse (Biorad) are used at a 1:5000 dilution. SuperSignal West Femto (Pierce) is used as Chemiluminescent Substrate and blots are imaged using a ChemiDoc Touch instrument (Biorad). For intracellular flow cytometry of XBP1s protein, 1-2 million splenocytes or dissociated cells from solid tumors or ascites are washed in cold PBS and stained with the Ghost Dye 510 fixable viability dye diluted 1:1000 in 1 ml PBS for 30 minutes on ice. The staining reaction is quenched with 2 mL of FACS buffer (PBS with 2% fetal bovine serum and 1 mM EDTA), cells pelleted by centrifugation at 300×g for 5 minutes, and then surface stained with antibodies directed at key lineage defining markers such as CD45/CD3/CD4/CD8 (for T cells) or CD45/CD11c/MHC-II (for DCs) for 30 minutes in FACS buffer on ice. Cells are washed twice with FACS buffer and then fixed and permeabilized for 30 minutes with the eBioscience FoxP3 nuclear staining kit according to the manufacturer's protocol. Cells are washed twice with 1× permeabilization buffer, then Fc receptors are blocked with Truestain FcX anti-mouse CD16/32 (Biolegend) for 15 minutes at room temperature. Finally, 5 microliters of XBP1s antibody (BD Pharmingen, clone Q3-695) or an equivalent molar amount of isotype control antibody are added directly to cells and stained for 30 minutes at room temperature protected from light. Cells are washed twice with 1× permeabilization buffer and resuspended in FACS buffer, then analyzed on a flow cytometer such as the BD LSR II.

Example 8: Ovarian Cancer Progression

Tumor progression is measured in parental ID8 and aggressive ID8-Defb29/Vegf-A mice administered vehicle or a compound from Table 1. Similar to Example 1, parental ID8 or aggressive ID8-Defb29/Vegf-A intraperitoneal ovarian tumors are generated. Briefly, 1-2×10$^6$ tumor cells are injected into wild type C57BL/6 mice. After 2 weeks, a first group of 8-10 tumor bearing mice (parental ID8 and ID8-Defb29/Vegf-A mice) and a separate group of naïve mice are injected intraperitoneally once per day with a compound from Table 1. Additional groups of tumor bearing mice and naïve mice are injected with PBS as a control. In combination therapy studies, additional groups of mice are injected every other day with 200 ug isotype control antibody or blocking antibodies against CTLA-4 or PD-1. A final group of mice receives a combination therapy consisting of compound from Table 1 and 200 ug checkpoint blocking antibody directed against either CTLA-4 or PD-1.

Tumor size, tumor volume, number of tumor masses as well as spleen size are then measured from vehicle or compound treated naïve mice, parental ID8 mice, and aggressive ID8-Defb29/Vegf-A mice. Naïve mice are monitored weekly for signs of morbidity or mortality from compound treatment. Malignant ascites accumulation is measured weekly as the percentage of body weight gain, and animals are euthanized once they reach 40% body weight gain. Survival of mice bearing parental ID8 tumors or aggressive ID8-Defb29/Vegf-A tumors that are treated with vehicle or a compound from Table 1 is calculated as the number of days required to reach 40% weight gain since the tumor cells are originally injected. Compounds listed in Table 1 are assessed for reduction in tumor-associated weight gain and an increase in overall survival time compared with vehicle control-treated animals.

Example 9: Lipid Analysis and Transcriptional Profiling

Lipid peroxidation byproducts are measured in mice described in Examples 1-2. Intracellular lipid content is evaluated via flow cytometry using 4,4-Difluorol,3,5,7,8-Pentamethyl-4-Bora-3a,4a-Diaza-s-Indacene (BODIPY 493/503; Life Technologies). Briefly, 5×10$^6$ splenic cells or dendritic cells from naïve mice, parental ID8 mice, and aggressive ID8-Defb29/Vegf-A mice that are administered vehicle or a compound from Table 1 are stained for surface markers using antibodies that do not overlap with BODIPY 493/503, namely CD11c-APC, CD45-APC-Cy7, and CD11b-Pacific Blue, followed by staining with 500 mL of BODIPY 493/503 at 0.5 mg/mL in PBS for 15 minutes at room temperature in the dark. BODIPY 493/503 staining is then detected in the PE or FITC channel. Lipid analysis is also performed using electron microscopy analysis and mass spectrometry. In addition to lipid content, intracellular reactive oxygen species (ROS) and 4-HNE adducts are measured with 2',7'-dichlorofluorescin diacetate (DCFDA) and a competitive ELISA assay (Cell Biolabs), respectively.

Transcriptional profiling is performed in naïve mice, parental ID8 mice, and aggressive ID8-Defb29/Vegf-A mice that are treated with vehicle or a compound from Table 1. Gene expression of genes that are involved in unfolded protein response (UPR)/endoplasmic reticulum (ER) stress and genes involved in lipid metabolism are measured in tDCs purified by FACS. These include but are not limited to Sec24d, Sec61a1, P4hb, Fasn, Agpat4, and Agpat6. XBP1 pathway activation and key effector functions are also measured by quantitative PCR in tumor-infiltrating lymphocytes purified by FACS. Compounds listed in Table 1 are assessed for reduction in XBP1s target gene expression and BODIPY 493/503 fluorescence in tumor-associated DCs.

Example 10: T Cell Activation

T cell activation is determined in ovarian cancer bearing mice following administration of compounds described herein. In vivo antigen presentation experiments are performed in wild-type C57BL/6 female mice bearing parental ID8 or ID8-Defb29/Vegf-A ovarian tumors. After three weeks, naïve mice, parental ID8 mice, or ID8-Defb29/Vegf-A mice are intraperitoneally injected with 0.6 mg of full length endotoxin-free ovalbumin (OVA) (SIGMA, grade VII). Mice are then injected with vehicle or a compound from Table 1 3 hours later. After 18 hours, mice receive intraperitoneally 2×10$^6$ CFSE-labeled T cells negatively purified from OT-1 transgenic mice. Peritoneal wash samples (10 mL) are collected after 72 hours and analyzed for CFSE dilution via FACS to calculate number of T cell divisions. Data are analyzed using FlowJo version 9 or 10.

In vitro antigen presentation experiments are performed with isolated tDCs from wild-type C57BL/6 female mice bearing parental ID8 or ID8-Defb29/Vegf-A ovarian tumors.

After 3-4 weeks of tumor burden, tDCs are purified by FACS from the peritoneal cavity of naïve mice, parental ID8 mice, or ID8-Defb29/Vegf-A, and are pulsed with full-length endotoxin-free ovalbumin protein (Sigma, grade VII) in cRPMI containing 25% cell-free ovarian cancer ascites supernatants overnight at 37° C. Antigen-loaded tDCs are then washed twice with cRPMI and co-cultured with CFSE-labeled OT-I CD8+ T cells immunopurified from OT-1 mice at a 1:10 (DC to T cell) ratio. After 3-5 days, cultures analyzed for CFSE dilution via FACS to calculate number of T cell divisions. Data are analyzed using FlowJo version 9 or 10. Isolated tDCs from animals treated with a compound from Table 1 are assessed for enhancement of T cell proliferation relative to tDCs isolated from vehicle-treated controls.

Example 11: Anti-Tumor Immunity

Effects of test compounds in inducing anti-tumor immunity are analyzed. Mice are intraperitoneally injected with ID8-Defb29/Vegf-A ovarian cancer cells and are treated with a compound from Table 1 (n=3-7/group) or vehicle daily starting at day 14 after tumor challenge. After 1-2 weeks of daily treatment, peritoneal lavage samples are analyzed for the number of metastatic cancer cells and tumor ascites accumulation in the peritoneal cavity.

The capacity for T cells to respond to tumor antigens is also measured. Freshly isolated ascites cells are cultured in 96-well flat bottom plates for 6 hours in the presence of PMA, Ionomycin and Brefeldin A to induce cytokine translation and retention within the secretory pathway. After this stimulation period, the cells are washed twice with FACS buffer (PBS+2% FBS and 1 mM EDTA) and stained for 30 minutes with Ghost Dye 510 Violet (Tonbo Biosciences) in PBS on ice according to the manufacturer's protocol. Cells are then washed twice more with FACS buffer and then stained with antibodies directed against CD45, CD3, CD4, CD8, and CD44 on ice for 30 minutes. Fc receptors are also blocked at this time with the TrueStain FcX Antibody (anti-CD16/32, Biolegend). After this staining period, cells are washed twice more with FACS buffer, resuspended in 1× Fix/Perm reagent (eBioscience Foxp3/Transcription Factor Staining Buffer Set), mixed well by pipetting 2-3 times and incubated for 30 minutes at room temperature protected from light. Cells are then washed twice with 1× permeabilization buffer and stained at room temperature with antibodies directed against murine Fc receptor CD16/32 (Fc Block), IFN-gamma and Granzyme-B for 30 minutes. After this incubation period, cells are washed once with 1× permeabilization buffer, once with FACS buffer, and resuspended in FACS buffer for analysis by flow cytometry. Data are analyzed using FlowJo version 9 or 10.

Total splenic T cells or Ficoll-enriched leukocytes (2-3× $10^5$) from peritoneal wash samples are cocultured in RPMI with 2-3×$10^4$ bone marrow-derived DCs that are pulsed overnight with ID8-Defb29/Vegf-A ovarian cancer cell lysates. Supernatants are collected after 48-72 hours of stimulation. IFN-γ and Granzyme B secretion is determined by ELISA using the Ready-SET-Go Kit (eBioscience). Tumor-resident T cells from animals treated with a compound from Table 1 are assessed for increased IFN-γ and Granzyme B production relative to T cells isolated from vehicle-treated controls.

Example 12: $IC_{50}$ Measurements for hERG Potassium Ion Channel

Blockade of the cardiac ion channel coded by the hERG gene can lead to cardiac arrhythmia. Many small compounds have been found to bind to the hERG gene leading to problems in the QT response. To determine the viability of the compounds disclosed herein as pharmacological agents that would not affect the hERG channel blockade, a standard automated planar clamp method was employed to determine the $IC_{50}$ for various test compounds on their inhibition of the channel. An electrophysiological assay was prepared to measure the electric current passing through the hERG channel expressed in a stable CHO cell line by applying the planar clamp method. This assay was performed using the automated QPatch platform (Sophion, Denmark) which allows fast and accurate electrophysiological characterization of the hERG ion channel and the determination of $IC_{50}$ values for the test compounds, as shown in Table 9. The significant separation (100-1000×) between effects against IRE1a-mediated XBP1 splicing in 293T cells and the effect on hERG channels suggest that there is a good safety margin for targeting IRE1a.

TABLE 9

| Compound Ref. No. | Mean $IC_{50}$ |
| --- | --- |
| 24; Formic Acid Salt | C |
| 37; HCl Salt | B |
| 69; Formic Acid Salt | B |

Note:
hERG channel blockade Mean $IC_{50}$ data are designated within the following ranges:
A: >50 uM; B: >10 uM to ≤50 uM; C: >1 uM to ≤10 uM; and D: ≤1 uM.

Example 13: Bioavailability Assay

Figure 3A:
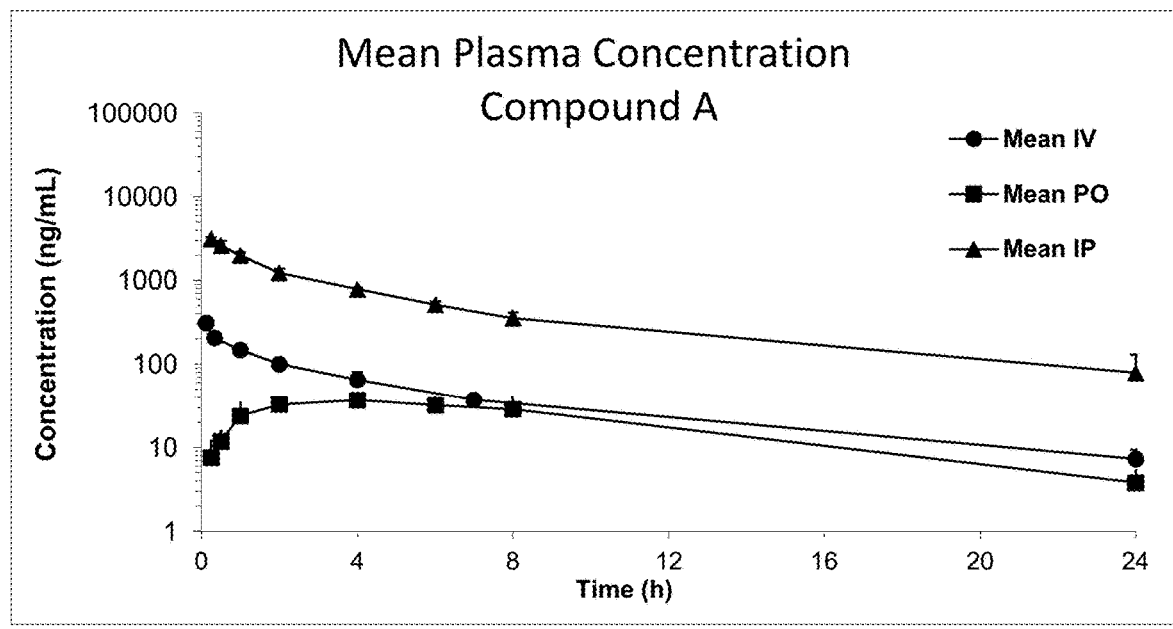
FIG. 3A depicts comparison of the mean plasma concentration of Compound A of the current disclosure after intravenous (IV), oral (PO), and intraperitoneal (IP) dosing.
Figure 3B:
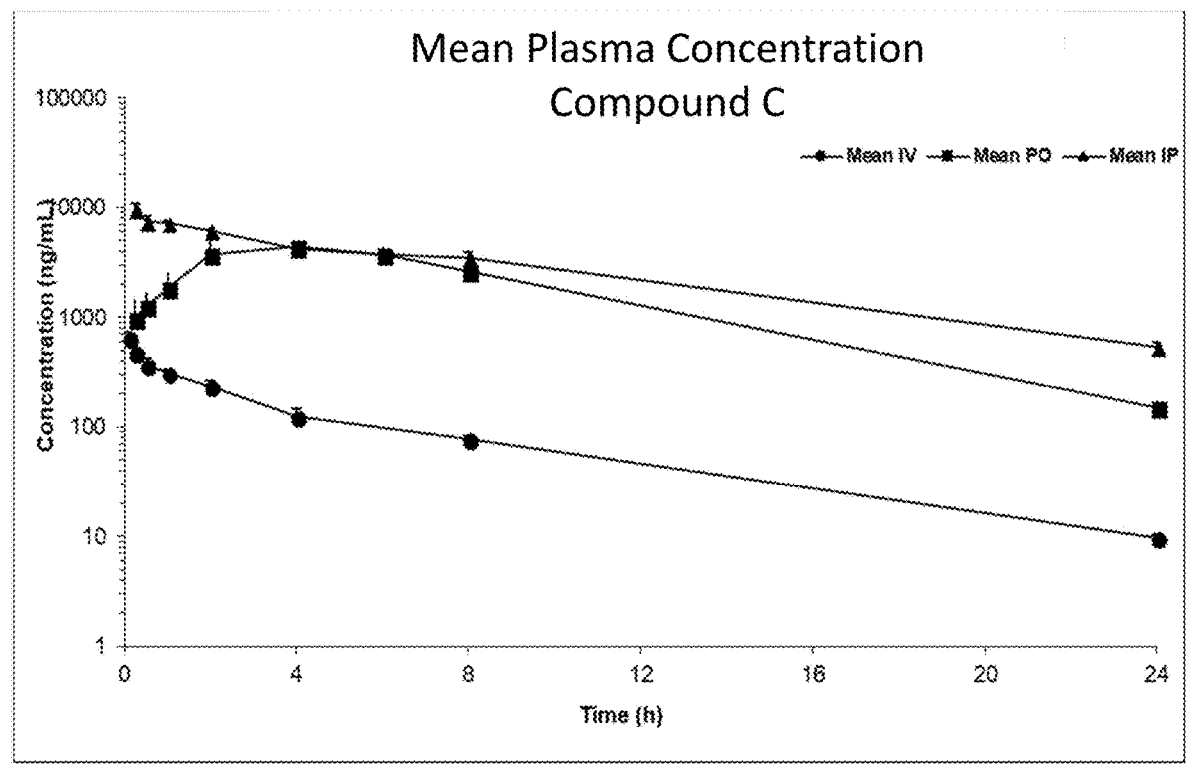
FIG. 3B depicts comparison of the mean plasma concentration of Compound C of the current disclosure after intravenous (IV), oral (PO), and intraperitoneal (IP) dosing.
Figure 4A:
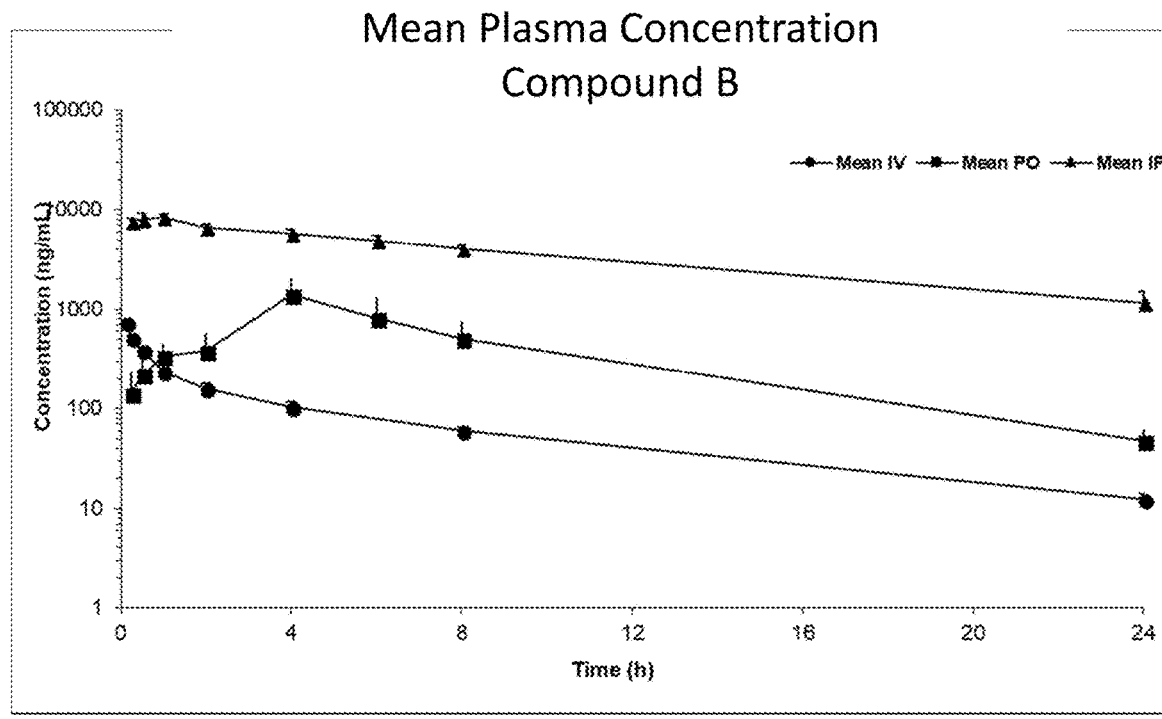
FIG. 4A depicts comparison of the mean plasma concentration of Compound B of the current disclosure after intravenous (IV), oral (PO), and intraperitoneal (IP) dosing.
Figure 4B:
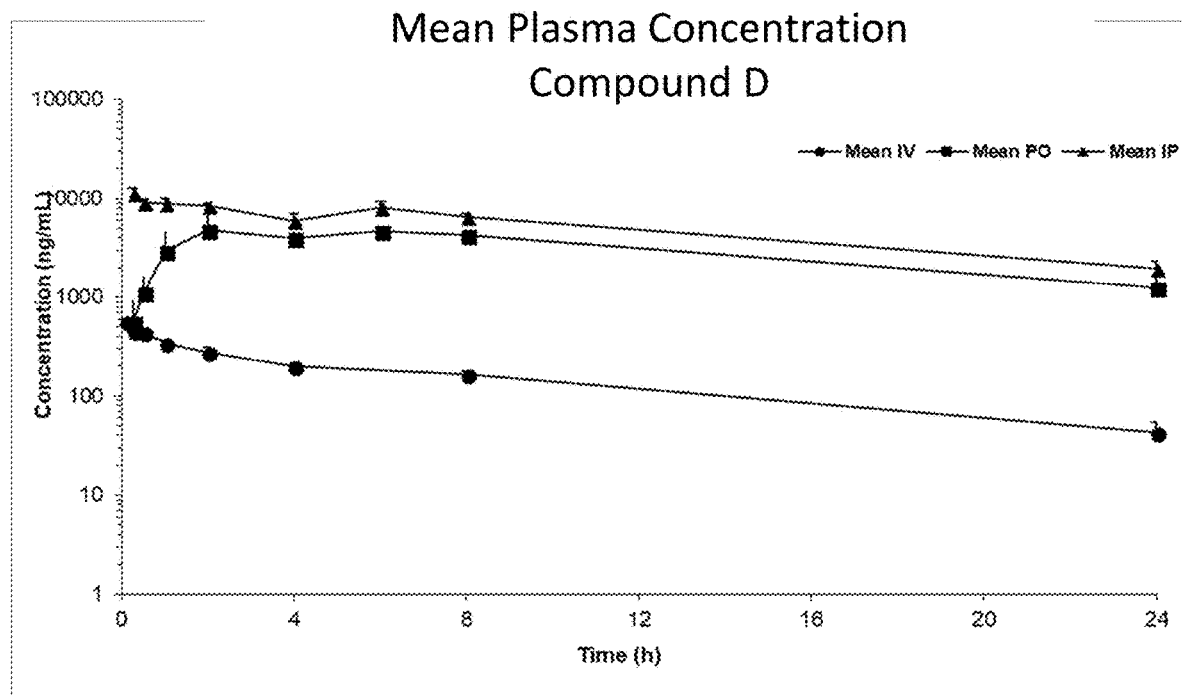
FIG. 4B depicts comparison of the mean plasma concentration of Compound D of the current disclosure after intravenous (IV), oral (PO), and intraperitoneal (IP) dosing.

Results from FRET assay and nano-luciferase assays showed that compounds having $R^6$ and $R^7$ N,N-dimethyl groups tend to be more potent at inhibiting IRE1 as versus their hydrogen analogs (data not shown). Compounds having $R^6$ and $R^7$ N,N-dimethyl groups were compared to their hydrogen analogs in an pharmacokinetic study and were similarly shown to have improved mouse oral bioavailability. For example, compound 91 (Compound C) had 66% oral bioavailability in a mouse study while the di-hydrogen version, N-(5-(2-(((1r,4r)-4-aminocyclohexyl)amino)-8-ethylquinazolin-6-yl)-6-methylpyridin-2-yl)-2-chlorobenzenesulfonamide (Compound A), had only 4% oral bioavailability. This can be seen in a plot of mean plasma concentrations of Compound A after intravenous (IV, 1 mg/kg), oral (PO, 10 mg/kg), and intraperitoneal (IP, 10 mg/kg) dosing (FIG. 3A) compared to Compound C after intravenous (IV, 1 mg/kg), oral (PO, 30 mg/kg), and intraperitoneal (IP, 30 mg/kg) dosing (FIG. 3B). In another example, compound 99 (Compound D) had 70% oral bioavailability while the di-hydrogen version compound 37 (Compound B) had only 17% oral bioavailability. This can be seen in a plot of mean plasma concentrations of Compound B after intravenous (IV, 1 mg/kg), oral (PO, 30 mg/kg), and intraperitoneal (IP, 30 mg/kg) dosing (FIG. 4A) compared to Compound D after intravenous (IV, 1 mg/kg), oral (PO, 30 mg/kg), and intraperitoneal dosing (IP, 30 mg/kg) (FIG. 4B).

In addition, metabolic assays of N,N-dimethyl compounds, such as Compounds C and D, showed removal of the methyl groups to arrive at compound similar to the dihydrogen analogs. (Data not shown.) This indicates that improved activities associated with N,N-dimethyl compounds in assays described herein are likely associate with their methylated state.

Example 14: Assay for Target Engagement in Pancreas and Salivary Gland

Figure 5:
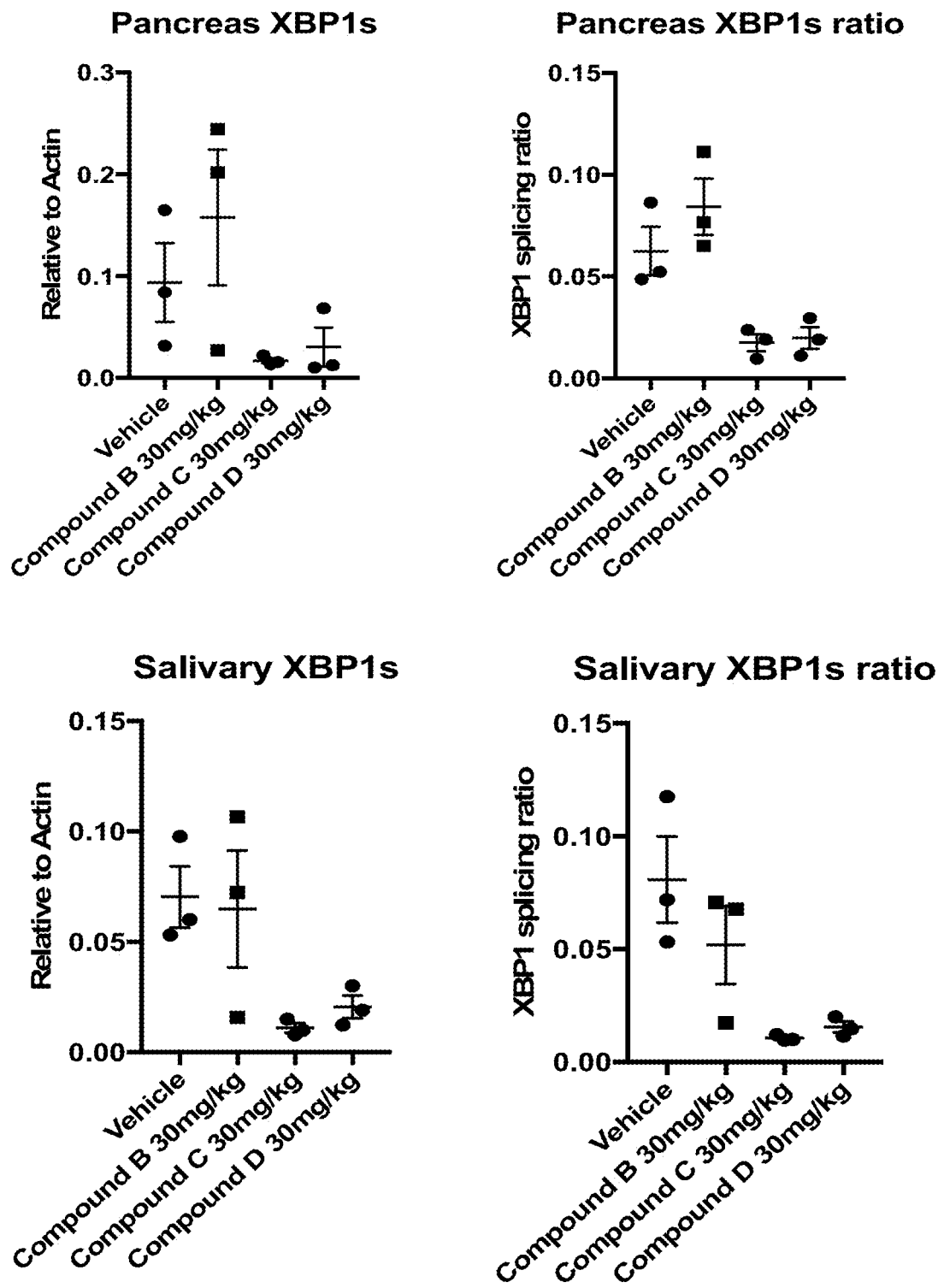
FIG. 5 depicts plots of gene expression analysis in pancreas tissue (upper plots) and salivary tissue (lower plots) following treatment with control, Compound B, Compound C or Compound D.

Mice (n=3 per group) were orally gavaged with 30 mg/kg vehicle control or IRE1 inhibitors dissolved in H$_2$O. After 6 hours, mice were euthanized and pancreas and salivary gland tissues were isolated, snap frozen on dry ice, and used for subsequent RT-qPCR analysis of beta-actin, XBP1s and total XBP1. Gene expression was evaluated by quantitative PCR for XBP1s and total XBP1 transcripts using the 2$^{(-\Delta CT)}$ method for calculating normalized gene expression. Gene expression levels were normalized to Actb transcripts. XBP1 splicing is calculated as XBP1s expression divided by total XBP1 expression. Compounds having R$^6$ and R$^7$ N,N-dimethyl groups (Compound C and Compound D) potently suppressed IRE1a-mediated XBP1 splicing in multiple tissue types after only 6 hours compared to the control and the di-hydrogen version of Compound D (Compound B). See FIG. 5.

Example 15: Assay for Inhibition of Endogenous XBP1 Splicing

Figure 6A:
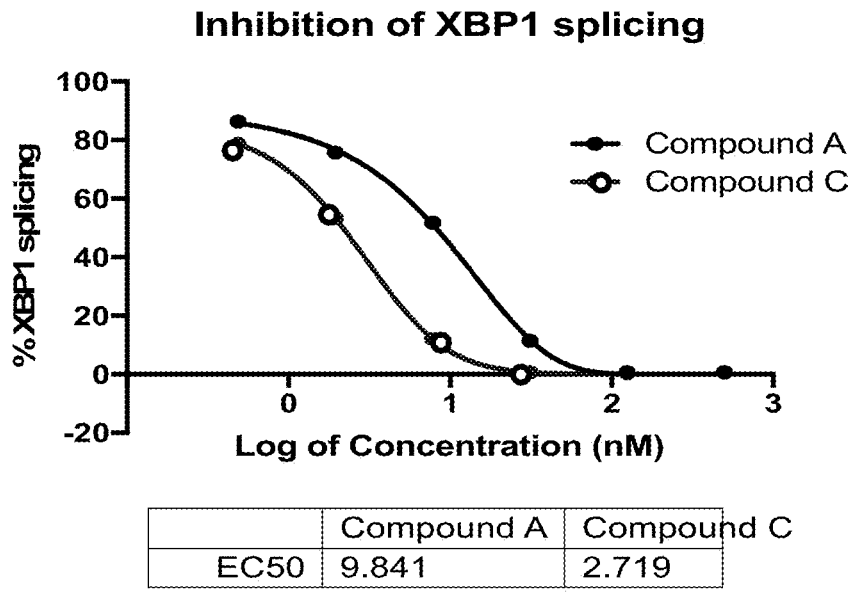
FIG. 6A depicts a plot from a pharmacokinetic assay of XBP1 splicing event occurrence in 293T cells treated with Compound A or Compound C after stress induction.
Figure 6B:
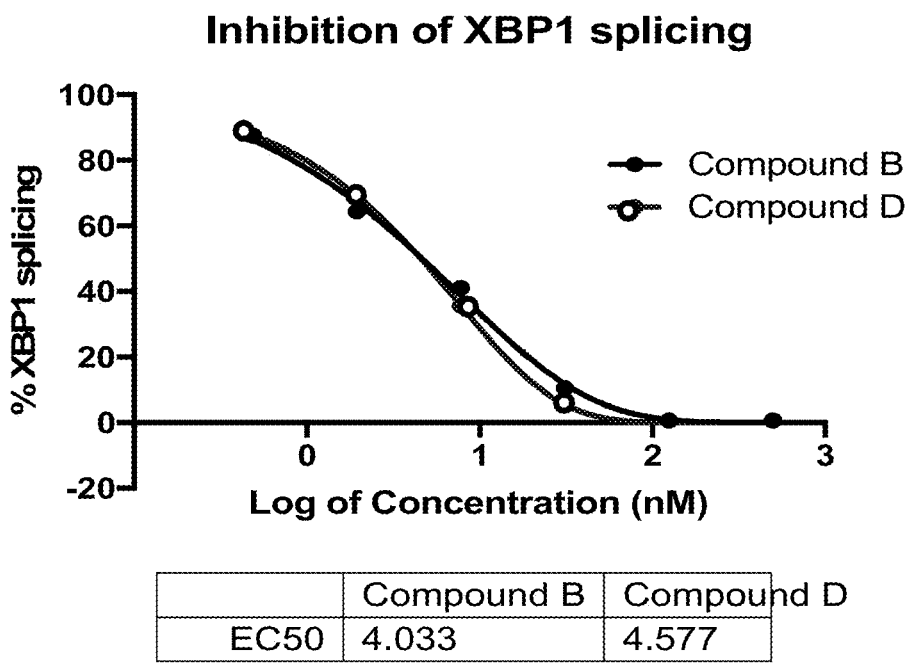
FIG. 6B depicts a plot from a pharmacokinetic assay of XBP1 splicing event occurrence in 293T cells treated with Compound B or Compound D after stress induction.

Dose-dependent inhibitor effects on the IRE1a/XBP1 pathway in 293T cells with or without tunicamycin (TM) (an ER stress inducer) were performed with compounds having R$^6$ and R$^7$ N,N-dimethyl groups (Compound C and Compound D) compared to their dihydrogen analogs (Compound A and Compound B, respectively) (FIG. 6A and FIG. 6B). Gene expression was evaluated by quantitative PCR for XBP1 s and total XBP1 transcripts using the 2$^{(-\Delta CT)}$ method for calculating normalized gene expression. Gene expression levels were normalized to ACTB transcripts. XBP1 splicing was calculated as actin-normalized XBP1 s expression divided by actin-normalized total XBP1 expression. The addition of methyl groups to compounds enhanced the inhibition of IRE1a in the human cell line 293T. The shift in potency observed between Compound A and Compound C was approximately 3.6x.

Example 16: IRE1a Phosphorylation Inhibition Assay

Figure 8:
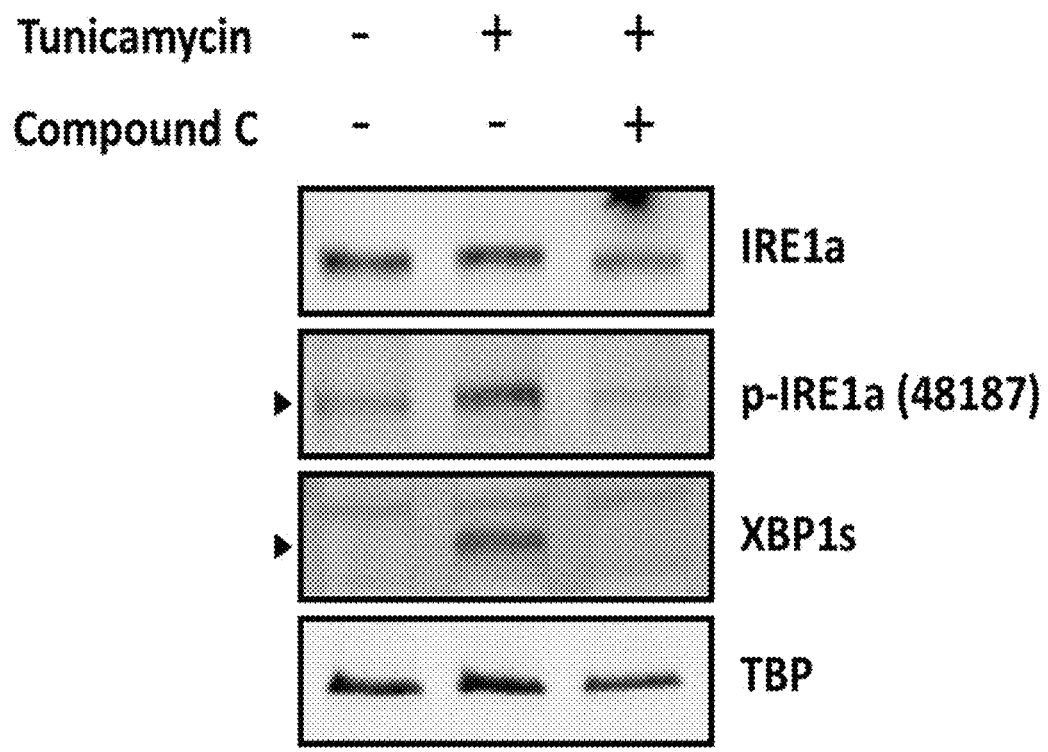
FIG. 8 depicts immunoblot analysis of lysates from tunicamycin treated and optionally Compound C treated 293T cells. Cells were stained for IRE1a, phosphorylated-IRE1a, XBP1, and TBP.

Inhibition of ER stress-induced IRE1a phosphorylation and XBP1s protein accumulation in human 293T cells was assessed. Immunoblot analysis was performed in human 293T cells lysates obtained from cells after exposure to the chemical ER stress-inducing agent tunicamycin, and optional treatment with Compound C. Lysates were probed with antibodies recognizing IRE1a, phosphorylated IRE1a, XBP1, or TATA-binding protein (TBP). TBP was blotted as a protein loading control. Pre-incubation with Compound C of the disclosure, having R$^6$ and R$^7$ N,N-dimethyl groups, strongly repressed IRE1a phosphorylation and completely abrogated the accumulation of XBP1s protein. See FIG. 8. 20 nM was sufficient to reduce XBP1s protein levels below the limit of detection in this assay.

Example 17: Protein Binding—Plasma Protein Binding Assay-HTD Method

The plasma protein binding is determined according to the following steps. Frozen plasma or freshly prepared plasma from various subjects are used as test matrix. They are purchased from commercial vendors or prepared in house from animals. Warfarin is used as a positive control. Other control compound(s) may be used according to specific requirement. One or more compounds from Table 1 are spiked into blank matrix at the final concentration of 2 µM (or other test concentrations based on specific requirement). Final organic solvent concentration is <1%. If plasma samples are collected from in-life studies, they are used as test matrix without spiking compounds. An appropriate volume of spiked plasma solution is removed before incubation for recovery calculation. An aliquot (e.g., 150 uL) of matrix sample is added to one side of the chamber (donor chamber) in a 96-well equilibrium dialyzer plate (HTD dialysis device) and an equal volume of dialysis buffer is added to the other side of the chamber (receiver chamber). Triplicate incubations are performed (or other replicate number according to specific requirement). The dialyzer plate is placed into a humidified incubator with 5% CO$_2$ and incubated at 37° C. for 4 to 6 hours. After incubation, samples are taken from the donor chamber as well as the receiver chamber. The plasma sample is matched with an appropriate volume of blank buffer; and buffer samples are matched with an appropriate volume of blank plasma. The matrix-matched samples are quenched with stop solution containing internal standard. Samples are analyzed by LC/MS/MS. Test compound concentrations in donor and receiver samples are expressed as peak area ratios of analyte/internal standard. If a quantitative analysis is needed, a set of calibration curve and quality controls could be included.

Example 18: Inhibition of Triple Negative Breast Cancer

XBP1 is known to binds directly to HIF1a in triple negative breast cancer, and this cooperative binding enhances the upregulation of HIF1a-dependent downstream target genes. Compounds in Table 1 are screened for impact on XBP1 protein level, thereby removing a key binding partner for HIF1a and reducing expression of HIF1a-dependent target genes such as VEGFA, PDK1, GLUT1, and JMJD1A. Specifically, human triple-negative breast cancer cell lines are treated with vehicle control or a compound shown in Table 1, then cultured under hypoxia (0.1% O$_2$) without glucose for 24 hours. Cells are then lysed with RLT buffer, RNA extracted with the RNeasy 96 kit (Qiagen) and complementary DNA generated from the pure RNA. Semi-quantitative PCR and quantitative PCR are then used to quantify spliced Xbp1 transcripts, total Xbp transcripts, target genes regulated by XBP1s (e.g. SEC61A1, P4HB, EDEM1, AND SEC24D) and target genes regulated by HIF1a (e.g. VEGFA, PDK1, GLUT1, and JMJD1A). The splicing ratio of XBP1 is calculated by determining the amount of spliced Xbp1 transcripts divided by the total number of spliced and unspliced Xbp1 transcripts, an indicator for compounds that inhibit critical intracellular signaling required for TNBC tumor-initiating cell function and metastatic capacity. Compounds shown in Table 1 are assessed for downregulation of XBP1s, XBP1 splicing ration, XBP1s-dependent target gene expression, and HIF1a target gene expression relative to DMSO control-treated samples.

Example 19: Soft Agar Colony Formation Assay

One hundred thousand triple negative breast cancer cells are mixed 4:1 (v/v) with 2.0% agarose in growth medium containing vehicle control or a compound listed in Table 1 for a final concentration of 0.4% agarose. The cell mixture is plated on top of a solidified layer of 0.8% agarose in growth medium. Cells are fed every 6-7 days with growth medium containing 0.4% agarose and vehicle control or a compound from Table 1, matching the initial plating conditions. The number of colonies are counted after 20 days, with the number of colonies visible at the end of the growth period to identify colonies with reduced growth.

Example 20: Inhibition of IRE1a-Dependent XBP1 Splicing in Ovarian Cancer Cells

Figure 7:
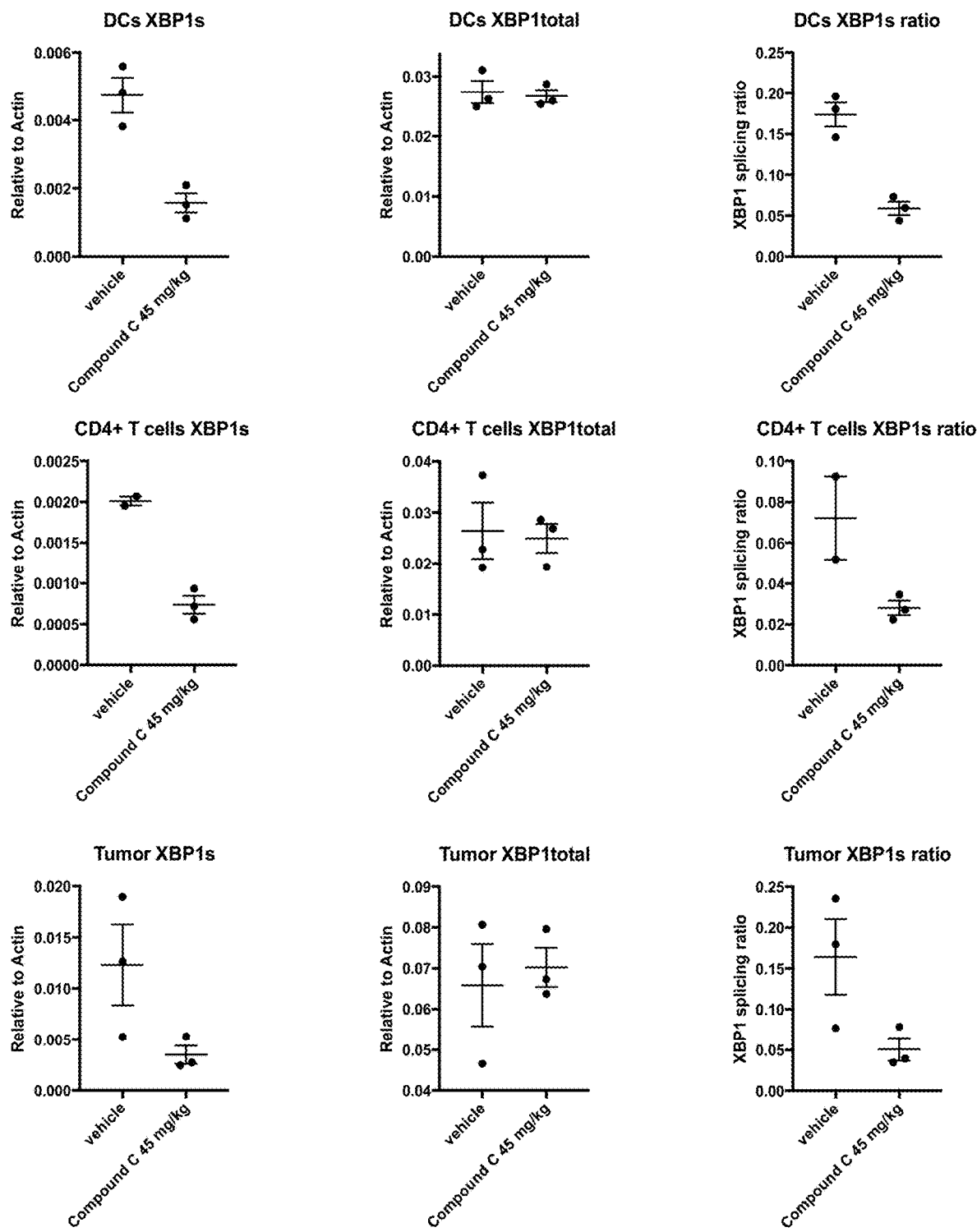
FIG. 7 depicts plots of metastatic ovarian tumor cells, dendritic cells (DCs), and CD4+ T cells treated with Compound C isolated by FACS and assayed for gene expression.

Mice (n=3) with established metastatic ovarian cancer were orally gavaged with 45 mg/kg vehicle control or inhibitor dissolved in $H_2O$. The inhibitor was Compound C. Compound C is 2-chloro-N-(5-(2-(((r,4r)-4-(dimethylamino)cyclohexyl)amino)-8-ethylquinazolin-6-yl)-6-methylpyridin-2-yl)benzenesulfonamide, Compound 91, described herein. After 24 hours, mice were euthanized, ascites-resident cells were extracted and tumor cells, dendritic cells (DCs), and CD4+ T cells were isolated by FACS. The samples were used for subsequent RT-qPCR analysis of beta-actin, XBP1 s and total XBP1. Gene expression was evaluated by quantitative PCR for XBP1 s and total XBP1 transcripts using the $2^{(-\Delta CT)}$ method for calculating normalized gene expression. Gene expression levels were normalized to Actb transcripts. XBP1 splicing is calculated as XBP1s expression divided by total XBP1 expression. A single oral dose of Compound C suppressed IRE1a-dependent XBP1 splicing in tumor cells and relevant immune cells in vivo over 24 hours, FIG. 7.

Figure 9:
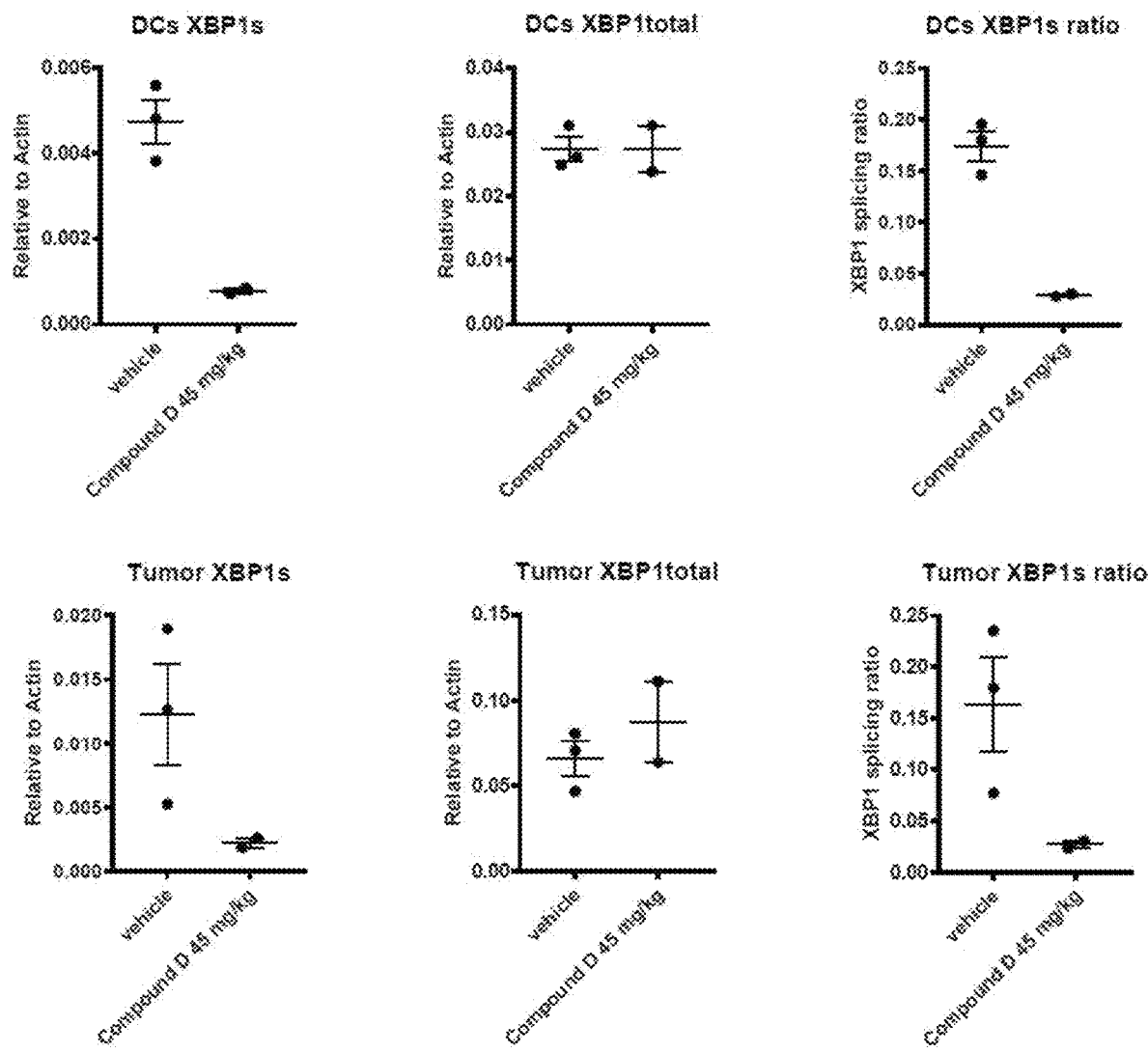
FIG. 9 depicts plots of metastatic ovarian tumor cells and dendritic cells (DCs) treated with Compound D isolated by FACS and assayed for gene expression.

Mice (n=3) with established metastatic ovarian cancer were orally gavaged with 45 mg/kg vehicle control or inhibitor dissolved in $H_2O$. The inhibitor was Compound D. Compound D is 2-chloro-N-(5-(2-(((r,4r)-4-(dimethylamino)cyclohexyl)amino)-8-ethylquinazolin-6-yl)-6-methoxypyridin-2-yl)benzenesulfonamide, Compound 99, described herein. After 24 hours, mice were euthanized, ascites-resident cells were extracted and tumor cells and dendritic cells (DCs) were isolated by FACS. The samples were used for subsequent RT-qPCR analysis of beta-actin, XBP1s, and total XBP1. Gene expression was evaluated by quantitative PCR for XBP1 s and total XBP1 transcripts using the $2^{(-\Delta CT)}$ method for calculating normalized gene expression. Gene expression levels were normalized to Actb transcripts. XBP1 splicing is calculated as XBP1s expression divided by total XBP1 expression. A single oral dose of Compound D suppressed IRE1a-dependent XBP1 splicing in tumor cells and in vivo over 24 hours, FIG. 9.

Example 21: Inhibition of Breast Cancer

Mice with established primary or metastatic breast cancer are administered each of the compounds in Table 1. After 12 hours, the tumors are excised, mechanically separated, and enzymatically digested to single cell suspensions. Flow-assisted cell sorting is then used to purify four populations of cells: tumor cells, dendritic cells (DC), CD4+ T cells, and CD8+ T cells. The cells are sorted directly into RLT buffer for instant cell lysis and RNase deactivation. Then, cellular RNA is purified with the RNeasy 96 kit (Qiagen), and complementary DNA generated from the pure RNA. Semi-quantitative PCR and quantitative PCR are then used to quantify spliced Xbp transcripts, total Xbp1 transcripts, and target genes regulated by XBP1s such as SEC61A1, P4HB, EDEM1, AND SEC24D. The splicing ratio of XBP1 is calculated by determining the amount of spliced Xbp transcripts divided by the total number of spliced and unspliced Xbp1 transcripts, an indicator for compounds that inhibit IRE1 in primary or metastatic breast cancer. Compounds shown in Table 1 are assessed for reduction in XBP1 s transcripts, XBP1 splicing and downstream XBP1 s target genes relative to vehicle control-treated mice.

Example 22: Inhibition of Lung Cancer

Mice with established primary or metastatic lung cancer are administered with each of the compounds in Table 1. After 12 or 24 hours, the tumors are excised, mechanically separated, and enzymatically digested to single cell suspensions. Flow-assisted cell sorting is then used to purify four populations of cells: tumor cells, dendritic cells (DC), CD4+ T cells, and CD8+ T cells. The cells are sorted directly into RLT buffer for instant cell lysis and RNase deactivation. Then, cellular RNA is purified with the RNeasy 96 kit (Qiagen), and complementary DNA generated from the pure RNA. Semi-quantitative PCR and quantitative PCR are then used to quantify spliced Xbp transcripts, total Xbp1 transcripts, and target genes regulated by XBP1s such as SEC61A1, P4HB, EDEM1, AND SEC24D. The splicing ratio of XBP1 is calculated by determining the amount of spliced Xbp transcripts divided by the total number of spliced and unspliced Xbp1 transcripts, an indicator for compounds that inhibit IRE1 in primary or metastatic lung cancer. Compounds shown in Table 1 are assessed for reduction in XBP1 s transcripts relative to vehicle control-treated mice.

Example 23: Inhibition of Bladder Cancer

Mice with established primary or metastatic bladder cancer are administered each of the compounds in Table 1. After 12 or 24 hours, the tumors are excised, mechanically separated, and enzymatically digested to single cell suspensions. Flow-assisted cell sorting is then used to purify four populations of cells: tumor cells, dendritic cells (DC), CD4+ T cells, and CD8+ T cells. The cells are sorted directly into RLT buffer for instant cell lysis and RNase deactivation. Then, cellular RNA is purified with the RNeasy 96 kit (Qiagen), and complementary DNA generated from the pure RNA. Semi-quantitative PCR and quantitative PCR are then used to quantify spliced Xbp transcripts, total Xbp1 transcripts, and target genes regulated by XBP1s such as SEC61A1, P4HB, EDEM1, AND SEC24D. The splicing ratio of XBP1 is calculated by determining the amount of spliced Xbp transcripts divided by the total number of spliced and unspliced Xbp1 transcripts, an indicator for compounds from that inhibit IRE1 in primary or metastatic bladder cancer. Compounds shown in Table 1 are assessed for reduction in XBP1 s transcripts, XBP1 splicing and downstream XBP1 s target genes relative to vehicle control-treated mice.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
SEQ ID NO: 1
MPARRLLLLLTLLLPGLGIFGSTSTVTLPETLLFVSTLDGSLHAVSKRTG
SIKWTLKEDPVLQVPTHVEEPAFLPDPNDGSLYTLGSKNNEGLTKLPFTI
PELVQASPCRSSDGILYMGKKQDIWYVIDLLTGEKQQTLSSAFADSLCPS
TSLLYLGRTEYTITMYDTKTRELRWNATYFDYAASLPEDDVDYKMSHFVS
NGDGLVVTVDSESGDVLWIQNYASPVVAFYVWQREGLRKVMHINVAVETL
RYLTFMSGEVGRITKWKYPFPKETEAKSKLTPTLYVGKYSTSLYASPSMV
HEGVAVVPRGSTLPLLEGPQTDGVTIGDKGECVITPSTDVKFDPGLKSKN
KLNYLRNYWLLIGHHETPLSASTKMLERFPNNLPKHRENVIPADSEKKSF
EEVINLVDQTSENAPTTVSRDVEEKPAHAPARPEAPVDSMLKDMATIILS
TFLLIGWVAFIITYPLSMHQQQQLQHQQFQKELEKIQLLQQQQQQLPFHP
PGDTAQDGELLDTSGPYSESSGTSSPSTSPRASNHSLCSGSSASKAGSSP
SLEQDDGDEETSVVIVGKISFCPKDVLGHGAEGTIVYRGMFDNRDVAVKR
ILPECFSFADREVQLLRESDEHPNVIRYFCTEKDRQFQYIAIELCAATLQ
EYVEQKDFAHLGLEPITLLQQTTSGLAHLHSLNIVHRDLKPHNILISMPN
AHGKIKAMISDFGLCKKLAVGRHSFSRRSGVPGTEGWIAPEMLSEDCKEN
PTYTVDIFSAGCVFYYVISEGSHPFGKSLQRQANILLGACSLDCLHPEKH
EDVIARELIEKMIAMDPQKRPSAKHVLKHPFFWSLEKQLQFFQDVSDRIE
KESLDGPIVKQLERGGRAVVKMDWRENITVPLQTDLRKFRTYKGGSVRDL
LRAMRNKKHHYRELPAEVRETLGSLPDDFVCYFTSRFPHLLAHTYRAMEL
CSHERLFQPYYFHEPPEPQPPVTPDAL

SEQ ID NO: 2
CAUGUCCGCAGCACAUG

SEQ ID NO: 3
CAUGUCCCCAGCACAUG
```

What is claimed is:

1. A compound of Formula (I), or a pharmaceutically acceptable salt thereof:

Formula (I)

wherein,
each Z is independently N or CR$^1$, provided that at least one Z is N;
each R$^1$ is independently H, —OR$^8$, or C$_1$-C$_4$alkyl;
R$^3$ is C$_1$-C$_4$alkyl, or —O-C$_1$-C$_4$alkyl;
R$^4$ is halogen, or C$_1$-C$_4$alkyl;
each R$^5$ is independently H, halogen, or C$_1$-C$_4$alkyl;
each R$^2$ is independently H, or C$_1$-C$_4$alkyl;
R$^6$ is H, or C$_1$-C$_4$alkyl;
R$^7$ is C$_3$-C$_6$cycloalkylalkyl, C$_1$-C$_4$alkyl, —CH$_2$CF$_3$, —CH$_2$-cyclopropyl, or —CH$_2$CH$_2$OCH$_3$;
each R$^8$ is C$_1$-C$_4$alkyl;
each R$^9$ is C$_1$-C$_4$alkyl;
R$^{A1}$ and R$^{A2}$ are each independently H, —OR$^9$, C$_1$-C$_4$alkyl, or C$_1$-C$_4$fluoroalkyl; provided that both R$^{A1}$ and R$^{A2}$ are not H;
n is, 1, 2, 3, or 4; and
q is 1, 2, 3, or 4.

2. The compound of claim 1, or a pharmaceutically acceptable salt thereof, wherein R$^7$ is methyl, ethyl, —CH$_2$CF$_3$, —CH$_2$-cyclopropyl, or —CH$_2$CH$_2$OCH$_3$.

3. The compound of claim 1, or a pharmaceutically acceptable salt thereof, wherein R$^6$ is C$_1$-C$_4$alkyl.

4. The compound of claim 2, or a pharmaceutically acceptable salt thereof, wherein R$^6$ is methyl.

5. The compound of claim 1, or a pharmaceutically acceptable salt thereof, wherein R$^6$ is H.

6. The compound of claim 1, or a pharmaceutically acceptable salt thereof, wherein each R$^1$ is independently H, or C$_1$-C$_4$alkyl.

7. The compound of claim 1, or a pharmaceutically acceptable salt thereof, wherein R$^3$ is methyl.

8. The compound of claim 1, or a pharmaceutically acceptable salt thereof, wherein R$^1$ is —OR$^8$.

9. The compound of claim 1, or a pharmaceutically acceptable salt thereof, wherein R$^4$ is Cl, F, Br, methyl, or ethyl.

10. The compound of claim 1, wherein the compound has the structure of formula (Ib), or a pharmaceutically acceptable salt thereof, (Ic)

(Id)

(Ie)

11. The compound of claim 1, or a pharmaceutically acceptable salt thereof, wherein R$^{A1}$ is H, or C$_1$-C$_4$alkyl.

12. The compound of claim 1, or a pharmaceutically acceptable salt thereof, wherein R$^{A2}$ is H, or C$_1$-C$_4$alkyl.

13. The compound of claim 12, or a pharmaceutically acceptable salt thereof, wherein R$^{A2}$ is ethyl.

14. The compound of claim 1, wherein the compound has the structure of formula (Ic), (Id), or (Ie), or a pharmaceutically acceptable salt thereof:

(Ic)

-continued

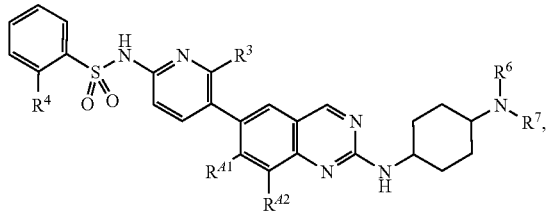

(Id)

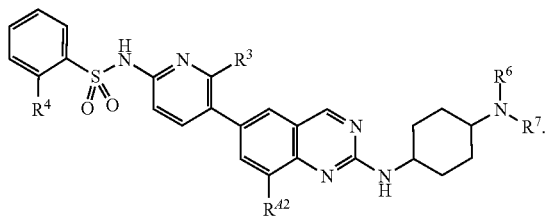

(Ie)

15. The compound of claim 1, or a pharmaceutically acceptable salt thereof, selected from:
2-chloro-N-(5-(2-(((1r,4r)-4-(dimethylamino)cyclohexyl) amino)-8-ethylquinazolin-6-yl)-6-methylpyridin-2-yl) benzenesulfonamide;
2-chloro-N-(5-(2-(((1r,4r)-4-(dimethylamino)cyclohexyl) amino)-8-ethylquinazolin-6-yl)-3-fluoro-6-methylpyridin-2-yl)benzenesulfonamide; and
2-chloro-N-(5-(2-(((1r,4r)-4-(dimethylamino)cyclohexyl) amino)-8-ethylquinazolin-6-yl)-6-methoxypyridin-2-yl)benzenesulfonamide.

16. The compound of claim 1, or a pharmaceutically acceptable salt thereof, selected from:
2-chloro-N-(5-(2-(((1r,4r)-4-(dimethylamino)cyclohexyl) amino)-7-methylquinazolin-6-yl)-6-methoxypyridin-2-yl)benzenesulfonamide;
2-chloro-N-(5-(8-ethyl-2-(((1r,4r)-4-(methylamino)cyclohexyl)amino)quinazolin-6-yl)-6-methoxypyridin-2-yl)benzenesulfonamide;
2-chloro-N-(5-(2-(((1r,4r)-4-(dimethylamino)cyclohexyl) amino)-8-ethylquinazolin-6-yl)-6-ethyl pyridin-2-yl) benzenesulfonamide;
N-(5-(8-ethyl-2-(((1r,4r)-4-(methylamino)cyclohexyl) amino)quinazolin-6-yl)-6-methoxypyridin-2-yl)-2-methylbenzenesulfonamide;
N-(5-(2-(((1r,4r)-4-(dimethylamino)cyclohexyl)amino)-8-ethylquinazolin-6-yl)-6-methoxypyridin-2-yl)-2-methylbenzenesulfonamide;
2-chloro-N-(5-(8-ethyl-2-(((1r,4r)-4-(methylamino)cyclohexyl)amino)quinazolin-6-yl)-6-methylpyridin-2-yl)benzenesulfonamide;
2-chloro-N-(5-(8-(1,1-difluoroethyl)-2-(((1r,4r)-4-(dimethylamino)cyclohexyl)amino)quinazolin-6-yl)-6-methoxypyridin-2-yl)benzenesulfonamide;
2-chloro-N-(5-(8-ethyl-2-(((1r,4r)-4-(ethyl(methyl) amino)cyclohexyl)amino)quinazolin-6-yl)-6-methylpyridin-2-yl)benzenesulfonamide;
2-chloro-N-(5-(8-ethyl-2-(((1r,4r)-4-(methyl(2,2,2-trifluoroethyl)amino)cyclohexyl)amino)quinazolin-6-yl)-6-methylpyridin-2-yl)benzenesulfonamide;
2-chloro-N-(5-(8-ethyl-2-(((1r,4r)-4-(methylamino)cyclohexyl)amino)quinazolin-6-yl)-3-fluoro-6-methoxypyridin-2-yl)benzenesulfonamide;
2-chloro-N-(5-(2-(((1r,4r)-4-(dimethylamino)cyclohexyl) amino)-8-ethylquinazolin-6-yl)-3-fluoro-6-methoxypyridin-2-yl)benzenesulfonamide;
2-chloro-N-(5-(2-(((1r,4r)-4-((cyclobutylmethyl)(methyl) amino)cyclohexyl)amino)-8-ethylquinazolin-6-yl)-6-methylpyridin-2-yl)benzenesulfonamide;
2-chloro-N-(5-(8-(1-difluoroethyl)-2-(((1r,4r)-4-(dimethylamino)cyclohexyl)amino)quinazolin-6-yl)-6-methylpyridin-2-yl)benzenesulfonamide;
2-chloro-N-(5-(8-ethyl-2-(((1r,4r)-4-((2-methoxyethyl) (methyl)amino)cyclohexyl)amino)quinazolin-6-yl)-6-methylpyridin-2-yl)benzenesulfonamide;
2-chloro-N-(5-(2-(((1r,4r)-4-(dimethylamino)cyclohexyl) amino)-8-methylquinazolin-6-yl)-6-methoxypyridin-2-yl)benzenesulfonamide;
2-chloro-N-(5-(2-(((1r,4r)-4-(dimethylamino)cyclohexyl) amino)-8-(trifluoromethyl)quinazolin-6-yl)-6-methoxypyridin-2-yl)benzenesulfonamide;
2-chloro-N-(5-(2-(((1r,4r)-4-(dimethylamino)cyclohexyl) amino)-8-(methoxymethyl)quinazolin-6-yl)-6-methoxypyridin-2-yl)benzenesulfonamide;
2-chloro-N-(5-(2-(((1s,4s)-4-(dimethylamino)cyclohexyl)amino)-8-methylquinazolin-6-yl)-6-methoxypyridin-2-yl)benzenesulfonamide;
2-chloro-N-(5-(2-(((1s,4s)-4-(dimethylamino)cyclohexyl)amino)-8-ethylquinazolin-6-yl)-6-methoxypyridin-2-yl)benzenesulfonamide;
2-chloro-N-(5-(2-(((1s,4s)-4-(dimethylamino)cyclohexyl)amino)-8-ethylquinazolin-6-yl)-3-fluoro-6-methoxypyridin-2-yl)benzenesulfonamide;
2-chloro-N-(5-(2-(((1s,4s)-4-(dimethylamino)-4-methylcyclohexyl)amino)-8-ethylquinazolin-6-yl)-6-methoxypyridin-2-yl)benzenesulfonamide;
2-chloro-N-(5-(2-(((1s,4s)-4-(dimethylamino)-4-methylcyclohexyl)amino)-8-ethylquinazolin-6-yl)-3-fluoro-6-methoxypyridin-2-yl)benzenesulfonamide;
2-chloro-N-(5-(2-(((1r,4r)-4-(dimethylamino)cyclohexyl) amino)-8-methylquinazolin-6-yl)-3-fluoro-6-methoxypyridin-2-yl)benzenesulfonamide; and
2-chloro-N-(5-(2-(((1s,4s)-4-(dimethylamino)cyclohexyl)amino)-8-methylquinazolin-6-yl)-3-fluoro-6-methoxypyridin-2-yl)benzenesulfonamide.

17. The compound of claim 1, or a pharmaceutically acceptable salt thereof, selected from:
N-(5-(2-(((1r,4r)-4-aminocyclohexyl)amino)-8-ethylquinazolin-6-yl)-4-methylpyrimidin-2-yl)-2-chlorobenzenesulfonamide;
N-(4-(2-(((1r,4r)-4-aminocyclohexyl)amino)-8-ethylquinazolin-6-yl)-2-fluorophenyl)-2-chlorobenzenesulfonamide;
N-(5-(2-(((1r,4r)-4-aminocyclohexyl)amino)-8-ethylquinazolin-6-yl)pyrazin-2-yl)-2-chlorobenzenesulfonamide;
N-(4-(2-(((1r,4r)-4-aminocyclohexyl)amino)quinazolin-6-yl)phenyl)-2-chlorobenzenesulfonamide;
N-(5-(2-(((1r,4r)-4-aminocyclohexyl)amino)-8-ethylquinazolin-6-yl)pyridin-2-yl)-2-chlorobenzenesulfonamide;
N-(6-(2-(((1r,4r)-4-aminocyclohexyl)amino)-8-ethylquinazolin-6-yl)pyridin-3-yl)-2-chlorobenzenesulfonamide;
N-(5-(2-(((1r,4r)-4-aminocyclohexyl)amino)-8-ethylquinazolin-6-yl)-1H-pyrazol-3-yl)-2-chlorobenzenesulfonamide;
N-(4-(2-(((1r,4r)-4-aminocyclohexyl)amino)-8-hydroxyquinazolin-6-yl)-3-methylphenyl)-chloro-N-methylbenzenesulfonamide;
N-(4-(2-(((1r,4r)-4-aminocyclohexyl)amino)-8-ethylquinazolin-6-yl)-3-methylphenyl)-2-chloro-N-methylbenzenesulfonamide;

N-(6-(2-(((1r,4r)-4-aminocyclohexyl)amino)-8-ethylquinazolin-6-yl)pyridazin-3-yl)-2-chlorobenzenesulfonamide;
N-(2-(2-(((1r,4r)-4-aminocyclohexyl)amino)-8-ethylquinazolin-6-yl)pyrimidin-5-yl)-2-chlorobenzenesulfonamide;
N-(4-(2-(((1r,4r)-4-aminocyclohexyl)amino)-8-ethylquinazolin-6-yl)-3-ethylphenyl)-2-chlorobenzenesulfonamide;
N-(4-(2-(((1r,4r)-4-aminocyclohexyl)amino)-8-ethylquinazolin-6-yl)-3-fluorophenyl)-2-chlorobenzenesulfonamide;
N-(4-(2-(((1r,4r)-4-aminocyclohexyl)amino)-8-methoxyquinazolin-6-yl)-3-methylphenyl)-2-chlorobenzenesulfonamide;
N-(5-(2-(((1r,4r)-4-aminocyclohexyl)amino)-8-ethylquinazolin-6-yl)-6-methoxypyridin-2-yl)-2-chlorobenzenesulfonamide;
N-(5-(2-(((1r,4r)-4-aminocyclohexyl)amino)-8-ethylquinazolin-6-yl)-4-methylthiazol-2-yl)-2-chlorobenzenesulfonamide;
N-(5-(2-(((1r,4r)-4-aminocyclohexyl)amino)-8-ethylquinazolin-6-yl)pyrimidin-2-yl)-2-chlorobenzenesulfonamide;
N-(5-(2-(((1r,4r)-4-aminocyclohexyl)amino)-8-isopropylquinazolin-6-yl)-1-methyl-i H-pyrazol-3-yl)-2-chlorobenzenesulfonamide;
N-(5-(2-(((1r,4r)-4-aminocyclohexyl)amino)-8-ethylquinazolin-6-yl)thiazol-2-yl)-2-chlorobenzenesulfonamide;
N-(4-(2-(((1r,4r)-4-aminocyclohexyl)amino)-8-ethylquinazolin-6-yl)-2-fluoro-5-methoxyphenyl)-2-chlorobenzenesulfonamide;
N-(1-(2-(((1r,4r)-4-aminocyclohexyl)amino)-8-ethylquinazolin-6-yl)-1H-pyrazol-4-yl)-2-chlorobenzenesulfonamide;
N-(5-(2-(((1r,4r)-4-aminocyclohexyl)amino)-8-ethylquinazolin-6-yl)isoxazol-3-yl)-2-chlorobenzenesulfonamide;
N-(5-(2-(((1r,4r)-4-aminocyclohexyl)amino)-8-methoxyquinazolin-6-y)-1-methyl-1H-pyrazol-3-yl)-2-chlorobenzenesulfonamide;
N-(5-(2-(((1r,4r)-4-aminocyclohexyl)amino)-8-ethylquinazolin-6-yl)-4-methoxypyrimidin-2-yl)-2-chlorobenzenesulfonamide;
N-(5-(2-(((1r,4r)-4-aminocyclohexyl)amino)-8-propylquinazolin-6-yl)-1-methyl-1H-pyrazol-3-yl)-2-chlorobenzenesulfonamide;
N-(4-(2-(((1r,4r)-4-aminocyclohexyl)amino)quinazolin-6-yl)-3-fluorophenyl)-2-chlorobenzenesulfonamide;
N-(6-(2-(((1r,4r)-4-aminocyclohexyl)amino)quinazolin-6-yl)pyridazin-3-yl)-2-chlorobenzenesulfonamide;
N-(4-(2-(((1r,4r)-4-aminocyclohexyl)amino)quinazolin-6-yl)-2-fluorophenyl)-2-chlorobenzenesulfonamide;
N-(6-(2-(((1r,4r)-4-aminocyclohexyl)amino)quinazolin-6-yl)-5-fluoropyridin-3-yl)-2-chlorobenzenesulfonamide;
N-(6-(2-(((1r,4r)-4-aminocyclohexyl)amino)-8-ethylquinazolin-6-yl)-5-fluoropyridin-3-yl)-2-chlorobenzenesulfonamide;
N-(4-(2-(((1r,4r)-4-aminocyclohexyl)amino)quinazolin-6-yl)-2,5-difluorophenyl)-2-chlorobenzenesulfonamide;
N-(5-(2-(((1r,4r)-4-aminocyclohexyl)amino)quinazolin-6-yl)-3-fluoropyridin-2-yl)-2-chlorobenzenesulfonamide;
N-(5-(2-(((1r,4r)-4-aminocyclohexyl)amino)-8-ethylquinazolin-6-yl)-3-fluoropyridin-2-yl)-2-chlorobenzenesulfonamide;
N-(4-(2-(((1r,4r)-4-aminocyclohexyl)amino)quinazolin-6-yl)-2,3-difluorophenyl)-2-chlorobenzenesulfonamide;
N-(4-(3-(((1r,4r)-4-aminocyclohexyl)amino)isoquinolin-7-yl)-2-fluorophenyl)-2-chlorobenzenesulfonamide;
(S)-2-amino-N-((1r,4S)-4-((6-(4-((2-chlorophenyl)sulfonamido)-3-fluorophenyl)-8-ethylquinazolin-2-yl)amino)cyclohexyl)-3-methylbutanamide;
N-((1r,4r)-4-((6-(4-((2-chlorophenyl)sulfonamido)-3-fluorophenyl)-8-ethylquinazolin-2-yl)amino)cyclohexyl)acetamide;
2-chloro-N-(4-(8-ethyl-2-(((1r,4r)-4-(methylamino)cyclohexyl)amino)quinazolin-6-yl)-2-fluorophenyl)benzenesulfonamide;
2-chloro-N-(6-(8-ethyl-2-(((1r,4r)-4-(methylamino)cyclohexyl)amino)quinazolin-6-yl)pyridazin-3-yl)benzenesulfonamide;
N-(4-(2-(((1r,4r)-4-aminocyclohexyl)amino)quinazolin-6-yl)-3,5-difluorophenyl)-2-chlorobenzenesulfonamide;
N-(4-(2-(((1r,4r)-4-aminocyclohexyl)amino)-8-ethylquinazolin-6-yl)-2,6-difluorophenyl)-2-chlorobenzenesulfonamide;
2-chloro-N-(6-(2-(((1r,4r)-4-(dimethylamino)cyclohexyl)amino)-8-ethylquinazolin-6-yl)pyridazin-3-yl)benzenesulfonamide;
N-(6-(2-(((1r,4r)-4-aminocyclohexyl)amino)-8-ethylquinazolin-6-yl)-5-methoxypyridazin-3-yl)-2-chlorobenzenesulfonamide;
N-(6-(2-(((1r,4r)-4-aminocyclohexyl)amino)-8-ethylquinazolin-6-yl)-4-methoxypyridazin-3-yl)-2-chlorobenzenesulfonamide;
N-(6-(2-(((1r,4r)-4-aminocyclohexyl)amino)-8-ethylquinazolin-6-yl)-5-methylpyridazin-3-yl)-2-chlorobenzenesulfonamide;
N-(5-(2-(((1r,4r)-4-aminocyclohexyl)amino)quinazolin-6-yl)-4-methylpyrimidin-2-yl)-2-chlorobenzenesulfonamide;
2-chloro-N-(4-(2-(((1r,4r)-4-(dimethylamino)cyclohexyl)amino)-8-ethylquinazolin-6-yl)-2-fluorophenyl)benzenesulfonamide;
N-(4-(2-(((1R,3R,4S)-4-amino-3-methylcyclohexyl)amino)-8-ethylquinazolin-6-yl)-2-fluorophenyl)-2-chlorobenzenesulfonamide;
N-(4-(2-(((1r,4r)-4-aminocyclohexyl)amino)-8-ethylquinazolin-6-yl)-2-fluoro-3-methylphenyl)-2-chlorobenzenesulfonamide;
N-(4-(2-(((1R,3S)-3-aminocyclohexyl)amino)-8-ethylquinazolin-6-yl)-2-fluorophenyl)-2-chlorobenzenesulfonamide;
(S)-2-chloro-N-(4-(8-ethyl-2-(piperidin-3-ylamino)quinazolin-6-y 1)-2-fluorophenyl)benzenesulfonamide;
N-(4-(2-(((1R,3R,4R)-4-amino-3-methylcyclohexyl)amino)-8-ethylquinazolin-6-yl)-2-fluorophenyl)-2-chlorobenzenesulfonamide;
N-(4-(2-(((1R,3S)-3-aminocyclohexyl)amino)quinazolin-6-yl)-2-fluorophenyl)-2-chlorobenzenesulfonamide;
(S)-2-chloro-N-(2-fluoro-4-2-(piperidin-3-ylamino)quinazolin-6-yl)phenyl)benzenesulfonamide;
N-(4-(2-(((1R,3R)-3-aminocyclopentyl)amino)quinazolin-6-yl)-2-fluorophenyl)-2-chlorobenzenesulfonamide;

N-(4-(2-(((1R,3R)-3-aminocyclopentyl)amino)-8-ethylquinazolin-6-yl)-2-fluorophenyl)-2-chlorobenzenesulfonamide;

N-(4-(2-(((1R,3S)-3-aminocyclopentyl)amino)-8-ethylquinazolin-6-yl)-2-fluorophenyl)-2-chlorobenzenesulfonamide;

N-(4-(2-(((1R,3S)-3-aminocyclopentyl)amino)quinazolin-6-yl)-2-fluorophenyl)-2-chlorobenzenesulfonamide;

N-(4-(2-((4-aminobicyclo[2.2.2]octan-1-yl)amino)quinazolin-6-yl)-2-fluorophenyl)-2-chlorobenzenesulfonamide;

N-(4-(2-(((2r,5r)-5-aminooctahydropentalen-2-yl)amino)-8-ethylquinazolin-6-yl)-2-fluorophenyl)-2-chlorobenzenesulfonamide;

N-(4-(2-(((2r,5r)-5-aminooctahydropentalen-2-y)amino)-8-ethylquinazolin-6-yl)-2-fluorophenyl)-2-chlorobenzenesulfonamide;

N-(4-(2-(((2s,5s)-5-aminooctahydropentalen-2-yl)amino)-8-ethylquinazolin-6-yl)-2-fluorophenyl)-2-chlorobenzenesulfonamide;

N-(4-(2-(((2s,5s)-5-aminooctahydropentalen-2-yl)amino)quinazolin-6-yl)-2-fluorophenyl)-2-chlorobenzenesulfonamide;

N-(4-(2-((4-aminobicyclo[2.2.1]heptan-1-yl)amino)quinazolin-6-yl)-2-fluorophenyl)-2-chlorobenzenesulfonamide;

N-(4-(2-((4-aminobicyclo[2.2.2]octan-1-yl)amino)-8-ethylquinazolin-6-yl)-2-fluorophenyl)-2-chlorobenzenesulfonamide;

2-chloro-N-(4-(8-ethyl-2-(((1r,4r)-4-(pyrrolidin-1-yl)cyclohexyl)amino)quinazolin-6-yl)-2-fluorophenyl)benzenesulfonamide;

N-(5-(2-(((1r,4r)-4-aminocyclohexyl)amino)quinazolin-6-yl)-1,3,4-thiadiazol-2-yl)-2-chlorobenzenesulfonamide;

N-(4-(2-(((1r,4r)-4-aminocyclohexyl)amino)-7-methylquinazolin-6-yl)-2-fluorophenyl)-2-chlorobenzenesulfonamide;

N-(5-(2-(((1r,4r)-4-aminocyclohexyl)amino)-8-ethylquinazolin-6-yl)-4-methoxypyridin-2-yl)-2-chlorobenzenesulfonamide;

N-(6-(2-(((1r,4r)-4-aminocyclohexyl)amino)-8-ethylquinazolin-6-yl)-5-methoxypyridin-3-yl)-2-chlorobenzenesulfonamide;

N-(5-(2-(((1r,4r)-4-aminocyclohexyl)amino)-8-ethylquinazolin-6-yl)-6-methylpyrazin-2-yl)-2-chlorobenzenesulfonamide;

2-chloro-N-(5-(2-(((1r,4r)-4-(dimethylamino)cyclohexyl)amino)-8-ethylquinazolin-6-yl)-3-fluoropyridin-2-yl)benzenesulfonamide;

N-(6-(2-(((1r,4r)-4-aminocyclohexyl)amino)-8-ethylquinazolin-6-yl)-5-ethylpyridazin-3-yl)-2-chlorobenzenesulfonamide; and N-(5-(2-(((1r,4r)-4-aminocyclohexyl)amino)-8-ethylquinazolin-6-yl)-6-methoxypyrazin-2-yl)-2-chlorobenzenesulfonamide.

18. The compound of claim 1, or a pharmaceutically acceptable salt thereof, selected from:

2-chloro-N-(5-(2-(((1r,4r)-4-(dimethylamino)cyclohexyl)amino)-8-fluoroquinazolin-6-yl)-6-methoxypyridin-2-yl)benzenesulfonamide;

2-chloro-N-(5-(2-(((1r,4r)-4-(dimethylamino)cyclohexyl)amino)quinazolin-6-yl)-3-fluoro-6-methoxypyridin-2-yl)benzenesulfonamide;

2-chloro-N-(3-fluoro-6-methoxy-5-(2-(((1r,4r)-4-(methylamino)cyclohexyl)amino)quinazolin-6-yl)pyridin-2-yl)benzenesulfonamide;

2-chloro-N-(5-(2-(((1S,2S,4S)-4-(dimethylamino)-2-fluorocyclohexyl)amino)-8-ethylquinazolin-6-yl)-6-methylpyridin-2-yl)benzenesulfonamide;

2,3-dichloro-N-(5-(2-(((1r,4r)-4-(dimethylamino)cyclohexyl)amino)-8-ethylquinazolin-6-yl)-6-methylpyridin-2-yl)benzenesulfonamide;

2-chloro-N-(5-(2-(((1r,4r)-4-(dimethylamino)cyclohexyl)amino)quinazolin-6-yl)-3-fluoro-6-methylpyridin-2-yl)benzenesulfonamide;

2-chloro-N-(5-(2-(((1r,4r)-4-(dimethylamino)cyclohexyl)amino)-8-ethylquinazolin-6-yl)-4-methoxypyrimidin-2-yl)benzenesulfonamide;

2-chloro-N-(5-(2-(((1r,4r)-4-(dimethylamino)cyclohexyl)amino)-8-fluoroquinazolin-6-yl)-3-fluoro-6-methoxypyridin-2-yl)benzenesulfonamide;

2-chloro-N-(5-(2-(((1r,4r)-4-(dimethylamino)cyclohexyl)amino)-8-fluoroquinazolin-6-yl)-3-fluoro-6-methylpyridin-2-yl)benzenesulfonamide;

2-chloro-N-(5-(2-(((1r,4r)-4-(dimethylamino)cyclohexyl)amino)-8-ethylquinazolin-6-yl)-6-methoxypyrazin-2-yl)benzenesulfonamide;

2-chloro-N-(5-(2-(((1r,4r)-4-(dimethylamino)cyclohexyl)amino)-8-ethylquinazolin-6-yl)-6-methylpyridin-2-yl)-3-fluorobenzenesulfonamide;

2-chloro-N-(6-(2-(((1r,4r)-4-(dimethylamino)cyclohexyl)amino)-8-ethylquinazolin-6-yl)-5-methoxypyridazin-3-yl)benzenesulfonamide;

2-chloro-N-(5-(2-(((1r,4r)-4-(dimethylamino)cyclohexyl)amino)-8-ethylquinazolin-6-yl)-6-methylpyridin-2-yl)-3-methylbenzenesulfonamide;

2-chloro-N-(5-(2-(((1r,4r)-4-(dimethylamino)cyclohexyl)amino)-8-ethyl-7-fluoroquinazolin-6-yl)-6-methylpyridin-2-yl)benzenesulfonamide;

2-chloro-N-(5-(2-(((1r,4r)-4-(dimethylamino)cyclohexyl)amino)-8-ethyl-7-fluoroquinazolin-6-yl)-3-fluoro-6-methylpyridin-2-yl)benzenesulfonamide; and 2-chloro-N-(5-(2-(((1r,4r)-4-(dimethylamino)cyclohexyl)amino)-8-ethyl-7-fluoroquinazolin-6-yl)-3-fluoro-6-methoxypyridin-2-yl)benzenesulfonamide.

19. The compound of claim 1 having Formula (Id*), or a pharmaceutically acceptable salt thereof:

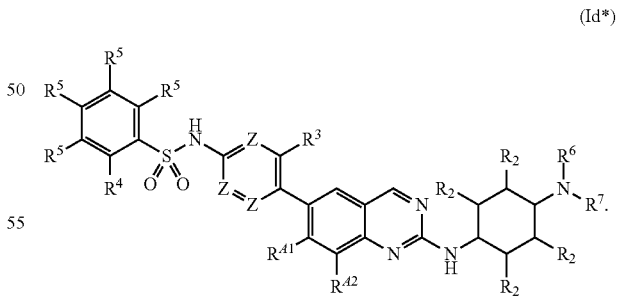

(Id*)

20. The compound of claim 19, or a pharmaceutically acceptable salt thereof,
wherein:
$R^3$ is $C_1$-$C_3$alkyl;
$R^{41}$ is hydrogen, or $C_1$-$C_3$alkyl;
$R^{42}$ is $C_1$-$C_3$alkyl, or hydrogen;
$R^4$ is chlorine or $C_1$-$C_3$alkyl; and
$R^1$ is hydrogen.

21. The compound of claim 19, or a pharmaceutically acceptable salt thereof, wherein:

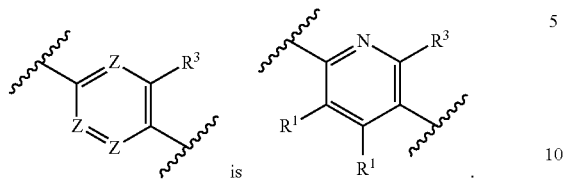

22. The compound of claim 19, or a pharmaceutically acceptable salt thereof, wherein;
   each $R^5$ is independently hydrogen, chlorine, fluorine, or —$CH_3$;
   $R^4$ is chlorine or —$CH_3$;
   $R^3$ is —$CH_3$, or —$CH_2CH_3$;
   $R^{41}$ is —$CH_3$;
   $R^{42}$ is hydrogen, —$CH_3$, —$CH_2CH_3$, or —$OCH_3$; and
   $R^1$ is hydrogen.

23. The compound of claim 19, or a pharmaceutically acceptable salt thereof, wherein
   each $R^5$ is hydrogen;
   $R^4$ is chlorine;
   each $R^2$ is hydrogen; and
   $R^1$ is hydrogen.

24. A pharmaceutical composition comprising a compound according to claim 1, or a pharmaceutically acceptable salt thereof, and one or more pharmaceutically acceptable excipients.

\* \* \* \* \*

SEQUENCE LISTING

<160> NUMBER OF SEQ ID NOS: 28

<210> SEQ ID NO 1
<211> LENGTH: 977
<212> TYPE: PRT
<213> ORGANISM: Homo sapiens

<400> SEQUENCE: 1

| Met | Pro | Ala | Arg | Arg | Leu | Leu | Leu | Leu | Thr | Leu | Leu | Leu | Pro | Gly |
|---|---|---|---|---|---|---|---|---|---|---|---|---|---|---|
| 1 | | | | 5 | | | | | 10 | | | | | 15 |

| Leu | Gly | Ile | Phe | Gly | Ser | Thr | Ser | Val | Thr | Leu | Pro | Glu | Thr | Leu |
|---|---|---|---|---|---|---|---|---|---|---|---|---|---|---|
| | | | | 20 | | | | 25 | | | | | 30 | |

| Leu | Phe | Val | Ser | Thr | Leu | Asp | Gly | Ser | Leu | His | Ala | Val | Ser | Lys | Arg |
|---|---|---|---|---|---|---|---|---|---|---|---|---|---|---|---|
| | | | 35 | | | | | 40 | | | | | 45 | | |

| Thr | Gly | Ser | Ile | Lys | Trp | Thr | Leu | Lys | Glu | Asp | Pro | Val | Leu | Gln | Val |
|---|---|---|---|---|---|---|---|---|---|---|---|---|---|---|---|
| | 50 | | | | | 55 | | | | | 60 | | | | |

| Pro | Thr | His | Val | Glu | Glu | Pro | Ala | Phe | Leu | Pro | Asp | Pro | Asn | Asp | Gly |
|---|---|---|---|---|---|---|---|---|---|---|---|---|---|---|---|
| 65 | | | | | 70 | | | | | 75 | | | | | 80 |

| Ser | Leu | Tyr | Thr | Leu | Gly | Ser | Lys | Asn | Asn | Glu | Gly | Leu | Thr | Lys | Leu |
|---|---|---|---|---|---|---|---|---|---|---|---|---|---|---|---|
| | | | | 85 | | | | | 90 | | | | | 95 | |

| Pro | Phe | Thr | Ile | Pro | Glu | Leu | Val | Gln | Ala | Ser | Pro | Cys | Arg | Ser | Ser |
|---|---|---|---|---|---|---|---|---|---|---|---|---|---|---|---|
| | | | | 100 | | | | | 105 | | | | | 110 | |

| Asp | Gly | Ile | Leu | Tyr | Met | Gly | Lys | Lys | Gln | Asp | Ile | Trp | Tyr | Val | Ile |
|---|---|---|---|---|---|---|---|---|---|---|---|---|---|---|---|
| | | | 115 | | | | | 120 | | | | | 125 | | |

| Asp | Leu | Leu | Thr | Gly | Glu | Lys | Gln | Gln | Thr | Leu | Ser | Ser | Ala | Phe | Ala |
|---|---|---|---|---|---|---|---|---|---|---|---|---|---|---|---|
| | | 130 | | | | | 135 | | | | | 140 | | | |

| Asp | Ser | Leu | Cys | Pro | Ser | Thr | Ser | Leu | Leu | Tyr | Leu | Gly | Arg | Thr | Glu |
|---|---|---|---|---|---|---|---|---|---|---|---|---|---|---|---|
| 145 | | | | | 150 | | | | | 155 | | | | | 160 |

| Tyr | Thr | Ile | Thr | Met | Tyr | Asp | Thr | Lys | Thr | Arg | Glu | Leu | Arg | Trp | Asn |
|---|---|---|---|---|---|---|---|---|---|---|---|---|---|---|---|
| | | | | 165 | | | | | 170 | | | | | 175 | |

| Ala | Thr | Tyr | Phe | Asp | Tyr | Ala | Ala | Ser | Leu | Pro | Glu | Asp | Asp | Val | Asp |
|---|---|---|---|---|---|---|---|---|---|---|---|---|---|---|---|
| | | | 180 | | | | | 185 | | | | | 190 | | |

| Tyr | Lys | Met | Ser | His | Phe | Val | Ser | Asn | Gly | Asp | Gly | Leu | Val | Val | Thr |
|---|---|---|---|---|---|---|---|---|---|---|---|---|---|---|---|
| | | 195 | | | | | 200 | | | | | 205 | | | |

| Val | Asp | Ser | Glu | Ser | Gly | Asp | Val | Leu | Trp | Ile | Gln | Asn | Tyr | Ala | Ser |
|---|---|---|---|---|---|---|---|---|---|---|---|---|---|---|---|
| 210 | | | | | 215 | | | | | 220 | | | | | |

| Pro | Val | Val | Ala | Phe | Tyr | Val | Trp | Gln | Arg | Glu | Gly | Leu | Arg | Lys | Val |
|---|---|---|---|---|---|---|---|---|---|---|---|---|---|---|---|
| 225 | | | | | 230 | | | | | 235 | | | | | 240 |

| Met | His | Ile | Asn | Val | Ala | Val | Glu | Thr | Leu | Arg | Tyr | Leu | Thr | Phe | Met |
|---|---|---|---|---|---|---|---|---|---|---|---|---|---|---|---|
| | | | | 245 | | | | | 250 | | | | | 255 | |

-continued

```
Ser Gly Glu Val Gly Arg Ile Thr Lys Trp Lys Tyr Pro Phe Pro Lys
            260                 265                 270

Glu Thr Glu Ala Lys Ser Lys Leu Thr Pro Thr Leu Tyr Val Gly Lys
            275                 280                 285

Tyr Ser Thr Ser Leu Tyr Ala Ser Pro Ser Met Val His Glu Gly Val
            290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                325                 330                 335

Ser Thr Asp Val Lys Phe Asp Pro Gly Leu Lys Ser Lys Asn Lys Leu
            340                 345                 350

Asn Tyr Leu Arg Asn Tyr Trp Leu Leu Ile Gly His His Glu Thr Pro
            355                 360                 365

Leu Ser Ala Ser Thr Lys Met Leu Glu Arg Phe Pro Asn Asn Leu Pro
            370                 375                 380

Lys His Arg Glu Asn Val Ile Pro Ala Asp Ser Glu Lys Lys Ser Phe
385                 390                 395                 400

Glu Glu Val Ile Asn Leu Val Asp Gln Thr Ser Glu Asn Ala Pro Thr
                405                 410                 415

Thr Val Ser Arg Asp Val Glu Glu Lys Pro Ala His Ala Pro Ala Arg
            420                 425                 430

Pro Glu Ala Pro Val Asp Ser Met Leu Lys Asp Met Ala Thr Ile Ile
            435                 440                 445

Leu Ser Thr Phe Leu Leu Ile Gly Trp Val Ala Phe Ile Ile Thr Tyr
450                 455                 460

Pro Leu Ser Met His Gln Gln Gln Leu Gln His Gln Gln Phe Gln
465                 470                 475                 480

Lys Glu Leu Glu Lys Ile Gln Leu Leu Gln Gln Gln Gln Gln Gln Leu
                485                 490                 495

Pro Phe His Pro Pro Gly Asp Thr Ala Gln Asp Gly Glu Leu Leu Asp
            500                 505                 510

Thr Ser Gly Pro Tyr Ser Glu Ser Ser Gly Thr Ser Ser Pro Ser Thr
            515                 520                 525

Ser Pro Arg Ala Ser Asn His Ser Leu Cys Ser Gly Ser Ser Ala Ser
530                 535                 540

Lys Ala Gly Ser Ser Pro Ser Leu Glu Gln Asp Asp Gly Asp Glu Glu
545                 550                 555                 560

Thr Ser Val Val Ile Val Gly Lys Ile Ser Phe Cys Pro Lys Asp Val
                565                 570                 575

Leu Gly His Gly Ala Glu Gly Thr Ile Val Tyr Arg Gly Met Phe Asp
            580                 585                 590

Asn Arg Asp Val Ala Val Lys Arg Ile Leu Pro Glu Cys Phe Ser Phe
            595                 600                 605

Ala Asp Arg Glu Val Gln Leu Leu Arg Glu Ser Asp Glu His Pro Asn
610                 615                 620

Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
                645                 650                 655

Asp Phe Ala His Leu Gly Leu Glu Pro Ile Thr Leu Leu Gln Gln Thr
            660                 665                 670

Thr Ser Gly Leu Ala His Leu His Ser Leu Asn Ile Val His Arg Asp
```

```
            675                 680                 685
Leu Lys Pro His Asn Ile Leu Ile Ser Met Pro Asn Ala His Gly Lys
    690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Val Pro Gly Thr Glu Gly
                725                 730                 735

Trp Ile Ala Pro Glu Met Leu Ser Glu Asp Cys Lys Glu Asn Pro Thr
                740                 745                 750

Tyr Thr Val Asp Ile Phe Ser Ala Gly Cys Val Phe Tyr Tyr Val Ile
                755                 760                 765

Ser Glu Gly Ser His Pro Phe Gly Lys Ser Leu Gln Arg Gln Ala Asn
770                 775                 780

Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
                805                 810                 815

Pro Gln Lys Arg Pro Ser Ala Lys His Val Leu Lys His Pro Phe Phe
                820                 825                 830

Trp Ser Leu Glu Lys Gln Leu Gln Phe Phe Gln Asp Val Ser Asp Arg
                835                 840                 845

Ile Glu Lys Glu Ser Leu Asp Gly Pro Ile Val Lys Gln Leu Glu Arg
850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
                900                 905                 910

Glu Leu Pro Ala Glu Val Arg Glu Thr Leu Gly Ser Leu Pro Asp Asp
                915                 920                 925

Phe Val Cys Tyr Phe Thr Ser Arg Phe Pro His Leu Leu Ala His Thr
930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Pro Val Thr Pro Asp Ala
                965                 970                 975

Leu

<210> SEQ ID NO 2
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 2
cauguccgca gcacaug                                                    17

<210> SEQ ID NO 3
<211> LENGTH: 17
<212> TYPE: RNA
<213> ORGANISM: Artificial Sequence
<220> FEATURE:
<223> OTHER INFORMATION: Description of Artificial Sequence: Synthetic
      probe
```

-continued

```
<400> SEQUENCE: 3
caugucccca gcacaug                                                  17

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acacgtttgg gaatggacac                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccatgggaag atgttctggg                                               20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcaggagga gcaatgatct tgat                                          24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taccaccatg tacccaggca                                               20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gacagagagt caaactaacg tgg                                           23

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 9
gtccagcagg caagaaggt                                                 19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagaacacgc ttgggaatgg                                                20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgcacctgc tgcggac                                                   17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctgagcccg gaggagaa                                                  18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcgagcagt ctgcgctg                                                  18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taaaagccct gatgctgaag c                                              21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```
tccgactatt ggcatccga                                                  19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctatttccag ggcttccgag t                                               21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aggtgttgta ctggcctcgg t                                               21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagccctctg gaacttgcg                                                  19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aacccaatgg cctgtctgg                                                  19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcatcggacg cacttggaa                                                  19

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
caaccacctt gaatggcaag a                                              21
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
gtccctagct tggctgacag a                                              21
```

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
tggagagcga gggctttg                                                  18
```

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
agcttgattg tcaacctcct g                                              21
```

<210> SEQ ID NO 25
<211> LENGTH: 434
<212> TYPE: PRT
<213> ORGANISM: Saccharomyces cerevisiae

<400> SEQUENCE: 25

Ser Arg Ile Ala Asn Ile Pro Asn Phe Glu Gln Ser Leu Lys Asn Leu
1               5                   10                  15

Val Val Ser Glu Lys Ile Leu Gly Tyr Gly Ser Ser Gly Thr Val Val
            20                  25                  30

Phe Gln Gly Ser Phe Gln Gly Arg Pro Val Ala Val Lys Arg Met Leu
        35                  40                  45

Ile Asp Phe Cys Asp Ile Ala Leu Met Glu Ile Lys Leu Leu Thr Glu
    50                  55                  60

Ser Asp His Pro Asn Val Ile Arg Tyr Tyr Cys Ser Glu Thr Thr
65                  70                  75                  80

Asp Arg Phe Leu Tyr Ile Ala Leu Glu Leu Cys Asn Leu Asn Leu Gln
                85                  90                  95

Asp Leu Val Glu Ser Lys Asn Val Ser Asp Glu Asn Leu Lys Leu Gln
            100                 105                 110

Lys Glu Tyr Asn Pro Ile Ser Leu Leu Arg Gln Ile Ala Ser Gly Val
        115                 120                 125

Ala His Leu His Ser Leu Lys Ile Ile His Arg Asp Leu Lys Pro Gln
    130                 135                 140

Asn Ile Leu Val Ser Thr Ser Ser Arg Phe Thr Ala Asp Gln Gln Thr
145                 150                 155                 160

Gly Ala Glu Asn Leu Arg Ile Leu Ile Ser Asp Phe Gly Leu Cys Lys
                165                 170                 175

Lys Leu Asp Ser Gly Gln Ser Ser Phe Arg Thr Asn Leu Asn Asn Pro
            180                 185                 190

Ser Gly Thr Ser Gly Trp Arg Ala Pro Glu Leu Leu Glu Glu Ser Asn
        195                 200                 205

Asn Leu Gln Thr Lys Arg Arg Leu Thr Arg Ser Ile Asp Ile Phe Ser
    210                 215                 220

Met Gly Cys Val Phe Tyr Tyr Ile Leu Ser Lys Gly Lys His Pro Phe
225                 230                 235                 240

Gly Asp Lys Tyr Ser Arg Glu Ser Asn Ile Ile Arg Gly Ile Phe Ser
                245                 250                 255

Leu Asp Glu Met Lys Cys Leu His Asp Arg Ser Leu Ile Ala Glu Ala
            260                 265                 270

Thr Asp Leu Ile Ser Gln Met Ile Asp His Asp Pro Leu Lys Arg Pro
        275                 280                 285

Thr Ala Met Lys Val Leu Arg His Pro Leu Phe Trp Pro Lys Ser Lys
    290                 295                 300

Lys Leu Glu Phe Leu Leu Lys Val Ser Asp Arg Leu Glu Ile Glu Asn
305                 310                 315                 320

Arg Asp Pro Pro Ser Ala Leu Leu Met Lys Phe Asp Ala Gly Ser Asp
                325                 330                 335

Phe Val Ile Pro Ser Gly Asp Trp Thr Val Lys Phe Asp Lys Ile Phe
            340                 345                 350

Met Asp Asn Leu Glu Arg Tyr Arg Lys Tyr His Ser Ser Lys Leu Met
        355                 360                 365

Asp Leu Leu Arg Ala Leu Arg Asn Lys Tyr His His Phe Met Asp Leu
    370                 375                 380

Pro Glu Asp Ile Ala Glu Leu Met Gly Pro Val Pro Asp Gly Phe Tyr
385                 390                 395                 400

Asp Tyr Phe Ile Lys Arg Phe Pro Asn Leu Leu Ile Gly Val Tyr Met
                405                 410                 415

Ile Val Lys Glu Asn Leu Ser Asp Asp Gln Ile Leu Arg Glu Phe Leu
            420                 425                 430

Tyr Ser

<210> SEQ ID NO 26
<211> LENGTH: 424
<212> TYPE: PRT
<213> ORGANISM: Homo sapiens

<400> SEQUENCE: 26

Asp Asp Gly Asp Glu Glu Thr Ser Val Val Ile Val Gly Lys Ile Ser
1               5                   10                  15

Phe Cys Pro Lys Asp Val Leu Gly His Gly Ala Glu Gly Thr Ile Val
                20                  25                  30

Tyr Arg Gly Met Phe Asp Asn Arg Asp Val Ala Val Lys Arg Ile Leu
            35                  40                  45

Pro Glu Cys Phe Ser Phe Ala Asp Arg Glu Val Gln Leu Leu Arg Glu
        50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

```
Glu Tyr Val Glu Gln Lys Asp Cys Phe Ala His Leu Gly Leu Glu Pro
                100                 105                 110

Ile Thr Leu Leu Gln Gln Thr Thr Ser Gly Leu Ala His Leu His Ser
            115                 120                 125

Leu Asn Ile Val His Arg Asp Leu Lys Pro His Asn Ile Leu Ile Ser
        130                 135                 140

Met Pro Asn Ala His Gly Lys Ile Lys Ala Met Ile Ser Asp Phe Gly
145                 150                 155                 160

Leu Cys Lys Lys Leu Ala Val Gly Arg His Ser Phe Ser Arg Arg Ser
                165                 170                 175

Gly Val Pro Gly Thr Glu Gly Trp Ile Ala Pro Glu Met Leu Ser Glu
            180                 185                 190

Asp Cys Lys Glu Asn Pro Thr Tyr Thr Val Asp Ile Phe Ser Ala Gly
        195                 200                 205

Cys Val Phe Tyr Tyr Val Val Ser Glu Gly Ser His Pro Phe Gly Lys
210                 215                 220

Ser Leu Gln Arg Gln Ala Asn Ile Leu Leu Gly Ala Cys Ser Leu Asp
225                 230                 235                 240

Cys Leu His Pro Glu Lys His Glu Asp Val Ile Ala Arg Glu Leu Ile
                245                 250                 255

Glu Lys Met Ile Ala Met Asp Pro Gln Lys Arg Pro Ser Ala Asn Asp
            260                 265                 270

Val Leu Lys His Pro Phe Phe Trp Ser Leu Glu Lys Gln Leu Gln Phe
        275                 280                 285

Phe Gln Asp Val Ser Asp Arg Ile Glu Lys Glu Ser Leu Asp Gly Pro
290                 295                 300

Ile Val Lys Gln Leu Glu Arg Gly Gly Arg Ala Val Val Lys Met Asp
305                 310                 315                 320

Trp Arg Glu Asn Ile Thr Asp Pro Leu Gln Thr Asp Leu Arg Lys Phe
                325                 330                 335

Arg Thr Tyr Lys Gly Gly Ser Val Arg Asp Leu Leu Arg Ala Met Arg
            340                 345                 350

Asn Lys Lys His His Tyr Arg Asp Leu Pro Glu Glu Val Arg Glu Thr
        355                 360                 365

Leu Gly Thr Leu Pro Asp Asp Phe Val Cys Tyr Phe Thr Ser Arg Phe
370                 375                 380

Pro His Leu Leu Ala His Thr Tyr Arg Ala Met Glu Leu Cys Ser His
385                 390                 395                 400

Glu Arg Leu Phe Gln Pro Tyr Tyr Phe His Glu Pro Pro Glu Pro Gln
                405                 410                 415

Pro Pro Val Thr Pro Asp Ala Leu
            420

<210> SEQ ID NO 27
<211> LENGTH: 423
<212> TYPE: PRT
<213> ORGANISM: Mus musculus

<400> SEQUENCE: 27

Asp Asp Glu Asp Glu Glu Thr Arg Met Val Ile Val Gly Lys Ile Ser
1               5                   10                  15

Phe Cys Pro Lys Asp Val Leu Gly His Gly Ala Glu Gly Thr Ile Val
            20                  25                  30

Tyr Lys Gly Met Phe Asp Asn Arg Asp Val Ala Val Lys Arg Ile Leu
        35                  40                  45
```

```
Pro Glu Cys Phe Ser Phe Ala Asp Arg Glu Val Gln Leu Leu Arg Glu
    50                  55                  60

Ser Asp Glu His Pro Asn Val Ile Arg Tyr Phe Cys Thr Glu Lys Asp
 65              70                  75                  80

Arg Gln Phe Gln Tyr Ile Ala Ile Glu Leu Cys Ala Ala Thr Leu Gln
                85                  90                  95

Glu Tyr Val Glu Gln Lys Asp Phe Ala His Leu Gly Leu Glu Pro Ile
                100                 105                 110

Thr Leu Leu His Gln Thr Thr Ser Gly Leu Ala His Leu His Ser Leu
            115                 120                 125

Asn Ile Val His Arg Asp Leu Lys Pro His Asn Ile Leu Leu Ser Met
        130                 135                 140

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
                165                 170                 175

Val Pro Gly Thr Glu Gly Trp Ile Ala Pro Glu Met Leu Ser Glu Asp
                180                 185                 190

Cys Lys Asp Asn Pro Thr Tyr Thr Val Asp Ile Phe Ser Ala Gly Cys
                195                 200                 205

Val Phe Tyr Tyr Val Ile Ser Glu Gly Asn His Pro Phe Gly Lys Ser
                210                 215                 220

Leu Gln Arg Gln Ala Asn Ile Leu Leu Gly Ala Cys Asn Leu Asp Cys
225                 230                 235                 240

Phe His Ser Asp Lys His Glu Asp Val Ile Ala Arg Glu Leu Ile Glu
                245                 250                 255

Lys Met Ile Ala Met Asp Pro Gln Gln Arg Pro Ser Ala Lys His Val
                260                 265                 270

Leu Lys His Pro Phe Phe Trp Ser Leu Glu Lys Gln Leu Gln Phe Phe
                275                 280                 285

Gln Asp Val Ser Asp Arg Ile Glu Lys Glu Ala Leu Asp Gly Pro Ile
                290                 295                 300

Val Arg Gln Leu Glu Arg Gly Gly Arg Ala Val Val Lys Met Asp Trp
305                 310                 315                 320

Arg Glu Asn Ile Thr Val Pro Leu Gln Thr Asp Leu Arg Lys Phe Arg
                325                 330                 335

Thr Tyr Lys Gly Gly Ser Val Arg Asp Leu Leu Arg Ala Met Arg Asn
                340                 345                 350

Lys Lys His His Tyr Arg Glu Leu Pro Ala Glu Val Gln Glu Thr Leu
                355                 360                 365

Gly Ser Ile Pro Asp Asp Phe Val Arg Tyr Phe Thr Ser Arg Phe Pro
370                 375                 380

His Leu Leu Ser His Thr Tyr Gln Ala Met Glu Leu Cys Arg His Glu
385                 390                 395                 400

Arg Leu Phe Gln Thr Tyr Tyr Trp His Glu Pro Thr Glu Pro Gln Pro
                405                 410                 415

Pro Val Ile Pro Tyr Ala Leu
                420

<210> SEQ ID NO 28
<211> LENGTH: 423
<212> TYPE: PRT
<213> ORGANISM: Rattus norvegicus
```

<400> SEQUENCE: 28

```
Asp Asp Glu Asp Glu Thr Arg Met Val Ile Val Gly Lys Ile Ser
1               5                   10                  15

Phe Cys Pro Lys Asp Val Leu Gly His Gly Ala Glu Gly Thr Ile Val
            20                  25                  30

Tyr Lys Gly Met Phe Asp Asn Arg Asp Val Ala Val Lys Arg Ile Leu
        35                  40                  45

Pro Glu Cys Phe Ser Phe Ala Asp Arg Glu Val Gln Leu Leu Arg Glu
    50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

Glu Tyr Val Glu Gln Lys Asp Phe Ala His Leu Gly Leu Glu Pro Ile
            100                 105                 110

Thr Leu Leu His Gln Thr Thr Ser Gly Leu Ala His Leu His Ser Leu
        115                 120                 125

Asn Ile Val His Arg Asp Leu Lys Pro His Asn Ile Leu Leu Ser Met
130                 135                 140

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
                165                 170                 175

Val Pro Gly Thr Glu Gly Trp Ile Ala Pro Glu Met Leu Ser Glu Asp
            180                 185                 190

Cys Lys Glu Asn Pro Thr Tyr Thr Val Asp Ile Phe Ser Ala Gly Cys
        195                 200                 205

Val Phe Tyr Tyr Val Ile Ser Glu Gly Asn His Pro Phe Gly Lys Ser
210                 215                 220

Leu Gln Arg Gln Ala Asn Ile Leu Leu Gly Ala Cys Ser Leu Asp Cys
225                 230                 235                 240

Phe His Ser Asp Lys His Glu Asp Val Ile Ala Arg Glu Leu Ile Glu
                245                 250                 255

Lys Met Ile Ala Met Asp Pro Gln Gln Arg Pro Ser Ala Lys His Val
            260                 265                 270

Leu Lys His Pro Phe Phe Trp Ser Leu Glu Lys Gln Leu Gln Phe Phe
        275                 280                 285

Gln Asp Val Ser Asp Arg Ile Glu Lys Glu Ser Leu Asp Gly Pro Ile
290                 295                 300

Val Arg Gln Leu Glu Arg Gly Gly Arg Ala Val Val Lys Met Asp Trp
305                 310                 315                 320

Arg Glu Asn Ile Thr Val Pro Leu Gln Thr Asp Leu Arg Lys Phe Arg
                325                 330                 335

Thr Tyr Lys Gly Gly Ser Val Arg Asp Leu Leu Arg Ala Met Arg Asn
            340                 345                 350

Lys Arg His His Tyr Arg Glu Leu Pro Leu Glu Val Gln Glu Thr Leu
        355                 360                 365

Gly Ser Ile Pro Asp Asp Phe Val Arg Tyr Phe Thr Ser Arg Phe Pro
370                 375                 380

His Leu Leu Ser His Thr Tyr Arg Ala Met Glu Leu Cys Arg His Glu
385                 390                 395                 400
```

Arg Leu Phe Gln Thr Tyr Tyr Trp His Glu Pro Thr Glu Ala Gln Pro
            405                 410                 415

Pro Gly Ile Pro Asp Ala Leu
            420

UNITED STATES PATENT AND TRADEMARK OFFICE
CERTIFICATE OF CORRECTION

PATENT NO. : 10,745,379 B2
APPLICATION NO. : 16/184916
DATED : August 18, 2020
INVENTOR(S) : Vacca et al.

Page 1 of 1

It is certified that error appears in the above-identified patent and that said Letters Patent is hereby corrected as shown below:

On the Title Page

In item (73), in "Assignee", in Column 1, Line 1, delete "Ithica," and insert --Ithaca,-- therefor In the Claims In Column 242, Lines 10-44, in Claim 10, delete " 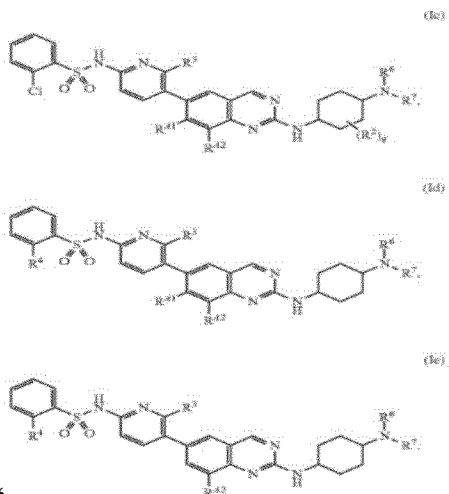 " and insert -- 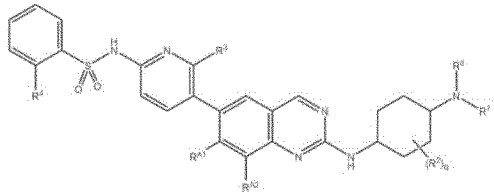 -- therefor Signed and Sealed this
Sixteenth Day of February, 2021

Drew Hirshfeld
*Performing the Functions and Duties of the
Under Secretary of Commerce for Intellectual Property and
Director of the United States Patent and Trademark Office*